United States Patent [19]

Thompson

[11] Patent Number: 4,756,742

[45] Date of Patent: Jul. 12, 1988

[54] HERBICIDAL ORTHO-HETEROCYCLIC THIOPHENESULFONAMIDES

[75] Inventor: Mark E. Thompson, Wilmington, Del.

[73] Assignee: E. I. Du Pont de Nemours and Company, Wilmington, Del.

[21] Appl. No.: 757,739

[22] Filed: Jul. 25, 1985

Related U.S. Application Data

[63] Continuation-in-part of Ser. No. 671,852, Nov. 15, 1984, abandoned.

[51] Int. Cl.$^4$ .................... C07D 409/14; A01N 47/36
[52] U.S. Cl. ........................................... 71/90; 71/91; 71/92; 71/93; 544/47; 544/207; 544/212; 544/253; 544/278; 544/320; 544/321; 544/324; 544/331; 546/276; 548/268
[58] Field of Search ............... 71/90, 91, 92; 544/320, 544/321, 324, 331, 47, 253, 278; 546/276; 548/268

[56] References Cited

U.S. PATENT DOCUMENTS

| | | | |
|---|---|---|---|
| 4,398,939 | 8/1983 | Levitt | 71/90 |
| 4,460,401 | 7/1984 | Sauers | 71/92 |
| 4,465,505 | 8/1984 | Wolf | 71/92 |
| 4,481,029 | 11/1984 | Levitt | 71/93 |
| 4,511,392 | 4/1985 | Rorer | 71/90 |
| 4,606,754 | 8/1986 | Shapiro | 71/92 |
| 4,609,397 | 9/1986 | Wexler | 71/92 |
| 4,657,578 | 4/1987 | Thompson | 71/90 |
| 4,664,695 | 5/1987 | Schurter et al. | 71/92 |
| 4,685,995 | 8/1987 | Christensen et al. | 71/92 |

FOREIGN PATENT DOCUMENTS

| | | | |
|---|---|---|---|
| 111442 | 6/1984 | European Pat. Off. | 71/90 |
| 838416 | 5/1984 | South Africa | 71/92 |

*Primary Examiner*—Robert Gerstl

[57] ABSTRACT

This invention relates to herbicidally active sulfonamide compounds having an ortho cyclic saturated or partially saturated group which includes a carbonyl or sulfonyl radical.

31 Claims, No Drawings

HERBICIDAL ORTHO-HETEROCYCLIC THIOPHENESULFONAMIDES

RELATED APPLICATION

This application is a continuation-in-part of copending application U.S. Ser. No. 671,852, filed Nov. 15, 1984 abandoned.

BACKGROUND OF THE INVENTION

U.S. Pat. No. 4,398,939, issued Aug. 16, 1983 to Levitt, discloses herbicidal thiophenesulfonylureas such as

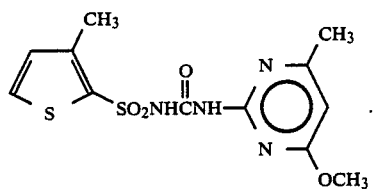

European Patent Application (EP-A) No. 30,142, published June 10, 1981, discloses herbicidal thiophene sulfonylureas such as

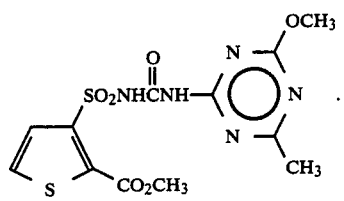

EP-A-No. 83,975, published July 20, 1983, and EP-A-No. 85,476, published Aug. 10, 1983, disclose herbicidal benzenesulfonamides of the formula

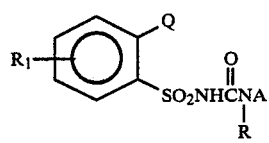

where Q is various 5- and 6-membered, saturated, unsaturated or partially unsaturated heterocyclic rings.

South African Patent Application No. 838,416 (published May, 1984) discloses herbicidal benzenesulfonamides of formula

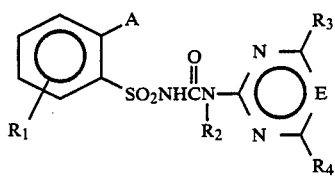

wherein
A is an unsaturated or only partially saturated 5- or 6-membered heterocyclic ring system which is bonded through a carbon atom and contains 1, 2 or 3 heteroatoms.

European Publication No. 116,518 (published 8/22/84; Swiss priority 2/4/83) discloses herbicidal sulfonylureas of the formula

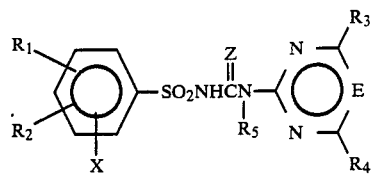

where, in part,
X is $-NR_6R_7$, $-N(SO_2R_9)_2$ or

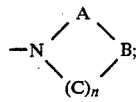

A is $-CO-$, $-SO_2-$, $-CONR_{23}-$ or $-CO_2-$;
B is $C_1-C_4$ alkylene or $C_2-C_4$ alkenylene;
C is $-CO-$, $CR_{21}R_{22}$ or $-SO_2-$; and
n is 0 or 1.

SUMMARY OF THE INVENTION

This invention pertains to novel compounds of Formula I, agriculturally suitable compositions containing them and their method of use as general and/or selective preemergent and/or postemergent herbicides or plant growth regulants.

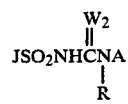

wherein
J is

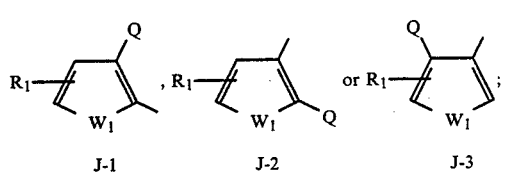

R is H or $CH_3$;
$R_1$ is H, $C_1-C_3$ alkyl, $C_1-C_3$ haloalkyl, halogen, nitro, $C_1-C_3$ alkoxy, $SO_2NR^IR^{II}$, $C_1-C_3$ alkylthio, $C_1-C_3$ alkylsulfinyl, $C_1-C_3$ haloalkoxy, $C_1-C_3$ haloalkylthio, amino, $C_1-C_3$ alkylamino, di($C_1-C_3$)alkylamino, $C_1-C_3$ alkylsulfonyl, $CO_2R^{III}$, $CH_2CN$, $CH_2OCH_3$ or $CH_2SCH_3$;
$W_1$ is O, S or $NR^{II}$;
$W_2$ is O or S;
$R^I$ is H, $C_1-C_4$ alkyl, $C_2-C_3$ cyanoalkyl, methoxy or ethoxy;
$R^{II}$ is H, $C_1-C_4$ alkyl or $C_3-C_4$ alkenyl; or
$R^I$ and $R^{II}$ may be taken together as $-(CH_2)_3-$, $-(CH_2)_4-$, $-(CH_2)_5-$ or $-CH_2CH_2OCH_2CH_2-$;
$R^{III}$ is $C_1-C_4$ alkyl, $C_3-C_4$ alkenyl, $C_3-C_4$ alkynyl, $C_2-C_4$ haloalkyl, $C_2-C_3$ cyanoalkyl, $C_5-C_6$ cycloalkyl, $C_4-C_7$ cycloalkylalkyl or $C_2-C_4$ alkoxyalkyl;
Q is

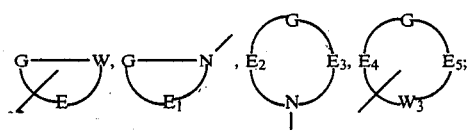

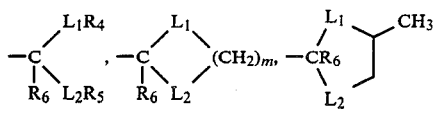

| Q₁ | Q₂ | Q₃ | Q₄ |

G is G=O or SO$_2$;

W is O, S, CHR$_2$ or NR$_3$;

W$_3$ is O, S, SO$_2$, CHR$_2$ or NR$_3$;

R$_2$ is H, C$_1$–C$_2$ alkyl, Cl, F or Br;

R$_3$ is H, C$_1$–C$_4$ alkyl, C$_1$–C$_4$ haloalkyl, C$_2$–C$_4$ alkoxyalkyl, C$_2$–C$_4$ cyanoalkyl, C$_3$–C$_4$ alkenyl or C$_3$–C$_4$ alkynyl;

E and E$_1$ are independently C$_3$–C$_4$ alkylene, C$_3$–C$_4$ alkenylene or C$_4$ alkenyldienyl;

E$_2$ and E$_4$ are independently C$_1$–C$_2$ alkylene or C$_2$ alkenylene;

E$_3$ and E$_5$ are independently C$_2$–C$_3$ alkylene or C$_2$–C$_3$ alkenylene; and E, E, E$_2$, E$_3$, E$_4$ and E$_5$ may optionally be substituted by 1–4 groups selected from C$_1$–C$_4$ alkyl, C$_1$–C$_4$ alkoxy, C$_1$–C$_4$ alkenyl, OH, halogen or C$_1$–C$_4$ haloalkoxy; further, when W is O, CHR$_2$ or NR$_3$, one of the carbon atoms of E may be in the form of a carbonyl group, and when W$_3$ is O, CHR$_2$ or NR$_3$, one of the carbon atoms of E$_4$ or E$_5$ may be in the form of a carbonyl group, provided that said carbonyl groups are not bonded directly to G;

A is

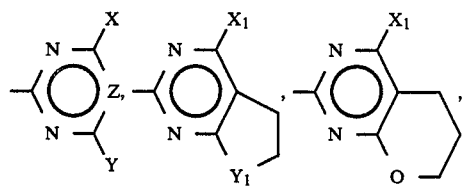

A-1    A-2    A-3

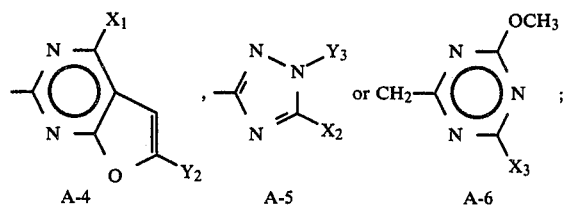

A-4    A-5    A-6

X is H, C$_1$–C$_4$ alkyl, C$_1$–C$_4$ alkoxy, C$_1$–C$_4$ haloalkoxy, C$_1$–C$_4$ haloalkyl, C$_1$–C$_4$ haloalkylthio, C$_1$–C$_4$ alkylthio, halogen, C$_2$–C$_5$ alkoxyalkyl, C$_2$–C$_5$ alkoxyalkoxy, amino, C$_1$–C$_3$ alkylamino or di(C$_1$–C$_3$ alkyl)amino;

Y is H, C$_1$–C$_4$ alkyl, C$_1$–C$_4$ alkoxy, C$_1$–C$_4$ haloalkoxy, C$_1$–C$_4$ haloalkylthio, C$_1$–C$_4$ alkylthio, halogen, C$_2$–C$_5$ alkoxyalkyl, C$_2$–C$_5$ alkoxyalkoxy, amino, C$_1$–C$_3$ alkylamino, di(C$_1$–C$_3$ alkyl)amino, C$_3$–C$_4$ alkenyloxy, C$_3$–C$_4$ alkynyloxy, C$_2$–C$_5$ alkylthioalkyl, C$_2$–C$_5$ alkylsulfinylalkyl, C$_2$–C$_5$ alkylsulfonylalkyl, C$_1$–C$_4$ haloalkyl, C$_3$–C$_5$ cycloalkyl, C$_2$–C$_4$ alkynyl, C(O)R$_6$, or N(OCH$_3$)CH$_3$;

m is 2 or 3;

L$_1$ and L$_2$ are independently O or S;

R$_4$ and R$_5$ are independently C$_1$–C$_2$ alkyl;

R$_6$ is H or CH$_3$;

Z is CH or N;

Y$_1$ is O or CH$_2$;

X$_1$ is CH$_3$, OCH$_3$, OC$_2$H$_5$ or OCF$_2$H;

Y$_2$ is H or CH$_3$;

X$_2$ is CH$_3$, OCH$_2$ or SCH$_3$;

Y$_3$ is CH$_3$, CH$_2$CH$_3$ or CH$_2$CF$_3$; and

X$_3$ is CH$_3$ or OCH$_3$;

and their agriculturally suitable salts; provided that
(a) when G is SO$_2$, then W is O, CHR$_2$ or NH$_3$;
(b) when E$_2$ or E$_4$ is C$_2$ alkylene or C$_2$ alkenylene, then E$_3$ or E$_5$ is C$_2$ alkylene or C$_2$ alkenylene;
(c) when X is Cl, F, Br or I, then Z is CH and Y is OCH$_3$, OC$_2$H$_5$, N(OCH$_3$)CH$_3$, NHCH$_3$, N(CH$_3$)$_2$ or OCF$_2$H;
(d) when X or Y is OCF$_2$H, then Z is CH;
(e) when the total number of carbon atoms of X and Y is greater than four, then the number of carbons of R$_1$ is less than or equal to two and the number of carbons of Q is less than or equal to eight; and
(f) when W$_2$ is S, then R is H, A is A-1, and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$, CH(OCH$_3$)$_2$ or

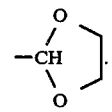

In the above definitions, the term "alkyl" used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers. C$_1$ alkenyl denotes an exocyclic double bond.

Alkynyl denotes straight chain or branched alkynes, e.g., ethynyl, 1-propynyl, 2-propynyl and the different butynyl isomers.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine.

In terms such as C$_2$–C$_3$ alkylthioalkyl, the specified number of carbon atoms is meant to define the total number of carbon atoms in that substituent group. For example, C$_2$–C$_3$ alkylthioalkyl would designate CH$_2$SCH$_3$, CH$_2$SC$_2$H$_5$, CH$_2$CH$_2$SCH$_3$ or CH(CH$_3$)SCH$_3$, and C$_2$–C$_5$ alkoxyalkoxy would represent OCH₂OCH₃ through O(CH₂)₄OCH₃ or OCH₂O(CH₂)₃CH₃ and the various structural isomers embraced therein.

C₄–C₇ cycloalkylalkyl means cyclopropylmethyl through cyclopropylbutyl or cyclohexylmethyl.

Alkylsulfonyl denotes methylsulfonyl, ethylsulfonyl and the different propylsulfonyl isomers.

Alkylthio, alkylsulfinyl, alkylamino, etc. are defined in an analogous manner.

Alkylene denotes methylene (—CH₂—), ethylene (—CH₂CH₂—), propylene or butylene; alkenylene denotes —CH=CH—, —CH=CHCH₂—, —CH=CHCH₂CH₂— or —CH₂CH=CHCH₂—; and alkenyldienyl denotes —CH=CH—CH=CH—.

Preferred for reasons of increased ease of synthesis and/or greater herbicidal efficacy are:
(1) Compounds of Formula I where W₂ is O and R is H;
(2) Compounds of Preferred 1 where
  W₁ is S;
  R₁ is H, Cl, Br, NO₂, CH₃, OCH₃, or CF₃;
  X is CH₃, OCH₃, OCH₂CH₃, Cl, F, Br, I, OCF₂H, CH₂F, OCH₂CH₂F, OCH₂CHF₂, OCH₂CF₃, CF₃, CH₂Cl or CH₂Br;
  Y is H, CH₃, OCH₃, OC₂H₅, CH₂OCH₃, NHCH₃, N(OCH₃)CH₃, N(CH₃)₂, CH₂CH₃, CF₃, SCH₃, CH(CH₃)₂, OCH₂CH=CH₂, OCH₂C≡CH, CH₂OCH₂CH₃, OCH₂CH₂OCH₃, CH₂SCH₃, —C(O)R₆,

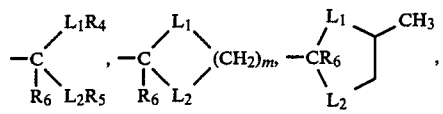

OCF₂H, SCF₂H, cyclopropyl, C≡CH or C≡CCH₃;
(3) Compounds of Preferred 2 where Q is Q₁;
(4) Compounds of Preferred 2 where Q is Q₂;
(5) Compounds of Preferred 2 where Q is Q₃;
(6) Compounds of Preferred 2 where Q is Q₄;
(7) Compounds of Preferred 2 where Q is

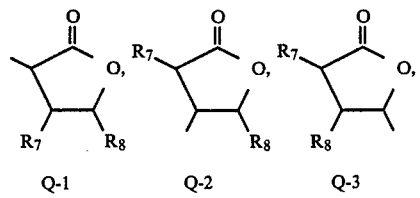

Q-1　　Q-2　　Q-3

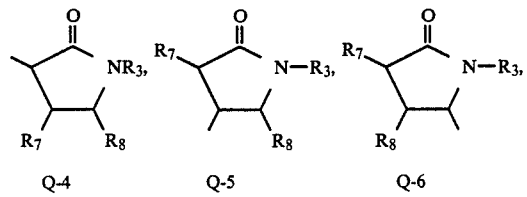

Q-4　　Q-5　　Q-6

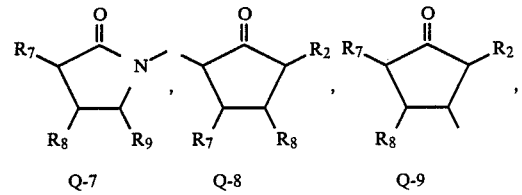

Q-7　　Q-8　　Q-9

-continued

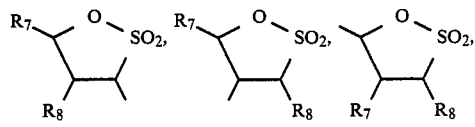

Q-10　　Q-11　　Q-12

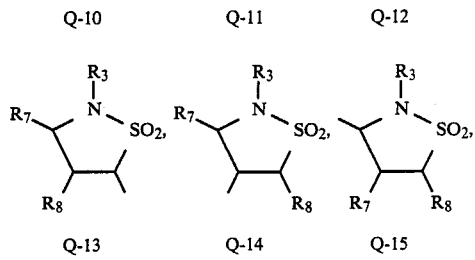

Q-13　　Q-14　　Q-15

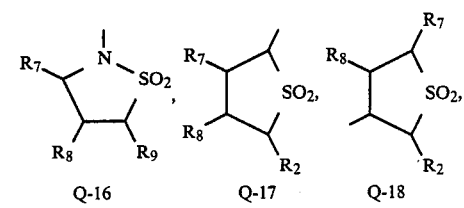

Q-16　　Q-17　　Q-18

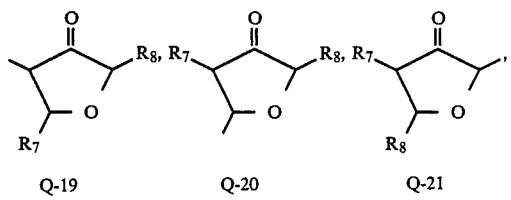

Q-19　　Q-20　　Q-21

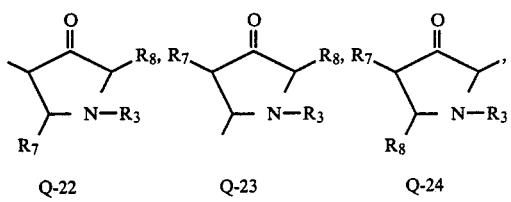

Q-22　　Q-23　　Q-24

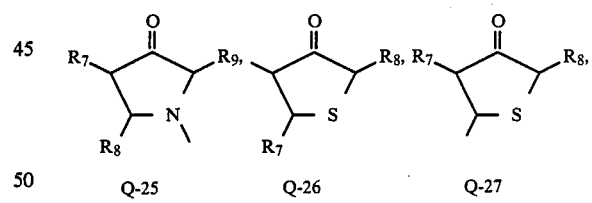

Q-25　　Q-26　　Q-27

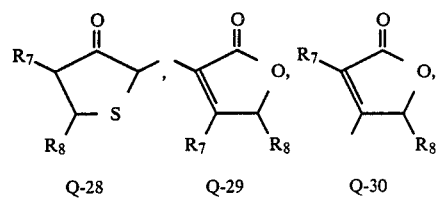

Q-28　　Q-29　　Q-30

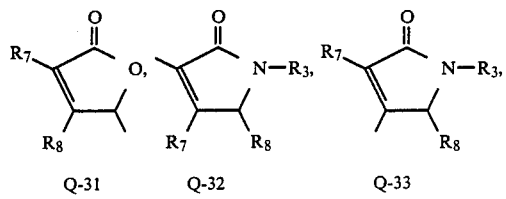

Q-31　　Q-32　　Q-33

-continued
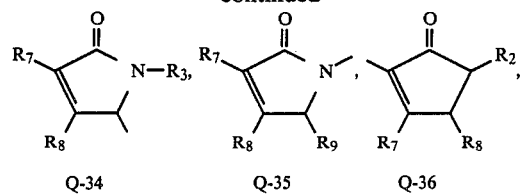
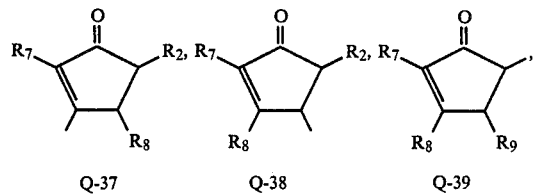
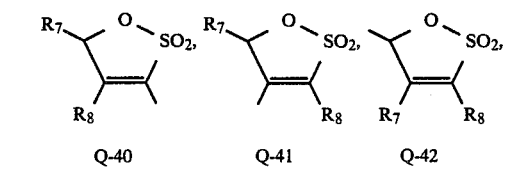
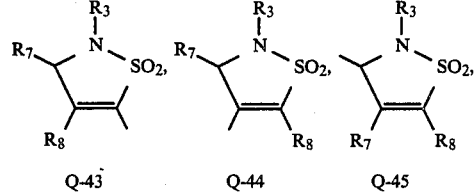
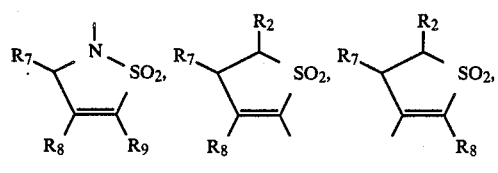
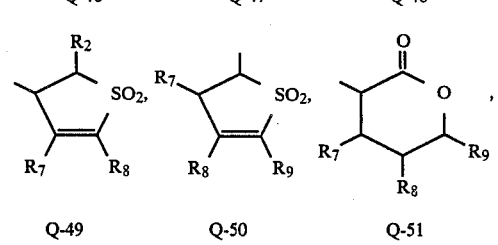
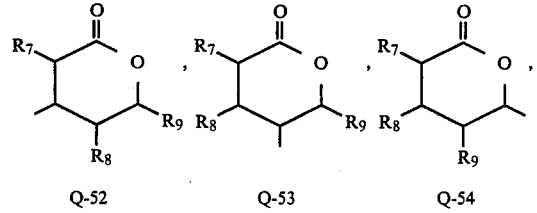
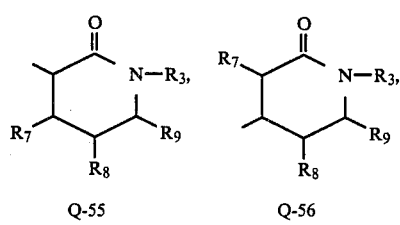
-continued
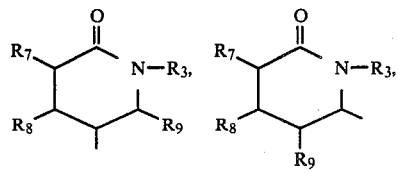
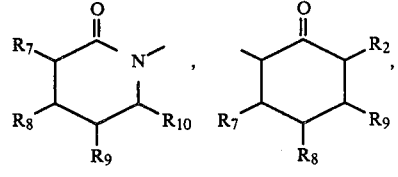
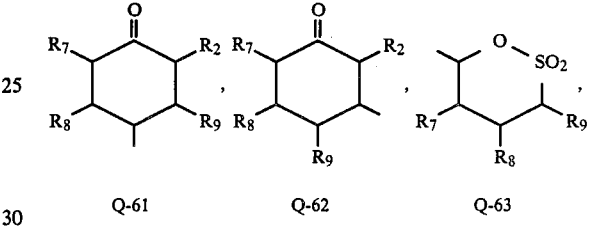
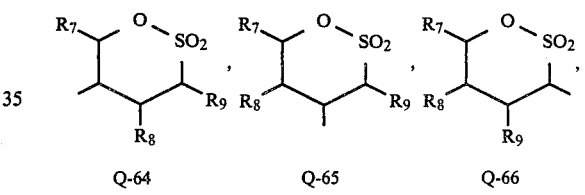
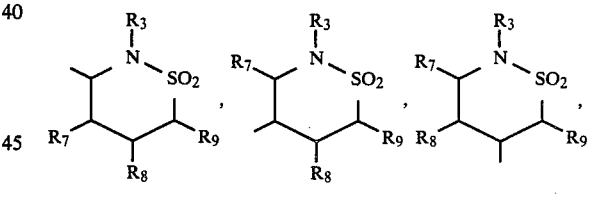
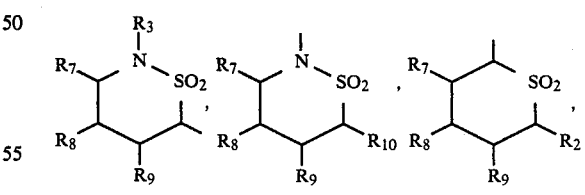
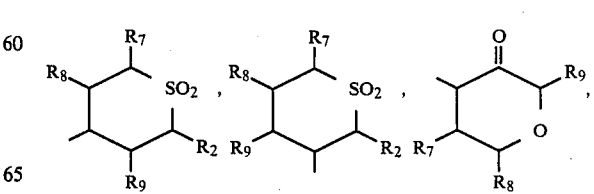

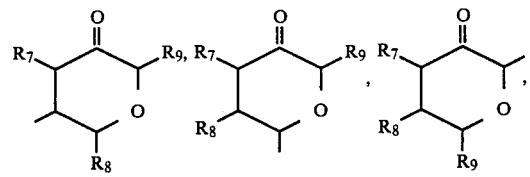
Q-76, Q-77, Q-78
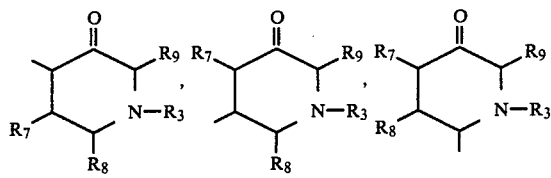
Q-79, Q-80, Q-81
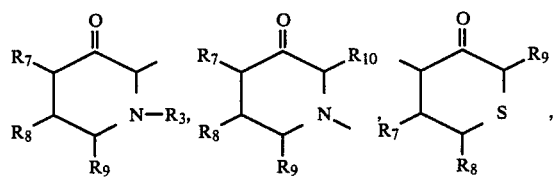
Q-82, Q-83, Q-84
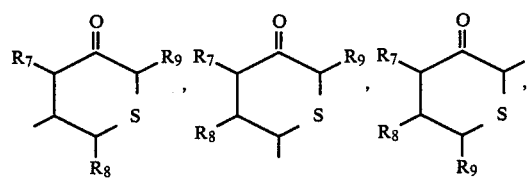
Q-85, Q-86, Q-87
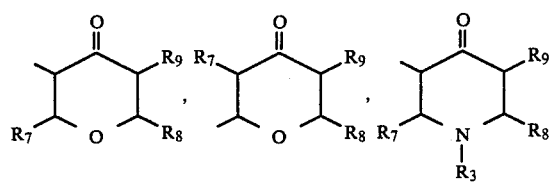
Q-88, Q-89, Q-90
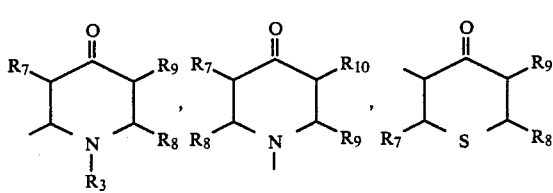
Q-91, Q-92, Q-93
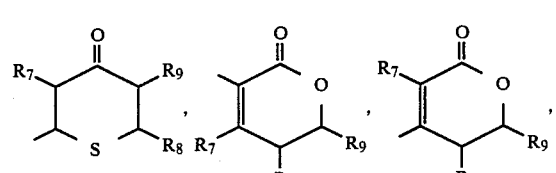
Q-94, Q-95, Q-96
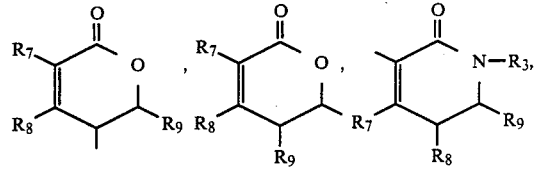
Q-97, Q-98, Q-99
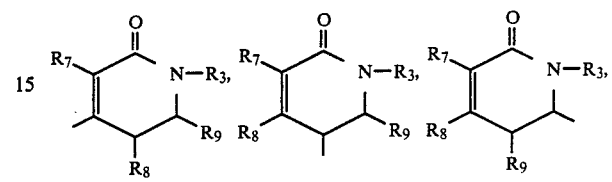
Q-100, Q-101, Q-102
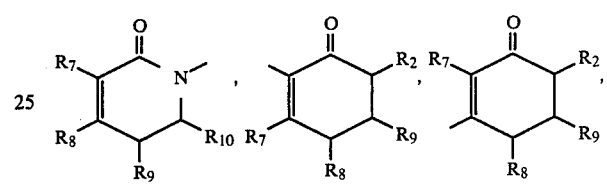
Q-103, Q-104, Q-105
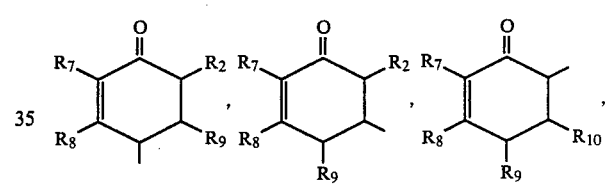
Q-106, Q-107, Q-108
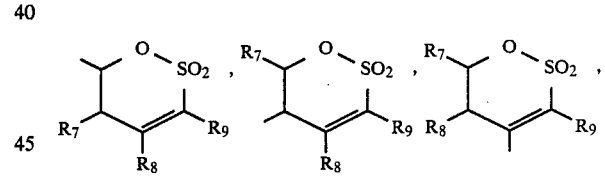
Q-109, Q-110, Q-111
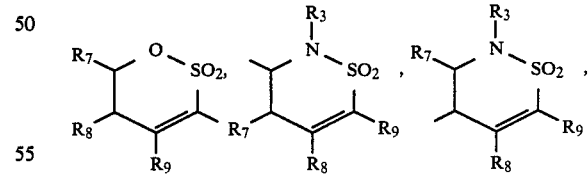
Q-112, Q-113, Q-114
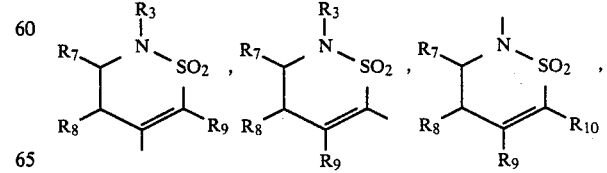
Q-115, Q-116, Q-117

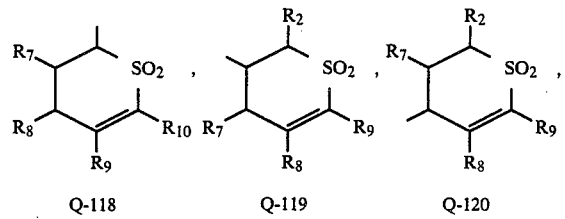
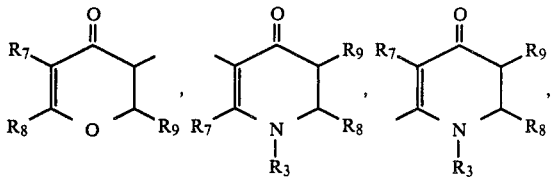
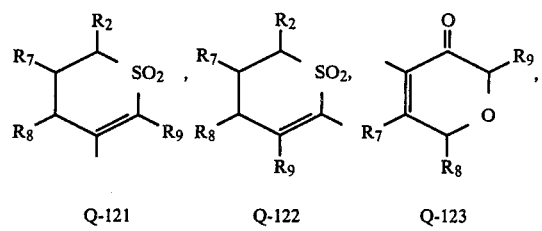
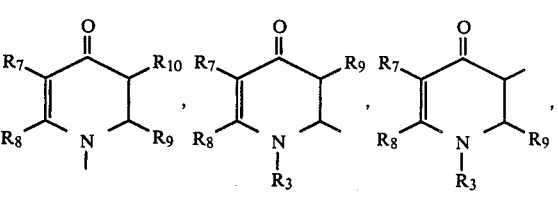
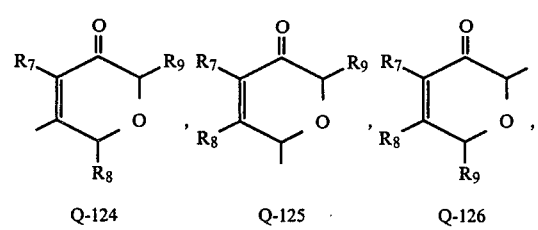
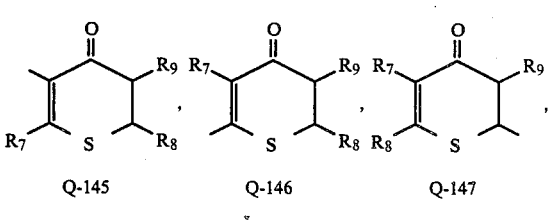
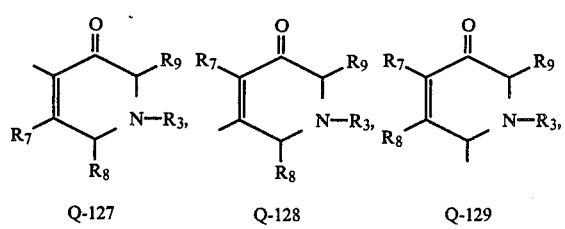
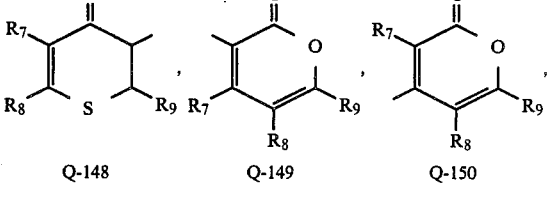
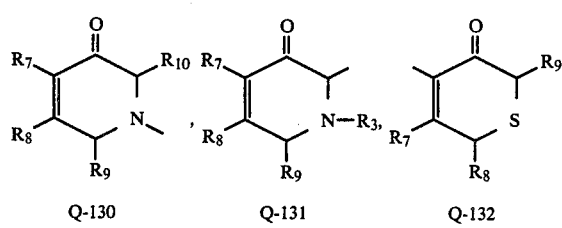
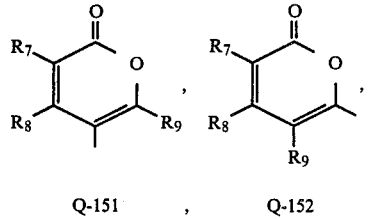
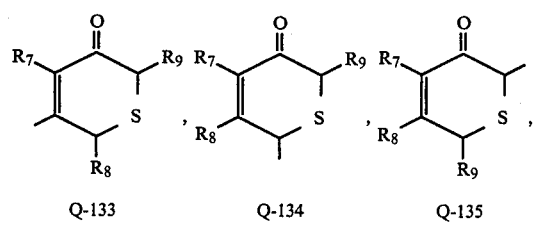
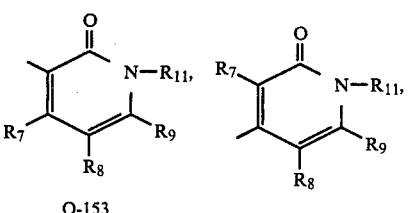
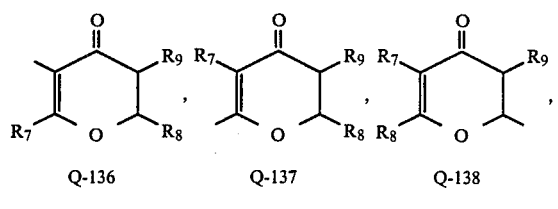
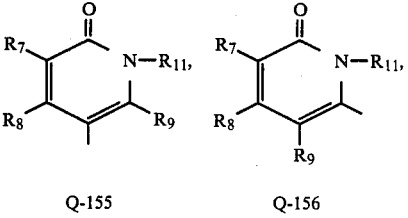

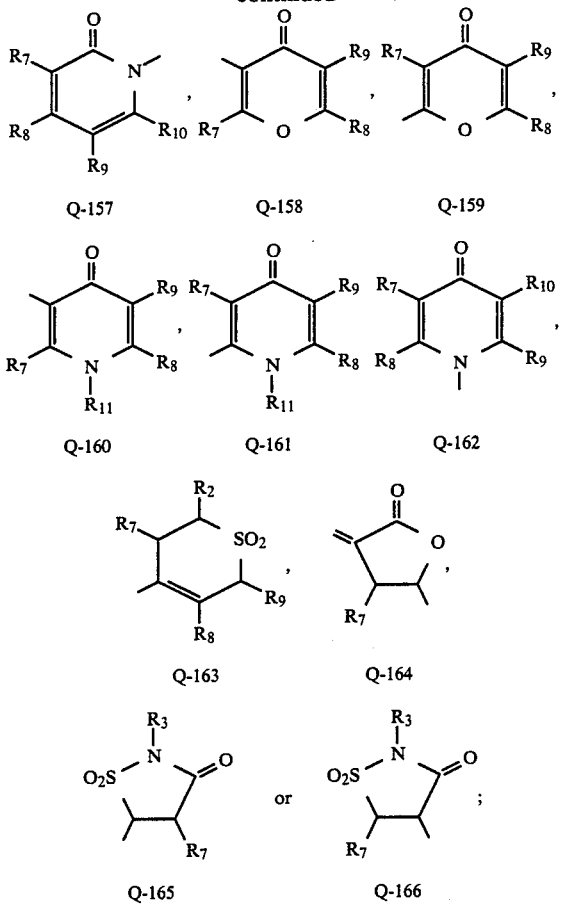

$R_7$, $R_8$, $R_9$ and $R_{10}$ are independently H or $CH_3$; and $R_{11}$ is H, $CH_3$ or $CH_2CH_3$;

(8) Compounds of Preferred 7 where J is J-1 or J-2;
(9) Compounds of Preferred 8 where $R_1$ is H, $CH_3$ or Cl and Y is $CH_3$, $OCH_3$, $C_2H_5$, $OC_2H_5$, $CH_2OCH_3$, $NHCH_3$, $CH(CH_3)_2$, $CH(OCH_3)_2$ or cyclopropyl;
(10) Compounds of Preferred 9 where $R_2$ is H or $CH_3$ and $R_3$ is H, $CH_3$ or $C_2H_5$;
(11) Compounds of Preferred 10 where X is $CH_3$; $OCH_3$, Cl or $OCF_2H$;
(12) Compounds of Preferred 11 where Q is Q-1;
(13) Compounds of Preferred 11 where Q is Q-2;
(14) Compounds of Preferred 11 where Q is Q-3;
(15) Compounds of Preferred 11 where Q is Q-4;
(16) Compounds of Preferred 11 where Q is Q-5;
(17) Compounds of Preferred 11 where Q is Q-6;
(18) Compounds of Preferred 11 where Q is Q-7;
(19) Compounds of Preferred 11 where Q is Q-8;
(20) Compounds of Preferred 11 where Q is Q-9;
(21) Compounds of Preferred 11 where Q is Q-10;
(22) Compounds of Preferred 11 where Q is Q-11;
(23) Compounds of Preferred 11 where Q is Q-12;
(24) Compounds of Preferred 11 where Q is Q-13;
(25) Compounds of Preferred 11 where Q is Q-14;
(26) Compounds of Preferred 11 where Q is Q-15;
(27) Compounds of Preferred 11 where Q is Q-16;
(28) Compounds of Preferred 11 where Q is Q-17;
(29) Compounds of Preferred 11 where Q is Q-18;
(30) Compounds of Preferred 11 where Q is Q-19;
(31) Compounds of Preferred 11 where Q is Q-20;
(32) Compounds of Preferred 11 where Q is Q-21;
(33) Compounds of Preferred 11 where Q is Q-22;
(34) Compounds of Preferred 11 where Q is Q-23;
(35) Compounds of Preferred 11 where Q is Q-24;
(36) Compounds of Preferred 11 where Q is Q-25;
(37) Compounds of Preferred 11 where Q is Q-26;
(38) Compounds of Preferred 11 where Q is Q-27;
(39) Compounds of Preferred 11 where Q is Q-28;
(40) Compounds of Preferred 11 where Q is Q-29;
(41) Compounds of Preferred 11 where Q is Q-30;
(42) Compounds of Preferred 11 where Q is Q-31;
(43) Compounds of Preferred 11 where Q is Q-32;
(44) Compounds of Preferred 11 where Q is Q-33;
(45) Compounds of Preferred 11 where Q is Q-34;
(46) Compounds of Preferred 11 where Q is Q-35;
(47) Compounds of Preferred 11 where Q is Q-36;
(48) Compounds of Preferred 11 where Q is Q-37;
(49) Compounds of Preferred 11 where Q is Q-38;
(50) Compounds of Preferred 11 where Q is Q-39;
(51) Compounds of Preferred 11 where Q is Q-40;
(52) Compounds of Preferred 11 where Q is Q-41;
(53) Compounds of Preferred 11 where Q is Q-42;
(54) Compounds of Preferred 11 where Q is Q-43;
(55) Compounds of Preferred 11 where Q is Q-44;
(56) Compounds of Preferred 11 where Q is Q-45;
(57) Compounds of Preferred 11 where Q is Q-46;
(58) Compounds of Preferred 11 where Q is Q-47;
(59) Compounds of Preferred 11 where Q is Q-48;
(60) Compounds of Preferred 11 where Q is Q-49;
(61) Compounds of Preferred 11 where Q is Q-50;
(62) Compounds of Preferred 11 where Q is Q-51;
(63) Compounds of Preferred 11 where Q is Q-52;
(64) Compounds of Preferred 11 where Q is Q-53;
(65) Compounds of Preferred 11 where Q is Q-54;
(66) Compounds of Preferred 11 where Q is Q-55;
(67) Compounds of Preferred 11 where Q is Q-56;
(68) Compounds of Preferred 11 where Q is Q-57;
(69) Compounds of Preferred 11 where Q is Q-58;
(70) Compounds of Preferred 11 where Q is Q-59;
(71) Compounds of Preferred 11 where Q is Q-60;
(72) Compounds of Preferred 11 where Q is Q-61;
(73) Compounds of Preferred 11 where Q is Q-62;
(74) Compounds of Preferred 11 where Q is Q-63;
(75) Compounds of Preferred 11 where Q is Q-64;
(76) Compounds of Preferred 11 where Q is Q-65;
(77) Compounds of Preferred 11 where Q is Q-66;
(78) Compounds of Preferred 11 where Q is Q-67;
(79) Compounds of Preferred 11 where Q is Q-68;
(80) Compounds of Preferred 11 where Q is Q-69;
(81) Compounds of Preferred 11 where Q is Q-70;
(82) Compounds of Preferred 11 where Q is Q-71;
(83) Compounds of Preferred 11 where Q is Q-72;
(84) Compounds of Preferred 11 where Q is Q-73;
(85) Compounds of Preferred 11 where Q is Q-74;
(86) Compounds of Preferred 11 where Q is Q-75;
(87) Compounds of Preferred 11 where Q is Q-76;
(88) Compounds of Preferred 11 where Q is Q-77;
(89) Compounds of Preferred 11 where Q is Q-78;
(90) Compounds of Preferred 11 where Q is Q-79;
(91) Compounds of Preferred 11 where Q is Q-80;
(92) Compounds of Preferred 11 where Q is Q-81;
(93) Compounds of Preferred 11 where Q is Q-82;
(94) Compounds of Preferred 11 where Q is Q-83;
(95) Compounds of Preferred 11 where Q is Q-84;
(96) Compounds of Preferred 11 where Q is Q-85;
(97) Compounds of Preferred 11 where Q is Q-86;
(98) Compounds of Preferred 11 where Q is Q-87;
(99) Compounds of Preferred 11 where Q is Q-88;
(100) Compounds of Preferred 11 where Q is Q-89;

(101) Compounds of Preferred 11 where Q is Q-90;
(102) Compounds of Preferred 11 where Q is Q-91;
(103) Compounds of Preferred 11 where Q is Q-92;
(104) Compounds of Preferred 11 where Q is Q-93;
(105) Compounds of Preferred 11 where Q is Q-94;
(106) Compounds of Preferred 11 where Q is Q-95;
(107) Compounds of Preferred 11 where Q is Q-96;
(108) Compounds of Preferred 11 where Q is Q-97;
(109) Compounds of Preferred 11 where Q is Q-98;
(110) Compounds of Preferred 11 where Q is Q-99;
(111) Compounds of Preferred 11 where Q is Q-100;
(112) Compounds of Preferred 11 where Q is Q-101;
(113) Compounds of Preferred 11 where Q is Q-102;
(114) Compounds of Preferred 11 where Q is Q-103;
(115) Compounds of Preferred 11 where Q is Q-104;
(116) Compounds of Preferred 11 where Q is Q-105;
(117) Compounds of Preferred 11 where Q is Q-106;
(118) Compounds of Preferred 11 where Q is Q-107;
(119) Compounds of Preferred 11 where Q is Q-108;
(120) Compounds of Preferred 11 where Q is Q-109;
(121) Compounds of Preferred 11 where Q is Q-110;
(122) Compounds of Preferred 11 where Q is Q-111;
(123) Compounds of Preferred 11 where Q is Q-112;
(124) Compounds of Preferred 11 where Q is Q-113;
(125) Compounds of Preferred 11 where Q is Q-114;
(126) Compounds of Preferred 11 where Q is Q-115;
(127) Compounds of Preferred 11 where Q is Q-116;
(128) Compounds of Preferred 11 where Q is Q-117;
(129) Compounds of Preferred 11 where Q is Q-118;
(130) Compounds of Preferred 11 where Q is Q-119;
(131) Compounds of Preferred 11 where Q is Q-120;
(132) Compounds of Preferred 11 where Q is Q-121;
(133) Compounds of Preferred 11 where Q is Q-122;
(134) Compounds of Preferred 11 where Q is Q-123;
(135) Compounds of Preferred 11 where Q is Q-124;
(136) Compounds of Preferred 11 where Q is Q-125;
(137) Compounds of Preferred 11 where Q is Q-126;
(138) Compounds of Preferred 11 where Q is Q-127;
(139) Compounds of Preferred 11 where Q is Q-128;
(140) Compounds of Preferred 11 where Q is Q-129;
(141) Compounds of Preferred 11 where Q is Q-130;
(142) Compounds of Preferred 11 where Q is Q-131;
(143) Compounds of Preferred 11 where Q is Q-132;
(144) Compounds of Preferred 11 where Q is Q-133;
(145) Compounds of Preferred 11 where Q is Q-134;
(146) Compounds of Preferred 11 where Q is Q-135;
(147) Compounds of Preferred 11 where Q is Q-136;
(148) Compounds of Preferred 11 where Q is Q-137;
(149) Compounds of Preferred 11 where Q is Q-138;
(150) Compounds of Preferred 11 where Q is Q-139;
(151) Compounds of Preferred 11 where Q is Q-140;
(152) Compounds of Preferred 11 where Q is Q-141;
(153) Compounds of Preferred 11 where Q is Q-142;
(154) Compounds of Preferred 11 where Q is Q-143;
(155) Compounds of Preferred 11 where Q is Q-144;
(156) Compounds of Preferred 11 where Q is Q-145;
(157) Compounds of Preferred 11 where Q is Q-146;
(158) Compounds of Preferred 11 where Q is Q-147;
(159) Compounds of Preferred 11 where Q is Q-148;
(160) Compounds of Preferred 11 where Q is Q-149;
(161) Compounds of Preferred 11 where Q is Q-150;
(162) Compounds of Preferred 11 where Q is Q-151;
(163) Compounds of Preferred 11 where Q is Q-152;
(164) Compounds of Preferred 11 where Q is Q-153;
(165) Compounds of Preferred 11 where Q is Q-154;
(166) Compounds of Preferred 11 where Q is Q-155;
(167) Compounds of Preferred 11 where Q is Q-156;
(168) Compounds of Preferred 11 where Q is Q-157;
(169) Compounds of Preferred 11 where Q is Q-158;
(170) Compounds of Preferred 11 where Q is Q-159;
(171) Compounds of Preferred 11 where Q is Q-160;
(172) Compounds of Preferred 11 where Q is Q-161;
(173) Compounds of Preferred 11 where Q is Q-162;
(174) Compounds of Preferred 11 where Q is Q-163;
(175) Compounds of Preferred 11 where Q is Q-164;
(176) Compounds of Preferred 11 where Q is Q-165;
(177) Compounds of Preferred 11 where Q is Q-166.

Specifically preferred for reasons of greatest ease of synthesis and/or greatest herbicidal efficacy are:
N-[(4,6-dimethoxypyrimidin-2-yl)aminocaronyl]-2-(tetrahydro-2-oxofuran-3-yl)-3-thiophenesulfonamide;
N-[(4-methoxy-6-methyltriazin-2-yl)aminocarbonyl]-2-(tetrahydro-2-oxofuran-3-yl)-3-thiophenesulfonamide; and
N-[(4,6-dimethylpyrimidin-2-yl)aminocarbonyl]-2-(3-oxo-1-cyclohexen-1-yl)-3-thiophenesulfonamide, m.p. 190°-192° C.

DETAILED DESCRIPTION OF THE INVENTION

Synthesis

Compounds of Formula I may be synthesized by one or more of the methods shown below in Equations 1, 2 and 3.

Equation 1 depicts the reaction of sulfonyl isocyanates and isothiocyanates II with the appropriate heterocyclic amines of Formula III to give the desired sulfonylureas I.

Equation 1

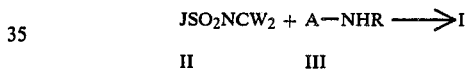

II   III wherein
J, R, $W_2$ and A are as previously defined.

The reaction of Equation 1 is best carried out in an inert aprotic solvent such as methylene chloride, tetrahydrofuran or acetonitrile at a temperature between 0° and 82° C. A catalytic amount of 1,4-diazabicyclo[2.2.2]octane (DABCO) may be used to accelerate the reaction. In the cases which the products are insoluble in the reaction solvent, they may be isolated by simple filtration. When the products are soluble, they may be isolated by evaporation of the solvent and trituration of the residue with solvents such as 1-chlorobutane, diethyl ether or ethyl acetate, and filtration.

Compounds of Formula I may also be prepared as shown below in Equation 2 by treating sulfonamides of Formula IV with the methyl ester of a pyrimidine or triazine carbamic acid of Formula V in the presence of an equimolar quantity of trimethylaluminum.

Equation 2

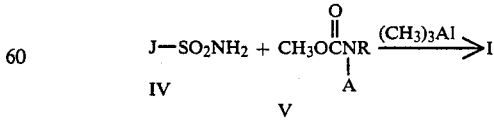

IV   V wherein
J and A are as previously defined, and R is H.

The reaction of Equation 2 is best carried out at temperatures between 25° and 83° C. in a solvent such as methylene chloride or 1,2-dichloroethane for 12 to 96 hours under an inert atmosphere, as taught in European Patent Application (EP-A) No. 84,244 (published July 27, 1983). The products of Formula I are most conveniently isolated by acidifying the reaction solution with dilute aqueous hydrochloric acid, and extraction with a suitable solvent such as methylene chloride or ethyl acetate. If necessary, purification may be achieved by recrystallization of column chromatography. The methyl carbamates V can be synthesized by treatment of the corresponding heterocyclic amines of Formula III with dimethyl carbonate or methyl chloroformate in the presence of a base such as sodium hydride or pyridine.

Alternatively, compounds of Formula I may be prepared as shown below in Equation 3 by the reaction of sulfonamides IV with the phenyl ester of the appropriate carbamic acid, VI, in the presence of an equimolar quantity of a tertiary amine base such as 1,8-diazabicyclo[5.4.0]undec-7-ene (DBU).

Equation 3

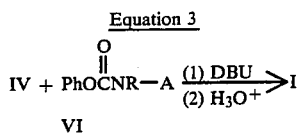

wherein
J and A are as previously defined, and R is H.

The reaction shown in Equation 3 is best carried out at about 25° C. in a suitable solvent such as dioxane or acetonitrile for 1–2 hours under an inert atmosphere as described in European Patent Application No. 70,804 (published Jan. 26, 1983). The desired products of Formula I may be most conveniently isolated by acidifying the reaction solution with dilute aqueous hydrochloric acid. In certain cases, the products are insoluble and may be filtered. Alternatively, the aqueous layer may be extracted with a solvent such as methylene chloride or ethyl acetate. Drying and evaporation of the solvent then affords the desired products. The phenyl carbamates VI can be synthesized by treatment of the corresponding heterocyclic amines of Formula III with diphenyl carbonate or phenyl chloroformate in the presence of a base such as sodium hydride, pyridine, or potassium carbonate with a catalytic amount of 4-dimethylaminopyridine. The mixture is stirred at temperatures between 25° and 65° C. in a suitable solvent such as tetrahydrofuran for 12–36 hours.

A judicious choice of the appropriate methods for preparing compounds of Formula I must take into account the nature of the substituents Q and $R_1$, and their chemical compatability with the reaction conditions of Equations 1–3. Such a decision would be obvious to one who is skilled in the art.

Sulfonyl isocyanates of Formula IIa may be prepared as shown in Equation 4 by the reaction of sulfonamides of general structure IV with phosgene in the presence of n-butyl isocyanate and a catalytic amount of 1,4-diazabicyclo[2.2.2]octane (DABCO).

Equation 4

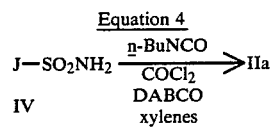

wherein

J is as previously defined and $W_2$ is O.

The reaction shown in Equation 4 is best carried out according to the procedure described in U.S. Pat. No. 4,238,621.

Alternatively, sulfonyl isocyanates IIa may be prepared via phosgenation of the preformed n-butylureas of Formula VII as represented in Equation 5.

Equation 5

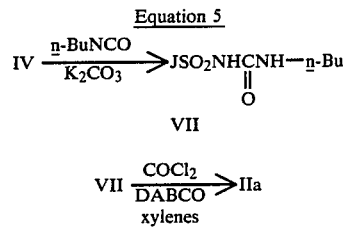

wherein
J is as previously defined and $W_2$ is O.

The compounds of Formula VII are conveniently prepared by stirring a mixture of the appropriate sulfonamide IV, anhydrous potassium carbonate, and n-butyl isocyanate in suitable solvent such as acetone or methyl ethyl ketone at 25° to 80° C. until all of the isocyanate has reacted. The product is isolated by quenching in dilute aqueous hydrochloric acid and recrystallizing the insoluble solid. The n-butylurea VII is then treated with phosgene and a catalytic amount of DABCO in refluxing xylenes or chlorobenzene in a manner analogous to that described in Equation 4.

Another, somewhat milder, method for the preparation of sulfonyl isocyanates IIa is shown in Equation 6. Treatment of sulfonamides of Formula IV with thionyl chloride gives intermediate N-sulfinylsulfonamides VIII, which afford sulfonyl isocyanates II upon exposure to phosgene in the presence of a catalytic amount of pyridine.

Equation 6

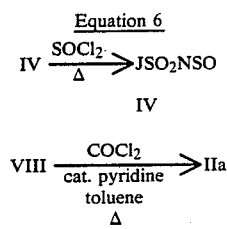

wherein
J is as previously defined and $W_2$ is O.

The reaction of Equation 6 may be performed according to the procedure of H. Ulrich, B. Tucker and A. Sayigh, *J. Org. Chem.*, 34, 3200 (1969).

Sulfonyl isothiocyanates of Formula II, where $W_2$ is S, can be prepared according to the method taught by K. Hartke, *Arch. Pharm.*, 299, 174 (1966).

A judicious choice of the appropriate method for preparing compounds of Formula II must take into account the nature of the substituents Q and $R_1$, and their chemical compatability with the reaction conditions of Equations 4–6. Such a decision would be obvious to one skilled in the art.

The requisite sulfonamides of Formula IV may be synthesized by one or more of the methods shown below in Equations 7, 8 and 9.

Equation 7 depicts the reaction of sulfonyl chlorides of Formula IX with ammonia to give sulfonamides of Formula IVa.

Equation 7

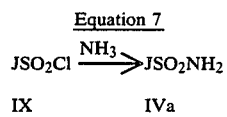

wherein
J is as previously defined.

The amination of Equation 7 is conveniently effected by adding at least two molar equivalents of either anhydrous ammonia or concentrated ammonium hydroxide to a solution of the sulfonyl chloride IX in a suitable solvent such as diethyl ether, tetrahydrofuran, or methylene chloride at temperatures between −30° and 25° C. The desired sulfonamides of Formula IVa are isolated either by filtration, in which case the by-product ammonium chloride is removed by washing with water, or extraction into a suitable organic solvent such as methylene chloride or ethyl acetate. Drying and evaporation of the solvent then affords the products IVa, which are usually sufficiently pure to be carried directly on to the next step.

Sulfonamides of Formula IVb may be prepared as shown in Equation 8 by treatment of the corresponding N-t-butylsulfonamides X with an appropriate acid such as trifluoroacetic (TFA), polyphosphoric (PPA), or p-toluenesulfonic acid (p-TSA).

Equation 8

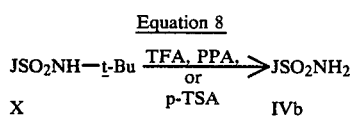

wherein
J is as previously defined.

The reaction of Equation 8 is conveniently carried out by stirring a solution of the compound of Formula X in excess trifluoroacetic acid (approximately 0.3M) at about 25° C. for 1-24 hours. The desired sulfonamides of Formula IVb are then isolated by removal of the volatiles in vacuo and crystallization from a suitable solvent such as diethyl ether, 1-chlorobutane, or ethyl acetate. Alternatively, the N-t-butylsulfonamides of Formula X may be treated with a catalytic amount of p-toluenesulfonic acid monohydrate in a solvent such as toluene or xylenes at reflux temperature for 1-6 hours. The desired products are then isolated in a manner analogous to the one described above. For use of polyphosphoric acid in the deprotection of N-t-butylsulfonamides, see J. G. Lombardino, *J. Org. Chem.*, 36, 1843 (1971); for use of trifluoroacetic acid, see J. D. Catt and W. L. Matier, *J. Org. Chem.*, 39, 566 (1974).

Alternatively, sulfonamides of Formula IVc, where Q is Q-1, may be synthesized via the two-step procedure represented below in Equation 9(a) starting from the thiazin-1,1-dioxides of Formula XI. In a similar fashion, sulfonamides of Formula IVd, where Q is Q-51, may be prepared via the two-step procedure shown in Equation 9(b) starting from the same compounds XI.

Equation 9

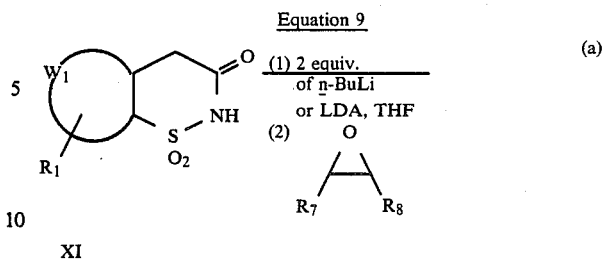

wherein $R_1$, $R_7$, $R_8$, and $R_9$ are as previously defined. In this and all subsequent equations,

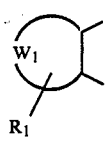

represents J as previously defined, and $W_1$ and $R_1$ are as previously defined.

Equation 9(a)

The transformation shown above in Equation 9(a) may be conveniently carried out by adding a suitable base such as n-butyllithium (n-BuLi) or lithium diisopropylamide (LDA) to a solution of the compound of general structure XI in a solvent such as tetrahydrofuran at −78° C. under an inert atmosphere. To ensure complete dianion formation, the reaction mixture is typically allowed to warm to about −30° C. over a period of 0.5 to 1 hour, and is then recooled and treated with the appropriate epoxide. After being stirred overnight at −78° to 25° C., the reaction solution is acidified with dilute aqueous hydrochloric acid and the water layer extracted with a suitable solvent such as diethyl ether or methylene chloride. Drying and evaporation of the organic extracts affords a crude residue which is immediately dissolved in an organic solvent such as tetrahydrofuran, and heated at reflux temperature in the presence of a mineral acid such as hydrochloric acid for 1 for 4 hours. The desired products of Formula IVc are isolated by extraction into an organic solvent such as diethyl ether or methylene chloride. Drying and evaporation of the organic extracts affords the crude sulfonamides IVc, which are typically purified by silica gel chromatography; elution is achieved with an appropriate solvent system such as 40–80% ethyl acetate-hexanes containing 1% methanol.

Equation 9(b)

The transformation depicted in Equation 9(b) is carried out in a manner analogous to the one described for Equation 9(a), except that a protected bromoalkanol is employed in the reaction with the dianions of thiazin 1,1-dioxides XI to give intermediates of Formula XIII. These compounds are then treated with aqueous acid as described above to afford the desired sulfonamides of Formula IVd, which may be purified by column chromatography if necessary.

The thiazin-1,1-dioxides XI may be prepared as shown below in Equation 10 by treatment of sulfonamides of Formula XIV with aqueous sodium hydroxide.

Equation 10

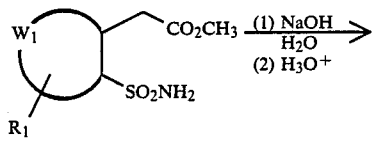

XIV

-continued
Equation 10

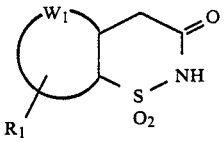

XI wherein
$W_1$, $R_1$ are as previously defined.

The ring-closure reaction shown in Equation 10 may be effected by stirring a solution of the compound of Formula XIV in excess 10% aqueous sodium hydroxide at about 25° C. for 1–2 hours. The products of Formula XI are then isolated by acidifying the cooled (0°–10° C.) reaction mixture with concentrated hydrochloric acid, and filtration. These compounds are generally sufficiently pure to be carried directly on to the next step.

Some sulfonyl chlorides of Formula IX may be prepared by one or more of the methods shown below in Equations 11, 12 and 13.

Equation 11 depicts the diazotization of appropriately substituted aminothiophene derivatives of Formula XV, where $W_1$ is S, and subsequent coupling with sulfur dioxide in the presence of either cupric or cuprous chloride to give the desired products of Formula IX.

Equation 11

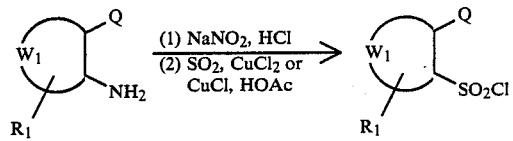

XV      IX wherein
Q and $R_1$ are as previously defined, and $W_1$ is S.

The reaction of Equation 11 is accomplished by treating a solution of the aminothiophene derivatives XV in concentrated hydrochloric acid with a solution of sodium nitrite in water at −5° to 5° C. After being stirred for 10–30 minutes at about 0° C., the solution is added to a mixture of excess sulfur dioxide and a catalytic amount of cupric chloride or cuprous chloride in glacial acetic acid at about 10° C. The temperature is maintained at about 10° C. for ¼–1 hour, then raised to 25° C. and stirred for 2–24 hours. This solution is then poured into a large excess of ice-water. The desired sulfonyl chlorides XI may be isolated by filtration, or by extraction into a solvent such as diethyl ether or methylene chloride, followed by drying and evaporation of the solvent.

Sulfonyl chlorides of Formula IX may also be prepared as shown below in Equation 12 by metalhalogen exchange of appropriately substituted thienyl or furanyl bromides XVIa, where $X_4$ is Br, and trapping with sulfuryl chloride.

Equation 12

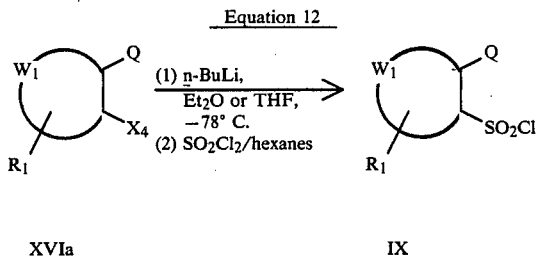

XVIa          IX wherein

Q, $W_1$, and $R_1$ are as previously defined, and $X_4$ is Br.

The lithiation shown in Equation 12 is best carried out by procedures analogous to those described by S. H. Bhattacharya, et al., *J. Chem. So. (C)*, 1265 (1968).

Alternatively, compounds of Formula IX may be prepared via oxidative chlorination of the appropriate thioethers of Formula XVIb, where $X_4$ is $SR_{12}$, as represented in Equation 13.

Equation 13

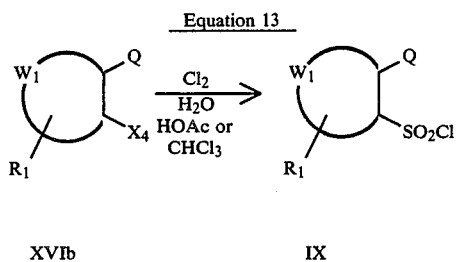

XVIb          IX wherein

Q, $W_1$ and $R_1$ are as previously defined, $X_4$ is $SR_{12}$, and $R_{12}$ is $C_2$-$C_4$ alkyl or benzyl.

The reaction of Equation 13 may be accomplished by treating a solution of the thioether XVIb in a suitable solvent such as chloroform or methylene chloride; in some cases, it is advantageous to use acetic acid as solvent. The reaction is carried out in the presence of at least 2.5 equivalents of water and at least 3 molar equivalents of chlorine at 0°–30° C. for 1 to 5 hours. The products may be isolated by removal of the solvent in vacuo and are generally sufficiently pure to be carried directly on to the next step.

The requisite aminothiophene derivatives of Formula XV may be prepared in a straightforward manner by reduction of the corresponding nitro compounds of Formula XVIc, where $X_4$ is $NO_2$, as shown in Equation 13a.

Equation 13a

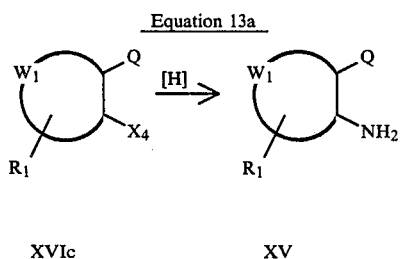

XVIc          XV wherein

Q and $R_1$ are as previously defined, $W_1$ is S, and $X_4$ is $NO_2$.

A wide variety of methods exists for effecting the reduction of aromatic nitro groups to the corresponding amino derivatives. One of the more common procedures involves treating the nitro compounds of Formula XVIc with a slight excess of stannous chloride dihydrate in concentrated hydrochloric acid at temperatures between 25° and 80° C. Alternatively, reduction may be accomplished with iron powder in glacial acetic acid as described by Hazlet and Dornfeld, *J. Am. Chem. Soc.*, 66, 1781 (1944), and by West, *J. Chem. Soc.*, 127, 494 (1925). For a general review, see Groggins in "Unit Processes in Organic Synthesis", McGraw-Hill Book Co., New York, 1947, pp. 73–128.

A judicious choice of the appropriate method for preparing compounds of Formula IX must take into account the nature of the substituents Q and $R_1$, and their chemical compatability with the reaction conditions of Equations 11–13a. Such a decision would be obvious to one who is skilled in the art.

Sulfonamides of Formulas XVIIa and XVIIb may be prepared as shown in Equations 14(a) and 14(b) by hydrogenolysis of the benzyl ethers XVIIIa and XVIIIb, followed by lactonization under acidic conditions.

Equation 14

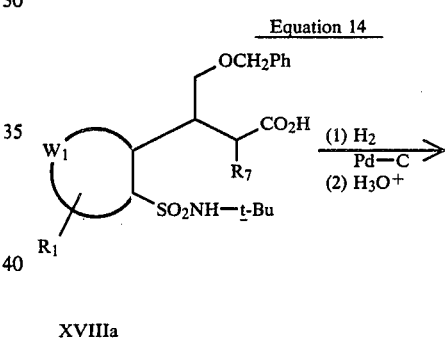 (a)

XVIIIa

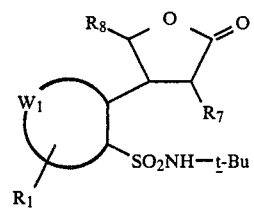

XVIIa

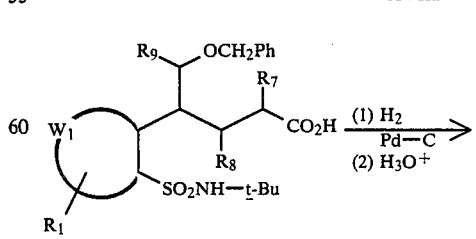 (b)

XVIIIb

-continued
Equation 14

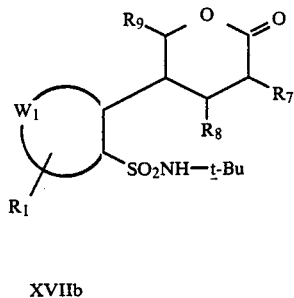

XVIIb wherein
$W_1$, $R_1$, $R_7$, $R_8$ and $R_9$ are as previously defined.

The hydrogenolysis of benzyl ethers to generate alcohols as shown in the first step of Equations 14(a) and 14(b) is well precedented in the literature and may be accomplished by subjecting compounds of Formulas XVIIIa and XVIIIb to a hydrogen atmosphere in the presence of a suitable catalyst such as palladium-on-carbon. For relevant references, see C. H. Heathcock and R. Ratcliffe, *J. Am. Chem. Soc.*, 93, 1746 (1971), and A. M. Felix, et al., *J. Org. Chem.*, 43, 4194 (1978). The second step represented above in Equations 14(a) and 14(b) involves the formation of 5- or 6-membered ring lactones from the corresponding 4- or 5-hydroxy carboxylic acids, an extremely facile cyclization which often occurs spontaneously. This lactonization process may be aided by heating the hydroxy acids in the presence of a suitable acid such as hydrochloric or sulfuric acid. For a discussion of this reaction and useful references, see J. March, "Advanced Organic Chemistry", 2nd Ed., McGraw-Hill Book Co., New York, 1977, pp. 363–365.

Alternatively, sulfonamides of Formula XVIIa may be synthesized via iodolactonization of the appropriate unsaturated carboxylic acids of Formula XIX, followed by reductive cleavage of the carbon-iodine bond as shown in Equation 15.

Equation 15

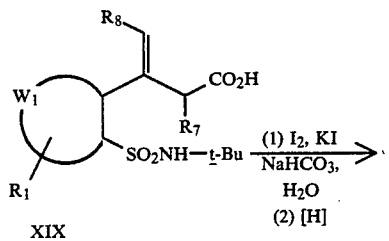

XIX

XVIIa wherein
$W_1$, $R_1$, $R_7$ and $R_8$ are as previously defined.

The first step of the reaction of Equation 15 may be accomplished according to the procedure of J. Klein, *J. Am. Chem. Soc.*, 81, 3611 (1959). The intermediate iodolactones obtained from this reaction are then treated with a suitable reducing agent such as zinc in acetic acid as described by C. Heathcock, et al., *J. Am. Chem. Soc.*, 92, 1326 (1970).

Sulfonamides of Formula XVIIc may be conveniently prepared as shown below in Equation 16, by a two-step procedure analogous to that shown in Equations 14(a) and 14(b) except that the starting carboxylic acids are those of Formula XVIIIc.

Equation 16

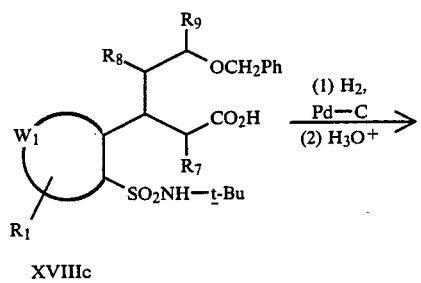

XVIIIc

XVIIc wherein
$W_1$, $R_1$, $R_7$, $R_8$, and $R_9$ are as previously defined.

The transformation shown above in Equation 16 may be effected in a manner identical to that described for Equations 14(a) and 14(b).

Sulfonamides of Formulas XVIId and XVIIe may be synthesized by the three-step sequence of reactions outlined below in Equations 17(a) and 17(b) which involves: (1) addition of the dianions of suitable N-t-butyl-thiophenesulfonamides of Formula XX to the appropriate β- or γ-formyl esters to give hydroxy esters XXIa and XXIb, (2) saponification of the esters XXIa and XXIb to afford the corresponding γ- or δ-hydroxy carboxylic acids, and (3) acid-induced lactonization.

Equation 17

(a)

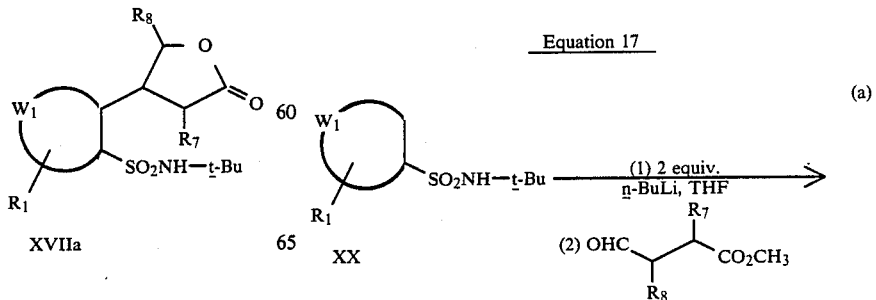

XX

-continued
Equation 17

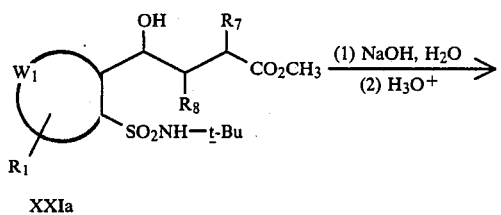

XXIa

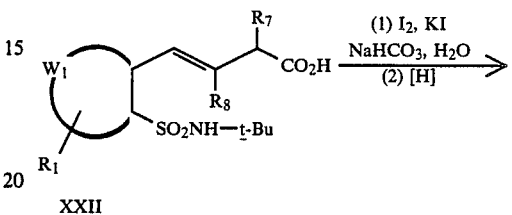

XVIId (b)

XX $\xrightarrow{\text{(1) 2 equiv.}}_{\underline{\text{n}}\text{-BuLi, THF}}$ (2) OHC–CHR$_9$–CHR$_8$–CHR$_7$–CO$_2$CH$_3$

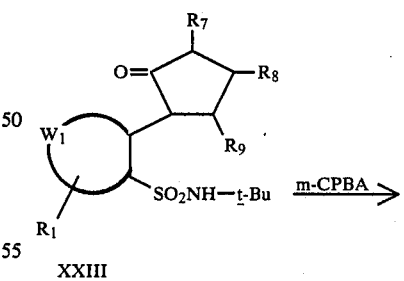

XXIb

XVIIe wherein
$R_1$, $R_7$, $R_8$, and $R_9$ are as previously defined, and $W_1$ is S.

The first step of Equations 17(a) and 17(b) may be carried out by treating the appropriate N-t-butylthiophenesulfonamide XX with n-butyllithium in a solvent such as tetrahydrofuran at 0°–25° C. by methods similar to the procedures of J. G. Lombardino, *J. Org. Chem.*, 36, 1843 (1971). Addition of suitably substituted β- or γ-formyl esters to these dianions affords the hydroxy esters of Formulas XXIa or XXIb. Saponification of these hydroxy esters may be most easily accomplished by treatment with excess aqueous sodium hydroxide solution at about 25° C. for 1–6 hours. The desired products are obtained by acidifying with concentrated hydrochloric acid (ice-water cooling) and either filtration or extraction into a suitable organic solvent such as methylene chloride, diethyl ether, or ethyl acetate. These γ- and β-hydroxy carboxylic acids may then spontaneously cyclize to give the desired products of Formulas XVIId and XVIIe; if not, lactonization may be achieved in a manner identical to that described for Equation 14 above.

Alternatively, sulfonamides of Formula XVIId may be prepared by iodolactonization of the appropriate unsaturated carboxylic acids of Formula XXII, followed by reductive cleavage of the carbon-iodine bond as shown in Equation 18.

Equation 18

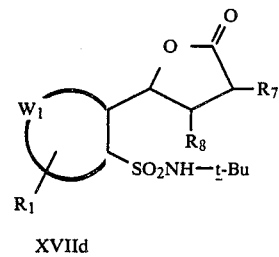

XXII

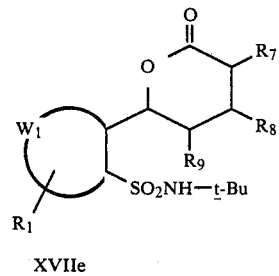

XVIId wherein
$R_1$, $R_7$ and $R_8$ are as previously defined, and $W_1$ is S.

The transformation shown in Equation 18 above may be achieved in a manner identical to that described for Equation 15.

Sulfonamides of Formula XVIIe may also be synthesized by a Baeyer-Villiger reaction on the appropriately substituted cyclopentanones XXIII as depicted in Equation 19.

Equation 19

XXIII $\xrightarrow{\underline{\text{m-CPBA}}}$

XVIIe wherein $R_1$, $R_7$, $R_8$, and $R_9$ are as previously defined, and $W_1$ is S.

The oxidation shown in Equation 19 may be carried out by treating a solution of the ketone XXIII in a suitable solvent such as chloroform or methylene chloride with m-chloroperoxybenzoic acid (m-CPBA) according to the methods described by S. L. Friess, *J. Am. Chem. Soc.*, 71, 2571 (1949), and S. L. Friess and P. E. Frankenburg, ibid., 74, 2679 (1952). For a review of the Baeyer-Villiger reaction, refer to C. H. Hassall, *Org. Reactions*, 9, 73 (1957).

It should be recognized that removal of the tert-butyl protecting group from compounds of Formulas XVIIa-XVIIe by one of the methods described above in Equation 8 will furnish the primary sulfonamides of Formula IVb, where Q is Q-2, Q-53, Q-52, Q-3 and Q-54, which may then be converted to compounds of Formula I with the corresponding Q substituents.

Compounds of Formula XXIV(a-g) may be prepared by treatment of the corresponding lactones IVc, XVIIa, XVIId, IVd, XVIIc, XVIIb and XVIIe, respectively, with ammonia or the appropriate primary amine, $R_3NH_2$, as shown below in Equation 20.

Equation 20

(a)
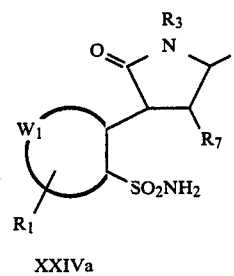
IVc (b)
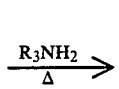
XVIIa

-continued

Equation 20

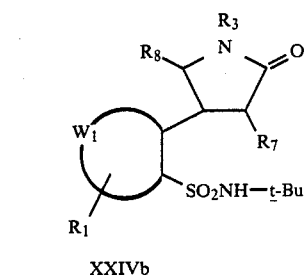
XXIVb (c)
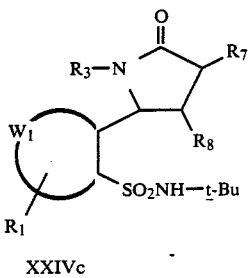
XVIId

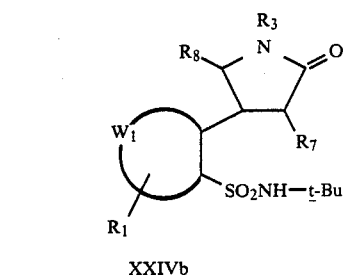
XXIVc (d)
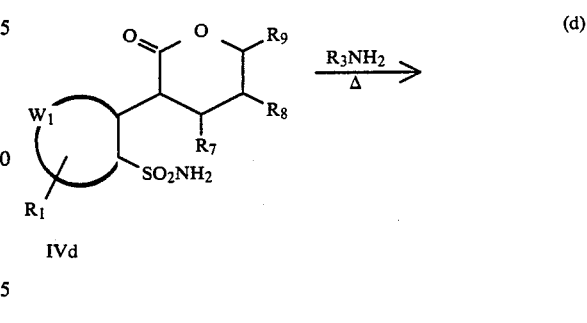
IVd

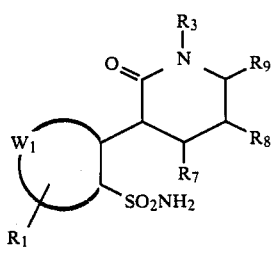
XXIVd

-continued

Equation 20

(e)
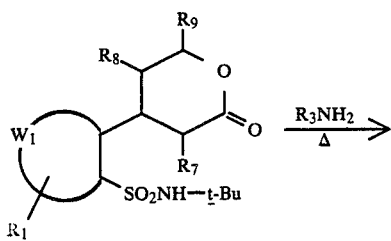
XVIIc

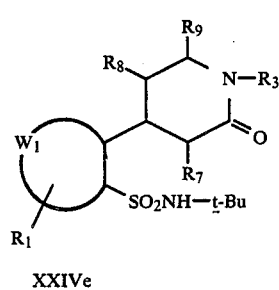
XXIVe (f)
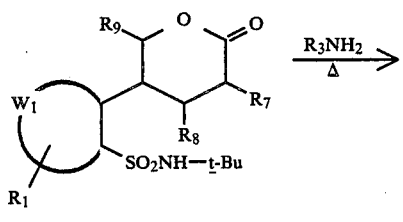
XVIIb

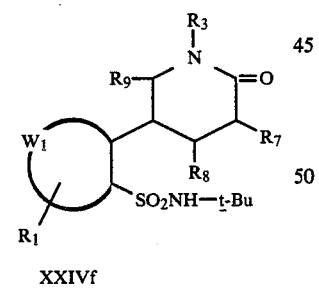
XXIVf

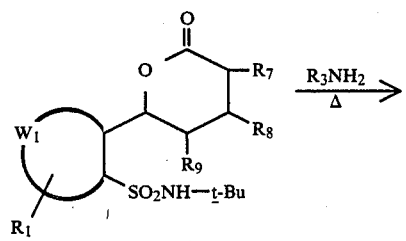
XVIIe

-continued

Equation 20

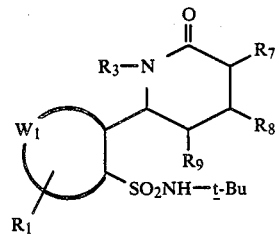
XXIVq wherein
$W_1$, $R_1$, $R_3$, $R_7$, $R_8$ and $R_9$ are as previously defined.

The conversion of lactones to lactams as shown in Equations 20(a)–20(g) is a well-known process and may be effectively carried out according to the procedures of Scott and Kearse, *J. Org. Chem.*, 5, 598 (1940), and Jones, et al., *J. Am. Chem. Soc.*, 48, 181 (1926); 49, 2528 (1927).

Lactams of Formulas XXIVh and XXIVi may be prepared as shown below in Equation 21 by an intramolecular N-acylation reaction of aminothiophene derivatives of Formulas XXVa and XXVb.

Equation 21

(a)
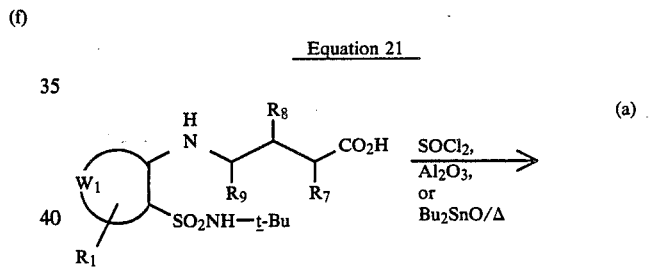
XXVa

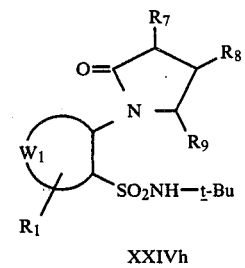
XXIVh (b)
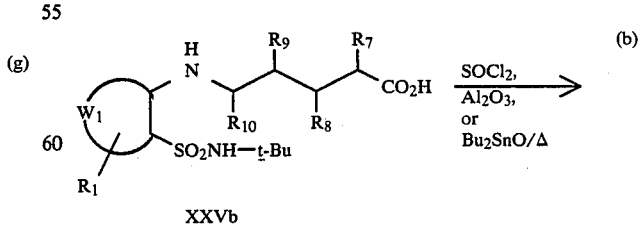
XXVb

-continued
Equation 21

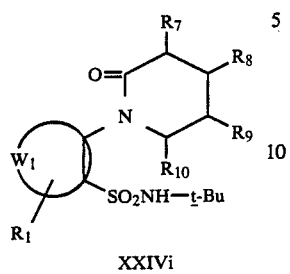

XXIVi wherein
$R_1$, $R_7$, $R_8$, $R_9$ and $R_{10}$ are as previously defined, and $W_1$ is S.

The reaction represented in Equations 21(a) and 21(b) may be accomplished by one or more of the following procedures: (1) treatment of compounds of Formulas XXVa and XXVb with thionyl chloride at reflux temperature to give intermediate acid chlorides which rapidly undergo cyclization (for related methods, see Kent and McElvain, *Org. Syntheses*, 25, 7 (1945); A. P. Martinez, et al., *J. Org. Chem.*, 26, 4501 (1961); W. B. Weaver and W. M. Whaley, *J. Am. Chem. Soc.*, 69, 515, 1144 (1947); and F. Falk, *J. Prakt. Chem.*, 15, 228 (1962)); (2) reaction of compounds of Formulas XXVa and XXVb with alumina or silica as described by A. Blade-Font, *Tetrahedron Lett.*, 21, 2443 (1980); and (3) treatment of compounds XXVa and XXVb with dibutyltin oxide as described by K. Steliou, et al., *J. Am. Chem. Soc.*, 102, 7578 (1980).

Subsequent treatment of N-t-butylsulfonamides of Formulas XXIVb, c and e-i according to one of the methods described in Equation 8 will furnish the primary sulfonamides of Formula IVb, where Q is Q-5, Q-6, Q-56, Q-57, Q-58, Q-7 and Q-59, which may then be converted to compounds of Formula I with the corresponding substituents.

Ketones of Formulas XXIIIa and XXIIIb may be prepared via the sequence shown below in Equations 22 and 23, from the appropriate N-t-butylthiophene- or furansulfonamides of Formula XX.

Equation 22

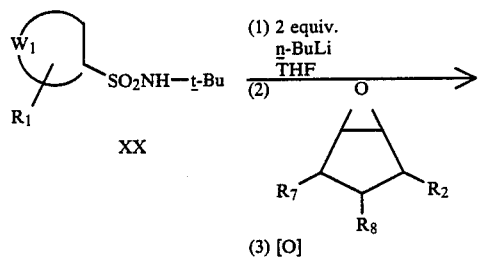

-continued
Equation 22

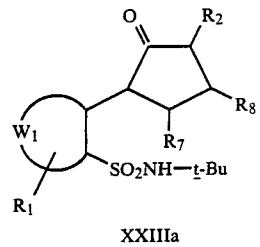

XXIIIa wherein
$W_1$, $R_1$, $R_2$, $R_7$ and $R_8$ are as previously defined.

Equation 23

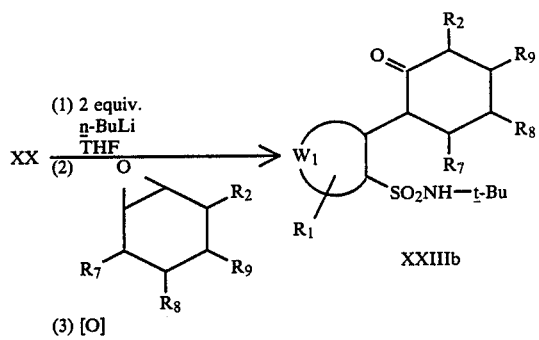

XXIIIb wherein
$W_1$, $R_1$, $R_2$, $R_7$, $R_8$ and $R_9$ are as previously defined.

The first step of Equations 22 and 23 may be carried out as described for Equation 17. Addition of the appropriate epoxide, and subsequent aqueous acid workup gives intermediate alcohols, which can be oxidized to the desired ketones of Formulas XXIIIa and XXIIIb by any one of numerous methods, e.g., with chromium trioxide in aqueous sulfuric acid (E. R. H. Jones, et al., *J. Chem. Soc.*, 2548 (1953)), chromium trioxide-pyridine (G. I. Poos, G. E. Arth, R. E. Beyler and L. H. Sareff, *J. Am. Chem. Soc.*, 75, 422 (1953)), or pyridinium chlorochromate (E. J. Corey and T. L. Suggs, *Tetrahedron Lett.*, 2647 (1975)).

Ketones of Formulas XXIIIc and XXIIId may be conveniently with dianions of N-t-butylsulfonamides XX. The result is a 1,4-addition to give the desired products of Formulas XXIIIIc and XXIIId as shown below in Equation 24.

Equation 24

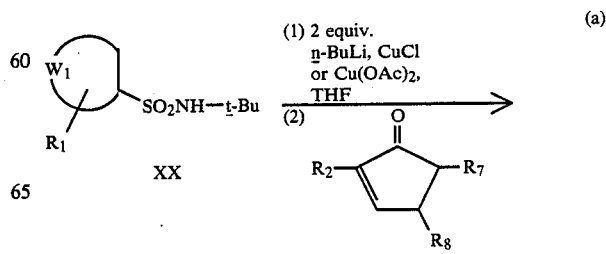
(a)

Equation 24

-continued

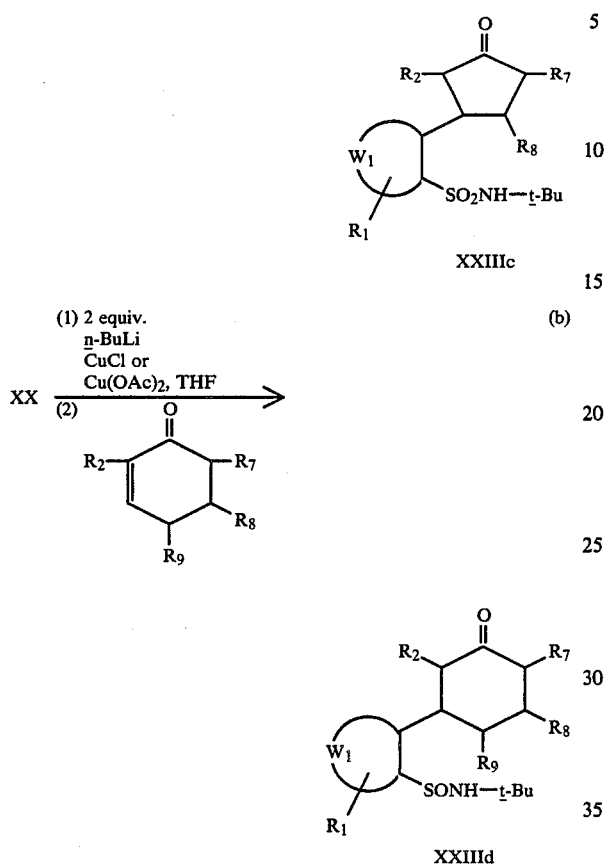

wherein
$W_1$, $R_1$, $R_2$, $R_7$, $R_8$ and $R_9$ are as previously defined.

The first step shown in Equations 24(a) and 24(b) involves the formation of N-t-butylthiophene- or furan-sulfonamide dianions as described for Equation 17. However, in the case of the reactions shown above in Equation 24, a suitable copper ion catalyst such as cuprous chloride or cupric acetate is added to form aryl copper reagents, which then undergo a conjugate addition to substituted cycloalkenones to generate the desired products of Formulas XXIIIc and XXIIId after aqueous workup. Such a transformation is well precedented in the literature; for relevant examples, see Gorlier, Harmon, Levisalles and Wagnon, Chem. Comm., 88 (1973); Posner, Org. Reactions, 19, 1 (1972); or House, Acc. Chem. Res., 9, 59 (1976).

Ketones of Formula XXIIIe, where $R_8$ is H, may be synthesized in a straightforward manner via the three-step sequence of reactions shown in Equation 25 involving: (a) selective reduction of esters of Formula XXVIII to aldehydes of Formula XXIX, (b) base-induced aldol condensation and dehydration to give enones of Formula XXX, and (c) selective reduction of the olefinic bond of enones XXX to provide the desired products.

Equation 25

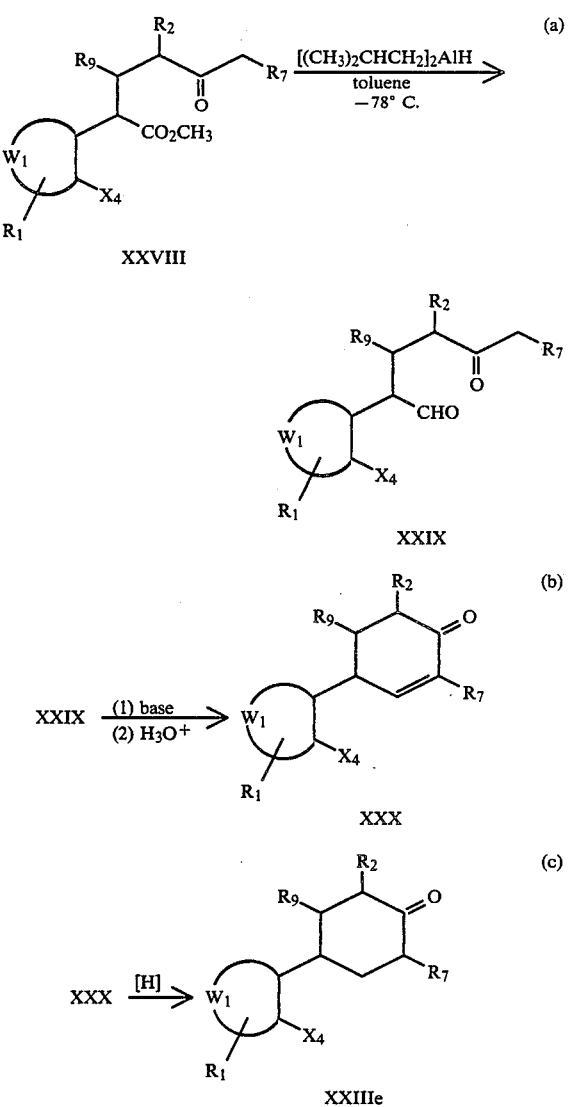

wherein
$W_1$, $R_1$, $R_2$, $R_7$ and $R_9$ are as previously defined, $X_4$ is Br, $SR_{12}$, or $NO_2$, and $R_{12}$ is $C_2$-$C_4$ alkyl or benzyl.

The selective reduction of carboxylic esters, such as those of Formula XXVIII, to the corresponding aldehydes of Formula XXIX as shown in Equation 25(a) may be achieved with diisobutylaluminum hydride (DIBAL) at low temperatures as described by E. J. Corey, K. C. Nicolaou and T. Toru, J. Am. Chem. Soc., 97, 2287 (1975). The intramolecular aldol condensation depicted in Equation 25(b) is effectively carried out by treating the compounds of Formula XXIX with a catalytic amount of a suitable base such as sodium methoxide or potassium tert-butoxide. Subsequent aqueous acid workup results in dehydration of the intermediate aldols to give the enones of Formula XXX. Alternatively, the aldol condensation may be achieved under conditions of acid catalysis, in which case the enones XXX are obtained directly. For a comprehensive review of this well-known reaction, see A. T. Nielsen and W. J. Houlihan, Org. Reactions, 16, 1 (1968). Equation 25(c) represents a selective reduction of the olefinic bond of α, β-unsaturated ketones XXX, and may be accomplished by any one of several methods. Two such methods are catalytic hydrogenation (see H. O. House, "Modern Synthetic Methods", 2nd Ed., W. A. Benjamin, Inc., Menlo Park, 1972, pp. 26–28), and reduction with potassium tri-s-butylborohydride (Fortunato and Ganem, *J. Org. Chem.*, 41, 2194 (1976)).

Ketones of Formula XXIIIf, where $R_8$ is as defined in the Summary of the Invention, may be synthesized by the 1,4-conjugate addition of appropriate cuprate reagents to enones of Formula XXX, as shown below in Equation 26.

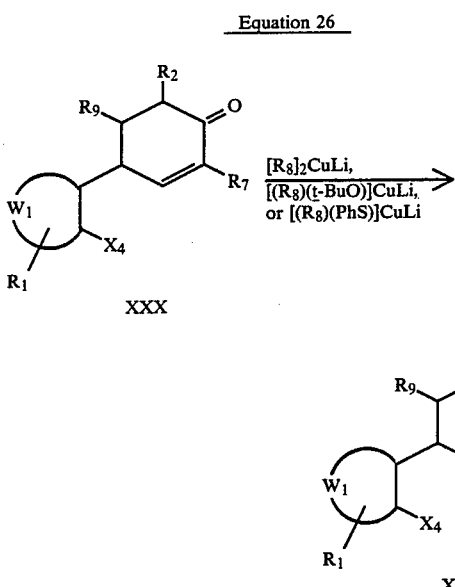

wherein
$W_1$, $R_1$, $R_2$, $R_7$, $R_8$ and $R_9$ are as previously defined, $X_4$ is Br, $SR_{12}$, or $NO_2$, and $R_{12}$ is $C_2$–$C_4$ alkyl or benzyl.

The 1,4-conjugate addition reaction of Equation 26 may be conveniently carried out according to the procedure described by House, Respess and Whitesides, *J. Org. Chem.*, 31, 3128 (1966) when the copper reagent is of the form $[R_8]_2CuLi$. For use of "mixed" copper reagents, see Posner and Whitten, *Tetrahedron Lett.*, 1815 (1973) (for the reagent $[(R_8)(t-BuO)]CuLi$), or Posner, Whitten and Sterling, *J. Am. Chem. Soc.*, 95, 7788 (1973) (for the $[(R_8)(Phs)]CuLi$ reagent).

It should be recognized that compounds of Formulas XXIIIe and XXIIIf may be treated according to one or both of the methods described in Equations 11 and 13 to afford the corresponding sulfonyl chlorides of Formula IX, where Q is Q-61. Similarly, removal of the tert-butyl group from compounds of Formulas XXIIIa–d by one or more of the procedures outlined in Equation 8 will furnish the primary sulfonamides of Formula IVb, where Q is Q-8, Q-60, Q-9 or Q-62, which may then be converted to compounds of Formula I with the corresponding Q substituents.

The requisite aminothiophene derivatives of Formulas XXVa and XXVb may be prepared in a straight-forward fashion by N-alkylation of compounds of formula XXXI with the appropriate γ- or δ-bromo esters, followed by saponification of the intermediate compounds of Formulas XXXIIa and XXXIIb, as shown below in Equation 27.

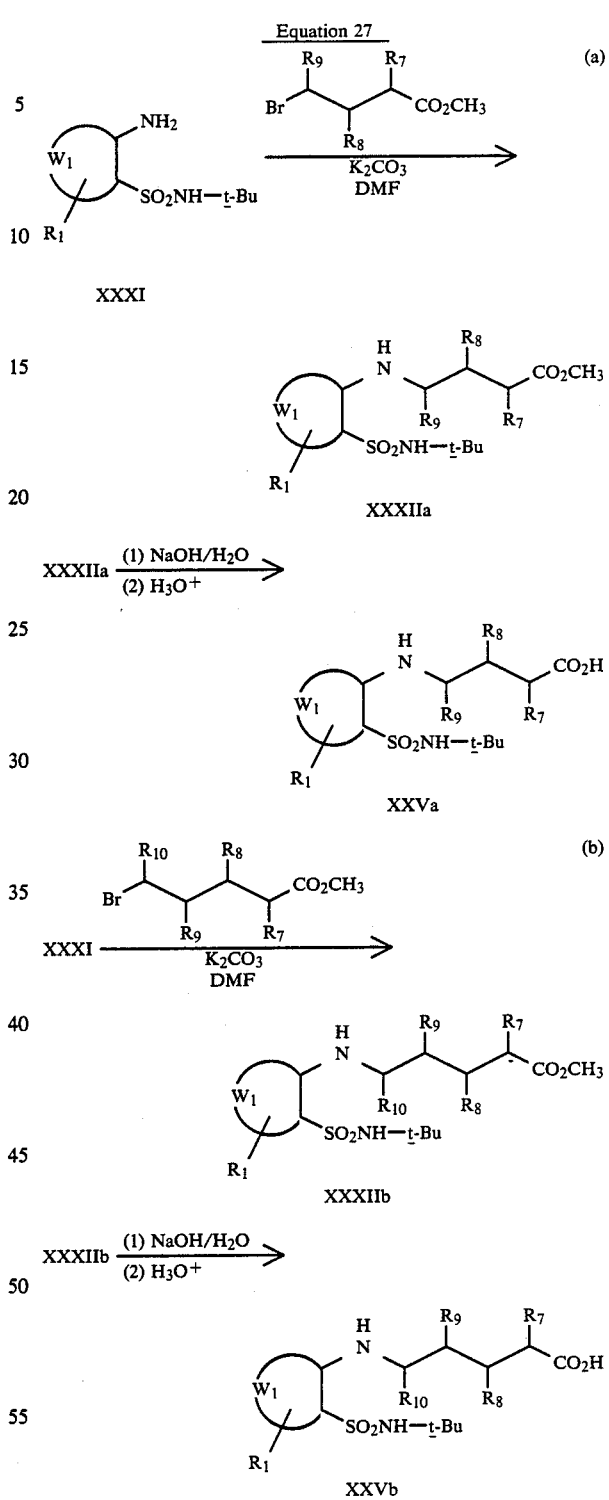

wherein
$R_1$, $R_7$, $R_8$, $R_9$ and $R_{10}$ are as previously defined, and $W_1$ is S.

The first step of Equations 27(a) and 27(b) is achieved by stirring a mixture of the aminothiophene derivative XXXI and the appropriate γ- or δ-bromo ester together in the presence of an excess of a suitable base such as anhydrous potassium carbonate in a polar solvent such as N,N-dimethylformamide at temperatures of 25°–110°

C. until all of the aminothiophene derivative has been consumed. The intermediate compounds of Formulas XXXIIa and XXXIIb may then be isolated by pouring the reaction mixture into ice-water, neutralizing by the addition of dilute aqueous mineral acid, and either filtration or extraction into a suitable organic solvent such as diethyl ether, methylene chloride, or ethyl acetate. These compounds of Formulas XXXIIa and XXXIIb are then treated with excess dilute aqueous sodium hydroxide solution at about 25° C. for 1-6 hours. Acidification with concentrated hydrochloric acid (ice-water cooling) followed by either filtration or extraction as described above and removal of the solvent in vacuo affords the desired aminothiophene derivatives of Formulas XXVa and XXVb.

The amino-N-t-butylthiophenesulfonamides of formulas XXXI may be prepared from the appropriate 2-nitrothiophenesulfonyl chlorides XXXIV by treatment with tert-butylamine, followed by reduction of the nitro group as depicted in Equation 28.

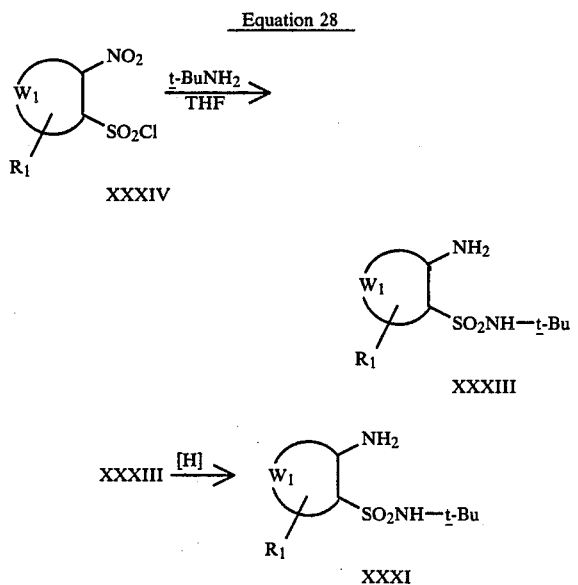

wherein
$R_1$ is as previously defined, and $W_1$ is S.

The first step of Equation 28 is effected by adding a solution of the appropriate nitrothiophenesulfonyl chloride XXXIV in a suitable solvent such as tetrahydrofuran or methylene chloride to a solution of excess tert-butylamine in the same solvent at about 0° C. After being stirred at 0°-25° C. for 2 to 24 hours, the reaction mixture is washed with water, and the organic layer dried and evaporated to give the desired intermediates of Formula XXXIII which are generally sufficiently pure to be carried directly on to the next step. The reduction of nitro compounds of Formula XXXIII to the corresponding aminothiophene derivatives XXXI may be accomplished by one or more of the methods described for Equation 13a.

Some of the sulfonyl chlorides of Formula XXXIV are known compounds. Those that are not known in the literature may be prepared by methods which are known to one skilled in the art.

The requisite unsaturated carboxylic acids of Formula XXII may be conveniently synthesized by dehydration of the appropriate hydroxy esters of Formula XXIa, followed by saponification as shown in Equation 29.

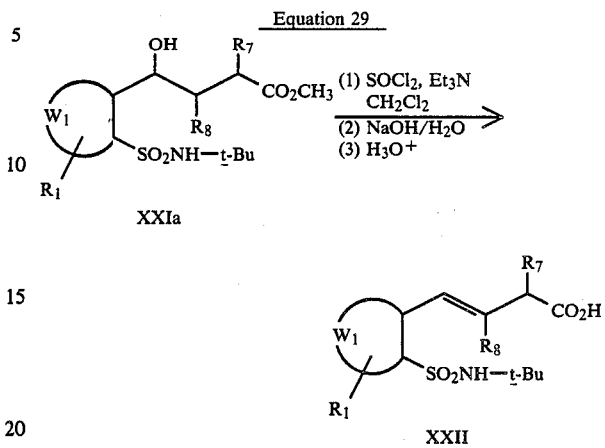

wherein
$W_1$, $R_1$, $R_7$ and $R_8$ are as previously defined.

The first step of Equation 29, dehydration of alcohols of Formula XXIa to give the corresponding olefins, may be carried out by treatment of the alcohols with thionyl chloride in the presence of a suitable acid scavenger such as triethylamine at 0°-25° C. The saponification shown in Equation 29 (steps 2 and 3) may be accomplished as described for the second step in Equations 17(a) and 17(b).

The carboxylic esters of Formula XXVIII may be prepared by treatment of the anions derived from thienyl- or furanylacetic esters of formula XXXV with the appropriate α, β-unsaturated ketones as shown below in Equation 30.

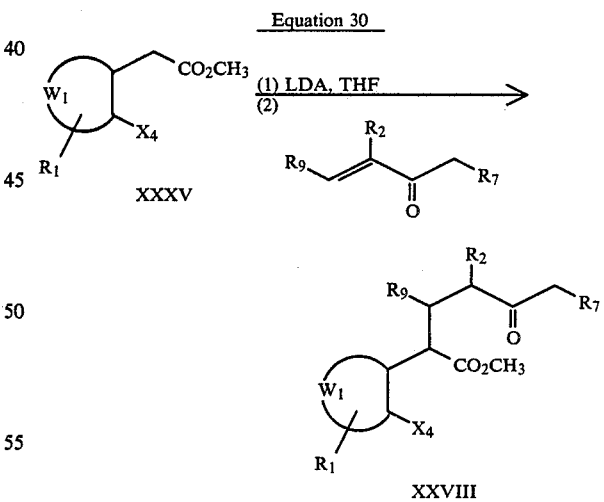

wherein
$W_1$, $R_1$, $R_2$, $R_7$ and $R_9$ are as previously defined, $X_4$ is Br, $SR_{12}$, or $NO_2$, and $R_{12}$ is $C_2$-$C_4$ alkyl or benzyl.

The reaction of Equation 30 is conveniently carried out by adding a solution of the acetic ester derivative XXXV in a suitable solvent such as tetrahydrofuran to a solution of a strong base such as lithium diisopropylamide (LDA) at −78° to 0° C. under an inert atmosphere. The mixture is stirred at temperatures below 0° C. for 0.5-1 hour to ensure complete anion formation and is then treated with an equimolar quantity of the appropriately substituted α,β-unsaturated ketone, which is prone to undergo reaction in a 1,4-conjugate manner. For a compilation of references dealing with this type of reaction, see Bergmann, Ginsburg, and Pappo, *Org. Reactions,* 10, 179 (1959).

The requisite N-t-butylsulfonamides of Formulas XVIIIa, XVIIIb, XVIIIc, and XIX may all be synthesized from common thienyl- or furanylacetic esters of Formula XXXVI via a sequence of reactions that entails the same seven basic processes. Equation 31 outlines this sequence of reactions leading to compounds of formula XVIIIa (where $R_7$ is H): (a) alkylation of the anion derived from the appropriate acetic ester derivatives of Formula XXXVI with aldehydes of Formula $R_8$CHO to give β-hydroxy acetic ester derivatives of Formula XXXVII, (b) protection of the alcohol with a suitable protecting group such as the benzyl ether of Formula XXXVIII, (c) reduction of the esters of Formula XXXVIII to afford primary alcohols of Formula XXXIX, (d) conversion of the hydroxyl group to a good leaving group such as the alkyl bromides of Formula XL, (e) conversion of the ortho substituent $X_4$ to a N-t-butylsulfamoyl group by one of the methods described previously, (f) displacement of the bromides of Formula XLI to give the corresponding nitriles of Formula XLII, and (g) hydrolysis of the nitriles XLII to afford the carboxylic acids of Formula XVIIIa, where $R_7$ is H.

Equation 31

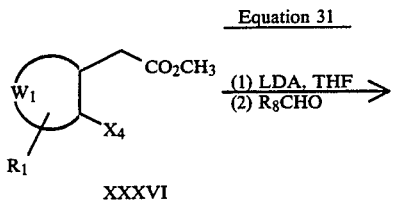

XXXVI

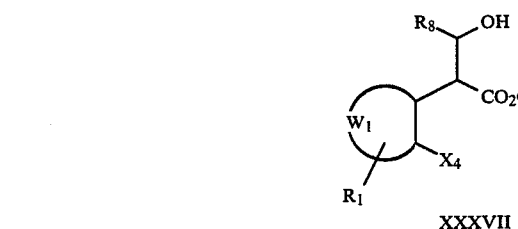

XXXVII

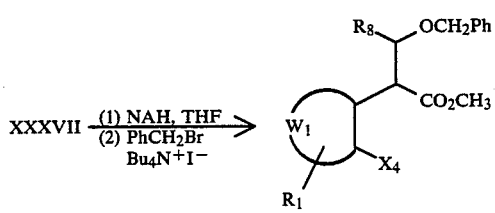

XXXVIII

XXXVIII $\xrightarrow{\text{LiAlH}_4}_{\text{Et}_2\text{O or THF}}$

XXXIX

-continued
Equation 31

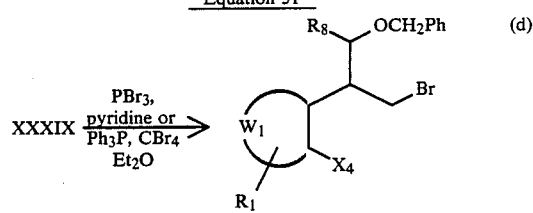

XL

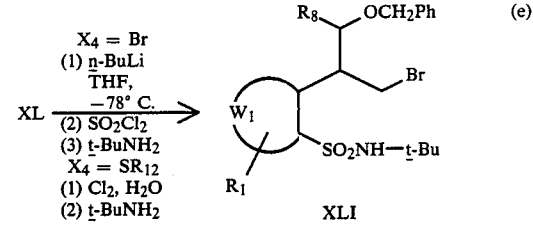

XLI

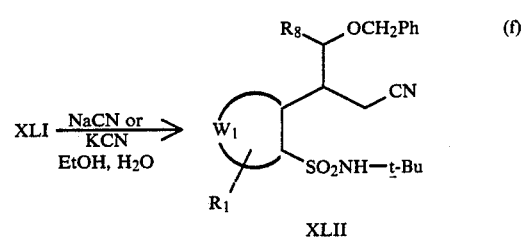

XLII

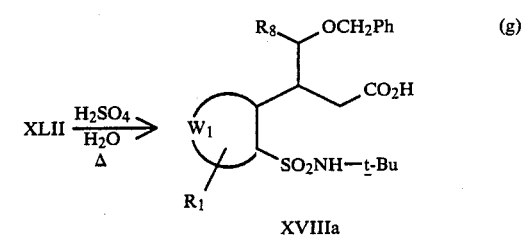

XVIIIa wherein $R_1$ and $R_8$ are as previously defined, $W_1$ is S or O, $X_4$ is Br or $SR_{12}$, and $R_{12}$ is $C_2$–$C_4$ alkyl or benzyl.

Equation 31(a)

Anions of acetic ester derivatives of Formula XXXVI may be formed as shown in Equation 31(a) by treatment with a suitable base such as lithium diisopropylamide (LDA). For a description of this procedure, see Equation 30. Other methods for the preparation and reaction of aliphatic ester enolates have been described by M. W. Rathke, *J. Am. Chem. Soc.,* 92, 3222 (1970), M. W. Rathke and D. F. Sullivan, ibid., 95, 3050 (1973), and M. W. Rathke and A. Lindert, ibid., 93, 2318 (1971). Addition of the appropriate aldehydes of structure $R_8$CHO to these anions gives the desired β-hydroxy esters XXXVII.

Equation 31(b)

The reaction is Equation 31(b) is accomplished by formation of the sodium alkoxide of alcohols XXXVII with sodium hydride, and treatment with benzyl bromide in the presence of a phase-transfer catalyst such as tetrabutylammonium iodide. For a description of this procedure, see S. Czernecki, C. Georgoulis and C. Provelenghiou, *Tetrahedron Lett.,* 3535 (1976).

Equation 31(c)

The reduction of carboxylic esters such as those of Formula XXXVIII with lithium aluminum hydride as shown in Equation 31(c) is a well-known process and may be carried out according to the procedures described by Gaylord, "Reduction with Complex Metal Hydrides", Interscience Publishers, Inc., New York, 1956, pp. 391–531.

Equation 31(d)

The transformation shown in Equation 31(d) may be achieved by one or more of the following procedures: treatment of alcohols of Formula XXXIX with phosphorus tribromide in pyridine (Shone, et al., *J. Am. Chem. Soc.*, 58, 585 (1936)), or with triphenyl phosphine-carbon tetrabromide (Lee and Downie, *Tetrahedron*, 23, 2789 (1967); Hooz and Gilani, *Can. J. Chem.*, 46, 86 (1968)).

Equation 31(e)

Compounds of Formula XL, where $X_4$ is Br, may be converted to the corresponding sulfonyl chlorides as described for Equation 12. Compounds of Formula XL, where $X_4$ is $SR_{12}$, are efficiently converted to the corresponding sulfonyl chlorides in a manner identical to that described in Equation 13. Treatment of these sulfonyl chlorides in a manner identical to that described in Equation 28 then affords the desired products of Formula XLI.

Equation 31(f)

The nulceophilic displacement reaction depicted in Equation 31(f) may be accomplished by treatment of bromides of Formula XLI with sodium or potassium cyanide according to the procedure of J. R. Ruhoff, *Org. Syntheses,* Coll. Vol. II, 292 (1943).

Equation 31(g)

Nitriles of Formula XLII may be conveniently converted to the corresponding acids of Formula XVIIIa, where $R_7$ is H, by treatment with sulfuric acid in the presence of water as described by Adams and Thal, *Org. Syntheses,* Coll. Vol. I, 436 (1941), and Wenner, *J. Org. Chem.*, 15, 548 (1950).

Compounds of Formula XVIIIa, where $R_7$ is other than H, may be conveniently prepared from the corresponding unsubstituted acids of Formula XVIIIa, where $R_7 = H$, by formation of the 0,α-dianion and subsequent trapping with the appropriate electrophile as shown in Equation 32.

Equation 32

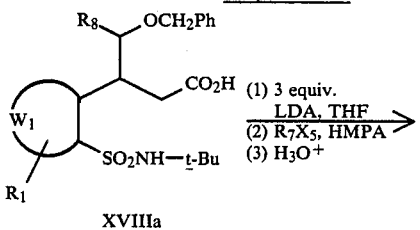

XVIIIa

-continued
Equation 32

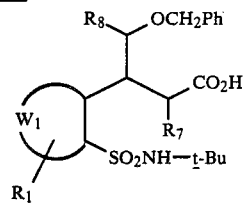

XVIIIa wherein
$W_1$, $R_1$, $R_7$ and $R_8$ are as defined above except $R_7$ is other than H, and $X_5$ is Cl, Br or I.

The alkylation of Equation 32 may be accomplished in a manner analogous to that described in Equation 31(a), except that 3 equivalents of a strong base such as LDA are required, and an electrophile of Formula $R_7X_5$, where $R_7$ is other than H and $X_5$ is Cl, Br, or I, is used to trap the enolate in lieu of an aldehyde. For relevant references, see J. C. Stowell, "Carbanions in Organic Synthesis", John Wiley and Sons, Inc., New York, 1979, pp 157–161.

As mentioned above, N-t-butylsulfonamides of Formulas XVIIIb, XVIIIc, and XIX may all be synthesized from the appropriate acetic ester derivatives of Formula XXXVI in multi-step reaction schemes analogous to that described in Equation 31 for compounds of Formula XVIIIa. The minor modifications in reaction conditions necessary to achieve these syntheses would be obvious to one who is skilled in the art.

Butenolides of Formula XLIIIa may be prepared as shown below in Equation 33 by oxidation of the α-phenylthioethers XLIVa, and subsequent thermolytic elimination.

Equation 33

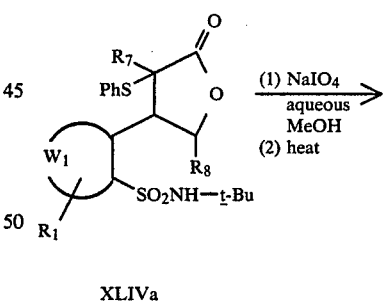

XLIVa

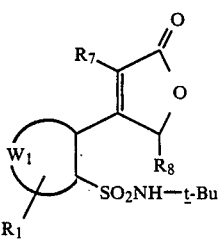

XLIIIa wherein
$W_1$, $R_1$, $R_7$ and $R_8$ are as previously defined.

The reactions of Equation 33 may be carried out according to the procedure of B. M. Trost and T. N. Salzmann, *J. Am. Chem. Soc.*, 95, 6840 (1973).

The requisite α-phenylthioethers XLIVa are readily obtained by treatment of the corresponding lactones of formula XVIIa with a suitable base to generate the enolates, followed by trapping with diphenyl disulfide or phenylsulfenyl chloride as outlined in Equation 34.

Equation 34

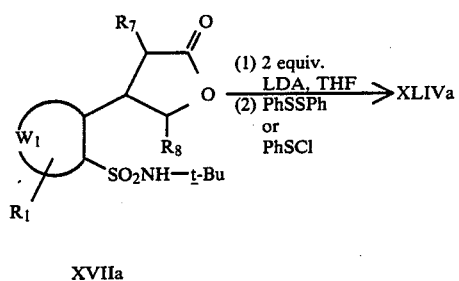

XVIIa wherein
$W_1$, $R_1$, $R_7$ and $R_8$ are as previously defined.

The α-alkylation of lactone enolates is a well-known process and may be successfully carried out according to G. H. Posner and G. L. Loomis, *Chem. Comm.*, 892 (1972), and K. Iwai, et al., *Chem. Letters*, 385 (1974). For use of diphenyl disulfide as the electrophile, see the reference cited for Equation 33. In the case of N-t-butylsulfonamides of Formula XVIIa, it is necessary to use two molar equivalents of base. The first equivalent of base removes the acidic N-H proton, and the second equivalent forms the lactone enolate.

By using processes analogous to those described above in Equations 33 and 34, or modifications thereof, it is possible for one skilled in the art to prepare α,β-unsaturated lactones of Formula XLIIIb–XLIIIe from the appropriate saturated precursors of Formulas XVIIb–XVIIe as represented in Equations 35(a–d).

Equation 35

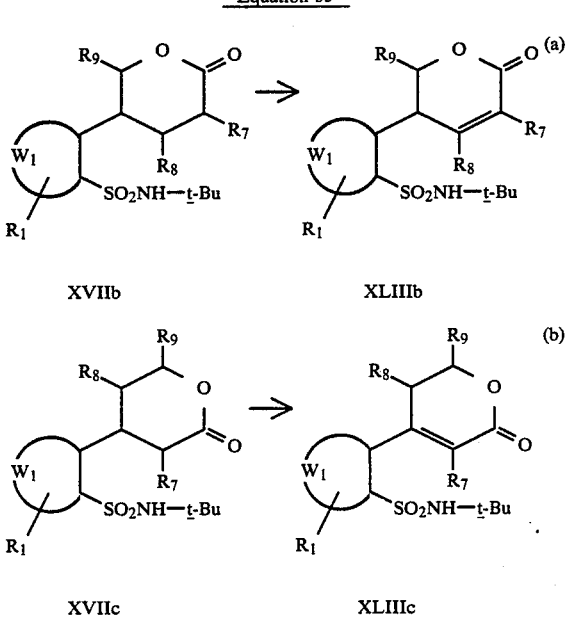

-continued
Equation 35

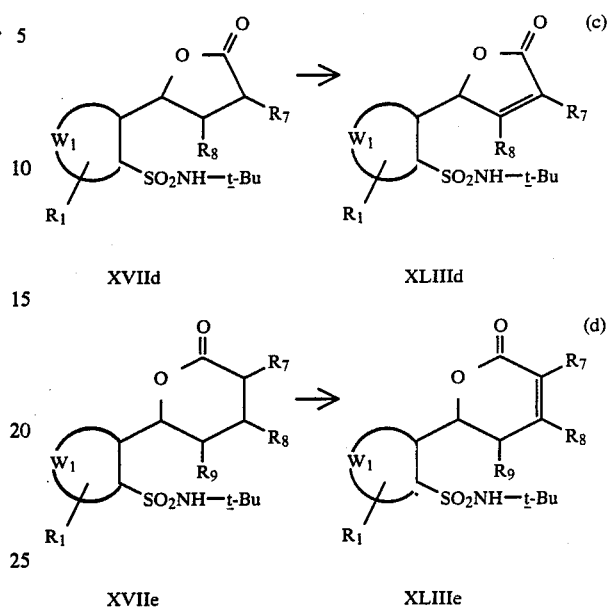

wherein
$W_1$, $R_1$, $R_7$, $R_8$ and $R_9$ are as previously defined.

An alternative route to the lactones of Formula XLIIIe above where $R_8$ is $C_1$–$C_4$ alkyl and $R_9$ is H involves the addition of the dienolates of the substituted crotonate esters of Formula XLIIIf to the aldehyde XLIIIg according to the procedure of R. W. Dugger and C. H. Heathcock, *J. Org. Chem.*, 45, 1181 (1980), as shown in Equation 35e. Aldehyde XLIIIg, can be synthesized by the addition of N,N-dimethylformamide (DMF) to the dianions of sulfonamides of Formula XX.

Equation 35e

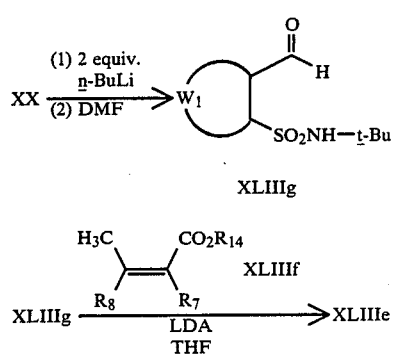

wherein
$W_1$, $R_1$, $R_7$, $R_8$ and $R_9$ are as previously defined,
$R_8$ and $R_{14}$ are $C_1$–$C_4$ alkyl, and
$R_9$ is H.

In a similar fashion, which is obvious to one skilled in the art, the lactams of Formulas XXIVa–XXIVi, where $R_3$ is other than H, may be converted to the corresponding α,β-unsaturated lactams of Formulas XLVa–XLVe as outlined in Equations 36(a–i).

Equation 36

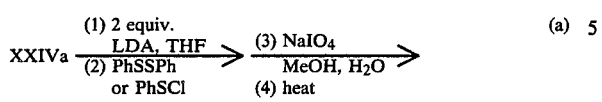
(a)

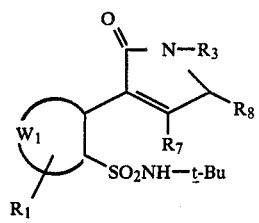

XLVa

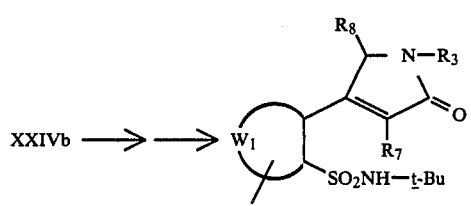

XLVb

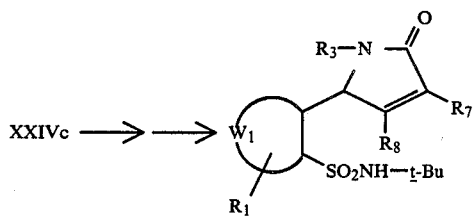

XLVc

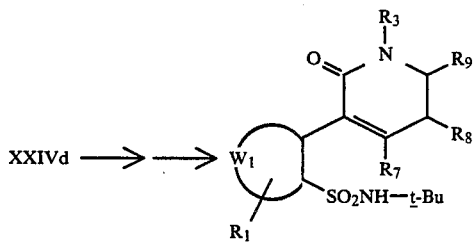

XLVd

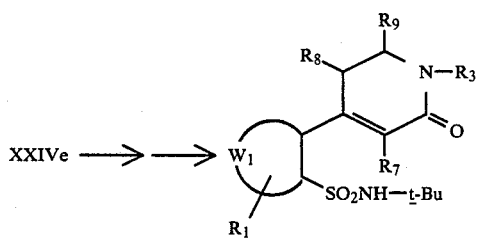

XLVe

-continued
Equation 36

XLVf

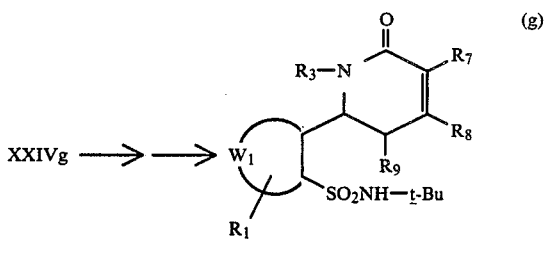

XLVg

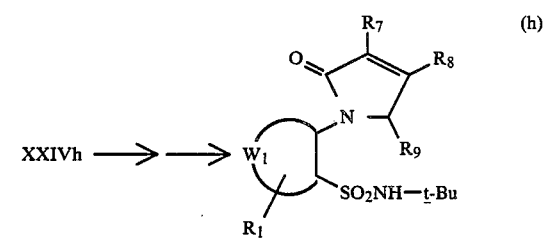

XLVh

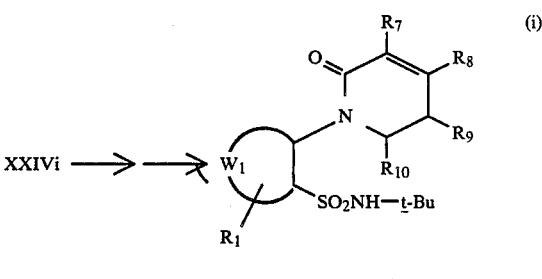

XLVi wherein
$W_1$, $R_1$, $R_3$, $R_7$, $R_8$, $R_9$ and $R_{10}$ are as previously defined except $R_3$ is other than H.

Unsaturated lactams of Formulas XLVa–XLVg, where $R_3$ is H, may be prepared by methods similar to those described in Equation 36. However, it is necessary to use one extra equivalent of a base such as lithium diisopropylamide (LDA) to generate the N, α-dianions XLVI, which may then be treated with diphenyl disulfide or phenylsulfenyl chloride in a manner identical to that described above to afford the desired products of Formulas XLVa–XLVg, where $R_3$ is H. Equation 37 depicts this procedure as it applies to the preparation of lactams of Formula XLVa ($R_3$=H) from the appropriate saturated precursors of Formula XXIVa.

Equation 37

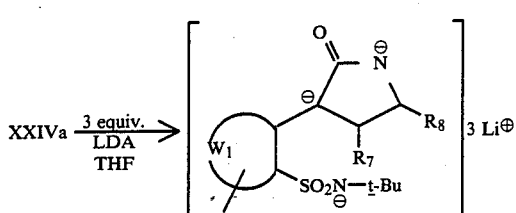

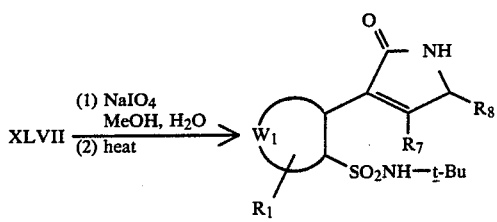

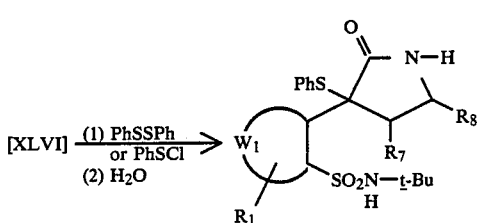

wherein
$W_1$, $R_1$, $R_7$ and $R_8$ are as previously defined.

For procedures dealing with the formation and alkylation of lactam α-anions such as those described in Equation 36, see P. A. Zoretic and F. Barcelos, *Tetrahedron Lett.*, 529 (1977), or B. M. Trost and R. A. Kunz, *J. Org. Chem.*, 39, 2475 (1974).

The method shown in Equation 37 may be applied to the synthesis of unsaturated lactams of Formulas XLVb–XLVg, where $R_3$ is H. For a relevant reference, see J-P. Depres, A. E. Greene and P. Crabbe, *Tetrahedron Lett.*, 2191 (1978).

Removal of the tert-butyl protecting group from compounds of Formulas XLIIIa–XLIIIe and XLVa–XLVi by one or more of the procedures described in Equation 8 will give the primary sulfonamides of Formula IVb, where Q is Q-30, Q-97, Q-96, Q-31, Q-98, Q-32, Q-33, Q-34, Q-99, Q-100, Q-101, Q-102, Q-35, or Q-103. These sulfonamides may then be converted to compounds of Formula I with the corresponding substituents.

Enones of Formulas XLVIIIa and XLVIIIb may be conveniently prepared as shown below in Equation 38 by an intramolecular aldol condensation of the appropriate carbonyl compounds of Formulas XLIXa and XLIXb.

Equation 38

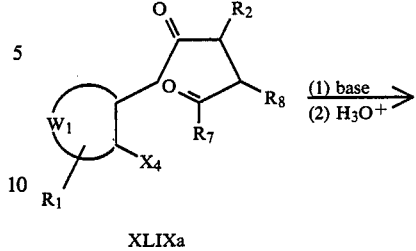

(a)

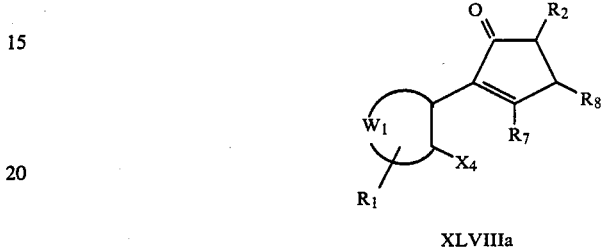

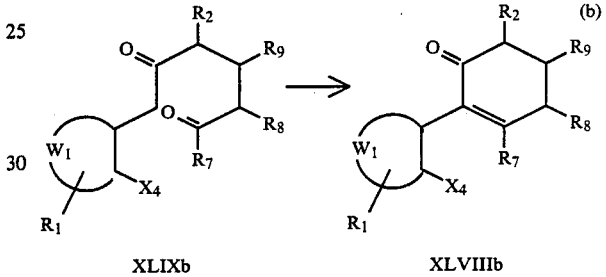

wherein
$W_1$, $R_1$, $R_2$, $R_7$, $R_8$ and $R_9$ are as previously defined, $X_4$ is Br, $SR_{12}$ or $NO_2$, and $R_{12}$ is $C_2$–$C_4$ alkyl or benzyl.

The aldol condensation depicted in Equations 38(a) and 38(b) may be carried out in a manner analogous to that described for Equation 25(b).

In a similar fashion, enones of Formulas XLVIIIc–XLVIIIi may be prepared from the appropriate carbonyl compounds of Formulas XLIXc–XLIXi as outlined below in Equation 39 (a–g).

Equation 39

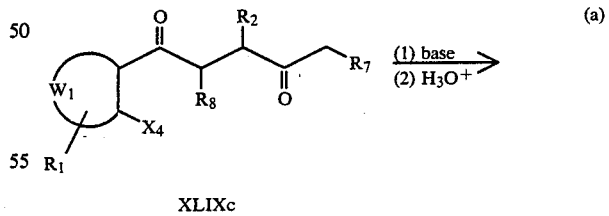

(a)

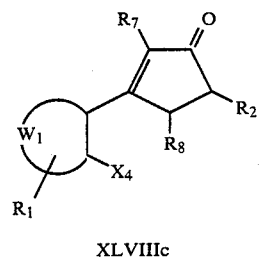

-continued
Equation 39

(b)
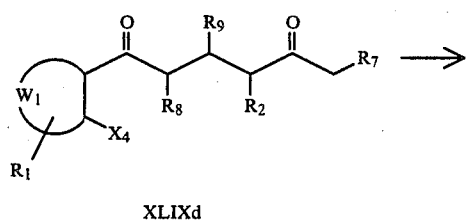
XLIXd

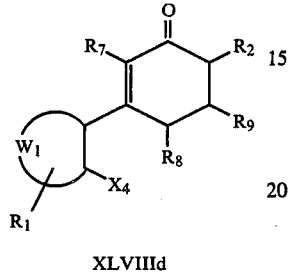
XLVIIId (c)
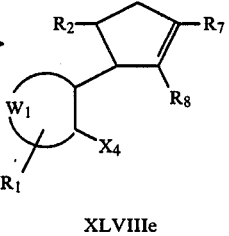 → 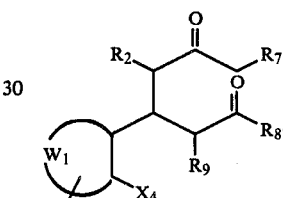
XLIXe          XLVIIIe (d)
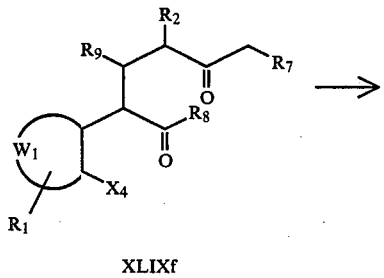
XLIXf

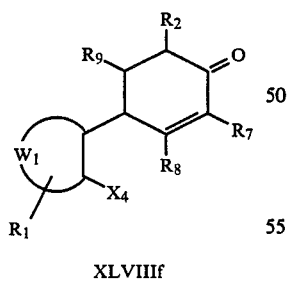
XLVIIIf (e)
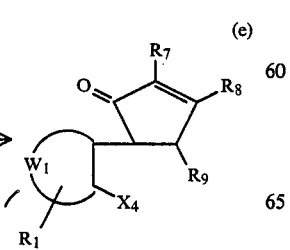
XLIXq          XLVIIIq

-continued
Equation 39

(f)
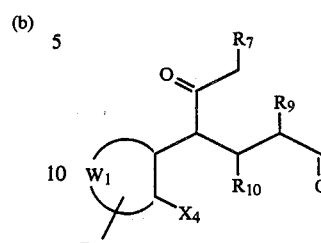
XLIXh

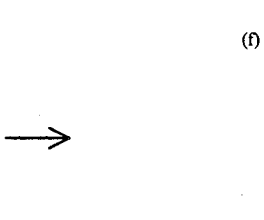
XLVIIIh (g)
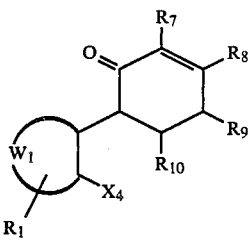 → 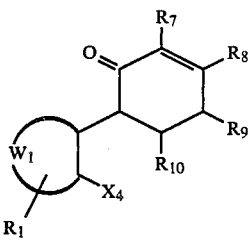
XLIXi          XLVIIIi wherein
$W_1$, $R_1$, $R_2$, $R_7$, $R_8$ and $R_9$ are as previously defined, $X_4$ is Br, $SR_{12}$ or $NO_2$, and $R_{12}$ is $C_2-C_4$ alkyl or benzyl.

Another route to the enones of Formula XLVIIIc and XLVIIId above is depicted in Equation 39h. The addition of 3-ethoxy-2-cyclohexenone or 3-ethoxy-2-cyclopentenone derivatives of Formula XLVIIIs and XLVIIIt respectively, to the dianions of sulfonamides of Formula XX followed by mild hydrolysis during workup affords the desired enones directly.

Equation 39h

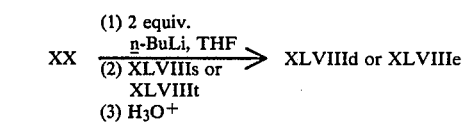

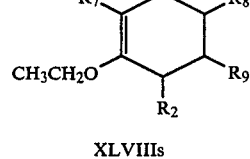   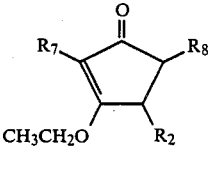
XLVIIIs            XLVIIIt wherein
$W_1$, $R_1$, $R_2$, $R_7$, $R_8$ and $R_9$ are as previously defined, and $X_4$ is $SO_2NH-t-Bu$.

Alternatively, many of the enones of Formulas XLVIIIj–XLVIIIr may be prepared from the corresponding saturated ketones of Formulas XXIIIa–XXIIIf via treatment with the appropriate base to form the α-carbanions, trapping with diphenyl disulfide or phenylsulfenyl chloride, and subsequent oxidative elimination. This sequence is depicted below in Equation 40 for the preparation of enones XLVIIIj or XLVIIIp from ketones of Formula XXIIIa or XXIIIa′.

Equation 40

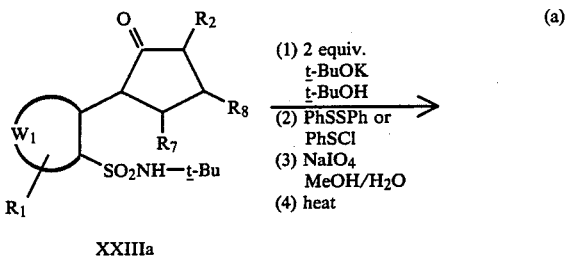

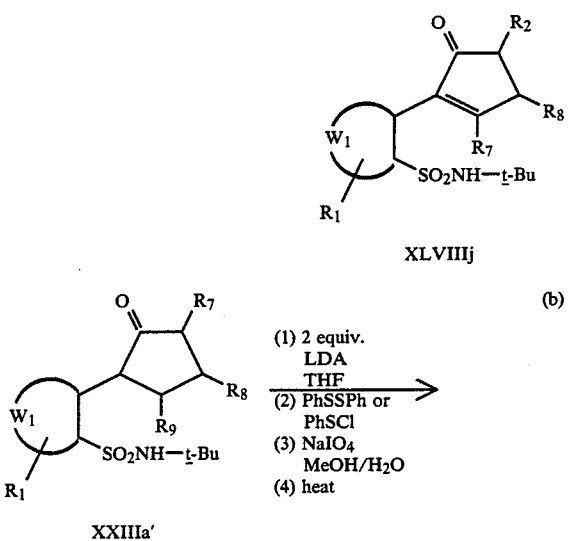

wherein
$W_1$, $R_1$, $R_2$, $R_7$, $R_8$ and $R_9$ are as previously defined.

Equation 40(a)

The transformation shown above in Equation 40(a) may be effectively carried out by treating ketones of Formula XXIIIa with two molar equivalents of a strong base such as potassium tert-butoxide (t-BuOK) in a suitable solvent such as t-butanol under an inert atmosphere at 0°–25° C. Such conditions are conducive to formation of the more stable, or thermodynamic, enolates. These anions are then treated in a manner analogous to that described in Equations 33 and 34.

Equation 40(b)

The transformation shown above in Equation 40(b) may be effectively carried out by treating ketones of Formula XXIIIa′ with two molar equivalents of a hindered base such a lithium diisopropylamide (LDA) in a suitable solvent such as tetrahydrofuran at low temperature (−78° C.) under an inert atmosphere. Such conditions are conducive to formation of the less stable, or kinetic, enolates. These anions are then treated in a manner analogous to that described in Equations 33 and 34.

For a discussion of the optimal conditions required for selectively generating thermodynamic or kinetic enolates, see J. C. Stowell, "Carbanions in Organic Synthesis", John Wiley and Sons, Inc., New York 1979, pp. 8–11, and references cited therein.

In a similar fashion, enones of Formulas XLVIIIk, XLVIIIl, XLVIIIm, XLVIIIn, XLVIIIo, XLVIIIq, and XLVIIIr may be prepared from the corresponding ketones of Formulas XXIIIb–XXIIIf by selection of the appropriate conditions for enolate formation.

Some of the requisite carbonyl compounds of Formulas XLIXa–XLIXi are known in the literature or may be prepared from known intermediates by methods obvious to one skilled in the art. The appropriately substituted acetic ester derivatives of Formula XXXVI will serve as useful precursors for most of the desired compounds of Formulas XLIXa–XLIXi, and may be transformed by methods similar to those described in Equation 31 or modifications thereof. Such methods would be obvious to one skilled in the art.

Sulfonamides of Formulas La and Lb may be prepared as shown in Equation 41 by treatment of compounds of Formulas LIa and LIb with base.

Equation 41

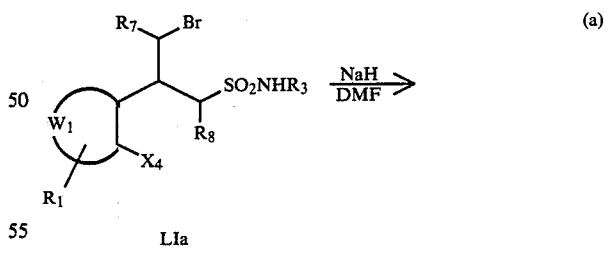

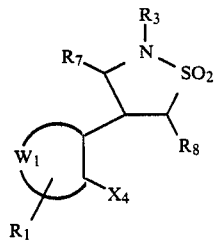

-continued
Equation 41

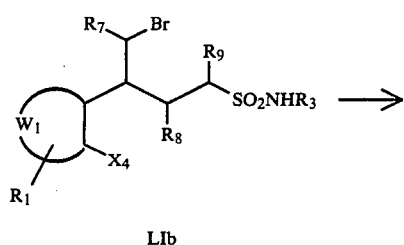

LIb (b)

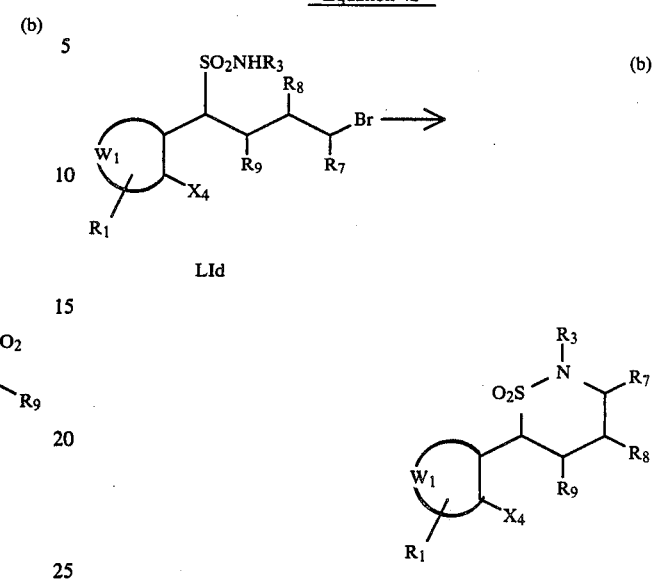

Equation 42 -continued (b)

LId

Ld

LIe (c)

Le

LIf (d)

Lf wherein $W_1$, $R_1$, $R_3$, $R_7$, $R_8$ and $R_9$ are as previously defined, $X_4$ is Br, $SR_{12}$ or $NO_2$, and $R_{12}$ is $C_2$-$C_4$ alkyl or benzyl.

The reactions of Equations 41(a) and 41(b) may be accomplished by adding a solution of sulfonamide LIa or LIb in a suitable solvent such as N,N-dimethylformamide (DMF) to a stirred suspension of a base such as sodium hydride at 0°-25° C. under an inert atmosphere. After being stirred at 25°-100° C. for several hours, or until all of the starting material has disappeared, the reaction mixture is cooled and poured into ice-water. The desired product of Formula La or Lb is then isolated by filtration or extraction with a suitable solvent such as diethyl ether, methylene chloride, or ethyl acetate, followed by drying and evaporation of the volatile components.

The sulfonamides of Formulas Lc–Lg may be synthesized in a manner identical to that described above in Equation 41 from the appropriate compounds of Formulas LIc–LIg as shown in Equations 42(a–e).

Equation 42

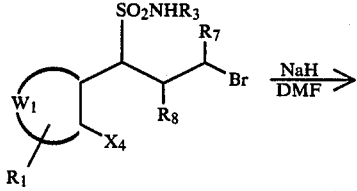

LIc

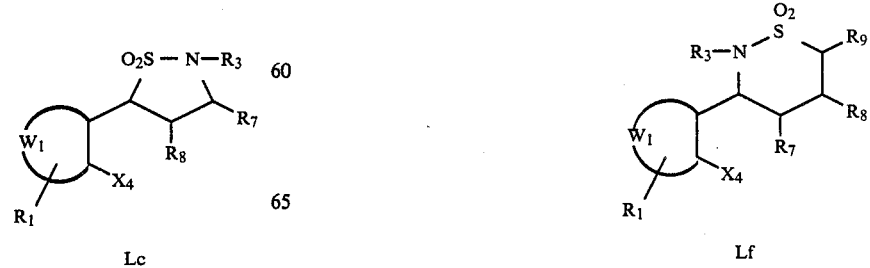

Lc

-continued
Equation 42

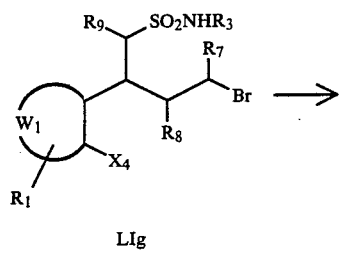

LIg

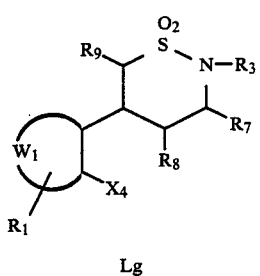

Lg wherein
$W_1$, $R_1$, $R_3$, $R_7$, $R_8$ and $R_9$ are as previously defined, $X_4$ is Br, $NO_2$, or $SR_{12}$, and $R_{12}$ is $C_2$-$C_4$ alkyl or benzyl.

Sulfonamides of Formulas Lh and Li may be prepared by treatment of the appropriate compounds of Formulas LIIa or LIIb with base to generate anions of Formulas LIIIa or LIIIb, and subsequent reaction with suitably substituted 2-nitrothienyl or 2-nitrofuranyl fluorides as shown in Equations 43(a) and 43(b).

Equation 43

(a)

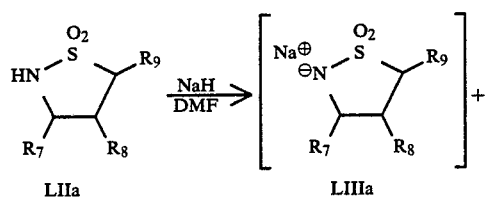

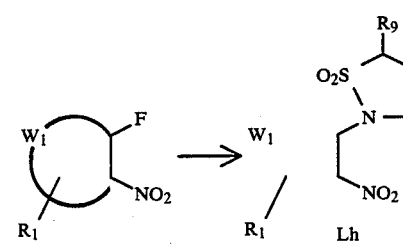

Lh (b)

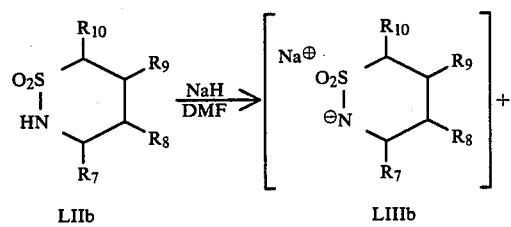

LIIb     LIIIb

-continued
Equation 43

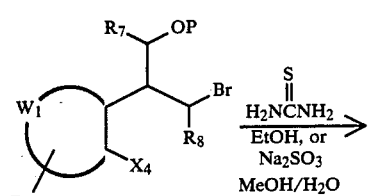
Li wherein
$R_1$, $R_7$, $R_8$, $R_9$ and $R_{10}$ are as previously defined, and $W_1$ is S or O.

The reactions of Equation 43 may be efficiently carried out by adding a solution of the appropriate sulfonamide LIIa or LIIb in a suitable solvent such as N,N-dimethylformamide (DMF) to a suspension of a base such as sodium hydride in the same solvent at 0°–25° C. under an inert atmosphere. When anion formation is complete, as evidenced by the cessation of hydrogen gas evolution, the reaction mixture is treated with the appropriate 2-nitrothienyl or 2-nitrofuranyl fluoride, and stirring is continued at 25°–100° C. for 2 to 24 hours. The desired products of Formulas Lh or Li are then isolated in a manner similar to that described above for Equation 42.

The requisite compounds of Formulas LIa-Lig may be synthesized via the same basic four-step sequence of reactions. Equation 44 depicts this synthetic scheme for the preparation of sulfonamides LIa, starting from the appropriate alkyl bromides of Formula LVIIa as a representative example.

Equation 44

(a)

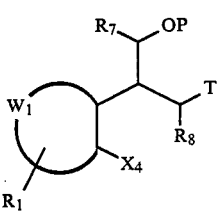

LVIIa

LVIa (T = —SCNH$_2$.HBr, or —SO$_3$Na)

-continued
Equation 44

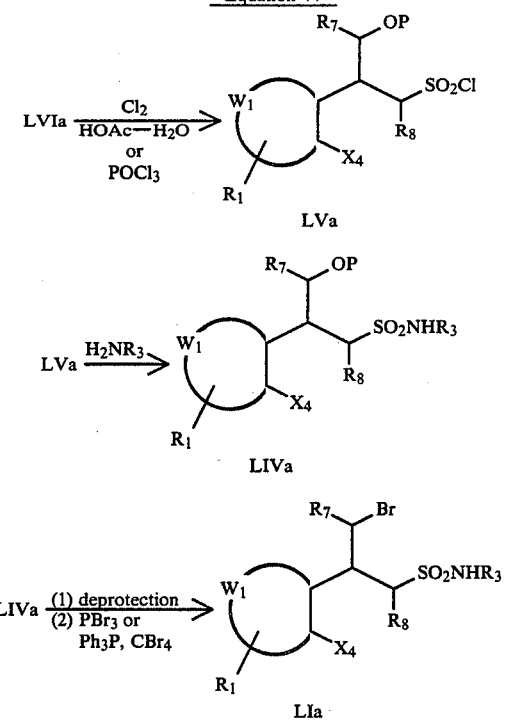

wherein $W_1$, $R_1$, $R_7$ and $R_8$ are as previously defined, $X_4$ is Br, $SR_{12}$ or $NO_2$, $R_{12}$ is $C_2$-$C_4$ alkyl or benzyl, and P is an appropriate alcohol protecting group such as $CH_2Ph$, $CH_3$, t-butyl, $Si(CH_3)_2(t$-Bu), etc.

Equation 44(a)

The displacement reaction of Equation 44(a) may be effected by treating the alkyl bromides of Formula LVIIa with either one molar equivalent of thiourea to give the corresponding isothiouronium salts LVIa, where T is $-SC(NH_2)=NH\cdot HBr$, or with sodium sulfite to yield the sodium sulfonate salts LVIa, where T is $-SO_3Na$. For detailed procedure relating to the preparation of isothiouronium salts, see Urquhart, Gates and Connor, *Org. Syntheses*, 21, 36 (1941), or Vogel, *J. Chem. Soc.*, 1822 (1948). For the use of sodium sulfite in the preparation of sodium sulfonate salts, see Reed and Tarter, *J. Am. Chem. Soc.*, 57, 571 (1935), or Latimer and Bost, *J. Org. Chem.*, 5, 24 (1940).

Equation 44(b)

The choice of chlorination conditions to be employed in the reaction of Equation 44(b) depends upon the nature of the substituent T. When T is $-SC(NH_2)=NH\cdot HBr$, the process may be effected with chlorine in an aqueous medium according to Johnson and Sprague, *J. Am. Chem. Soc.*, 58, 1348 (1936); 59, 1837, 2439 (1937). When T is $-SO_3Na$, the reaction may be carried out using phosphorous oxychloride according to the procedure of Westlake and Dougherty, *J. Am. Chem. Soc.*, 63, 658 (1941).

Equation 44(c)

The reaction shown in Equation 44(c) is conveniently accomplished in a manner identical to that described for Equation 7. For useful references, see Huntress and Carter, *J. Am. Chem. Soc.*, 62, 511 (1940), or Huntress and Autenrieth, ibid., 63, 3446 (1941).

Equation 44(d)

The first step of Equation 44(d) involves removal of the hydroxyl protecting group to release an alcohol substituent. Selection of a suitable protecting group must take into account the nature of other substituents in the molecule and would be obvious to one skilled in the art. For a compilation of references describing the wide variety of protecting groups available for alcohols, see T. W. Greene, "Protective Groups in Organic Synthesis", John Wiley and Sons, Inc., New York, 1981, pp. 10–72. The second step shown in Equation 44(d) involves the preparation of the desired products of Formula LIa from the corresponding alcohols with either phosphorous tribomide or triphenylphosphine-carbon tetrabromide. For relevant procedures, see Equation 31(d).

The requisite alkyl bromides of Formula LVIIa, where $R_8$ is H, may be synthesized in a manner analogous to that described in Equation 31 for compounds of Formula XL. Alternatively, the alkyl bromides of Formula LVIIa, where $R_8$ is other than H, are conveniently obtained as shown in Equation 45, starting from the appropriate esters of Formula XXXVIIIa.

Equation 45

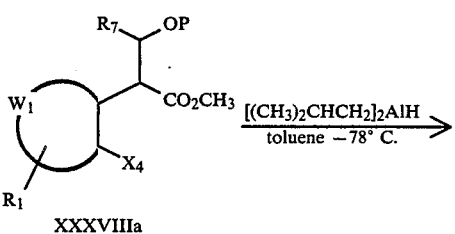

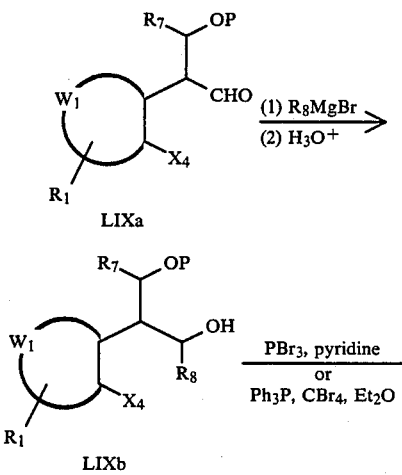

wherein $W_1$, $R_1$, $R_7$ and $R_8$ are as previously defined, $X_4$ is Br, $SR_{12}$ or $NO_2$, $R_{12}$ is $C_2$–$C_4$ alkyl or benzyl, and P is a protecting group as defined above in Equation 44.

The reduction of carboxylic esters such as those of Formula XXXVIIIa to the corresponding aldehydes with diisobutylaluminum hydride may be carried out as described in Equation 25(a). The second step of Equation 45 involves the addition of appropriate Grignard reagents, $R_8MgBr$, to aldehydes of Formula LIXa to afford the corresponding alcohols LIXb after aqueous workup. This is a well-known reaction and may be accomplished by following the procedures compiled in Patai, "The Chemistry of the Carbonyl Group", Vol. 1, Interscience Publishers, New York, 1969, pp. 621–693, Kharasch and Reinmuth, "Grignard Reactions of Nonmetallic Substances", Prentice-Hall, Inc., Englewood Cliffs, N.J. 1954, pp. 138–528. The third step shown in Equation 45 involves the conversion of alcohols LIXb to the corresponding alkyl bromides LVIIa, and has been described above in Equation 31(d).

Compounds of Formulas LIb–LIg may be prepared by methods analogous to those described in Equations 44 and 45 with suitable modifications which would be obvious to one skilled in the art.

Equation 46 depicts the intramolecular reaction of γ- and δ-hydroxysulfonyl chlorides of Formulas LXa and LXb to afford the sulfonates of Formulas LXIa and LXIb.

Equation 46

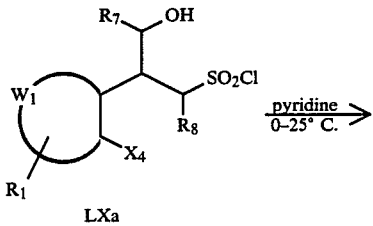

LXa

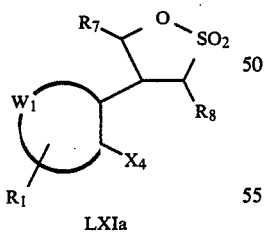

LXIa (b)

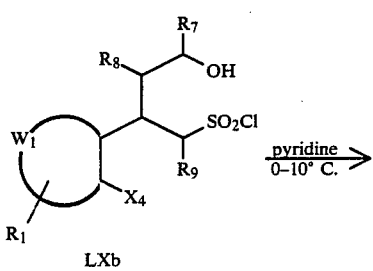

LXb

-continued
Equation 46

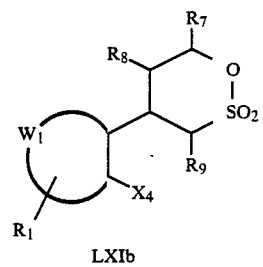

LXIb wherein
$W_1$, $R_1$, $R_7$, $R_8$ and $R_9$ are as previously defined, $X_4$ is Br, $NO_2$ or $SR_{12}$, and $R_{12}$ is $C_2$–$C_4$ alkyl or benzyl.

The cyclization shown in Equations 46(a) and 45(b) may be achieved according to the procedures of Tipson, J. Org. Chem., 9, 235 (1944). Marvel and Sekera, Org. Syntheses, 20, 50 (1940), or Sekera and Marvel, J. Am. Chem. Soc., 55, 346 (1933).

In a similar fashion, sulfonates of Formulas LXIc–LXIg may be prepared by base-induced cyclization of the appropriate or γ- or δ-hydroxysulfonyl chlorides of Formulas LXc–LXg, as shown below in Equations 47(a–e).

Equation 47

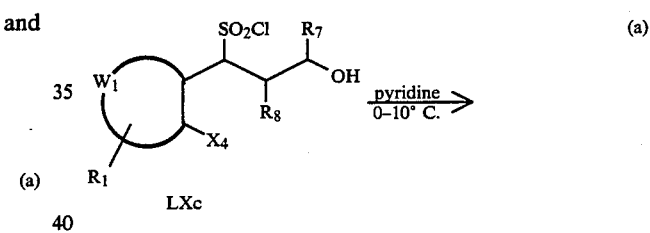

LXc

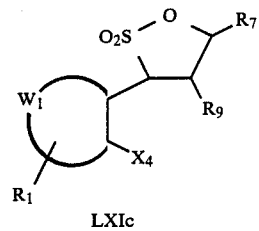

LXIc (b)

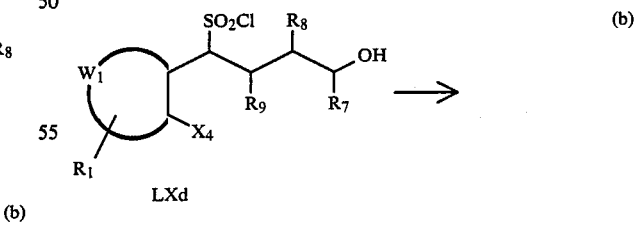

LXd

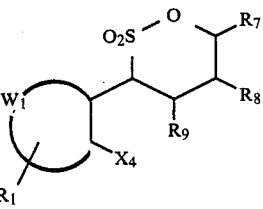

LXId

-continued

Equation 47

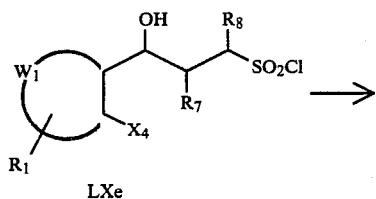
LXe (c)

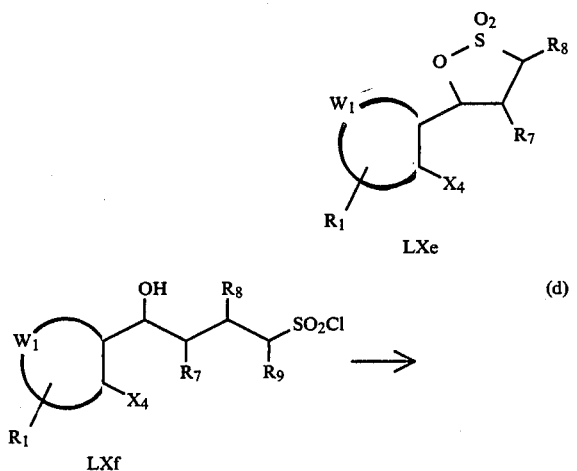
LXe

LXf

LXIf

LXq

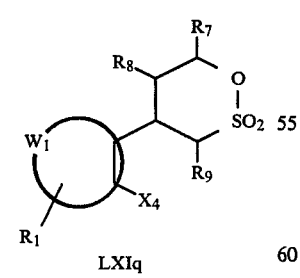
LXIq wherein $W_1$, $R_1$, $R_7$, $R_8$ and $R_9$ are as previously defined, $X_4$ is Br, $NO_2$ or $SR_{12}$, and $R_{12}$ is $C_2$–$C_4$ alkyl or benzyl.

The synthesis of the requisite hydroxysulfonyl chlorides has been described previously. For example, γ-hydroxysulfonyl chlorides of Formula LXa may be obtained from the corresponding protected compounds of Formula LVa (Equation 44). In a similar fashion, the requisite hydroxysulfonyl chlorides LXb–LXg may be prepared from the appropriate protected alcohols by methods which would be obvious to one skilled in the art.

sulfones of Formulas LXIIa–LXIIe may be conveniently prepared as shown in Equation 48 by oxidation of the appropriate 5- and 6-membered ring thioethers of Formulas LXIIIa–LXIIIe.

Equation 48

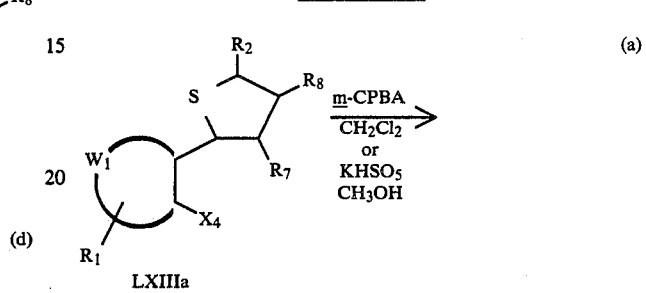
LXIIIa

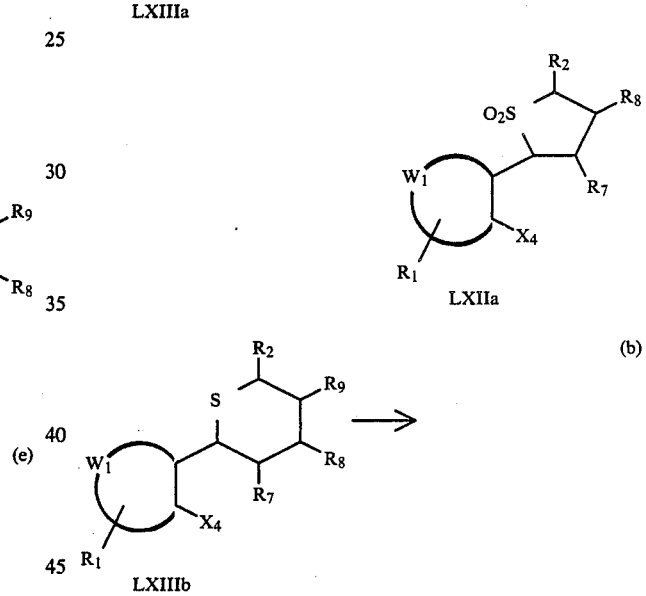
LXIIa

LXIIIb

LXIIb

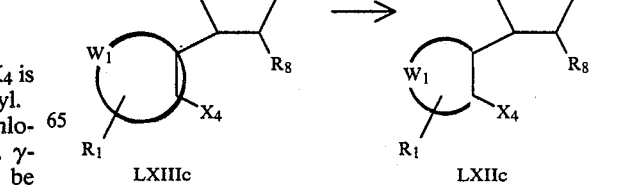
LXIIIc   LXIIc

-continued
Equation 48

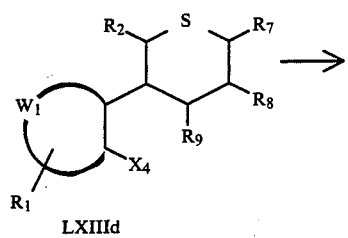
LXIIId

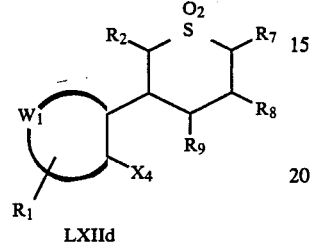
LXIId

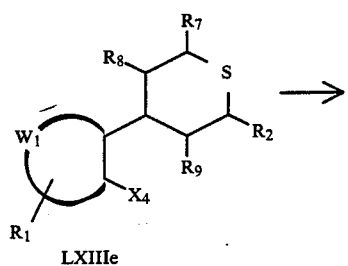
LXIIIe

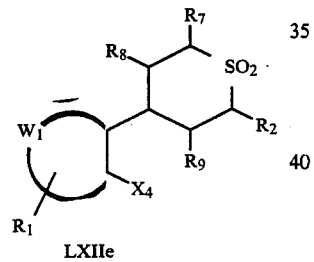
LXIIe wherein
$W_1$, $R_1$, $R_2$, $R_7$, $R_8$ and $R_9$ are as previously defined, and $X_4$ is $NO_2$ or $SO_2NH$—t—Bu.

The oxidation shown in Equation 48 is most conveniently carried out by adding a solution of at least two molar equivalents of m-chloroperoxybenzoic acid (m-CPBA) in a suitable solvent such as methylene chloride or chloroform to a solution of the sulfide LXIII(a–e) in the same solvent at 0°–25° C. After the reaction mixture has been stirred at about 25° C. for 1–4 hours, excess oxidant is destroyed by the addition of saturated aqueous sodium bisulfite (ice-water cooling). The reaction mixture is then filtered to remove the by-product m-chlorobenzoic acid, and the filtrate is washed several times with portions of saturated aqueous sodium bicarbonate. The desired products of Formula LXII(a–e) are isolated by drying and evaporation of the organic layer, and are often sufficiently pure to be carried directly on to the next step. Alternatively, the oxidation of Equation 48 may be accomplished by the use of potassium hydrogen persulfate as described by B. M. Trost and D. P. Curran, *Tetrahedron Lett.,* 1287 (1981).

The requisite sulfides of Formulas LXIIIa and LXIIIb may be prepared as shown in Equation 49, by conversion of the appropriate diols of Formulas LXIVa and LXIVb to the corresponding dibromides LXVa and LXVb, respectively, and subsequent treatment with sodium sulfide to effect cyclization.

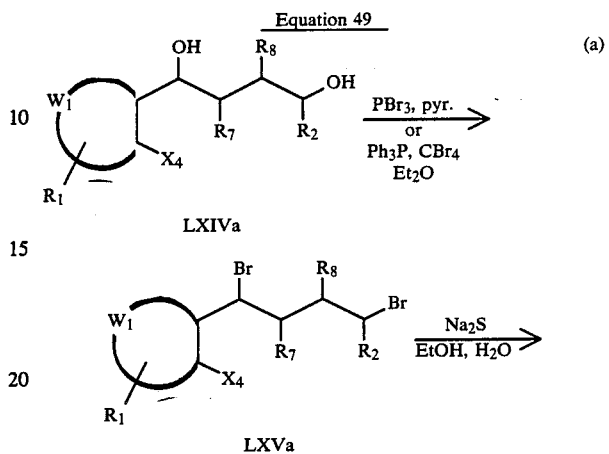

wherein
$W_1$, $R_1$, $R_2$, $R_7$, $R_8$ and $R_9$ are as previously defined, and $X_4$ is $NO_2$ or $SO_2NH$—t—Bu.

The first step of Equations 49(a) and 49(b) may be effected in a manner analogous to that described for Equation 31(d) except that two molar equivalents of the appropriate brominating agent are required. The second step shown above in Equations 49(a) and 49(b) may be conveniently carried out according to the method of Tarbell and Weaver, *J. Am. Chem. Soc.*, 63, 2940 (1941), or Naylor, *J. Chem. Soc.*, 1107 (1947).

In a similar manner, the requisite sulfides of Formulas LXIIIc–LXIIIe may be prepared via conversion of the appropriate diols to the corresponding dibromides, and subsequent cyclization by treatment with sodium sulfide.

Diols such as those of Formulas LXIVa and LXIVb may be prepared from the appropriately substituted intermediates, many of which have already been described. Methods needed to effect these transformations would be obvious to one skilled in the art.

The γ,β-unsaturated sulfonamides, represented by Formula LXVIIa, may be prepared by a procedure identical to that described for the synthesis of α,β-unsaturated lactams of Formulas XLVa–XLVi as shown above in Equations 36 and 37. For example, treatment of sulfonamides of Formula La with base, addition of diphenyl disulfide or phenylsulfenyl chloride, and subsequent oxidative elimination gives the unsaturated compounds of Formula LXVIIa as shown in Equation 50.

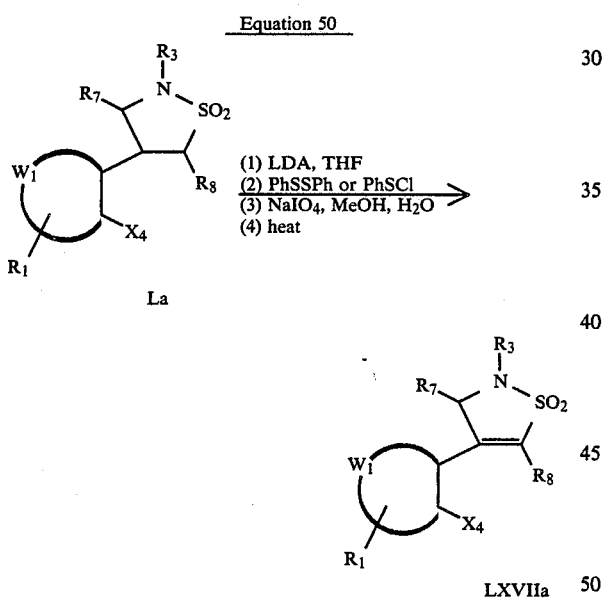

wherein
$W_1$, $R_1$, $R_3$, $R_7$ and $R_8$ are as previously defined, and $X_4$ is Br or $NO_2$.

The transformation depicted in Equation 50 is conveniently carried out in a manner analogous to that described in Equations 36 and 37. When $R_3$ is H in Equation 50, it is necessary to use one extra molar equivalent of lithium diisopropylamide (LDA) to form the α,N-dianions of sulfonamides La–Li. This procedure may be applied to the preparation of the remaining α,β-unsaturated analogues of sulfonamides Lb–Li.

The α,β-unsaturated sulfonates of Formulas LXVIIIa–LXVIIIg may be synthesized via the four-step sequence of reactions shown below in Equations 51(a–g), starting from the saturated compounds of Formula LXIa–LXIg.

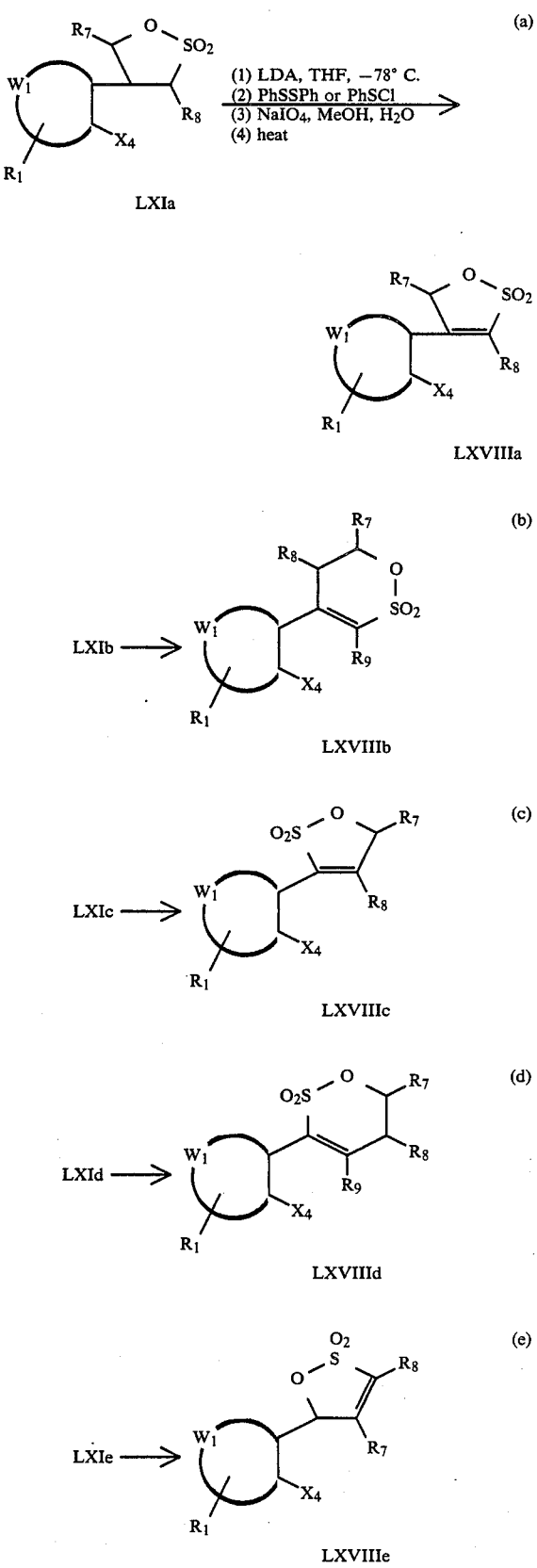

-continued
Equation 51

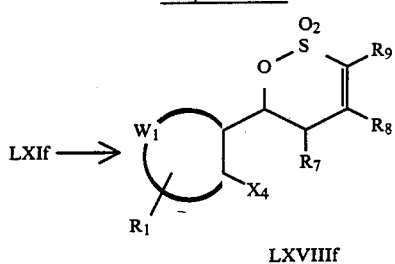

LXIf ⟶

LXVIIIf (f)

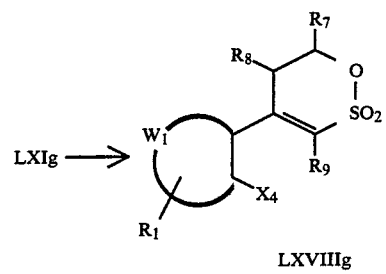

LXIg ⟶

LXVIIIg (g)

wherein
$W_1$, $R_1$, $R_7$, $R_8$ and $R_9$ are as previously defined and $X_4$ is Br, or $NO_2$.

The formation of anions alpha to the sulfonyl group of alkyl sulfonates such as those of Formulas LXIa–LXIg is a process with considerable precedent in the literature. For related examples, refer to Truce, Hollister, Lindy and Parr, *J. Org. Chem.*, 33, 43 (1968); Truce and Vrencur, *Can. J. Chem.*, 47, 860 (1969), *J. Org. Chem.*, 35, 1226 (1970); Julia and Arnould, *Bull. Soc. Chim. Fr.*, 743, 746 (1973); and Bird and Stirling, *J. Chem. Soc. (B)*, 111 (1968). Reaction of these sulfonate anions with diphenyl disulfide or phenylsulfenyl chloride and subsequent oxidative elimination may be effected as described for Equations 36 and 37.

Compounds of Formulas LXXa–LXXe may be synthesized as shown in Equation 52 by the reaction of appropriate α,β-unsaturated carbonyl compounds LXXIa–LXXIe with α-chloroketene acetals of Formulas LXXIIa or LXXIIb.

Equation 52

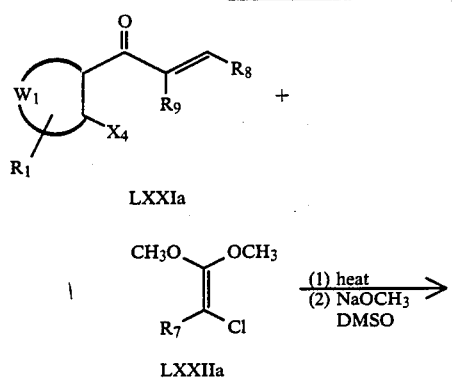

LXXIa

CH₃O  OCH₃

\  (1) heat
   (2) NaOCH₃ ⟶
       DMSO

LXXIIa

-continued
Equation 52

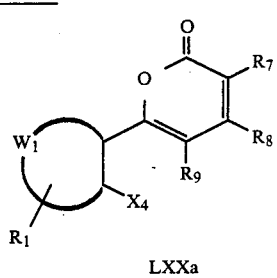

LXXa (a)

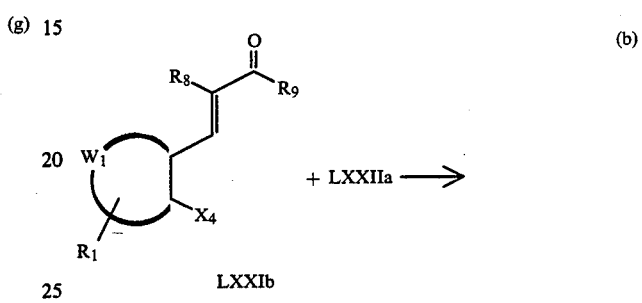

+ LXXIIa ⟶

LXXIb (b)

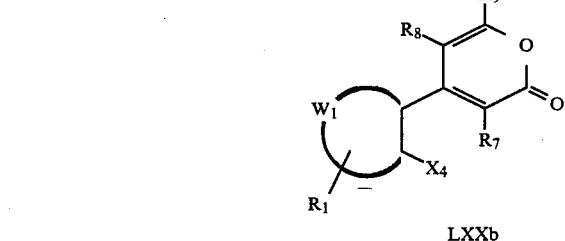

LXXb

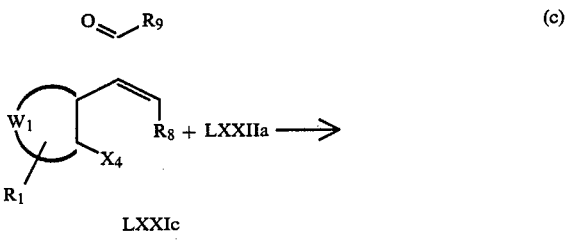

+ LXXIIa ⟶

LXXIc (c)

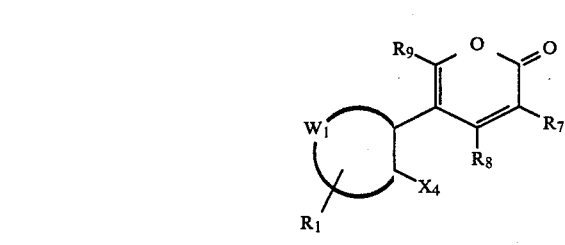

LXXc

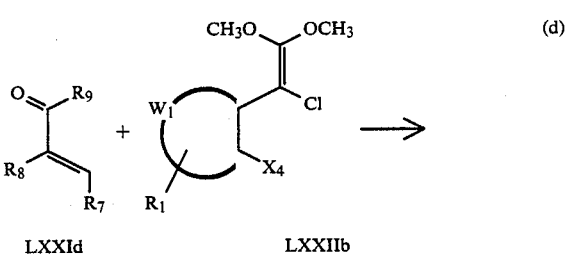

LXXId       LXXIIb (d)

-continued
Equation 52

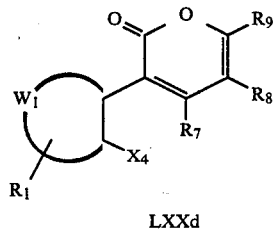

LXXd wherein $W_1$, $R_1$, $R_7$, $R_8$ and $R_9$ are as previously defined, $X_4$ is Br, $NO_2$, or $SR_{12}$, and $R_{12}$ is $C_2$–$C_4$ alkyl or benzyl.

The transformations outlined in Equation 52 may be conveniently carried out by the procedure of A. Belanger and P. Brassard, Chem. Comm., 863 (1972). Other syntheses of α-pyrones are known in the literature and have been reviewed by J. Fried in "Heterocyclic Compounds", ed. R. C. Elderfield, Wiley, New York, 1950, Vol. I, pp. 358–370, and L. F. Cavalieri, Chem. Rev., 41, 525 (1947).

The requisite α,β-unsaturated carbonyl compounds of Formulas LXXIa–LXXId and the α-chloroketene acetals of Formula LXXIIb may be prepared by methods known to one skilled in the art.

The α-pyrones of Formulas LXXIIIa and LXXIIIb may be prepared by one or more of several methods which have been reviewed by J. Fried in "Heterocyclic Compounds", ed. R. C. Elderfield, Wiley, New York, Vol. I, pp. 379–391. A more recent procedure involves the reaction of suitable potassium enolates of Formulas LXXIVa and LXXIVb with the appropriate acid chlorides of Formulas LXXVa and LXXVb, as shown in Equation 53.

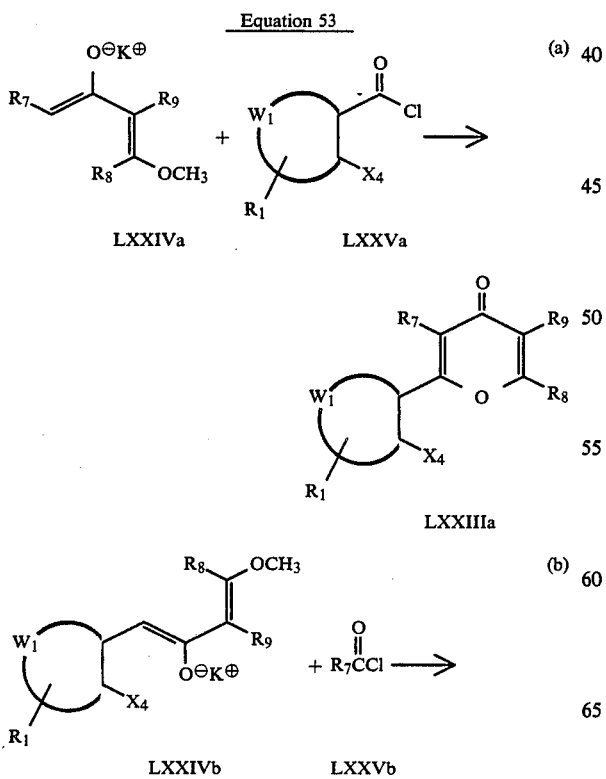

-continued
Equation 53

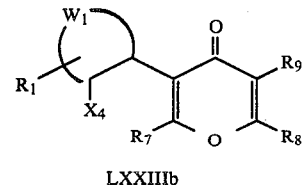

LXXIIIb wherein $W_1$, $R_1$, $R_7$, $R_8$ and $R_9$ are as previously defined, $X_4$ is Br, $NO_2$ or $SR_{12}$, and $R_{12}$ is $C_2$–$C_4$ alkyl or benzyl.

The reactions shown above in Equations 53(a) and 53(b) may be carried out according to the procedures described by T. A. Morgan and B. Ganem, Tetrahedron Lett., 21, 2773 (1980). For a closely-related method, refer to M. Koreeda and H. Akagi, Tetrahedron Lett., 21, 1197 (1980).

The requisite potassium enolates of Formulas LXXIVa and LXXIVb may be most conveniently prepared by treatment of the appropriate unsaturated ketones of Formulas LXXVIa and LXXVIb with a suitable base such as potassium tert-butoxide as shown in Equation 54.

Equation 54

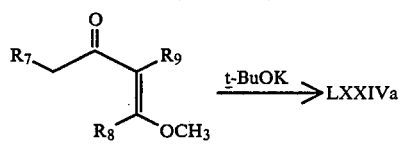

LXXVIa

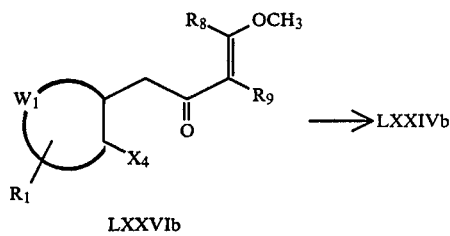

LXXVIb wherein $W_1$, $R_1$, $R_7$, $R_8$ and $R_9$ are as previously defined. $X_4$ is Br, $NO_2$ or $SR_{12}$, and $R_{12}$ is $C_2$–$C_4$ alkyl or benzyl.

The reaction shown in Equation 54 may be carried out according to the method described in Morgan and Ganem, Tetrahedron Lett., 21, 2773 (footnote 6) (1980).

The requisite unsaturated ketones of Formulas LXXVIa and LXXVIb, as well as the acid chlorides of Formula LXXVa, may be synthesized by methods known to one skilled in the art.

α-Pyridones of Formulas LXXVIIa–LXXVIId may be prepared in a straightforward manner by treatment of the appropriate α-pyrones of Formulas LXXa–LXXd with suitable amines, $H_2NR_{11}$, as represented below in Equation 55(a–d).

Equation 55

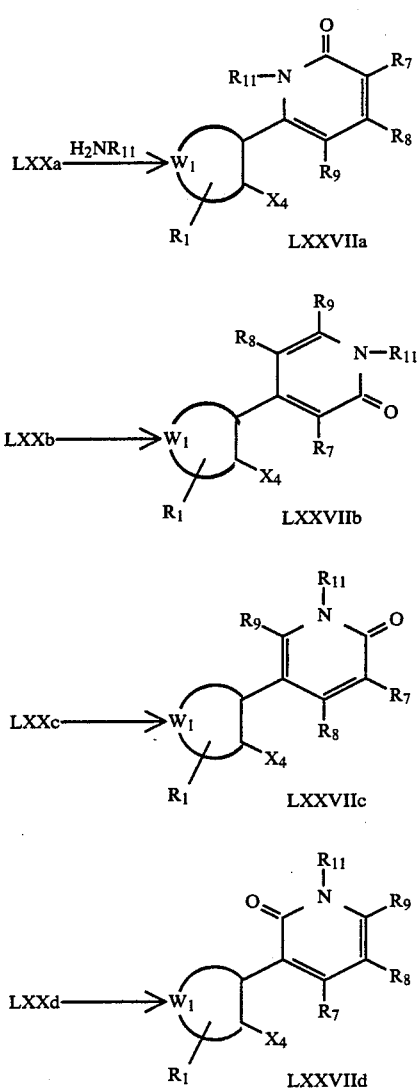

wherein $W_1$, $R_1$, $R_7$, $R_8$, $R_9$ and $R_{11}$ are as previously defined, $X_4$ is Br, $NO_2$ or $SR_{12}$, and $R_{12}$ is $C_2$–$C_4$ alkyl or benzyl.

The conversion of α-pyrones to the corresponding pyridones as shown in Equation 55 is a well-precedented process in the literature. For detailed descriptions of the procedure, see the following references: J. A. Leben, Ber., 29, 1673, (1896); von Pechmann and W. Welsh, Ber., 17, 2391 (1884); and J. H. Boyer and W. Schoen, *Org. Syntheses*, Coll. Vol. IV, 532 (1963).

Compounds of Formula LXXVIIe may be conveniently prepared as shown in Equation 56 by the reaction of α-pyrones of Formula LXXX with the anions LXXIX of the appropriate aminothiophene derivatives of Formula LXXVIII.

Equation 56

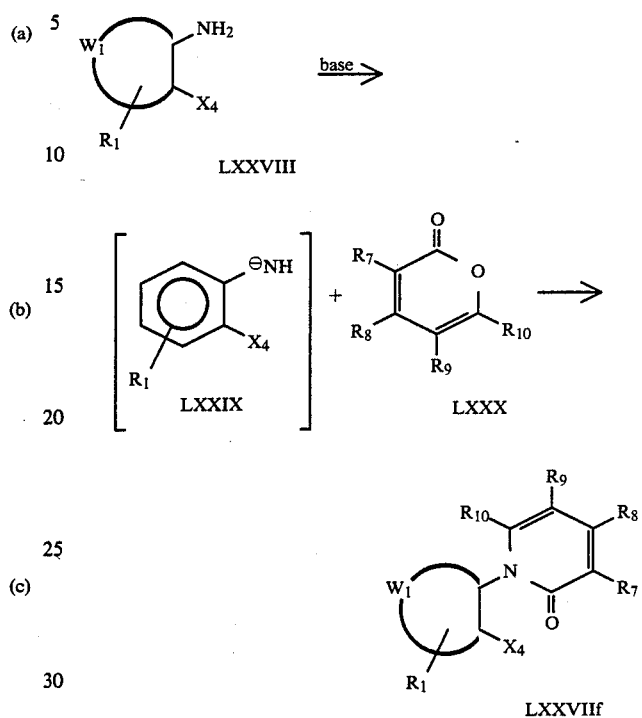

wherein $R_1$, $R_7$, $R_8$, $R_9$ and $R_{10}$ are as previously defined, $W_1$ is S, $X_4$ is Br, $NO_2$ or $SR_{12}$ and $R_{12}$ is $C_2$–$C_4$ alkyl or benzyl.

The first step of Equation 56, formation of the anions LXXIX of amino derivatives LXXVIII by treatment with a suitable base such as ethoxide ion, may be carried out according to the methods described by DeFeo and Strickler, *J. Org. Chem.*, 28, 2915 (1963), Yang, Cannon and Rose. *Tetrahedron Lett.*, 1791 (1970), or Singh, *Tetrahedron Lett.*, 321 (1971). The second step of Equation 56 may be effected in a manner analogous to that described in Equation 55.

γ-Pyridones of Formulas LXXXIa and LXXXIb may be synthesized from the corresponding γ-pyrones of Formulas LXXIIIa and LXXIIIb by treatment with the appropriate amines, $H_2NR_{11}$. This transformation is depicted in Equation 57.

Equation 57

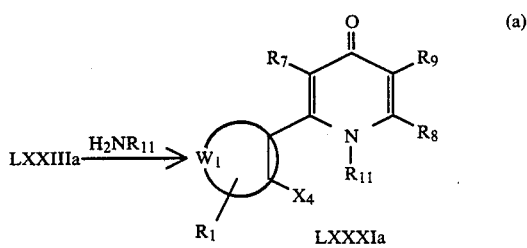

Equation 57 -continued

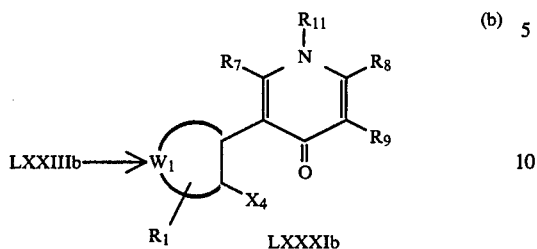

wherein
$W_1$, $R_1$, $R_7$, $R_8$, $R_9$ and $R_{11}$ are as previously defined, $X_4$ is Br, $NO_2$ or $SR_{12}$, and $R_{12}$ is $C_2$–$C_4$ alkyl or benzyl.

The reactions of Equations 57(a) and 57(b) may be conveniently carried out as described by C. F. Rassweiler and R. Adams, *J. Am. Chem. Soc.*, 46, 2758 (1924).

γ-Pyridones of Formula LXXXIc may be prepared in a manner analogous to that outlined above in Equation 56. Thus, addition of the anions of Formula LXXIX to γ-pyrones of Formula LXXXII, as shown in Equation 58, affords the desired products of Formula LXXXIc.

Equation 58

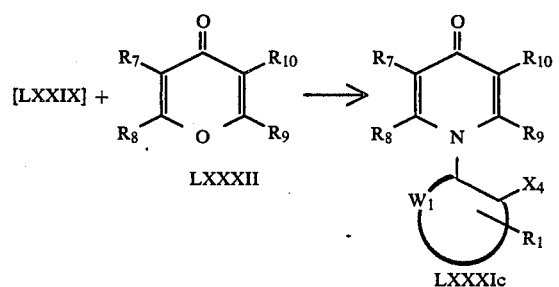

wherein
$W_1$, $R_1$, $R_7$, $R_8$, $R_9$ and $R_{10}$ are as previously defined, $X_4$ is Br, $NO_2$ or $SR_{12}$ and $R_2$ is $C_2$–$C_4$ alkyl or benzyl.

Compounds of Formula LXXXIIIa, where $R_8$ is H, may be prepared as shown in Equation 59 by the three-step sequence of reactions involving: (a) conversion of suitably protected carboxylic acids of Formula LXXXVI to the acid chlorides LXXXV, (b) treatment with diazomethane to give diazoketones of Formula LXXXIV, and (c) acid-induced cyclization.

Equation 59

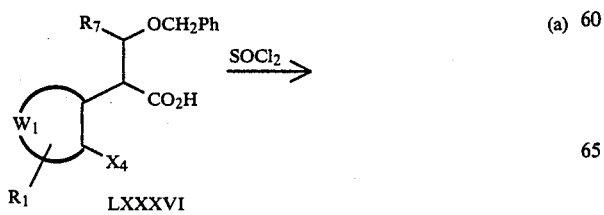

Equation 59 -continued

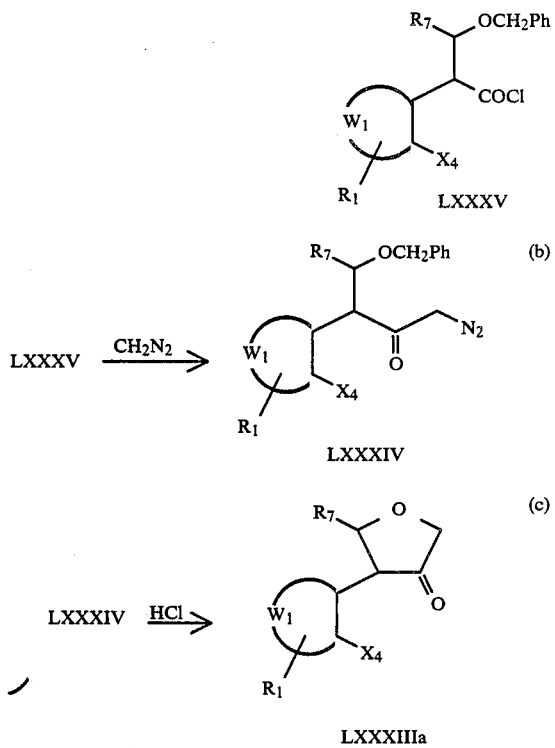

wherein
$W_1$, $R_1$ and $R_7$ are as previously defined, $X_4$ is Br, $NO_2$ or $SR_{12}$, and $R_{12}$ is $C_2$–$C_4$ alkyl or benzyl.

The transformations outlined in Equations 59(a–c) may be achieved according to the procedure of V. Luhmann and W. Luttke, *Chem. Ber.*, 105, 1350 (1972).

Compounds of Formula LXXXIIIb may be prepared via an intramolecular epoxide opening reaction followed by oxidation of the resulting alcohol as depicted in Equation 60.

Equation 60

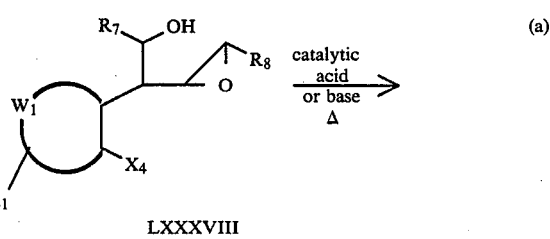

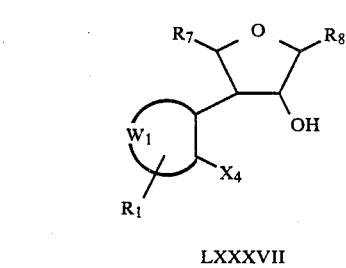

Equation 60

LXXXVII $\xrightarrow{CrO_3}$ 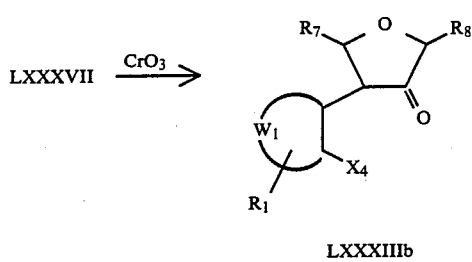 (b)

LXXXIIIb wherein $W_1$, $R_1$, $R_7$ and $R_8$ are as previously defined, $X_4$ is Br, $NO_2$ or $SR_{12}$, and $R_{12}$ is $C_2$–$C_4$ alkyl or benzyl.

Equation 60(a)

The reaction of Equation 60(a) involves the intramolecular alcoholysis of epoxides of Formula LXXXVIII, and may be accomplished by treatment with either a catalytic amount of a suitable base such as potassium tert-butoxide, or with a catalytic amount of a suitable acid such as sulfuric acid. For relevant procedures, refer to Chitwood and Freure, *J. Am. Chem. Soc.*, 68, 680 (1946), Sexton and Britton, ibid., 70 3606 (1948), or Winstein and Henderson, ibid., 65, 2196 (1943).

Equation 60(b)

The oxidation of 3-hydroxytetrahydrofurans, such as those of Formula LXXXVII, to the corresponding furanones of Formula LXXXIIIb, may be accomplished with chromium trioxide as described by V. Luhmann and W. Luttke, *Chem. Ber.*, 105, 1350 (1972).

Furanones of Formula LXXXIIIc may be synthesized as depicted in Equation 61 via a three-step process involving: (a) o-alkylation of the appropriate alcohols of Formula XCI, (b) Dieckmann cyclization to give α-carboethoxy furanones LXXXIX, and (c) hydrolysis and decarboxylation of esters LXXXIX with sulfuric acid.

Equation 61

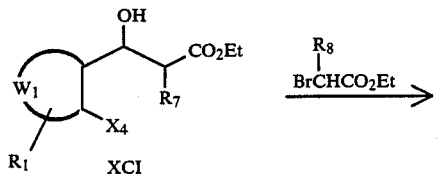 $\xrightarrow[BrCHCO_2Et]{R_8}$ (a)

XCI

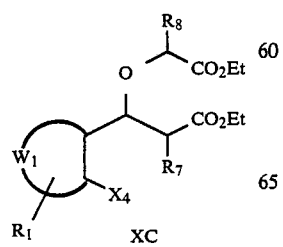

XC

Equation 61 -continued

XC $\xrightarrow{NaH}$ 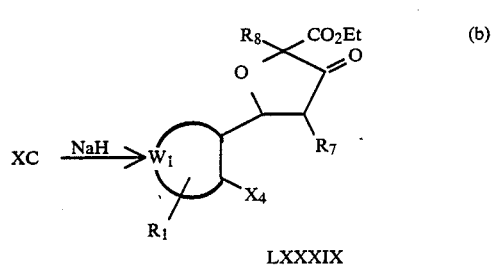 (b)

LXXXIX

LXXXIX $\xrightarrow{H_2SO_4}$ 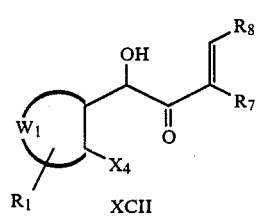 (c)

LXXXIIIc wherein $W_1$, $R_1$, $R_7$ and $R_8$ are as previously defined. $X_4$ is Br, $NO_2$ or $SR_{12}$, and $R_{12}$ is $C_2$–$C_4$ alkyl or benzyl.

The transformation outlined above in Equation 61(a–c) may be effectively accomplished by the procedure of V. Luhmann and W. Luttke, *Chem. Ber.*, 105, 1350 (1972).

Furanones of Formula LXXXIIId may be prepared as shown in Equation 62 by addition of anions of Formula XCIII to the appropriate aldehydes XCIV, and subsequent acid-induced cyclization of the resultant α-hydroxyenones of Formula XCII.

Equation 62

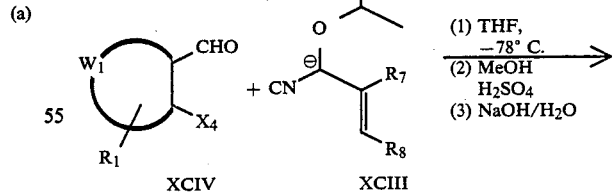 
(1) THF, −78° C.
(2) MeOH $H_2SO_4$
(3) NaOH/$H_2O$

XCIV    XCIII

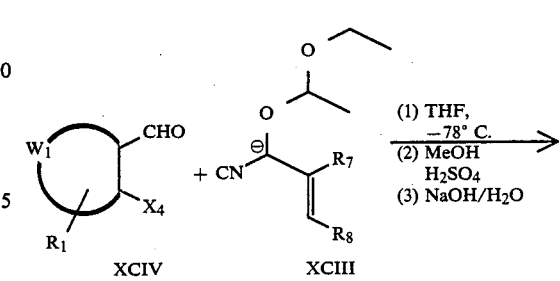

XCII

-continued
Equation 62

XCII ⟶ 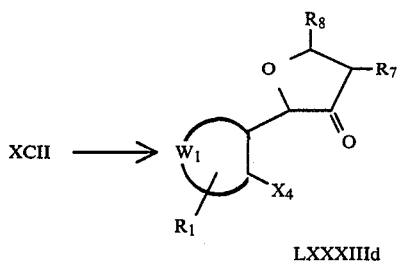

LXXXIIId (b)

wherein
$W_1$, $R_1$, $R_7$ and $R_8$ are as previously defined. $X_4$ is Br, $NO_2$ or $SR_{12}$, and $R_{12}$ is $C_2$-$C_4$ alkyl or benzyl.

Equation 62(a)

The addition of protected cyanohydrin anions of Formula XCIII to aldehydes of Formula XCIV and subsequent hydrolysis to afford α-hydroxyenones of Formula XCII may be carried out according to the procedure of G. Stork and L. Maldonado, *J. Am. Chem. Soc.*, 93, 5286 (1971). Also, refer to Stork and Maldonado, ibid., 96, 5272 (1974).

Equation 62(b)

The cyclization of Equation 62(b) may be carried out by heating a solution of the hydroxyenone of Formula XCII in a suitable solvent such as tetrahydrofuran in the presence of a catalytic amount of an appropriate acid such as hydrochloric or sulfuric acid. Alternatively, compounds of Formula XCII may be heated in a suitable solvent such as toluene at reflux temperature in the presence of a catalytic amount of p-toluenesulfonic acid.

Compounds of Formulas LXXXIIIe-LXXXIIIh, which are homologs of furanones LXXXIIIa-LXXXIIId, may be prepared by methods analogous to those described above in Equations 59, 60, 61 and 62. The minor modifications needed to implement these syntheses would be obvious to one skilled in the art. Equations 63(a)-63(d) depict the procedures for the preparation of compounds LXXXIIIe-LXXXIIIh.

Equation 63 (a)

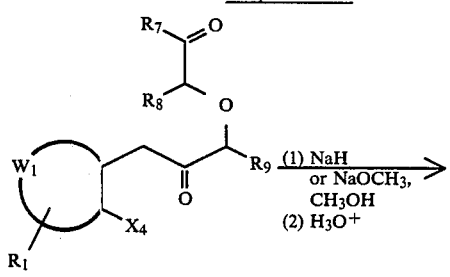

XCVI

-continued
Equation 63

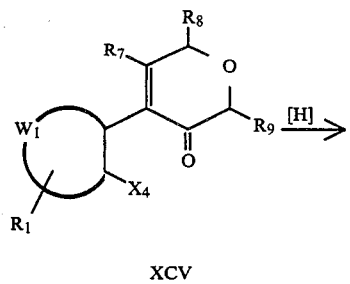

XCV

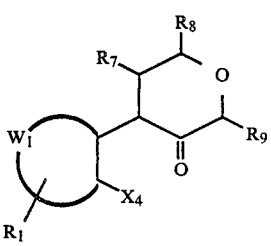

LXXXIIIe (b)

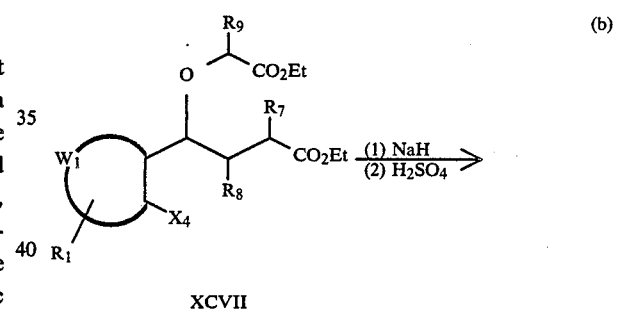

XCVII

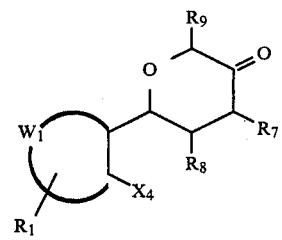

LXXXIIIf (c)

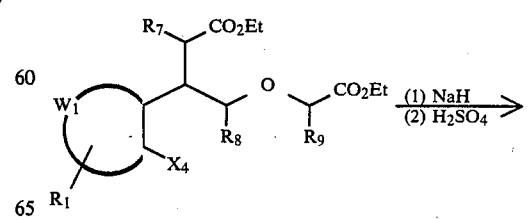

XCVIII

-continued
Equation 63

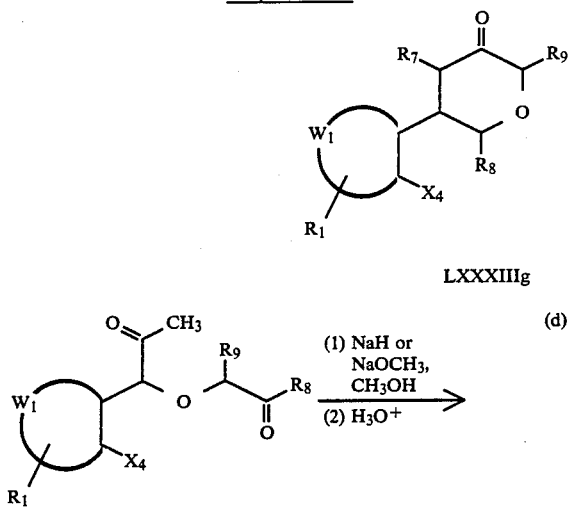

LXXXIIIg (d)

C

XCIX

LXXXIIIh wherein
$W_1$, $R_1$, $R_7$, $R_8$ and $R_9$ are as previously defined, $X_4$ is Br, $NO_2$ or $SR_{12}$, $R_2$ is $C_2$–$C_4$ alkyl or benzyl, and $X_5$ is Cl, Br, or I.

Equation 63(a)

The first step of Equation 63(a) is an intramolecular aldol condensation and may be carried out in a manner analogous to that described for Equation 25(b). The second step of Equation 63(a) involves a selective 1,4-reduction of an α,β-unsaturated ketone and may be achieved by methods described in Equation 25(c).

Equations 63(b)–63(d)

For a description of the procedures for carrying out the reactions of Equations 63(b)–63(d), see the reference cited for Equation 61. The reductive alkylation process shown in the second step of Equation 63(d), whereby unsaturated ketones of Formula XCIX are converted to the desired products of Formula LXXXIIIh, may conveniently be effected according to the method of V. I. Mel'nikova and K. K. Pivnitskii, *J. Org. Chem.* USSR (Engl. Trans.), 6, 2635 (1970).

The pyrrolidones of Formulas CIa–CId may be synthesized as shown in Equation 64 via hydroboration/oxidation of the appropriate Δ²-pyrrolines of Formulas CIIa–CIIb.

Equation 64

(a)

CIIa (1) $BH_3$, THF
(2) $H_2O_2$, NaOH
(3) [O]

CIa (b)

CIIb

CIb (c)

CIIc

-continued

Equation 64

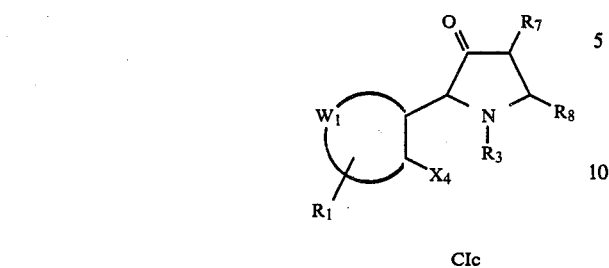

CIc (d)

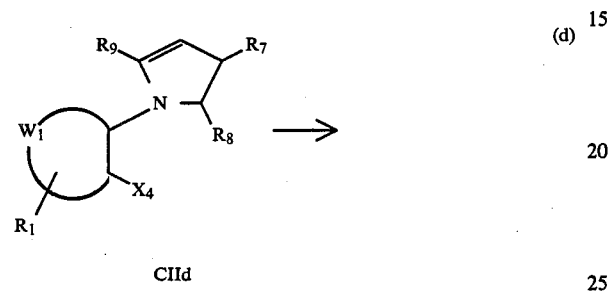

CIId

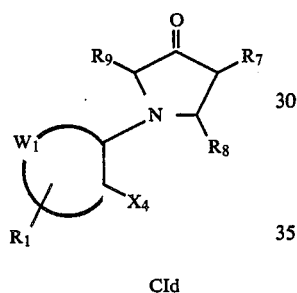

CId wherein
$W_1$, $R_1$, $R_3$, $R_7$, $R_8$ and $R_9$ are as previously defined, and $X_4$ is Br or $NO_2$.

The reactions of Equations 64(a)–(d) may conveniently be carried out according to the method of I. J. Borowitz and G. J. Williams, *J. Org. Chem.*, 32, 4157 (1967).

In a similar fashion, the compounds of Formulas CIe–CIi may be prepared from the appropriate enamines of Formulas CIIIa–CIIIe as represented in Equation 65(a–e).

Equation 65

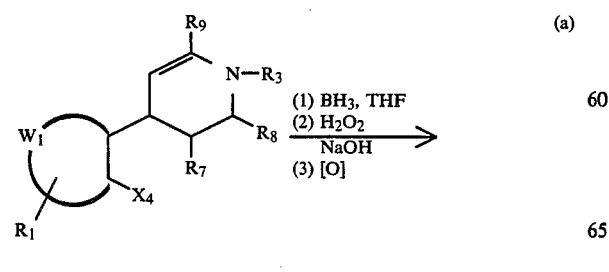

CIIIa (1) $BH_3$, THF
(2) $H_2O_2$ / NaOH
(3) [O]

-continued

Equation 65

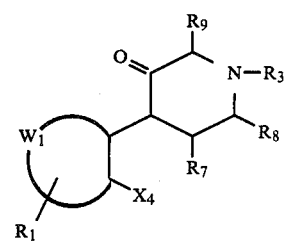

CIe

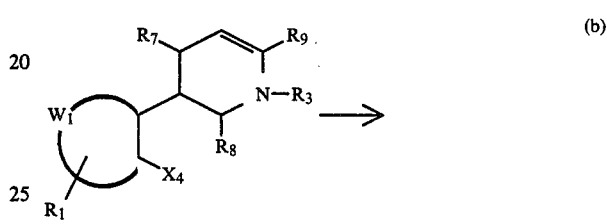

CIIIb

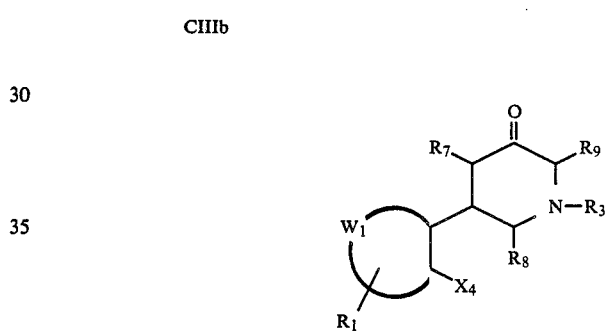

CIf

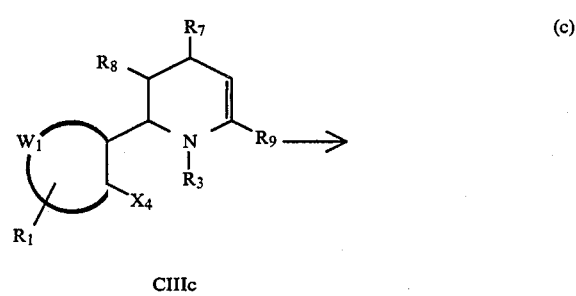

CIIIc

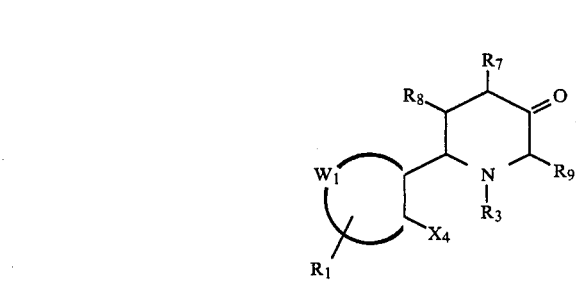

CIq (a)

(b)

(c)

Equation 65

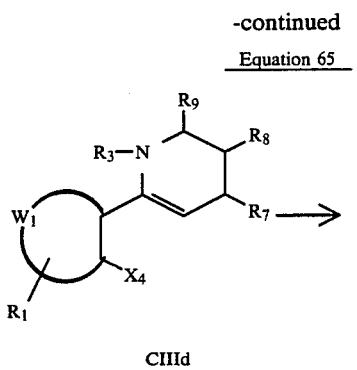

CIIId

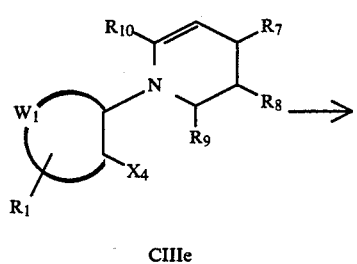

CIIIe

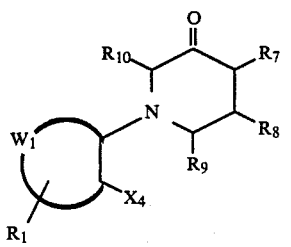

CIi wherein $W_1$, $R_1$, $R_3$, $R_7$, $R_8$, $R_9$ and $R_{10}$ are as previously defined, and $X_4$ is Br or $NO_2$.

The requisite compounds of Formulas CIIa–CIId and CIIIa–CIIIe may be prepared by the method shown in Equation 66. For example, treatment of the appropriate compounds of Formulas CIVa or CIVb with suitable amines, $H_2NR_3$, affords the desired pyrrolines or tetrahydropyridines of Formulas CIIa and CIIIa, respectively.

Equation 66

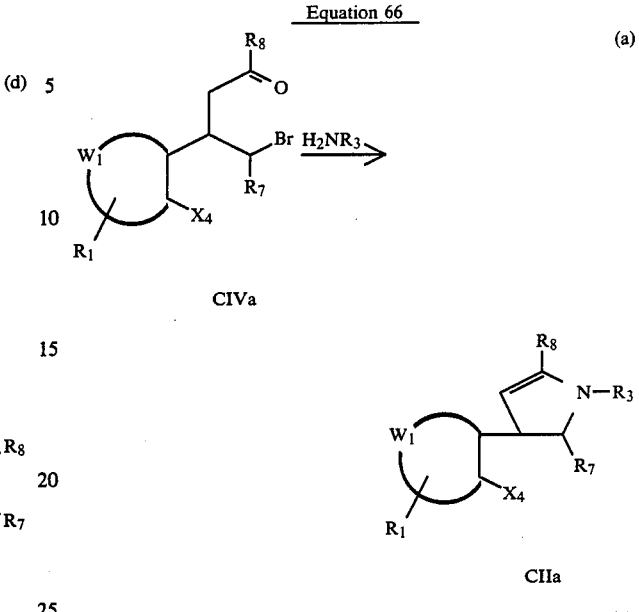

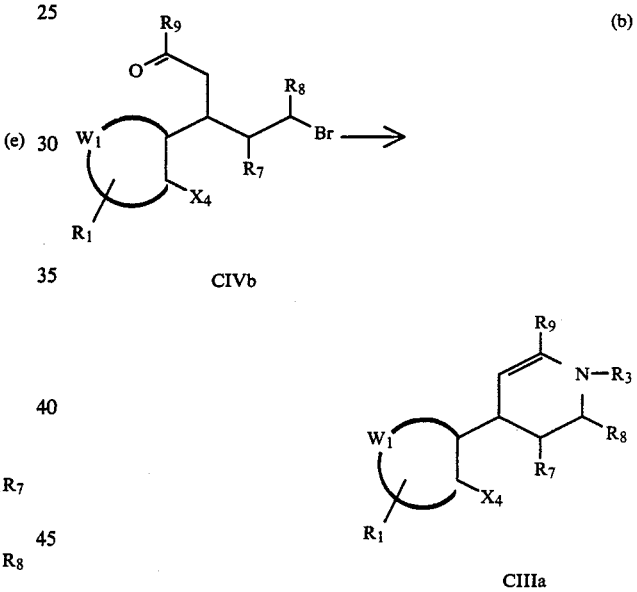

wherein $W_1$, $R_1$, $R_3$, $R_7$, $R_8$ and $R_9$ are as previously defined, and $X_4$ is Br or $NO_2$.

The reactions of Equations 66(a) and 66(b) may be conveniently carried out according to procedures described in the following references: J. Cloke, *J. Am. Chem. Soc.*, 51, 1174 (1929); A. Wohl, Ber., 34, 1914 (1901); A. Kipp. Ber., 18, 3284 (1895), and 25, 2190 (1892); and S. Gabriel, Ber., 41, 2010 (1908).

The transformations depicted above in Equation 66 may be applied in a straightforward manner to the synthesis of the related compounds of Formulas CIIb–CIId and CIIIb–CIIIe.

The $\alpha,\beta$-unsaturated compounds of Formulas CVa may be prepared by the same type of process described above in Equations 33 and 34 to synthesize unsaturated lactones of Formulas XLIII. Thus, treatment of compounds CIe with a kinetic base such as lithium diisopropylamide (LDA) will generate the corresponding enolates of Formula CVI. Trapping with diphenyl disulfide or phenylsulfenyl chloride, and subsequent oxidative elimination gives the desired compounds of Formula CVa, as shown in Equation 67.

Equation 67

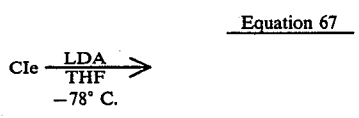

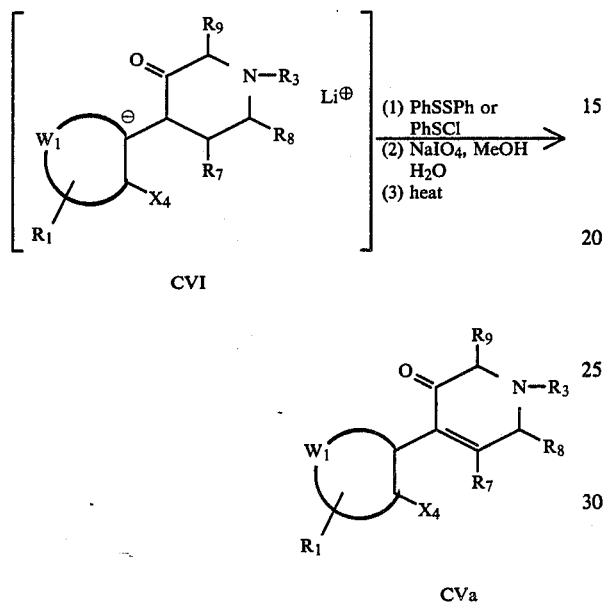

wherein
$W_1$, $R_1$, $R_3$, $R_7$, $R_8$ and $R_9$ are as previously defined, and $X_4$ is Br, $NO_2$, or $SO_2NH-t-Bu$.

It should be noted in Equation 67 that for compounds of Formula CIe, where $R_3$ is H, one extra molar equivalent of base must be employed to generate the dianions. For a procedure describing the formation of enolates of 3-piperidones such as those of Formulas CIe-CIi, see McElvain, *J. Am. Chem. Soc.*, 55, 1233 (1933), and McElvain and Vozza, ibid., 71, 896 (1949).

The procedure shown in Equation 67 may be quite easily applied to compounds of Formulas CIf-CIi. In this manner, the corresponding α,β-unsaturated derivatives may be synthesized and further transformed into the appropriate sulfonamides of Formula IVa or IVb, where Q is Q-128, Q-129, Q-131, and Q-130.

In an analogous fashion, compounds of Formulas LXXXIIIe-LXXXIIIh may be treated according to the procedures described in Equations 33 and 34 to give the corresponding α,β-unsaturated derivatives. Further elaboration of these compounds then affords the primary sulfonamides of Formula IVa, or IVb, where Q is Q-123, Q-125, Q-124, and Q-126.

Compounds of Formulas CVIIa and CVIIb may be conveniently prepared as shown in Equation 68(a and b) by a Dieckmann cyclization of the appropriate sulfides of Formulas CVIIIa and CVIIIb, followed by hydrolysis and decarboxylation.

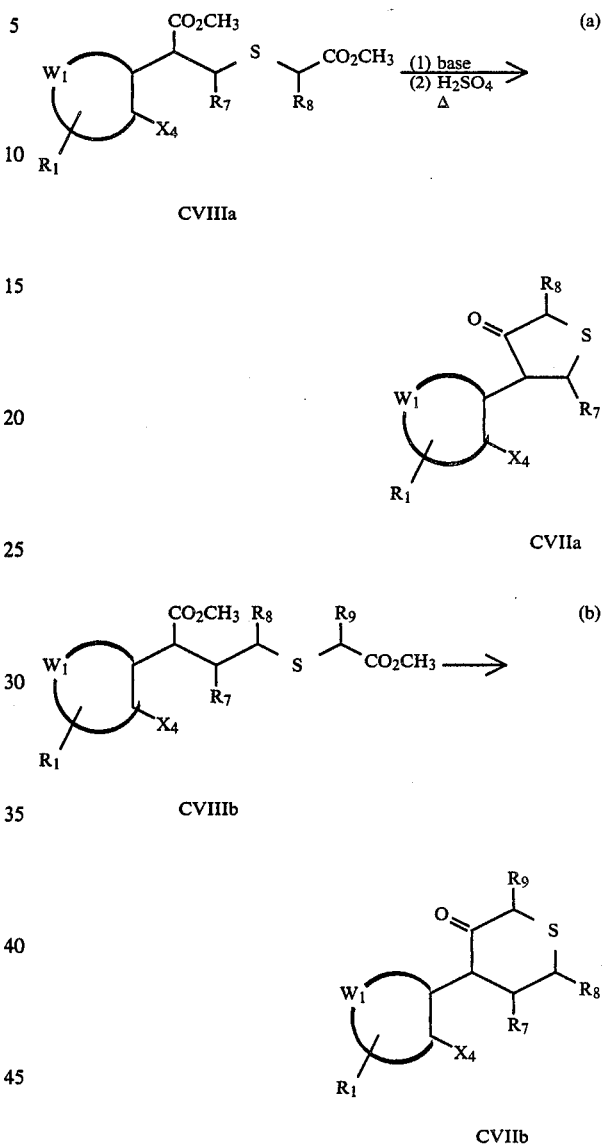

wherein
$W_1$, $R_1$, $R_7$, $R_8$ and $R_9$ are as previously defined, and $X_4$ is Br, $NO_2$ or $SO_2NH-t-Bu$.

The reactions of Equations 68(a) and 68(b) may be carried out according to the procedure of Woodward and Eastman, *J. Am. Chem. Soc.*, 68, 2229 (1946), and Woodward and Eastman, ibid., 66, 849 (1944). For a review of syntheses of these ring system, see Wolf and Folkers, *Org. Reactions*, Vol. 6, 1951, pp. 443–468.

In a similar fashion, the 3-ketothiolanes of Formulas CVIIc-CVIIg may be prepared via Dieckmann cyclization of the appropriate sulfides of Formulas CVIIIc-CVIIIg as outlined below in Equation 69(a-e).

Equation 69

(a)
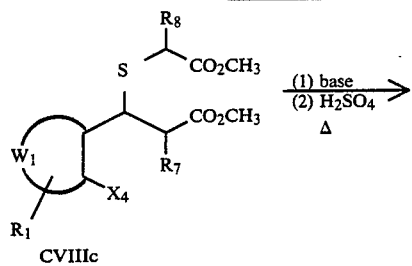
CVIIIc
(1) base
(2) $H_2SO_4$
Δ

(d)
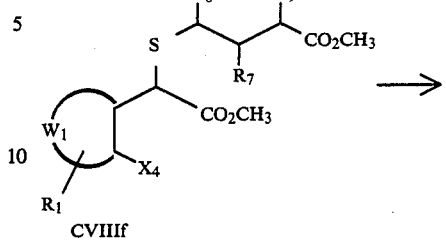
CVIIIf

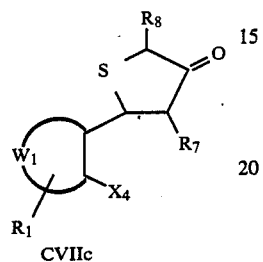
CVIIc

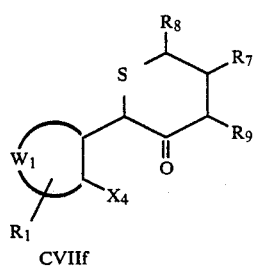
CVIIf (b)
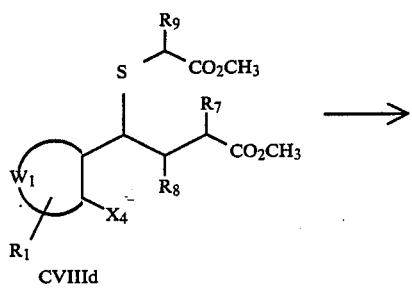
CVIIId (e)
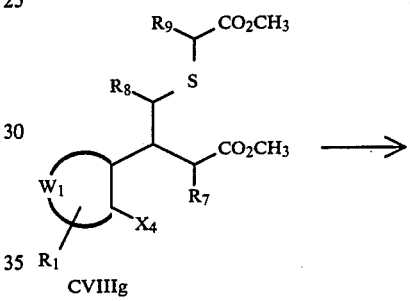
CVIIIg

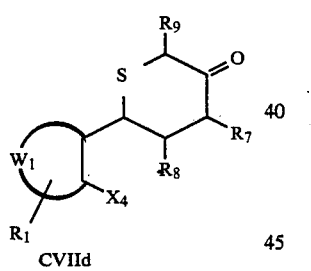
CVIId

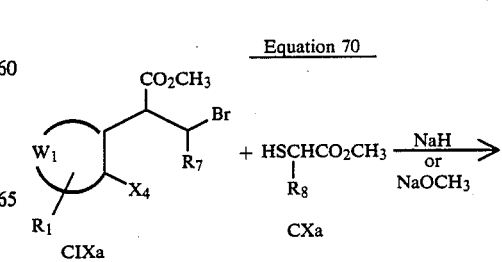
CVIIg (c)
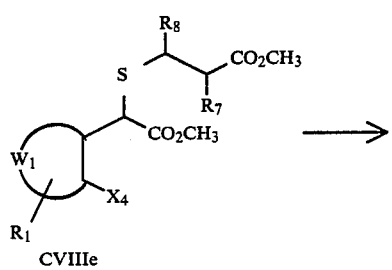
CVIIIe wherein
$W_1$, $R_1$, $R_7$, $R_8$ and $R_9$ are as previously defined, and $X_4$ is Br, $NO_2$, or $SO_2NH-t-Bu$.

The requisite sulfides of Formulas CVIIIa–CVIIIg may be prepared by the reaction of appropriate alkyl bromides of Formula CIX with substituted mercaptans of Formula CX. Equation 70 shows this reaction for the example CVIIIa.

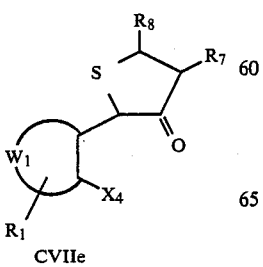
CVIIe

Equation 70

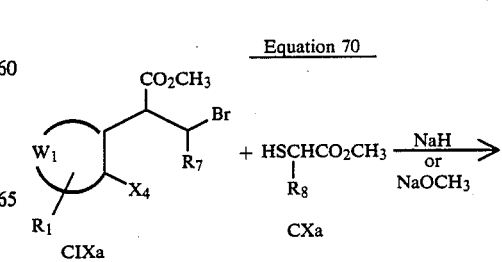
CIXa      CXa
$\xrightarrow{\text{NaH or NaOCH}_3}$

Equation 70 -continued

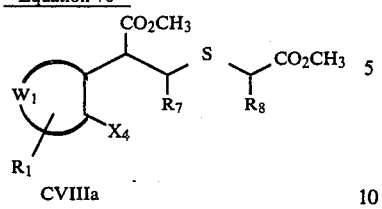

CVIIIa wherein
$W_1$, $R_1$, $R_7$ and $R_8$ are as previously defined, and $X_4$ is Br, $NO_2$, or $SO_2NH$—t—Bu.

The alkylation of mercaptans such as those of Formula CXa with alkyl halides is a well-known process with considerable precedent in the literature. For relevant references, see Shriner, Struck and Jorison, *J. Am. Chem. Soc.*, 52, 2066 (1930); Kirner and Richter, ibid., 51, 3135 (1929); Kipnis and Ornfelt, ibid., 71, 3571 (1949); and Fehnel and Carmack, ibid., 71, 92 (1949).

By applying the procedures described above in Equation 70, one skilled in the art may prepare the requisite sulfides of Formulas CVIIIb–CVIIIg from the appropriate alkyl bromides and mercaptans.

In an analogous manner, the requisite ethers of Formulas XC, XCVI, XCVII, XCVIII and C may be prepared via treatment of the appropriate alkyl bromides of Formula CXI with the sodium salts of the appropriate alcohols of Formula CXII. This reaction is shown below in Equation 71 for the synthesis of compounds XCVI as a representative example.

Equation 71

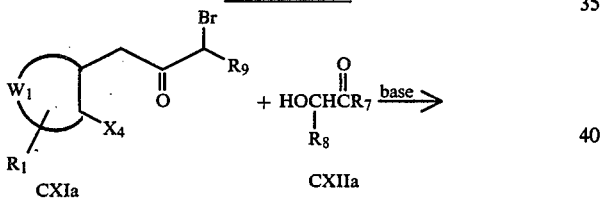

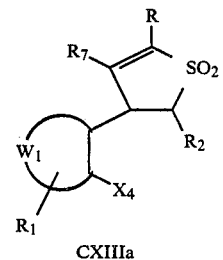

XCVI wherein
$W_1$, $R_1$, $R_7$, $R_8$ and $R_9$ are as previously defined, $X_4$ is Br, $NO_2$ or $SR_{12}$ and $R_2$ is $C_2$–$C_4$ alkyl or benzyl.

For a compilation of references dealing with the reaction of Equation 71, see R. B. Wagner and H. D. Zook, "Synthetic Organic Chemistry", John Wiley and Sons, Inc., New York, 1953, pp. 226–228.

Unsaturated sulfones of Formulas CXIIIa and CXIIIb may be prepared as shown in Equation 72 by a three-step sequence of reactions involving: (1) addition of the appropriate organometallic reagents, $R_8M$ or $R_7M$, to compounds of Formula CVIIa or CVIIb, (2) oxidation of the adducts of Formula CXVa or CXVb, and (3) dehydration of the sulfones CXVIa or CXVIb to the corresponding products of Formula CXIIIa or CXIIIb.

Equation 72 (a)

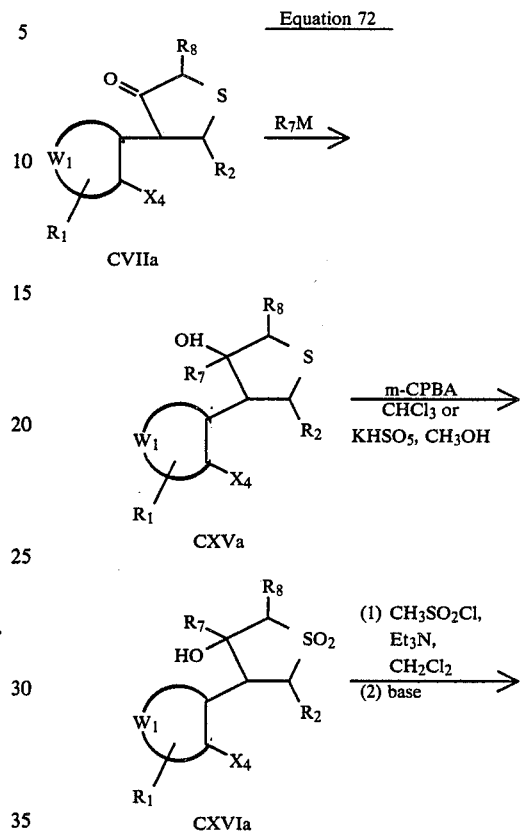

(b)

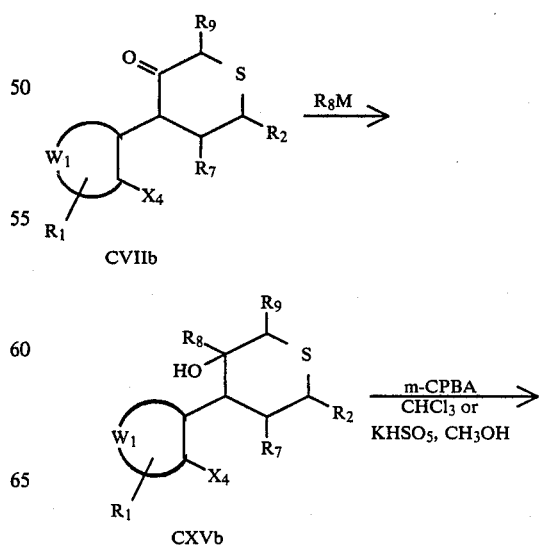

-continued
Equation 72

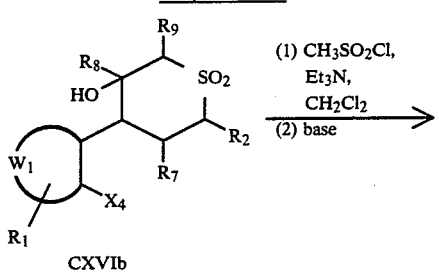

CXVIb

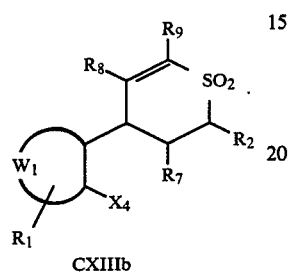

CXIIIb wherein $W_1$, $R_1$, $R_2$, $R_7$, $R_8$ and $R_9$ are as previously defined, $X_4$ is Br or $NO_2$, and M is MgBr or Li.

The transformations shown above in Equations 72(a) and 72(b) may be effected according to the method of T. Takaya, et. al., *Bull. Chem. Soc. Japan*, 41, 2086 (1968).

In a similar fashion, compounds of Formulas CVIIc–CVIIg may be treated according to the procedures described above in Equations 72(a) and 72(b) to afford the corresponding unsaturated sulfones. Further elaboration of the unsaturated sulfones derived from the compounds of Formulas CVIIa–CVIIg by methods described previously yields the primary sulfonamides of Formula IVa or IVb, where Q is Q-49, Q-120, Q-50, Q-118, Q-47, Q-122, and Q-119.

The unsaturated sulfones of Formulas CXIIIc and CXIIId may be prepared as shown in Equation 73 by: (1) addition of the dianions of N-t-butylthienyl or N-t-butylfuranyl sulfonamides XX to the appropriately substituted compounds of Formulas CXVIIa and CXVIIb, and (2) oxidation and dehydration of the resultant adducts of Formulas CXVc and CXVd.

Equation 73                                          (a)

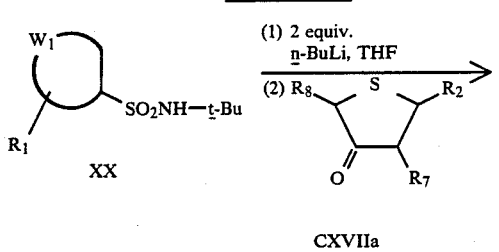

-continued
Equation 73

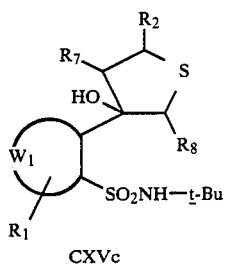

CXVc

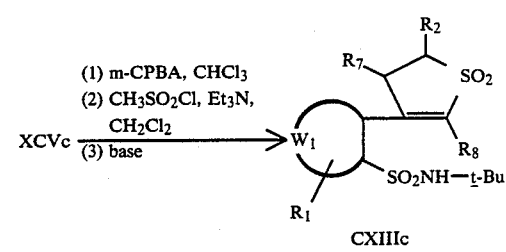

CXIIIc

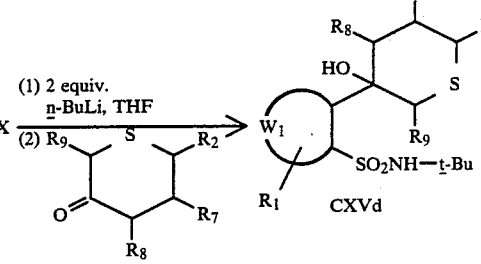                                  (b)

CXVIIb                                                CXVd

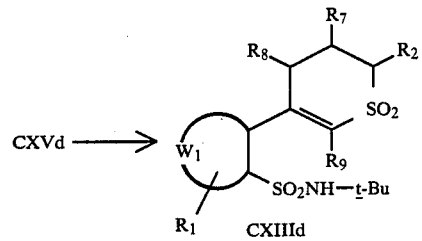

CXVd ⟶

CXIIId wherein $R_1$, $R_2$, $R_7$, $R_8$ and $R_9$ are as previously defined, and $W_1$ is S or O.

The first step of the reactions of Equations 73(a) and 73(b) may be conveniently carried out according to the procedure of J. G. Lombardino, *J. Org. Chem.*, 36, 1843 (1971). The second step shown in Equations 73(a) and 73(b) is accomplished by the method described in Equation 72.

Dihydrothiopyran-3-ones of Formulas CXVIIIa–CXVIIId may be synthesized as depicted below in Equation 74(a–d) by a Dieckmann-type cyclization of the appropriate sulfides of Formulas CXIXa–CXIXd, and subsequent acid-induced hydrolysis and decarboxylation.

Equation 74

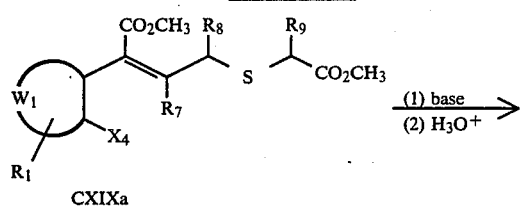
(a)

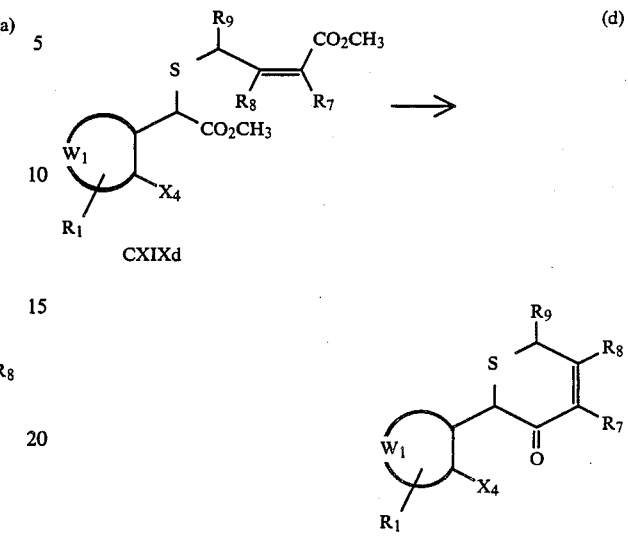
(d)

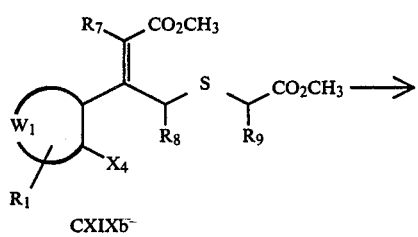
(b)

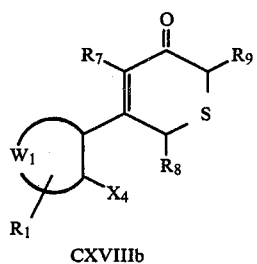

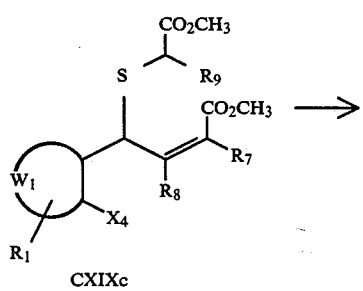
(c)

wherein
$W_1$, $R_1$, $R_7$, $R_8$ and $R_9$ are as previously defined, and $X_4$ is Br, $NO_2$ or $SO_2NH-t-Bu$.

The reaction of Equation 74(a-d) may be carried out according to the procedure of S. Rossi and G. Pagani, *Tetrahedron Lett.*, 2129 (1966).

The requisite sulfides of Formulas CXIXa-CXIXd may be prepared in a manner analogous to that described in Equation 70 for the preparation of compounds CVIIa.

Dihydropyrones of Formulas CXXa-CXXd may be conveniently prepared as shown in Equation 75 by reaction of the appropriate potassium enolates of Formulas CXXIa-CXXId with suitable acid chlorides of Formulas CXXIIa-CXXIIc.

Equation 75

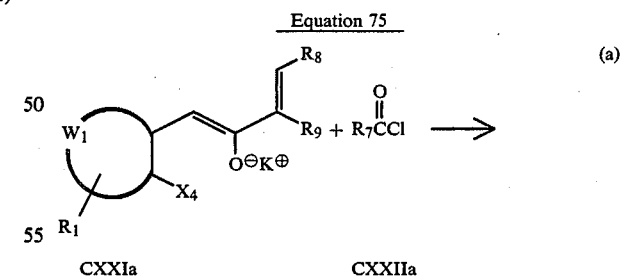
(a)

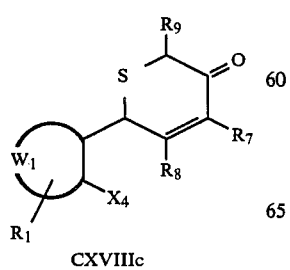

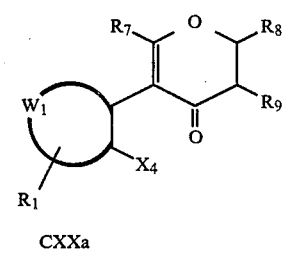

-continued
Equation 75

(b) CXXIb + R₈CCl → CXXIIb

CXXb (c) CXXIc + R₈CCl → CXXIIb

CXXc (d) CXXId + CXXIIc →

CXXd wherein $W_1$, $R_1$, $R_7$, $R_8$ and $R_9$ are as previously defined, $X_4$ is Br, $NO_2$ or $SR_{12}$, and $R_{12}$ is $C_2$-$C_4$ alkyl or benzyl.

The reactions of Equation 75 may be carried out in a manner analogous to that described for Equation 53.

An alternative method for the preparation of dihydropyrones of Formula CXXb above where $R_8$ is H involves the Lewis acid catalyzed hetero-Diels-Alder reaction of sulfonamide XCIV with dienes of Formula CXXe followed by mild hydrolysis as depicted in Equation 75e. Suitable Lewis acids include magnesium bromide, zinc chloride, and (6,6,7,7,8,8,8-heptafluoro-2,2-dimethyl-3,5-octanedionato)europium[Eu(fod)₃]. For typical procedures for carrying out the cyclocondensations, see M. Bednarski and S. Danishefsky, *J. Am. Chem. Soc.*, 105, 5716 (1983).

Equation 75e

XCIV + CXXe $\xrightarrow[(3) H_3O^+]{(1) (CH_3)_3SiO, (2) Eu(fod)_3}$ CXXb wherein $W_1$, $R_1$, $R_7$ and $R_9$ are as previously defined,
$R_8$ is H,
$X_4$ is Br, $NO_2$, $SR_{12}$ or $SO_2NH$—t—Bu, and
$R_{12}$ is $C_2$-$C_4$ alkyl or benzyl.

Reduction of dihydropyrones of Formulas CXXa-CXXd gives the corresponding tetrahydropyrones as shown in Equation 76 for the specific example of CXXa.

Equation 76

CXXa $\xrightarrow[\text{catalyst}]{H_2}$ CXXIII wherein $W_1$, $R_1$, $R_7$, $R_8$ and $R_9$ are as previously defined, $X_4$ is Br, $NO_2$ or $SR_{12}$, and $R_{12}$ is $C_2$-$C_4$ alkyl or benzyl.

The reduction shown in Equation 76 may be carried out in the presence of a suitable catalyst such as colloidal palladium (cf., Borsche, Ber., 48, 682 (1915); 56, 2012, 2132 (1923); 59, 237 (1926)) or palladized strontium carbonate (see Cawley and Plant, *J. Chem. Soc.*, 1214 (1938); Attenburrow, et al., ibid., 571 (1945)).

In a similar fashion, compounds of Formulas CXXb-CXXd may be reduced to afford the corresponding tetrahydropyrones. Further elaboration of the compounds by methods described previously then yields the primary sulfonamides IVa or IVb, where Q is Q-88 or Q-89.

Compounds of Formulas CXXIVa-CXXIVe may be synthesized as shown in Equation 77 by condensation of 1,3-diketones of Formulas CXXVa-CXXVe with the appropriate imines of Formulas CXXVIa-CXXVId.

Equation 77

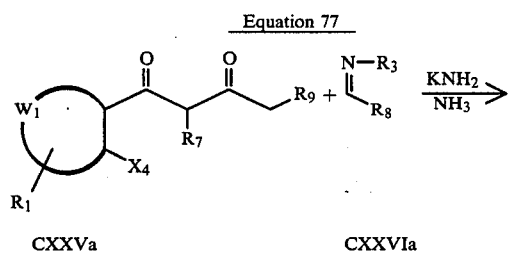 (a)

CXXVa + CXXVIa $\xrightarrow{\text{KNH}_2 / \text{NH}_3}$

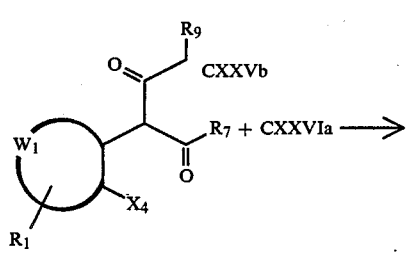

CXXIVa

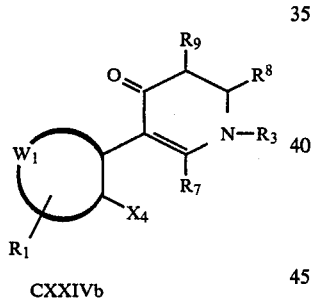 (b)

CXXVb + CXXVIa $\longrightarrow$

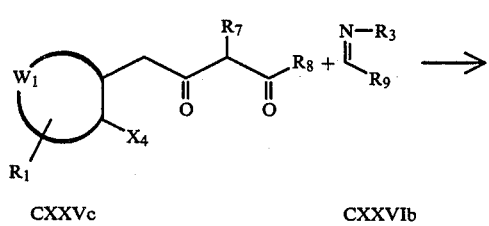

CXXIVb

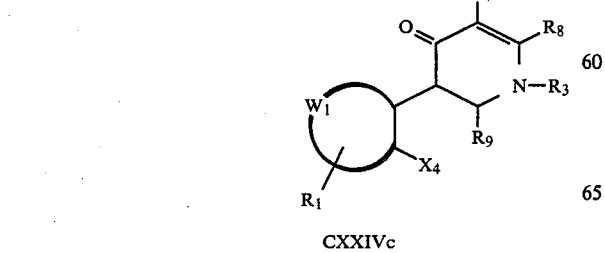 (c)

CXXVc + CXXVIb $\longrightarrow$

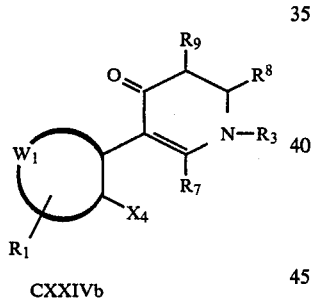

CXXIVc

-continued
Equation 77

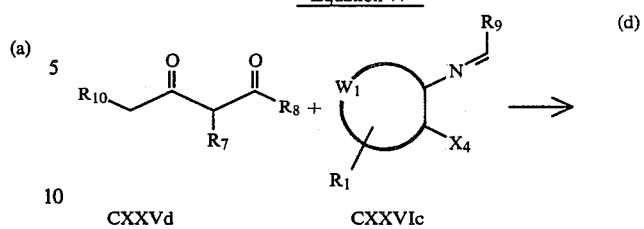 (d)

CXXVd + CXXVIc $\longrightarrow$

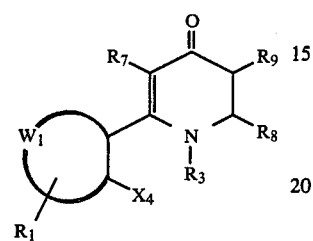

CXXIVd

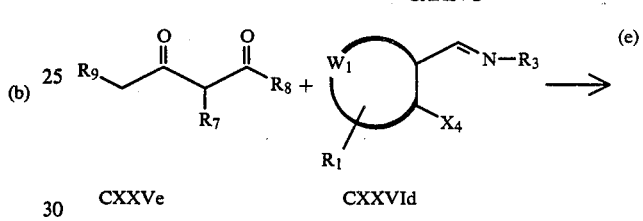 (e)

CXXVe + CXXVId $\longrightarrow$

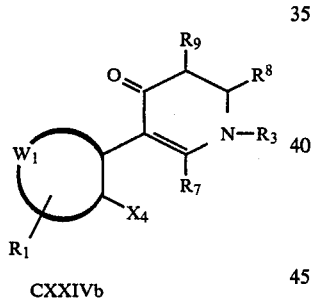

CXXIVe wherein
$W_1$, $R_1$, $R_3$, $R_7$, $R_8$, $R_9$ and $R_{10}$ are as previously defined, $X_4$ is Br, $NO_2$ or $SR_{12}$, and $R_{12}$ is $C_2$–$C_4$ alkyl or benzyl.

The reactions of Equation 77 are carried out by the procedure described by N. Sugiyama, M. Yamamoto and C. Kashima, *Bull. Chem. Soc. Japan*, 42, 1357 (1969).

Dihydropyridone CXXIVe above (when $R_8$ is H) may also be prepared in an analogous manner to Equation 75e as depicted in Equation 77f. The Lewis acid catalyzed Diels-Alder reaction of imines of Formula CXXVId with dienes CXXe results in the desired dihydropyridones.

Equation 78f

CXXVId $\xrightarrow[\text{ZnCl}_2]{\text{CXXe}}$ CXXIVe wherein
$W_1$, $R_1$, $R_3$, $R_7$, $R_9$ and $R_{10}$ are as previously defined, $R_8$ is H, $X_4$ is Br, $NO_2$, $SR_{12}$ or $SO_2NH$-t-Bu, and $R_{12}$ is $C_2$–$C_4$ alkyl or benzyl.

Dihydropyridones, such as those of Formulas CXXIVa–CXXIVe, may also be prepared by reduction of the appropriate pyridones of Formulas LXXXIa and LXXXIb with lithium aluminum hydride (E. Winterfeldt, *Ber. deutsch Chem. Ges.*, 97, 2463 (1964)), lithium triethoxyaluminum hydride (Y,. Tamura, et al., *Chem. and Ind.*, 168 (1972)), or catalytic hydrogenation (see J. Hebky and J. Kejha, CA, 50, 15532c).

Piperidones of Formulas CXXVIIa–CXXVIIc may be prepared in a straightforward manner via reduction of the appropriate dihydropyridones of Formulas CXXIVa–CXXIVe. Equation 78 depicts the reduction of compounds of Formula CXXIVa with lithium aluminum hydride to give piperidones of Formula CXXVIIa.

Equation 78

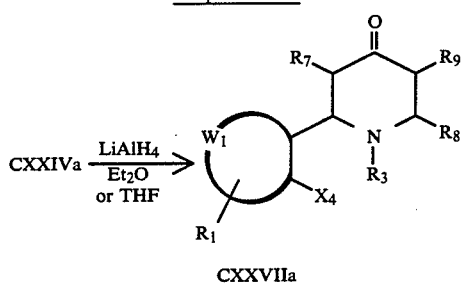

CXXVIIa wherein $W_1$, $R_1$, $R_3$, $R_7$, $R_8$ and $R_9$ are as previously defined, $X_4$ is Br, $NO_2$ or $SR_{12}$, and $R_{12}$ is $C_2$–$C_4$ alkyl or benzyl.

The 1,4-reduction of enaminones such as those of Formula CXXIVa may be achieved with lithium aluminum hydride and a variety of other reagents. For a review of these methods, see J. V. Greenhill, *Chem. Soc. Rev.*, 6, 277 (1977).

The tetrahydrothiopyrones of Formulas CXXVIIIa and CXXVIIIb may be prepared as shown in Equation 79 by a Dieckmann-type cyclization of the appropriate sulfides of Formulas CXXIXa and CXXIXb, followed by acid- or base-induced ester cleavage and decarboxylation.

Equation 79

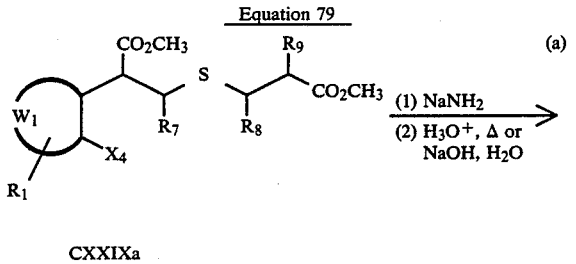

CXXIXa

CXXVIIIa

-continued
Equation 79

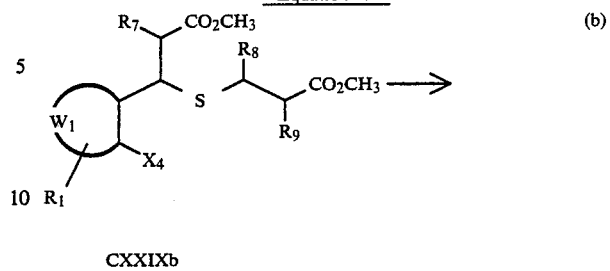

CXXIXb

CXXVIIIb wherein
$W_1$, $R_1$, $R_7$, $R_8$ and $R_9$ are as previously defined, and $X_4$ is Br, $NO_2$ or $SO_2NH$-t-Bu.

The reactions of Equations 79(a) and 79(b) may be effectively accomplished by the procedure of G. M. Bennett and L. V. D. Scorah, *J. Chem. Soc.*, 194 (1927).

The requisite sulfides of Formulas CXXIXa and CXXIXb may be readily synthesized by either of the methods shown in Equation 80. Thus, treatment of the mercaptide salts of Formula CXXX with either (a) α,β-unsaturated esters of Formula CXXXI, or (b) alkyl halides of Formula CXXXII affords the desired products of Formula CXXIXa.

Equation 80

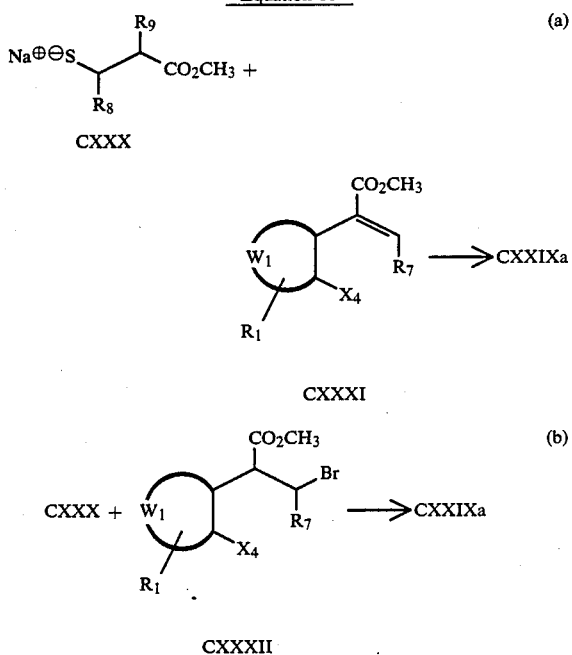

CXXXII wherein $W_1$, $R_1$, $R_7$, $R_8$ and $R_9$ are as previously defined, and $X_4$ is Br, $NO_2$ or $SO_2NH$-t-Bu.

The reaction of Equation 80 may be carried out according to the procedures discussed by Bruson, Org. Reactions, 5 (1949), pp. 95–97 and 129–130.

The dihydrothiopyrones of Formulas CXXXIIIa–CXXXIIId may be prepared from the appropriate tetrahydropyrones of Formulas CXXVIIa and CXXVIIb by oxidation with N-chlorosuccinimide (NCS) as shown in Equations 81(a) and 81(b).

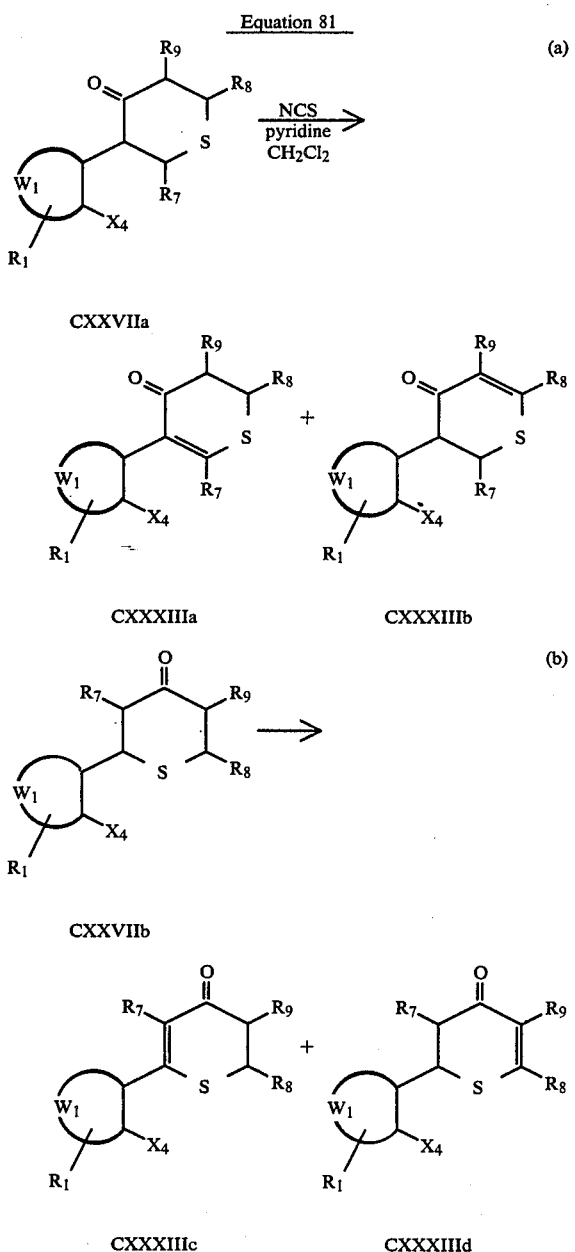

wherein
$W_1$, $R_1$, $R_7$, $R_8$ and $R_9$ are as previously defined, and $X_4$ is Br, $NO_2$ or $SO_2NH$-t-Bu.

The reaction of Equation 81 may be carried out according to the procedure of C. H. Chen, G. A. Reynolds and J. A. Van Allan, J. Org. Chem., 42 2777 (1977). It should be noted that the reaction shown in Equation 81, when applied to unsymmetrical tetrahydropyrones such as those of Formulas CXXVIIa and CXXVIIb, gives mixtures of isomers. These compounds may be separated by recrystallization from a suitable solvent such as diethyl ether, benzene, or ethyl acetate, or by column chromatography.

The synthesis of heterocyclic amines such as those represented by Formula III has been reviewed in "The Chemistry of Heterocyclic Compounds," a series published by Interscience Publ., New York and London. Aminopyrimidines are described by D. J. Brown in "The Pyrimidines", Vol. XVI of the series mentioned above which is herein incorporated by reference. The 2-amino-1,3,5-triazines of Formula III, where A is A-1 and Z is N, may be prepared according to methods described by E. M. Smolin and L. Rapaport in "s-Triazines and Derivatives," Vol. XIII.

Pyrimidines of Formula III, where A is A-1 and Y is an acetal or thioacetal substituent, may be prepared by methods taught in European Patent Application No. 84,224 (published July 27, 1983).

Pyrimidines of Formula III, where A is A-1 and Y is cyclopropyl or $OCF_2H$, may be synthesized according to the methods taught in South African Patent Application No. 837,434 and South African Publication No. 82,5045, respectively.

Compounds of Formula III, where A is A-2 or A-3, may be prepared by procedures disclosed in U.S. Pat. No. 4,339,267.

Compounds of Formula III, where A is A-4, may be prepared by methods taught in European Patent Application No. 46,677 (published Mar. 3, 1982).

Additional references dealing with the synthesis of bicyclic pyrimidines of Formula III, were A is A-2, A-3, or A-4 are Braker, Sheehan, Spitzmiller and Lott. J. Am. Chem. Soc., 69, 3072 (1947); Mitler and Bhattachanya, Quart. J. Indian Chem. Soc., 4, 152 (1927); Shrage and Hitchings, J. Org. Chem., 16, 1153 (1951); Caldwell, Kornfeld and Donnell, J. Am. Chem. Soc., 63, 2188 (1941); and Fissekis, Myles and Brown, J. Org. Chem., 29, 2670 (1964).

Compounds of Formula III, where A is A-5, may be prepared by methods taught in U.S. Pat. No. 4,421,550.

Compounds of Formula III, where A is A-6, may be prepared by methods taught in European Patent Application No. 94,260 (published Nov. 16, 1983).

Agriculturally suitable salts of compounds of Formula I are also useful herbicides and may be prepared in a number of ways known to the art. For example, metal salts may be made by treating compounds of Formula I with a solution of an alkali or alkaline earth metal salt having a sufficiently basic anion (e.g., hydroxide, alkoxide, carbonate or hydride). Quaternary amine salts may be made by similar techniques. Detailed examples of such techniques are given in U.S. Pat. No. 4,127,405.

The compounds of this invention and their preparation are further illustrated by the following examples.

EXAMPLE 1

N-(1,1-Dimethylethyl)-2-(3-oxo-1-cyclohexen-1-yl)-3-thiophenesulfonamide

A solution of 3-t-butylthiophenesulfonamide (5.0 g, 0.0228 mole) in 100 mL THF was cooled to −78° C. and stirred while n-butyllithium (1.37M, 35 mL, 0.046 mole) was added rapidly in a dropwise manner. The solution was warmed to 0° C. for 1 hour, stirred at room temperature for 1 hour, and was recooled to −10° C. and treated with a solution of 3-ethoxy-2-cyclohexenone in 10 mL THF. After being warmed to room temperature and stirred for 4 hours, the mixture was treated with 100 mL of ice-water followed by enough 1N HCl to bring to pH to ca 4. The mixture was then extracted with ether (3×200 mL) and the combined ether extracts were washed with brine and dried (MgSO₄). Concentration gave an oil that was crystallized with 20% ethyl acetate in hexane to yield 4.37 g white solid, m.p. 157°–158° C.

EXAMPLE 2

2-(3-Oxo-1-cyclohexen-1-yl)-3-thiophenesulfonamide

A solution of the product from Example 1 (6.0 g, 0.0192 mole) in trifluoroacetic acid (20 mL) was stirred at room temperature overnight, was stripped to an oil, and crystallized with ethyl acetate/ether to yield 2.87 g solid, m.p. 140°–147° C.

EXAMPLE 3

N-[(4,6-Dimethylpyrimidin-2-yl)aminocarbonyl]-2-(3-oxo-1-cyclohexen-1-yl)-3-thiophenesulfonamide A mixture of the product from Example 2 (0.30 g, 1.17 mole) and N-(4,6-dimethylpyrimidin-2-yl)phenyl carbamate (0.30 g, 1.23 mmole) in acetonitrile (30 mL) was treated with DBU (184 μl, 1.23 mmole) at room temperature overnight. The solution was poured into water and acidified with acetic acid. The solid which precipitated was collected on a glass funnel and washed with water, butylchloride, and ether to yield 0.15 g white solid; m.p. 190°–192° C.; NMR (CDCl₃)δ: 2.0–2.2 (m, 2H), 2.3–2.5 (m, with s at δ2.44, 8H), 2.7–2.8 (m, 2H), 6.25 (s, 1H), 6.77 (s, 1H), 7.36 and 7.66 (AB q, J=5.4 Hz, 2H); IR cm⁻¹ (nujol): 1730, 1700 (shoulder at 1685 and 1675), 1605, 1550, 1170, 1140.

By applying the procedures of Examples 1–3 and Equations 1–81, one skilled in the art may prepare the compounds shown in Tables 1–7.

General Formulas for Tables

General Formula 1
W₂ is O unless indicated by *, wherein W₂ is S
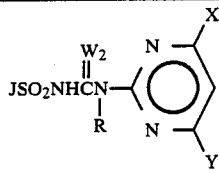

General Formula 2
W₂ is O unless indicated by *, wherein W₂ is S
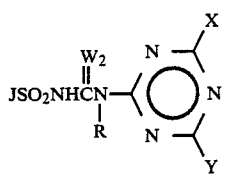

General Formula 3
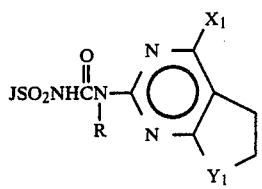

General Formula 4
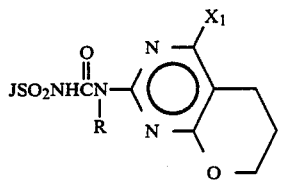

General Formula 5
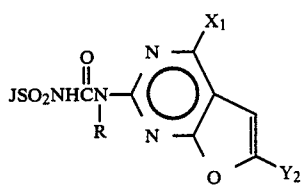

General Formula 6
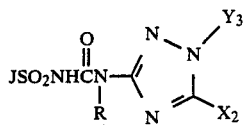

General Formula 7
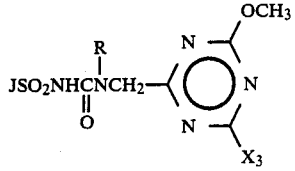

TABLE 1

General Formula 1

| J | W₁ | Q | R | R₁ | X | Y | m.p. (°C.) |
|---|---|---|---|---|---|---|---|
| J-1 | S | Q-1 (R₇ = H, R₈ = H) | H | H | CH₃ | CH₃ | |
| J-2 | S | Q-1 (R₇ = H, R₈ = H) | H | H | OCH₃ | CH₃ | |
| J-1 | S | Q-1 (R₇ = H, R₈ = H) | H | H | OCH₃ | OCH₃ | |
| J-2 | S | Q-1 (R₇ = H, R₈ = H) | CH₃ | H | OCH₃ | OCH₃ | |
| J-1 | S | Q-1 (R₇ = H, R₈ = H) | CH₃ | H | OCH₃ | CH₃ | |
| J-2 | S | Q-1 (R₇ = H, R₈ = H) | H | 5-CH₃ | OCH₃ | OCH₃ | |
| J-1 | S | Q-1 (R₇ = H, R₈ = H) | H | 5-CH₂F | OCH₃ | OCH₃ | |
| J-2 | S | Q-1 (R₇ = H, R₈ = H) | H | 5-CH₂CH₂Br | OCH₃ | OCH₃ | |
| J-3 | O | Q-1 (R₇ = H, R₈ = H) | H | 5-CH(CH₃)(CH₂Cl) | OCH₃ | OCH₃ | |
| J-1 | S | Q-1 (R₇ = H, R₈ = H) | H | 4-NH₂ | OCH₃ | OCH₃ | |
| J-2 | S | Q-1 (R₇ = H, R₈ = H) | H | 4-N(CH₃)₂ | OCH₃ | OCH₃ | |
| J-1 | NH | Q-1 (R₇ = H, R₈ = H) | H | 5-Cl | OCH₃ | OCH₃ | |
| J-2 | S | Q-1 (R₇ = H, R₈ = H) | H | 4-F | OCH₃ | OCH₃ | |
| J-1 | S | Q-1 (R₇ = H, R₈ = H) | H | 5-I | OCH₃ | OCH₃ | |
| J-2 | O | Q-1 (R₇ = H, R₈ = H) | H | 4-NO₂ | OCH₃ | OCH₃ | |
| J-1 | S | Q-1 (R₇ = H, R₈ = H) | H | 5-CF₃ | OCH₃ | OCH₃ | |
| J-2 | S | Q-1 (R₇ = H, R₈ = H) | H | H | OCH₃ | CH₂CH₃ | |
| J-1 | S | Q-1 (R₇ = H, R₈ = H) | H | H | OCH₃ | CH(CH₃)₂ | |
| J-2 | S | Q-1 (R₇ = H, R₈ = H) | H | H | OCH₃ | (CH₂)₃CH₃ | |
| J-1 | S | Q-1 (R₇ = H, R₈ = H) | H | H | OCH₃ | CH₂CH₃ | |
| J-2 | S | Q-1 (R₇ = H, R₈ = H) | H | H | OCH₃ | OCH(CH₃)₂ | |
| J-1 | S | Q-1 (R₇ = H, R₈ = H) | H | H | OCH₃ | O(CH₂)₃CH₃ | |
| J-2 | S | Q-1 (R₇ = H, R₈ = H) | H | H | OCF₂H | OCH₃ | |
| J-1 | S | Q-1 (R₇ = H, R₈ = H) | H | H | OCH₂CH₂F | OCH₃ | |
| J-2 | S | Q-1 (R₇ = H, R₈ = H) | H | H | OCH₂CHF₂ | OCH₃ | |
| J-1 | S | Q-1 (R₇ = H, R₈ = H) | H | H | OCH₂CF₃ | OCH₃ | |
| J-2 | S | Q-1 (R₇ = H, R₈ = H) | H | H | OCH(CH₃)(CH₂Cl) | OCH₃ | |
| J-1 | S | Q-1 (R₇ = H, R₈ = H) | H | H | O(CH₂)₃CH₂Br | OCH₃ | |
| J-2 | S | Q-1 (R₇ = H, R₈ = H) | H | H | CH₂F | OCH₃ | |
| J-1 | S | Q-1 (R₇ = H, R₈ = H) | H | H | CH₂Cl | OCH₃ | |
| J-2 | O | Q-1 (R₇ = H, R₈ = H) | H | H | CH₂Br | OCH₃ | |
| J-1 | S | Q-1 (R₇ = H, R₈ = H) | H | H | CF₃ | OCH₃ | |
| J-2 | S | Q-1 (R₇ = H, R₈ = H) | H | H | CH₂CH₂Br | OCH₃ | |
| J-1 | S | Q-1 (R₇ = H, R₈ = H) | H | H | CH(CH₃)(CH₂Cl) | OCH₃ | |
| J-2 | S | Q-1 (R₇ = H, R₈ = H) | H | H | (CH₂)₃CH₃ | OCH₃ | |
| J-1 | S | Q-1 (R₇ = H, R₈ = H) | H | H | SCH₃ | OCH₃ | |
| J-2 | S | Q-1 (R₇ = H, R₈ = H) | H | H | SCH₂CH₃ | OCH₃ | |
| J-1 | O | Q-1 (R₇ = H, R₈ = H) | H | H | SCH(CH₃)₂ | OCH₃ | |
| J-2 | S | Q-1 (R₇ = H, R₈ = H) | H | H | S(CH₂)₃CH₃ | OCH₃ | |
| J-1 | S | Q-1 (R₇ = H, R₈ = H) | H | H | SCHF₂ | OCH₃ | |
| J-2 | S | Q-1 (R₇ = H, R₈ = H) | H | H | SCH₂CH₂Br | OCH₃ | |
| J-1 | S | Q-1 (R₇ = H, R₈ = H) | H | H | SCH(CH₃)(CH₂Cl) | OCH₃ | |
| J-2 | S | Q-1 (R₇ = H, R₈ = H) | H | H | S(CH₂)₃CH₂F | OCH₃ | |
| J-1 | S | Q-1 (R₇ = H, R₈ = H) | H | H | Cl | OCH₃ | |
| J-2 | S | Q-1 (R₇ = H, R₈ = H) | H | H | Br | OCH₃ | |
| J-1 | S | Q-1 (R₇ = H, R₈ = H) | H | H | F | OCH₃ | |
| J-2 | S | Q-1 (R₇ = H, R₈ = H) | H | H | I | OCH₃ | |
| J-1 | S | Q-1 (R₇ = H, R₈ = H) | H | H | OCH₃ | CH₂OCH₃ | |
| J-2 | S | Q-1 (R₇ = H, R₈ = H) | H | H | OCH₃ | CH₂CH₂OCH(CH₃)₂ | |
| J-1 | O | Q-1 (R₇ = H, R₈ = H) | H | H | OCH₃ | CH(CH₃)(CH₂OCH₃) | |
| J-3 | S | Q-1 (R₇ = H, R₈ = H) | H | H | OCH₃ | (CH₂)₄CH₂OCH₂CH₃ | |

TABLE 1-continued

General Formula 1

| J | W₁ | Q | R | R₁ | X | Y | m.p. (°C.) |
|---|---|---|---|---|---|---|---|
| J-1 | S | Q-1 (R₇ = H, R₈ = H) | H | H | OCH₂O(CH₂)₃CH₃ | OCH₃ | |
| J-2 | S | Q-1 (R₇ = H, R₈ = H) | H | H | OCH₂CH₂OCH(CH₃)₂ | OCH₃ | |
| J-1 | S | Q-1 (R₇ = H, R₈ = H) | H | H | OCH(CH₃)(CH₂OCH₃) | OCH₃ | |
| J-2 | S | Q-1 (R₇ = H, R₈ = H) | H | H | O(CH₂)₄CH₂OCH₂CH₃ | OCH₃ | |
| J-1 | S | Q-1 (R₇ = H, R₈ = H) | H | H | OCH₃ | NH₂ | |
| J-2 | S | Q-1 (R₇ = H, R₈ = H) | H | H | OCH₃ | NHCH₃ | |
| J-1 | S | Q-1 (R₇ = H, R₈ = H) | H | H | OCH₃ | NHCH₂CH₃ | |
| J-2 | O | Q-1 (R₇ = H, R₈ = H) | H | H | OCH₃ | NHCH(CH₃)₂ | |
| J-1 | S | Q-1 (R₇ = H, R₈ = H) | H | H | OCH₃ | N(CH₃)₂ | |
| J-2 | S | Q-1 (R₇ = H, R₈ = H) | H | H | OCH₃ | N(CH₃)(CH₂CH₃) | |
| J-1 | S | Q-1 (R₇ = H, R₈ = H) | H | H | OCH₃ | N(CH₃)(CH(CH₃)₂) | |
| J-3 | S | Q-1 (R₇ = H, R₈ = H) | H | H | OCH₃ | (CH₂)₄CH₂OCH₂CH₃ | |
| J-2 | S | Q-1 (R₇ = H, R₈ = H) | H | H | H | OCH₃ | |
| J-1 | O | Q-1 (R₇ = H, R₈ = H) | H | H | OCH₃ | OCH₂CH=CH₂ | |
| J-1 | S | Q-1 (R₇ = H, R₈ = H) | H | H | OCH₃ | OCH₂C(CH₃)=CH₂ | |
| J-2 | S | Q-1 (R₇ = H, R₈ = H) | H | H | OCH₃ | OCH₂C≡CH | |
| J-1 | S | Q-1 (R₇ = H, R₈ = H) | H | H | OCH₃ | OCH₂C≡CCH₃ | |
| J-2 | S | Q-1 (R₇ = H, R₈ = H) | H | H | OCH₃ | CH₂S(CH₂)₃CH₃ | |
| J-1 | O | Q-1 (R₇ = H, R₈ = H) | H | H | OCH₃ | CH₂CH₂SCH(CH₃)₂ | |
| J-3 | S | Q-1 (R₇ = H, R₈ = H) | H | H | OCH₃ | CH(CH₃)(CH₂SCH₃) | |
| J-1 | S | Q-1 (R₇ = H, R₈ = H) | H | H | OCH₃ | (CH₂)₄CH₂SCH₂CH₃ | |
| J-2 | S | Q-1 (R₇ = H, R₈ = H) | H | H | OCH₃ | cyclopropyl | |
| J-1 | S | Q-1 (R₇ = H, R₈ = H) | H | H | OCH₃ | 2-methylcyclopropyl | |
| J-2 | S | Q-1 (R₇ = H, R₈ = H) | H | H | OCH₃ | cyclopentyl | |
| J-1 | S | Q-1 (R₇ = H, R₈ = H) | H | H | OCH₃ | C≡CH | |
| J-1 | S | Q-1 (R₇ = H, R₈ = H) | H | H | OCH₃ | C≡CCH₃ | |
| J-2 | S | Q-1 (R₇ = H, R₈ = H) | H | H | OCH₃ | —CHO | |
| J-1 | O | Q-1 (R₇ = H, R₈ = H) | H | H | OCH₃ | —COCH₃ | |
| J-1 | S | Q-1 (R₇ = H, R₈ = H) | H | H | OCH₃ | —CH(OCH₃)₂ | |
| J-2 | S | Q-1 (R₇ = H, R₈ = H) | H | H | OCH₃ | —CH(SCH₃)(OCH₂CH₃) | |
| J-1 | O | Q-1 (R₇ = H, R₈ = H) | H | H | OCH₃ | —CH(SCH₃)(SCH₃)₂ | |
| J-1 | S | Q-1 (R₇ = H, R₈ = H) | H | H | OCH₃ | —C(CH₃)(SCH₃)₂ | |
| J-3 | S | Q-1 (R₇ = H, R₈ = H) | H | H | OCH₃ | —CH(SCH₂CH₃)₂ | |
| J-1 | S | Q-1 (R₇ = H, R₈ = H) | H | H | OCH₃ | 1,3-dioxolan-2-yl | |
| J-1 | S | Q-1 (R₇ = H, R₈ = H) | H | H | OCH₃ | 2-methyl-1,3-oxa-thiolan-2-yl | |
| J-2 | S | Q-1 (R₇ = H, R₈ = H) | H | H | OCH₃ | 1,3-oxathian-2-yl | |
| J-1 | S | Q-1 (R₇ = H, R₈ = H) | H | H | OCH₃ | 2-methyl-1,3-dithian-2-yl | |
| J-2 | S | Q-1 (R₇ = H, R₈ = H) | H | H | OCH₃ | 4-methyl-1,3-dioxolan-2-yl | |
| J-1 | S | Q-1 (R₇ = H, R₈ = H) | H | H | OCH₃ | 4-methyl-1,3-oxathiolan-2-yl | |
| J-2 | S | Q-1 (R₇ = H, R₈ = H) | H | H | OCH₃ | 2,4-dimethyl-1,3-dithiolan-2-yl | |
| J-1 | O | Q-1 (R₇ = H, R₈ = H) | H | H | OCH₃ | N(OCH₃)(CH₃)₂ | |
| J-2 | S | Q-1 (R₇ = H, R₈ = CH₃) | H | H | OCH₃ | OCH₃ | |
| J-1 | S | Q-1 (R₇ = H, R₈ = CH₃) | H | H | CH₃ | CH₃ | |
| J-2 | S | Q-1 (R₇ = H, R₈ = CH₃) | H | H | CH₃ | OCH₃ | |
| J-1 | S | Q-1 (R₇ = H, R₈ = CH₂CH₃) | H | H | OCH₃ | OCH₃ | |
| J-3 | S | Q-1 (R₇ = H, R₈ = CH(CH₃)₂) | H | H | OCH₃ | OCH₃ | |
| J-2 | S | Q-1 (R₇ = H, R₈ = (CH₂)₃CH₃) | H | H | OCH₃ | OCH₃ | |

TABLE 1-continued

| J | W₁ | Q | | R | R₁ | X | Y | m.p. (°C.) |
|---|---|---|---|---|---|---|---|---|
| | | | | General Formula 1 | | | | |
| J-1 | S | Q-1 | (R₇ = CH₃, R₈ = CH₃) | H | H | OCH₃ | OCH₃ | |
| J-1 | S | Q-2 | (R₇ = H, R₈ = H) | H | H | OCH₃ | OCH₃ | |
| J-1 | S | Q-2 | (R₇ = H, R₈ = H) | CH₃ | H | OCH₃ | OCH₃ | |
| J-1 | O | Q-2 | (R₇ = H, R₈ = CH₃) | H | 5-CH₃ | OCH₃ | OCH₃ | |
| J-2 | S | Q-2 | (R₇ = H, R₈ = CH₃) | H | H | OCH₃ | OCH₃ | |
| J-1 | S | Q-3 | (R₇ = H, R₈ = H) | H | H | OCF₂H | CH₃ | |
| J-1 | S | Q-3 | (R₇ = C₂H₅, R₈ = H) | H | H | OCH₃ | CH₃ | |
| J-2 | S | Q-3 | (R₇ = CH₃, R₈ = H) | H | 5-Cl | OCH₃ | OCH₃ | |
| J-1 | S | Q-4 | (R₇ = H, R₈ = H, R₃ = CH₃) | H | H | CH₃ | OCH₃ | |
| J-3 | S | Q-4 | (R₇ = H, R₈ = H, R₃ = C₂H₅) | H | H | CH₃ | OCH₃ | |
| J-1 | S | Q-4 | (R₇ = H, R₈ = H, R₃ = i-C₃H₇) | H | 5-CH₃ | OCH₃ | OCH₃ | |
| J-1 | S | Q-5 | (R₇ = H, R₈ = H, R₃ = H) | H | H | Cl | OCH₃ | |
| J-1 | S | Q-5 | (R₇ = H, R₈ = H, R₃ = CH₃) | CH₃ | H | CH₃ | OCH₃ | |
| J-2 | O | Q-6 | (R₇ = CH₃, R₈ = H, R₃ = CH₃) | H | H | CH₃ | OCH₃ | |
| J-1 | S | Q-6 | (R₇ = C₂H₅, R₈ = H, R₃ = C₂H₅) | H | H | CH₃ | OCH₃ | |
| J-2 | S | Q-7 | (R₇ = H, R₈ = H, R₉ = H) | H | H | OCH₃ | OCH₃ | |
| J-1 | NCH₃ | Q-7 | (R₇ = i-C₃H₇, R₈ = H, R₉ = CH₃) | H | H | OCH₃ | OCH₃ | |
| J-2 | S | Q-7 | (R₇ = H, R₈ = C₂H₅, R₉ = H) | H | H | OCH₃ | OCF₂H | |
| J-3 | S | Q-8 | (R₇ = H, R₈ = H, R₂ = H) | H | H | OCH₃ | OCH₃ | |
| J-1 | S | Q-8 | (R₇ = CH₃, R₈ = H, R₂ = OCH₃) | H | H | OCH₃ | OCH₃ | |
| J-2 | S | Q-8 | (R₇ = H, R₈ = H, R₂ = OCH(CH₃)CH₂CH₃) | H | 5-CH₃ | OCH₃ | OCH₃ | |
| J-1 | S | Q-9 | (R₇ = H, R₈ = H, R₂ = H) | H | H | OCH₃ | OCH₃ | |
| J-2 | O | Q-9 | (R₇ = CH₃, R₈ = H, R₂ = CH₃) | H | H | OCH₃ | CH₃ | |
| J-1 | S | Q-9 | (R₇ = H, R₈ = H, R₂ = Cl) | H | 5-Cl | OCH₃ | CH₃ | |
| J-2 | S | Q-10 | (R₇ = H, R₈ = H) | CH₃ | H | OCH₃ | OCH₃ | |
| J-1 | S | Q-10 | (R₇ = CH₃, R₈ = H) | H | 5-CH₃ | OCH₃ | OCH₃ | |
| J-2 | S | Q-10 | (R₇ = H, R₈ = CH₃) | H | H | OCH₃ | CH₃ | |
| J-1 | S | Q-11 | (R₇ = n-C₄H₉, R₈ = H) | H | 5-Cl | OCF₂H | OCH₃ | |
| J-1 | S | Q-11 | (R₇ = CH₃, R₈ = CH₃) | H | H | OCH₃ | OCH₃ | |
| J-2 | S | Q-11 | (R₇ = H, R₈ = H) | H | 5-CH₃ | CH₃ | OCH₃ | |
| J-1 | O | Q-12 | (R₇ = CH₃, R₈ = H) | H | H | CH₃ | OCH₃ | |
| J-2 | S | Q-12 | (R₇ = H, R₈ = C₂H₅) | CH₃ | H | CH₃ | CH₃ | |
| J-1 | S | Q-13 | (R₇ = H, R₈ = H, R₃ = H) | H | H | OCH₃ | CH₃ | |
| J-2 | S | Q-13 | (R₇ = CH₃, R₈ = H, R₃ = CH₃) | H | 5-CH₃ | OCH₃ | OCH₃ | |
| J-1 | S | Q-13 | (R₇ = H, R₈ = CH₃, R₃ = CH₃) | H | H | OCH₃ | OCH₃ | |
| J-2 | S | Q-14 | (R₇ = CH₃, R₈ = H, R₃ = C₂H₅) | H | H | OCH₃ | OCH₃ | |
| J-1 | S | Q-14 | (R₇ = H, R₈ = CH₃, R₃ = CH₃) | H | 5-CH₃ | OCH₃ | OCH₃ | |
| J-2 | S | Q-15 | (R₇ = CH₃, R₈ = H, R₃ = H) | H | H | OCH₃ | OCH₃ | |
| J-1 | S | Q-15 | (R₇ = C₂H₅, R₈ = CH₃, R₃ = CH₃) | H | H | OCH₃ | OCH₃ | |
| J-2 | O | Q-15 | (R₇ = CH₃, R₈ = H, R₉ = H) | H | 5-Cl | OCH₃ | OCF₂H | |
| J-1 | S | Q-16 | (R₇ = H, R₈ = CH₃, R₉ = H) | H | H | OCH₃ | OCH₃ | |
| J-2 | S | Q-16 | (R₇ = CH₃, R₈ = CH₃, R₉ = H) | CH₃ | 5-CH₃ | OCH₃ | OCH₃ | |
| J-1 | S | Q-17 | (R₇ = H, R₈ = H, R₂ = CH₃) | H | H | OCH₃ | OCH₃ | |
| J-3 | S | Q-17 | (R₇ = CH₃, R₈ = H, R₂ = C₂H₅) | H | H | OCH₃ | CH₃ | |
| J-1 | O | Q-17 | (R₇ = H, R₈ = H, R₂ = C₂H₅) | H | 5-Cl | OCF₂H | CH₃ | |
| J-2 | S | Q-18 | (R₇ = H, R₈ = H, R₂ = OC₂H₅) | H | H | CH₃ | CH₃ | |
| J-3 | S | Q-18 | (R₇ = H, R₈ = H, R₂ = H) | H | H | CH₃ | OCH₃ | |
| J-1 | S | Q-18 | (R₇ = H, R₈ = OC₂H₅, R₂ = H) | H | H | CH₃ | OCH₃ | |

TABLE 1-continued

| | | | General Formula 1 | | | | |
|---|---|---|---|---|---|---|---|
| J | W$_1$ | Q | R | R$_1$ | X | Y | m.p. (°C.) |
| J-2 | S | Q-18 (R$_7$ = CH$_3$, R$_9$ = OCH(CH$_3$)$_2$, R$_2$ = CH$_3$) | H | 5-CH$_3$ | OCH$_3$ | OCH$_3$ | |
| J-1 | O | Q-19 (R$_7$ = H, R$_8$ = H) | H | H | OCH$_3$ | OCH$_3$ | |
| J-2 | S | Q-19 (R$_7$ = CH$_3$, R$_8$ = H) | H | H | Cl | OCH$_3$ | |
| J-1 | S | Q-19 (R$_7$ = H, R$_8$ = CH$_3$) | H | H | CH$_3$ | OCH$_3$ | |
| J-1 | S | Q-20 (R$_7$ = CH$_3$, R$_8$ = H) | CH$_3$ | H | CH$_3$ | OCH$_3$ | |
| J-2 | S | Q-20 (R$_7$ = H, R$_8$ = CH$_3$) | H | H | OCH$_3$ | OCH$_3$ | |
| J-1 | S | Q-20 (R$_7$ = H, R$_8$ = H) | H | H | OCH$_3$ | OCH$_3$ | |
| J-1 | S | Q-21 (R$_7$ = CH$_3$, R$_8$ = H) | H | H | OCH$_3$ | OCH$_3$ | |
| J-1 | S | Q-21 (R$_7$ = H, R$_8$ = CH$_3$) | H | 5-CH$_3$ | OCH$_3$ | OCH$_3$ | |
| J-3 | S | Q-22 (R$_7$ = H, R$_8$ = H, R$_3$ = H) | H | H | OCH$_3$ | OCH$_3$ | |
| J-1 | S | Q-22 (R$_7$ = CH$_3$, R$_8$ = CH$_3$, R$_3$ = CH$_3$) | H | H | OCH$_3$ | OCF$_2$H | |
| J-1 | O | Q-22 (R$_7$ = H, R$_8$ = CH$_3$, R$_3$ = C$_2$H$_5$) | H | 5-Cl | OCH$_3$ | OCH$_3$ | |
| J-2 | S | Q-23 (R$_7$ = H, R$_8$ = H, R$_3$ = H) | H | H | OCH$_3$ | OCH$_3$ | |
| J-1 | S | Q-23 (R$_7$ = H, R$_8$ = CH$_3$, R$_3$ = CH$_3$) | CH$_3$ | 5-CH$_3$ | OCH$_3$ | OCH$_3$ | |
| J-2 | S | Q-23 (R$_7$ = CH$_3$, R$_8$ = H, R$_3$ = n-C$_4$H$_9$) | H | H | OCH$_3$ | OCH$_3$ | |
| J-1 | S | Q-24 (R$_7$ = H, R$_8$ = H, R$_3$ = CH$_3$) | H | 5-Cl | OCH$_3$ | CH$_3$ | |
| J-2 | S | Q-24 (R$_7$ = CH$_3$, R$_8$ = CH$_3$, R$_3$ = C$_2$H$_5$) | H | H | CH$_3$ | CH$_3$ | |
| J-1 | S | Q-24 (R$_7$ = CH$_3$, R$_8$ = CH$_3$, R$_3$ = i-C$_3$H$_7$) | H | H | CH$_3$ | OCH$_3$ | |
| J-3 | S | Q-25 (R$_7$ = H, R$_8$ = H, R$_9$ = H) | H | 5-CH$_3$ | OCF$_2$H | OCF$_2$H | |
| J-1 | S | Q-25 (R$_7$ = CH$_3$, R$_8$ = H, R$_9$ = H) | H | H | OCH$_3$ | OCH$_3$ | |
| J-1 | S | Q-25 (R$_7$ = H, R$_8$ = H, R$_9$ = C$_2$H$_5$) | H | H | CH$_3$ | CH$_3$ | |
| J-2 | S | Q-26 (R$_7$ = H, R$_8$ = H) | H | H | CH$_3$ | CH$_3$ | |
| J-1 | O | Q-26 (R$_7$ = CH$_3$, R$_8$ = CH$_3$) | H | H | OCH$_3$ | OCH$_3$ | |
| J-2 | S | Q-27 (R$_7$ = H, R$_8$ = H) | H | H | Cl | OCH$_3$ | |
| J-1 | S | Q-27 (R$_7$ = CH$_3$, R$_8$ = H) | CH$_3$ | H | CH$_3$ | OCH$_3$ | |
| J-2 | S | Q-27 (R$_7$ = H, R$_8$ = CH$_3$) | H | H | CH$_3$ | CH$_3$ | |
| J-1 | S | Q-28 (R$_7$ = H, R$_8$ = H) | H | H | OCH$_3$ | OCH$_3$ | |
| J-2 | S | Q-28 (R$_7$ = CH$_3$, R$_8$ = CH$_3$) | H | 5-CH$_3$ | OCH$_3$ | OCH$_3$ | |
| J-1 | S | Q-29 (R$_7$ = CH$_3$, R$_8$ = H) | H | 5-Cl | OCH$_3$ | OCF$_2$H | |
| J-1 | S | Q-29 (R$_7$ = H, R$_8$ = CH$_3$) | H | H | OCH$_3$ | OCH$_3$ | |
| J-2 | O | Q-30 (R$_7$ = H, R$_8$ = H) | H | 5-CH$_3$ | OCH$_3$ | OCH$_3$ | |
| J-1 | S | Q-30 (R$_7$ = CH$_3$, R$_8$ = H, R$_3$ = H) | CH$_3$ | H | OCH$_3$ | OCH$_3$ | |
| J-2 | S | Q-30 (R$_7$ = C$_2$H$_5$, R$_8$ = H, R$_3$ = C$_2$H$_5$) | H | H | OCH$_3$ | CH$_3$ | |
| J-1 | S | Q-31 (R$_7$ = H, R$_8$ = H) | H | 5-CH$_3$ | OCH$_3$ | OCH$_3$ | |
| J-2 | S | Q-31 (R$_7$ = i-C$_3$H$_7$, R$_8$ = H) | H | H | CH$_3$ | CH$_3$ | |
| J-1 | S | Q-31 (R$_7$ = H, R$_8$ = n-C$_4$H$_9$) | H | 5-Cl | CH$_3$ | CH$_3$ | |
| J-2 | S | Q-32 (R$_7$ = CH$_3$, R$_8$ = H, R$_3$ = H) | H | H | CH$_3$ | OCH$_3$ | |
| J-1 | S | Q-32 (R$_7$ = H, R$_8$ = CH$_3$, R$_3$ = C$_2$H$_5$) | H | 5-CH$_3$ | OCH$_3$ | OCH$_3$ | |
| J-1 | O | Q-32 (R$_7$ = H, R$_8$ = CH$_3$, R$_3$ = CH$_3$) | H | H | OCH$_3$ | OCH$_3$ | |
| J-2 | S | Q-33 (R$_7$ = CH$_3$, R$_8$ = H, R$_3$ = i-C$_3$H$_7$) | H | H | OCH$_3$ | OCH$_3$ | |
| J-1 | S | Q-33 (R$_7$ = C$_2$H$_5$, R$_8$ = H, R$_3$ = n-C$_4$H$_9$) | CH$_3$ | 5-Cl | Cl | OCH$_3$ | |
| J-2 | S | Q-33 (R$_7$ = CH$_3$, R$_8$ = CH$_3$, R$_3$ = H) | H | H | CH$_3$ | CH$_3$ | |
| J-1 | S | Q-34 (R$_7$ = C$_2$H$_5$, R$_8$ = H, R$_3$ = H) | H | H | CH$_3$ | CH$_3$ | |
| J-1 | S | Q-34 (R$_7$ = i-C$_3$H$_7$, R$_8$ = H, R$_3$ = CH$_3$) | CH$_3$ | H | CH$_3$ | OCH$_3$ | |
| J-2 | S | Q-34 (R$_7$ = H, R$_8$ = n-C$_4$H$_9$, R$_3$ = H) | H | 5-CH$_3$ | OCH$_3$ | OCH$_3$ | |
| J-2 | S | Q-35 (R$_7$ = H, R$_8$ = H, R$_9$ = H) | H | H | OCH$_3$ | OCH$_3$ | |
| J-1 | S | Q-35 (R$_7$ = CH$_3$, R$_8$ = H, R$_9$ = H) | H | H | OCH$_3$ | OCH$_3$ | |

TABLE 1-continued

General Formula 1

| J | W₁ | Q | R | R₁ | X | Y | m.p. (°C.) |
|---|---|---|---|---|---|---|---|
| J-2 | S | Q-35 (R₇ = CH₃, R₈ = CH₃, R₉ = CH₃) | H | 5-CH₃ | OCH₃ | OCH₃ | |
| J-1 | O | Q-36 (R₇ = H, R₈ = H, R₂ = H) | H | H | OCH₃ | OCH₃ | |
| J-2 | S | Q-36 (R₇ = CH₃, R₈ = H, R₂ = CH₃) | H | H | OCH₃ | OCF₂H | |
| J-2 | S | Q-36 (R₇ = H, R₈ = H, R₂ = C₂H₅) | H | 5-Cl | OCH₃ | OCH₃ | |
| J-1 | S | Q-37 (R₇ = H, R₈ = H, R₂ = H) | H | H | OCH₃ | CH₃ | 196-199 |
| J-2 | S | Q-37 (R₇ = H, R₈ = H, R₂ = H) | H | H | CH₃ | CH₃ | 202-204 |
| J-2 | S | Q-37 (R₇ = H, R₈ = H, R₂ = H) | H | H | OCH₃ | OCH₃ | 160-163 |
| J-2 | S | Q-37 (R₇ = H, R₈ = H, R₂ = H) | H | H | OCH₃ | Cl | 208-210 |
| J-3 | S | Q-37 (R₇ = H, R₈ = H, R₂ = H) | CH₃ | H | OCH₃ | OCH₃ | 144-147 |
| J-2 | S | Q-37 (R₇ = H, R₈ = H, R₂ = i-C₃H₇) | H | 5-CH₃ | OCH₃ | OCH₃ | |
| J-1 | S | Q-37 (R₇ = H, R₈ = H, R₂ = n-C₄H₉) | H | H | OCH₃ | OCH₃ | |
| J-2 | S | Q-37 (R₇ = H, R₈ = H, R₂ = OCF₂H) | H | H | OCH₃ | OCH₃ | |
| J-1 | S | Q-38 (R₇ = CH₃, R₈ = H, R₂ = OCH₂CH₂F) | H | H | OCF₂H | OCH₃ | |
| J-2 | S | Q-38 (R₇ = H, R₈ = H, R₂ = Cl) | H | 5-Cl | OCH₃ | OCH₃ | |
| J-1 | S | Q-39 (R₇ = H, R₈ = H, R₉ = H) | H | H | CH₃ | CH₃ | |
| J-2 | O | Q-39 (R₇ = C₂H₅, R₈ = H, R₉ = H) | H | H | CH₃ | CH₃ | |
| J-2 | S | Q-39 (R₇ = H, R₈ = H, R₉ = CH₃) | H | H | OCH₃ | OCH₃ | |
| J-3 | NH | Q-40 (R₇ = H, R₈ = H) | H | H | OCH₃ | OCH₃ | |
| J-1 | S | Q-40 (R₇ = CH₃, R₈ = CH₃) | H | 5-CH₃ | Cl | OCH₃ | |
| J-2 | S | Q-41 (R₇ = H, R₈ = CH₃) | H | H | CH₃ | CH₃ | |
| J-1 | S | Q-41 (R₇ = CH₃, R₈ = CH₃) | CH₃ | H | CH₃ | CH₃ | |
| J-2 | S | Q-41 (R₇ = H, R₈ = C₂H₅) | H | H | OCH₃ | OCH₃ | |
| J-1 | S | Q-42 (R₇ = H, R₈ = H) | H | 5-Cl | OCH₃ | OCH₃ | |
| J-2 | S | Q-42 (R₇ = CH₃, R₈ = CH₃) | H | H | OCH₃ | OCH₃ | |
| J-2 | O | Q-42 (R₇ = C₂H₅, R₈ = C₂H₅) | H | H | OCH₃ | OCH₃ | |
| J-2 | S | Q-43 (R₇ = H, R₈ = H, R₃ = H) | H | 5-CH₃ | OCH₃ | OCH₃ | |
| J-1 | S | Q-43 (R₇ = CH₃, R₈ = H, R₃ = CH₃) | H | H | OCH₃ | OCF₂H | |
| J-2 | S | Q-43 (R₇ = CH₃, R₈ = H, R₃ = CH₃) | H | H | OCH₃ | OCH₃ | |
| J-2 | S | Q-44 (R₇ = H, R₈ = H, R₃ = H) | H | H | OCH₃ | OCH₃ | |
| J-1 | O | Q-44 (R₇ = CH₃, R₈ = H, R₃ = C₂H₅) | CH₃ | 5-CH₃ | OCH₃ | CH₃ | |
| J-2 | S | Q-45 (R₇ = CH₃, R₈ = H, R₃ = H) | H | H | OCH₃ | CH₃ | |
| J-1 | S | Q-45 (R₇ = H, R₈ = CH₃, R₃ = CH₃) | H | 5-Cl | OCH₃ | CH₃ | |
| J-2 | S | Q-46 (R₇ = H, R₈ = H, R₉ = H) | H | H | OCF₂H | CH₃ | |
| J-1 | O | Q-46 (R₇ = CH₃, R₈ = CH₃, R₉ = H) | H | 5-CH₃ | OCH₃ | CH₃ | |
| J-2 | S | Q-47 (R₇ = H, R₈ = H, R₂ = H) | H | H | CH₃ | CH₃ | |
| J-2 | S | Q-47 (R₇ = CH₃, R₈ = H, R₂ = CH₃) | H | 5-Cl | CH₃ | CH₃ | |
| J-3 | S | Q-47 (R₇ = H, R₈ = H, R₂ = C₂H₅) | H | H | Cl | CH₃ | |
| J-2 | S | Q-48 (R₇ = H, R₈ = H, R₂ = H) | CH₃ | 5-CH₃ | CH₃ | CH₃ | |
| J-1 | O | Q-48 (R₇ = H, R₈ = C₂H₅, R₂ = C₂H₅) | H | H | OCH₃ | OCH₃ | |
| J-2 | S | Q-49 (R₇ = CH₃, R₈ = H, R₉ = H) | H | H | OCH₃ | OCH₃ | |
| J-1 | S | Q-49 (R₇ = CH₃, R₈ = CH₃, R₉ = H) | H | 5-CH₃ | OCH₃ | OCH₃ | |
| J-2 | S | Q-49 (R₇ = CH₃, R₈ = H, R₂ = H) | H | H | OCH₃ | OCH₃ | |
| J-1 | O | Q-50 (R₇ = CH₃, R₈ = H, R₂ = H) | H | H | OCH₃ | OCH₃ | |
| J-2 | S | Q-50 (R₇ = CH₃, R₈ = CH₃, R₂ = H) | H | H | OCH₃ | OCF₂H | |
| J-1 | S | Q-50 (R₇ = CH₃, R₈ = CH₃, R₂ = CH₃) | H | 5-Cl | OCH₃ | OCH₃ | |

TABLE 1-continued

General Formula 1

| J | W₁ | Q | R | R₁ | X | Y | m.p. (°C.) |
|---|---|---|---|---|---|---|---|
| J-2 | S | Q-51 (R₇ = H, R₈ = H, R₉ = H) | H | H | OCH₃ | OCH₃ | |
| J-3 | S | Q-51 (R₇ = H, R₈ = H, R₉ = CH₃) | CH₃ | H | OCH₃ | OCH₃ | |
| J-1 | S | Q-51 (R₇ = H, R₈ = H, R₉ = s-C₄H₉) | H | 5-CH₃ | OCH₃ | OCH₃ | |
| J-1 | S | Q-52 (R₇ = CH₃, R₈ = H, R₉ = H) | H | H | OCH₃ | OCH₃ | |
| J-2 | O | Q-52 (R₇ = H, R₈ = H, R₉ = CH₃) | H | H | OCF₂H | CH₃ | |
| J-1 | S | Q-52 (R₇ = H, R₈ = H, R₉ = H) | H | 5-Cl | OCH₃ | CH₃ | |
| J-2 | S | Q-53 (R₇ = H, R₈ = CH₃, R₉ = CH₃) | H | H | CH₃ | OCH₃ | |
| J-1 | S | Q-53 (R₇ = H, R₈ = H, R₉ = CH₃) | H | 5-CH₃ | CH₃ | OCH₃ | |
| J-1 | S | Q-54 (R₇ = H, R₈ = H, R₉ = H) | H | H | OCH₃ | OCH₃ | |
| J-2 | S | Q-54 (R₇ = CH₃, R₈ = H, R₉ = H) | H | H | Cl | OCH₃ | |
| J-3 | S | Q-55 (R₇ = H, R₈ = H, R₉ = i-C₃H₇) | H | H | CH₃ | OCH₃ | |
| J-1 | S | Q-55 (R₇ = H, R₈ = H, R₃ = H) | H | H | CH₃ | OCH₃ | |
| J-2 | S | Q-55 (R₇ = H, R₈ = H, R₉ = CH₃, R₃ = CH₃) | H | H | OCH₃ | OCH₃ | |
| J-1 | S | Q-55 (R₇ = H, R₈ = H, R₉ = s-C₄H₉, R₃ = H) | H | H | OCH₃ | OCH₃ | |
| J-2 | O | Q-56 (R₇ = H, R₈ = H, R₃ = C₂H₅) | H | H | OCH₃ | OCH₃ | |
| J-1 | S | Q-56 (R₇ = CH₃, R₈ = H, R₉ = H, R₃ = H) | H | 5-CH₃ | OCH₃ | OCH₃ | |
| J-2 | S | Q-56 (R₇ = H, R₈ = H, R₉ = CH₃, R₃ = CH₃) | H | H | OCH₃ | OCH₃ | |
| J-1 | S | Q-57 (R₇ = H, R₈ = H, R₉ = H, R₃ = i-C₃H₇) | H | H | OCH₃ | OCF₂H | |
| J-2 | S | Q-57 (R₇ = H, R₈ = CH₃, R₉ = CH₃, R₃ = H) | H | 5-Cl | OCH₃ | OCH₃ | |
| J-3 | S | Q-57 (R₇ = H, R₈ = H, R₉ = CH₃, R₃ = CH₃) | H | H | OCH₃ | OCH₃ | |
| J-1 | S | Q-58 (R₇ = CH₃, R₈ = H, R₉ = H, R₃ = H) | CH₃ | 5-CH₃ | CH₃ | CH₃ | |
| J-2 | S | Q-58 (R₇ = H, R₈ = H, R₉ = i-C₃H₇, R₃ = CH₃) | H | H | OCH₃ | OCH₃ | |
| J-1 | S | Q-59 (R₇ = H, R₈ = H, R₉ = H, R₃ = H) | H | H | OCH₃ | OCH₃ | |
| J-2 | O | Q-59 (R₇ = CH₃, R₈ = H, R₉ = H, R₃ = CH₃) | H | 5-CH₃ | OCH₃ | OCH₃ | |
| J-1 | S | Q-59 (R₇ = H, R₈ = H, R₉ = H, R₁₀ = s-C₄H₉) | H | H | OCF₂H | CH₃ | |
| J-2 | S | Q-60 (R₇ = H, R₈ = H, R₉ = H, R₁₀ = CH₃) | H | 5-Cl | OCH₃ | CH₃ | |
| J-1 | S | Q-60 (R₇ = H, R₈ = H, R₉ = H, R₂ = H) | H | H | CH₃ | CH₃ | |
| J-2 | S | Q-60 (R₇ = H, R₈ = H, R₉ = H, R₂ = H) | H | H | CH₃ | OCH₃ | |
| J-1 | S | Q-60 (R₇ = H, R₈ = H, R₉ = H, R₂ = Br) | H | H | OCH₃ | OCH₃ | 110-117 |
| J-2 | S | Q-60 (R₇ = CH₃, R₈ = H, R₉ = H, R₂ = O(CH₂)₃CH₂Br) | H | 5-CH₃ | OCH₃ | OCH₃ | 123-133 |
| J-1 | S | Q-61 (R₇ = H, R₈ = H, R₉ = H, R₂ = H) | H | H | OCH₃ | OCH₃ | 124-132 |
| J-2 | S | Q-61 (R₇ = CH₃, R₈ = H, R₉ = H, R₂ = OCH₂F) | H | H | OCH₃ | OCH₃ | 150-162 |
| J-1 | S | Q-61 (R₇ = H, R₈ = CH₃, R₉ = H, R₂ = O(CH₂)₃CH₃) | H | H | OCH₃ | OCH₃ | |
| J-2 | S | Q-62 (R₇ = H, R₈ = H, R₉ = H, R₂ = H) | H | H | OCH₃ | OCH₃ | |
| J-1 | S | Q-62 (R₇ = H, R₈ = H, R₉ = H, R₂ = CH₃) | CH₃ | H | OCH₃ | OCH₃ | |
| J-2 | O | Q-62 (R₇ = Cl, R₈ = H, R₉ = H, R₂ = H) | H | H | OCH₃ | OCH₃ | |
| J-1 | S | Q-63 (R₇ = H, R₈ = H, R₉ = H) | H | H | Cl | Cl | |
| J-2 | S | Q-63 (R₇ = CH₃, R₈ = H, R₉ = H) | H | 5-CH₃ | OCH₃ | OCH₃ | |
| J-1 | S | Q-64 (R₇ = H, R₈ = H, R₉ = CH₃) | H | H | CH₃ | OCH₃ | |
| J-2 | S | Q-64 (R₇ = C₂H₅, R₈ = H, R₉ = H) | H | H | CH₃ | CH₃ | |
| J-1 | S | Q-65 (R₇ = H, R₈ = H, R₉ = C₂H₅) | H | 5-Cl | CH₃ | OCH₃ | |
| J-2 | S | Q-65 (R₇ = n-C₄H₉, R₈ = H, R₉ = H) | H | 5-CH₃ | OCH₃ | OCH₃ | |
| J-3 | S | Q-65 (R₇ = H, R₈ = CH₃, R₉ = i-C₃H₇) | CH₃ | H | OCH₃ | OCH₃ | |
| J-1 | S | Q-66 (R₇ = H, R₈ = H, R₉ = H) | H | H | OCH₃ | OCH₃ | |
| J-2 | O | Q-66 (R₇ = i-C₃H₇, R₈ = H, R₉ = H) | H | 5-CH₃ | OCF₂H | OCF₂H | |
| J-2 | S | Q-66 (R₇ = H, R₈ = C₂H₅, R₉ = CH₃) | H | 5-Cl | OCH₃ | CH₃ | |

TABLE 1-continued

General Formula 1

| J | W₁ | Q | R | R₁ | X | Y | m.p. (°C.) |
|---|---|---|---|---|---|---|---|
| J-1 | S | Q-67 (R₇ = H, R₈ = H, R₉ = H, R₃ = H) | H | H | CH₃ | OCH₃ | |
| J-2 | S | Q-67 (R₇ = CH₃, R₈ = H, R₉ = H, R₃ = CH₃) | H | H | OCH₃ | OCH₃ | |
| J-1 | S | Q-67 (R₇ = H, R₈ = H, R₉ = CH₃, R₃ = C₂H₅) | H | 5-CH₃ | OCH₃ | OCH₃ | |
| J-2 | S | Q-67 (R₇ = H, R₈ = H, R₉ = H, R₃ = CH₃) | H | H | OCH₃ | OCH₃ | |
| J-1 | S | Q-68 (R₇ = C₂H₅, R₈ = H, R₉ = H, R₃ = i-C₃H₇) | H | H | Cl | OCH | |
| J-3 | S | Q-68 (R₇ = H, R₈ = H, R₉ = C₂H₅, R₃ = n-C₄H₉) | H | H | CH₃ | OCH | |
| J-1 | O | Q-69 (R₇ = H, R₈ = H, R₉ = H, R₃ = CH₃) | CH₃ | H | CH₃ | OCH₃ | |
| J-2 | S | Q-69 (R₇ = n-C₄H₉, R₈ = CH₃, R₉ = H, R₃ = C₂H₅) | H | H | CH₃ | OCH₃ | |
| J-1 | S | Q-69 (R₇ = H, R₈ = CH₃, R₉ = i-C₃H₇, R₃ = H) | H | H | OCH₃ | OCH | |
| J-2 | S | Q-70 (R₇ = H, R₈ = H, R₉ = H, R₃ = CH₃) | H | H | OCH₃ | OCH₃ | |
| J-1 | S | Q-70 (R₇ = i-C₃H₇, R₈ = H, R₉ = CH₃, R₃ = CH₃) | H | 5-CH₃ | OCH₃ | OCH₃ | |
| J-2 | S | Q-70 (R₇ = H, R₈ = C₂H₅, R₉ = H, R₁₀ = H) | H | H | OCH₃ | OCF₂H | |
| J-1 | NCH₃ | Q-71 (R₇ = H, R₈ = H, R₉ = H, R₁₀ = H) | H | H | OCH₃ | OCH₃ | |
| J-1 | S | Q-71 (R₇ = CH₃, R₈ = H, R₉ = H, R₁₀ = CH₃) | H | H | OCH₃ | OCH₃ | |
| J-2 | S | Q-71 (R₇ = H, R₈ = H, R₉ = H, R₁₀ = CH₃) | H | 5-Cl | OCH₃ | OCH₃ | |
| J-1 | S | Q-72 (R₇ = H, R₈ = H, R₉ = H, R₂ = H) | H | H | OCH₃ | CH₃ | |
| J-2 | S | Q-72 (R₇ = CH₃, R₈ = H, R₉ = H, R₂ = CH₃) | H | H | OCH₃ | OCH₃ | |
| J-3 | O | Q-72 (R₇ = H, R₈ = H, R₉ = H, R₂ = H) | H | H | OCH₃ | OCH₃ | |
| J-1 | S | Q-73 (R₇ = H, R₈ = H, R₉ = H, R₂ = H) | H | 5-CH₃ | OCH₃ | OCH₃ | |
| J-2 | S | Q-73 (R₇ = H, R₈ = CH₃, R₉ = H, R₂ = C₂H₅) | H | H | OCH₃ | CH₃ | |
| J-1 | S | Q-73 (R₇ = CH₃, R₈ = H, R₉ = CH₃, R₂ = H) | H | 5-Cl | OCF₂H | CH₃ | |
| J-1 | S | Q-74 (R₇ = H, R₈ = H, R₉ = H, R₂ = H) | H | H | OCH₃ | OCH₃ | |
| J-2 | S | Q-74 (R₇ = CH₃, R₈ = H, R₉ = H, R₂ = CH₃) | H | H | CH₃ | OCH₃ | |
| J-1 | S | Q-74 (R₇ = C₂H₅, R₈ = H, R₉ = H, R₂ = C₂H₅) | H | 5-CH₃ | CH₃ | OCH₃ | |
| J-2 | S | Q-75 (R₇ = H, R₈ = H, R₉ = H) | H | H | OCH₃ | OCH₃ | |
| J-1 | S | Q-75 (R₇ = CH₃, R₈ = H, R₉ = CH₃) | H | H | Cl | OCH₃ | |
| J-2 | S | Q-76 (R₇ = H, R₈ = H, R₉ = H) | H | 5-CH₃ | CH₃ | OCH₃ | |
| J-1 | O | Q-76 (R₇ = H, R₈ = H, R₉ = H) | H | 5-Cl | CH₃ | OCH₃ | |
| J-3 | S | Q-76 (R₇ = C₂H₅, R₈ = H, R₉ = C₂H₅) | H | H | OCH₃ | OCH₃ | |
| J-1 | S | Q-77 (R₇ = H, R₈ = H, R₉ = n-C₃H₇) | H | H | OCH₃ | OCH₃ | |
| J-2 | S | Q-77 (R₇ = CH₃, R₈ = H, R₉ = H) | H | H | OCH₃ | OCH₃ | |
| J-1 | S | Q-77 (R₇ = H, R₈ = CH₃, R₉ = H) | H | 5-CH₃ | OCH₃ | OCH₃ | |
| J-1 | S | Q-78 (R₇ = H, R₈ = H, R₉ = H) | H | 5-Cl | OCH₃ | OCH₃ | |
| J-2 | S | Q-78 (R₇ = n-C₃H₇, R₈ = H, R₉ = H) | H | H | OCH₃ | OCF₂H | |
| J-1 | S | Q-79 (R₇ = H, R₈ = H, R₉ = H, R₃ = H) | CH₃ | H | OCH₃ | OCH₃ | |
| J-2 | S | Q-79 (R₇ = H, R₈ = H, R₉ = H, R₃ = CH₃) | H | H | OCH₃ | OCH₃ | |
| J-1 | S | Q-79 (R₇ = CH₃, R₈ = H, R₉ = H, R₃ = C₂H₅) | H | 5-CH₃ | OCH₃ | OCH₃ | |
| J-3 | S | Q-80 (R₇ = CH₃, R₈ = H, R₉ = H, R₃ = CH₃) | H | H | OCH₃ | OCH₃ | |
| J-1 | S | Q-80 (R₇ = H, R₈ = H, R₉ = CH₃, R₃ = C₂H₅) | H | H | OCF₂H | OCH₃ | |
| J-2 | S | Q-80 (R₇ = H, R₈ = H, R₉ = H, R₃ = CH₃) | H | 5-CH₃ | OCH₃ | OCH₃ | |
| J-1 | S | Q-81 (R₇ = H, R₈ = CH₃, R₉ = H, R₃ = CH₃) | H | 5-Cl | CH₃ | CH₃ | |
| J-1 | S | Q-81 (R₇ = CH₃, R₈ = H, R₉ = H, R₃ = i-C₃H₇) | H | H | CH₃ | CH₃ | |
| J-1 | S | Q-82 (R₇ = H, R₈ = H, R₉ = H, R₃ = CH₃) | H | 5-CH₃ | CH₃ | CH₃ | |
| J-2 | S | Q-82 (R₇ = CH₃, R₈ = H, R₉ = C₂H₅, R₃ = CH₃) | H | H | Cl | OCH₃ | |
| J-1 | S | Q-82 (R₇ = H, R₈ = H, R₉ = H, R₁₀ = H) | H | H | CH₃ | OCH₃ | |
| J-1 | S | Q-83 (R₇ = CH₃, R₈ = H, R₉ = H, R₁₀ = CH₃) | CH₃ | H | CH₃ | OCH₃ | |
| J-2 | O | Q-83 (R₇ = H, R₈ = H, R₉ = H, R₁₀ = H) | H | H | CH₃ | OCH₃ | |
| J-3 | S | Q-83 (R₇ = CH₃, R₈ = CH₃, R₉ = H, R₁₀ = H) | H | H | OCH₃ | OCH₃ | |

TABLE 1-continued

General Formula 1

| J | W₁ | Q | R | R₁ | X | Y | m.p. (°C.) |
|---|---|---|---|---|---|---|---|
| J-1 | S | Q-84 (R₇ = H, R₈ = H, R₉ = H) | H | H | OCH₃ | OCH₃ | |
| J-2 | S | Q-84 (R₇ = H, R₈ = H, R₉ = CH₃) | H | H | OCH₃ | OCH₃ | |
| J-1 | S | Q-84 (R₇ = H, R₈ = C₂H₅, R₉ = H) | H | 5-CH₃ | OCH₃ | OCH₃ | |
| J-2 | S | Q-85 (R₇ = CH₃, R₈ = H, R₉ = H) | H | H | OCH₃ | OCF₂H | |
| J-1 | S | Q-85 (R₇ = H, R₈ = H, R₉ = C₂H₅) | H | 5-Cl | OCH₃ | OCH₃ | |
| J-2 | O | Q-85 (R₇ = H, R₈ = H, R₉ = H) | H | H | OCH₃ | OCH₃ | |
| J-1 | S | Q-86 (R₇ = CH₃, R₈ = H, R₉ = H) | CH₃ | H | OCH₃ | OCH₃ | |
| J-2 | S | Q-86 (R₇ = H, R₈ = H, R₉ = C₂H₅) | H | 5-CH₃ | OCH₃ | OCH₃ | |
| J-1 | S | Q-87 (R₇ = H, R₈ = H, R₉ = H) | H | H | OCH₃ | CH₃ | |
| J-2 | S | Q-87 (R₇ = CH₃, R₈ = H, R₉ = CH₃) | H | H | OCF₂H | CH₃ | |
| J-3 | S | Q-87 (R₇ = H, R₈ = H, R₉ = H) | H | 5-Cl | OCH₃ | OCH₃ | |
| J-1 | S | Q-88 (R₇ = CH₃, R₈ = H, R₉ = H) | H | H | CH₃ | OCH₃ | |
| J-2 | S | Q-88 (R₇ = H, R₈ = H, R₉ = CH₃) | H | 5-CH₃ | OCH₃ | OCH | |
| J-1 | S | Q-89 (R₇ = H, R₈ = H, R₉ = H) | H | H | OCH₃ | OCH₃ | |
| J-2 | O | Q-89 (R₇ = CH₃, R₈ = H, R₉ = C₂H₅) | H | H | Cl | OCH | |
| J-1 | S | Q-90 (R₇ = H, R₈ = H, R₉ = H, R₃ = CH₃) | H | H | CH₃ | OCH₃ | |
| J-2 | S | Q-90 (R₇ = CH₃, R₈ = H, R₉ = H, R₃ = C₂H₅) | CH₃ | H | CH₃ | OCH₃ | |
| J-1 | S | Q-90 (R₇ = H, R₈ = H, R₉ = CH₃, R₃ = CH₃) | H | H | CH₃ | OCH₃ | |
| J-3 | S | Q-91 (R₇ = H, R₈ = H, R₉ = H, R₃ = CH₃) | H | 5-CH₃ | OCH₃ | OCH₃ | |
| J-1 | S | Q-91 (R₇ = CH₃, R₈ = H, R₉ = H, R₃ = H) | H | H | CH₃ | OCH₃ | |
| J-2 | S | Q-91 (R₇ = H, R₈ = CH₃, R₃ = CH₃) | H | H | OCH₃ | OCH₃ | |
| J-1 | S | Q-92 (R₇ = H, R₈ = H, R₉ = H, R₁₀ = H) | H | 5-CH₃ | OCH₃ | OCH₃ | |
| J-2 | S | Q-92 (R₇ = H, R₈ = CH₃, R₉ = H, R₁₀ = CH₃) | H | H | OCH₃ | OCH₃ | |
| J-1 | O | Q-92 (R₇ = CH₃, R₈ = H, R₉ = H, R₁₀ = H) | H | 5-Cl | OCH₃ | OCF₂H | |
| J-2 | S | Q-93 (R₇ = H, R₈ = H, R₉ = H) | H | H | OCH₃ | OCH₃ | |
| J-1 | S | Q-93 (R₇ = CH₃, R₈ = H, R₉ = CH₃) | CH₃ | H | OCH₃ | OCH₃ | |
| J-2 | S | Q-93 (R₇ = H, R₈ = H, R₉ = H) | H | 5-CH₃ | OCH₃ | OCH₃ | |
| J-1 | NH | Q-94 (R₇ = H, R₈ = H, R₉ = H) | H | H | OCF₂H | CH₃ | |
| J-2 | S | Q-94 (R₇ = CH₃, R₈ = H, R₉ = n-C₄H₉) | H | H | OCH₃ | CH₃ | |
| J-3 | S | Q-95 (R₇ = H, R₈ = H, R₉ = H) | H | 5-Cl | CH₃ | CH₃ | |
| J-1 | S | Q-95 (R₇ = H, R₈ = H, R₉ = CH₃) | H | H | CH₃ | OCH₃ | |
| J-2 | S | Q-95 (R₇ = CH₃, R₈ = H, R₉ = s-C₄H₉) | H | 5-CH₃ | OCH₃ | OCH₃ | |
| J-1 | O | Q-96 (R₇ = H, R₈ = H, R₉ = H) | H | H | Cl | OCH₃ | |
| J-2 | S | Q-96 (R₇ = CH₃, R₈ = H, R₉ = H) | H | 5-Cl | CH₃ | OCH₃ | |
| J-1 | S | Q-97 (R₇ = H, R₈ = H, R₉ = H) | H | H | CH₃ | OCH₃ | |
| J-2 | S | Q-97 (R₇ = CH₃, R₈ = H, R₉ = CH₃, R₉ = CH₃) | CH₃ | H | CH₃ | OCH₃ | |
| J-1 | S | Q-98 (R₇ = H, R₈ = H, R₉ = H) | H | 5-CH₃ | OCH₃ | OCH₃ | |
| J-2 | S | Q-98 (R₇ = CH₃, R₈ = H, R₉ = H) | H | H | OCH₃ | OCH₃ | |
| J-1 | O | Q-98 (R₇ = H, R₈ = H, R₉ = i-C₃H₇) | H | H | OCH₃ | OCH₃ | |
| J-2 | S | Q-99 (R₇ = H, R₈ = H, R₉ = H, R₃ = H) | H | 5-CH₃ | OCH₃ | OCH₃ | |
| J-1 | S | Q-99 (R₇ = H, R₈ = H, R₉ = H, R₃ = H) | H | H | OCH₃ | OCF₂H | |
| J-2 | O | Q-99 (R₇ = H, R₈ = H, R₉ = s-C₄H₉, R₃ = H) | H | 5-Cl | OCH₃ | OCH | |
| J-1 | S | Q-100 (R₇ = H, R₈ = H, R₉ = H, R₃ = C₂H₅) | CH₃ | H | OCH₃ | CH₃ | |
| J-2 | S | Q-100 (R₇ = H, R₈ = CH₃, R₉ = H, R₃ = H) | CH₃ | H | OCH₃ | CH₃ | |
| J-1 | S | Q-100 (R₇ = H, R₈ = H, R₉ = CH₃, R₃ = CH₃) | H | 5-CH₃ | OCH₃ | OCH₃ | |

TABLE 1-continued

General Formula 1

| J | W$_1$ | Q | R | R$_1$ | X | Y | m.p. (°C.) |
|---|---|---|---|---|---|---|---|
| J-2 | S | Q-101 (R$_7$ = H, R$_8$ = H, R$_9$ = H, R$_3$ = i-C$_3$H$_7$) | H | H | OCH$_3$ | OCH$_3$ | |
| J-1 | S | Q-101 (R$_7$ = CH$_3$, R$_8$ = H, R$_9$ = CH$_3$, R$_3$ = H) | H | H | OCF$_2$H | CH$_3$ | |
| J-2 | S | Q-101 (R$_7$ = H, R$_8$ = H, R$_9$ = CH$_3$, R$_3$ = CH$_3$) | H | 5-Cl | OCH$_3$ | CH$_3$ | |
| J-3 | S | Q-102 (R$_7$ = CH$_3$, R$_8$ = H, R$_9$ = H, R$_3$ = H) | H | H | CH$_3$ | OCH$_3$ | |
| J-2 | O | Q-102 (R$_7$ = H, R$_8$ = H, R$_9$ = H, R$_3$ = CH$_3$) | H | H | CH$_3$ | OCH$_3$ | |
| J-1 | S | Q-102 (R$_7$ = H, R$_8$ = H, R$_9$ = i-C$_3$H$_7$, R$_3$ = CH$_3$) | H | 5-CH$_3$ | OCH$_3$ | OCH$_3$ | |
| J-2 | S | Q-103 (R$_7$ = CH$_3$, R$_8$ = H, R$_9$ = H, R$_{10}$ = H) | H | H | OCH$_3$ | OCH$_3$ | |
| J-2 | S | Q-103 (R$_7$ = H, R$_8$ = H, R$_9$ = H, R$_{10}$ = CH$_3$) | H | H | Cl | OCH$_3$ | |
| J-1 | S | Q-103 (R$_7$ = H, R$_8$ = H, R$_9$ = H, R$_{10}$ = s-C$_4$H$_9$) | H | H | CH$_3$ | OCH$_3$ | |
| J-2 | S | Q-104 (R$_7$ = CH$_3$, R$_8$ = H, R$_9$ = H, R$_2$ = H) | CH$_3$ | H | CH$_3$ | OCH$_3$ | |
| J-1 | S | Q-104 (R$_7$ = H, R$_8$ = H, R$_9$ = H, R$_2$ = OC$_2$H$_5$) | H | H | OCH$_3$ | OCH$_3$ | |
| J-2 | S | Q-104 (R$_7$ = H, R$_8$ = H, R$_9$ = H, R$_2$ = Br) | H | H | OCH$_3$ | OCH$_3$ | |
| J-2 | S | Q-105 (R$_7$ = CH$_3$, R$_8$ = H, R$_9$ = H, R$_2$ = H) | H | H | OCH$_3$ | OCH$_3$ | |
| J-3 | S | Q-105 (R$_7$ = H, R$_8$ = H, R$_9$ = H, R$_2$ = CH$_3$) | H | 5-CH$_3$ | CH$_3$ | CH$_3$ | 190–192 |
| J-2 | S | Q-105 (R$_7$ = H, R$_8$ = CH$_3$, R$_9$ = H, R$_2$ = H) | H | H | CH$_3$ | CH$_3$ | 186–188 |
| J-1 | S | Q-105 (R$_7$ = H, R$_8$ = H, R$_9$ = H, R$_2$ = H) | H | H | OCH$_3$ | OCH$_3$ | 182–183 |
| J-2 | S | Q-105 (R$_7$ = H, R$_8$ = H, R$_9$ = H, R$_2$ = C$_2$H$_5$) | H | H | OCH$_3$ | Cl | 170–173 |
| J-1 | S | Q-106 (R$_7$ = CH$_3$, R$_8$ = H, R$_9$ = H, R$_2$ = CH$_3$) | H | H | OCH$_3$ | OCH$_3$ | |
| J-2 | S | Q-106 (R$_7$ = Cl, R$_8$ = H, R$_9$ = H, R$_2$ = H) | H | 5-Cl | OCH$_3$ | OCF$_2$H | |
| J-1 | O | Q-107 (R$_7$ = CH$_3$, R$_8$ = H, R$_9$ = H, R$_2$ = H) | CH$_3$ | H | OCH$_3$ | OCH$_3$ | |
| J-2 | S | Q-107 (R$_7$ = H, R$_8$ = H, R$_9$ = H, R$_2$ = CH$_3$) | H | 5-CH$_3$ | OCH$_3$ | OCH$_3$ | |
| J-2 | S | Q-108 (R$_7$ = H, R$_8$ = CH$_3$, R$_9$ = H, R$_2$ = H) | H | H | OCH$_3$ | OCH$_3$ | |
| J-1 | S | Q-108 (R$_7$ = H, R$_8$ = H, R$_9$ = H, R$_2$ = Cl) | H | 5-Cl | OCH$_3$ | Cl | |
| J-2 | S | Q-108 (R$_7$ = H, R$_8$ = H, R$_9$ = H, R$_2$ = CH$_3$) | H | 5-CH$_3$ | CH$_3$ | CH$_3$ | |
| J-2 | O | Q-109 (R$_7$ = H, R$_8$ = H, R$_9$ = H) | H | H | OCF$_2$H | CH$_3$ | |
| J-1 | S | Q-109 (R$_7$ = CH$_3$, R$_8$ = H, R$_9$ = H) | CH$_3$ | H | OCH$_3$ | CH$_3$ | |
| J-2 | S | Q-109 (R$_7$ = H, R$_8$ = CH$_3$, R$_9$ = H) | H | H | CH$_3$ | OCH$_3$ | |
| J-2 | S | Q-110 (R$_7$ = H, R$_8$ = H, R$_9$ = H) | H | H | OCH$_3$ | OCH$_3$ | |
| J-1 | S | Q-110 (R$_7$ = CH$_3$, R$_8$ = H, R$_9$ = H) | H | 5-CH$_3$ | OCH$_3$ | OCH$_3$ | |
| J-2 | S | Q-110 (R$_7$ = H, R$_8$ = CH$_3$, R$_9$ = H) | H | H | CH$_3$ | CH$_3$ | |
| J-2 | S | Q-111 (R$_7$ = H, R$_8$ = H, R$_9$ = H) | H | H | Cl | OCH | |
| J-1 | S | Q-111 (R$_7$ = CH$_3$, R$_8$ = H, R$_9$ = H) | CH$_3$ | 5-Cl | CH$_3$ | OCH$_3$ | |
| J-2 | S | Q-112 (R$_7$ = H, R$_8$ = H, R$_9$ = H) | H | H | OCH$_3$ | OCH$_3$ | |
| J-2 | O | Q-112 (R$_7$ = H, R$_8$ = CH$_3$, R$_9$ = CH$_3$) | CH$_3$ | 5-CH$_3$ | OCH$_3$ | OCH$_3$ | |
| J-1 | S | Q-113 (R$_7$ = H, R$_8$ = H, R$_9$ = H, R$_3$ = CH$_3$) | H | H | OCH$_3$ | OCH$_3$ | |
| J-2 | S | Q-113 (R$_7$ = C$_2$H$_5$, R$_8$ = H, R$_9$ = H, R$_3$ = i-C$_3$H$_7$) | H | 5-Cl | OCH$_3$ | OCF$_2$H | |
| J-2 | S | Q-113 (R$_7$ = H, R$_8$ = H, R$_9$ = C$_2$H$_5$, R$_3$ = n-C$_4$H$_9$) | H | 5-CH$_3$ | OCH$_3$ | OCH$_3$ | |
| J-1 | S | Q-114 (R$_7$ = H, R$_8$ = H, R$_9$ = H, R$_3$ = CH$_3$) | H | H | OCH$_3$ | OCH$_3$ | |
| J-2 | S | Q-114 (R$_7$ = n-C$_4$H$_9$, R$_8$ = H, R$_9$ = H, R$_3$ = C$_2$H$_5$) | H | 5-Cl | CH$_3$ | CH$_3$ | |
| J-1 | S | Q-114 (R$_7$ = H, R$_8$ = CH$_3$, R$_8$ = i-C$_3$H$_7$, R$_3$ = H) | CH$_3$ | 5-CH$_3$ | OCH$_3$ | OCH$_3$ | |
| J-2 | S | Q-115 (R$_7$ = i-C$_3$H$_7$, R$_8$ = H, R$_9$ = H, R$_3$ = CH$_3$) | H | 5-Cl | OCF$_2$H | OCH$_3$ | |
| J-1 | S | Q-115 (R$_7$ = H, R$_8$ = C$_2$H$_5$, R$_9$ = CH$_3$, R$_3$ = H) | H | H | OCH$_3$ | OCH$_3$ | |
| J-1 | O | Q-116 (R$_7$ = CH$_3$, R$_8$ = H, R$_9$ = H, R$_{10}$ = H) | H | H | CH$_3$ | CH$_3$ | |
| J-2 | S | Q-116 (R$_7$ = H, R$_8$ = H, R$_9$ = H, R$_{10}$ = H) | H | H | CH$_3$ | OCH$_3$ | |

TABLE 1-continued

| | | | General Formula 1 | | | | |
|---|---|---|---|---|---|---|---|
| J | W₁ | Q | R | R₁ | X | Y | m.p. (°C.) |
| J-3 | NCH₃ | Q-116 (R₇ = H, R₈ = H, R₉ = H, R₁₀ = CH₃) | H | 5-CH₃ | OCH₃ | OCH₃ | |
| J-1 | S | Q-117 (R₇ = H, R₈ = H, R₉ = H, R₂ = H) | H | H | OCH₃ | OCH₃ | |
| J-2 | S | Q-117 (R₇ = H, R₈ = CH₃, R₉ = H, R₂ = CH₃) | H | H | Cl | OCH₃ | |
| J-1 | S | Q-117 (R₇ = CH₃, R₈ = H, R₉ = H, R₂ = H) | CH₃ | H | CH₃ | OCH₃ | |
| J-2 | S | Q-118 (R₇ = H, R₈ = H, R₉ = H, R₁₀ = H) | H | H | CH₃ | OCH₃ | |
| J-1 | S | Q-118 (R₇ = CH₃, R₈ = H, R₉ = H, R₁₀ = CH₃) | CH₃ | H | OCH₃ | OCH | |
| J-1 | S | Q-119 (R₇ = H, R₈ = H, R₉ = H, R₁₀ = H) | H | H | OCH₃ | OCH₃ | |
| J-2 | O | Q-119 (R₇ = H, R₈ = H, R₉ = H, R₂ = CH₃) | H | H | OCH₃ | OCH₃ | |
| J-1 | S | Q-119 (R₇ = H, R₈ = CH₃, R₉ = H, R₂ = C₂H₅) | H | 5-CH₃ | OCH₃ | OCH₃ | |
| J-3 | S | Q-120 (R₇ = H, R₈ = H, R₉ = H, R₂ = H) | H | H | OCH₃ | OCH₃ | |
| J-1 | S | Q-120 (R₇ = H, R₈ = H, R₉ = CH₃, R₂ = CH₃) | H | H | OCH₃ | OCF₂H | |
| J-1 | S | Q-120 (R₇ = H, R₈ = H, R₉ = H, R₂ = CH₃) | H | 5-Cl | OCH₃ | OCH₃ | |
| J-2 | S | Q-121 (R₇ = H, R₈ = H, R₉ = H, R₂ = C₂H₅) | H | H | OCH₃ | OCH₃ | |
| J-1 | S | Q-121 (R₇ = CH₃, R₈ = CH₃, R₉ = H, R₂ = H) | CH₃ | 5-CH₃ | OCH₃ | CH₃ | |
| J-2 | S | Q-121 (R₇ = H, R₈ = H, R₉ = H, R₂ = H) | H | H | OCH₃ | OCH₃ | |
| J-1 | O | Q-122 (R₇ = CH₃, R₈ = CH₃, R₉ = H, R₂ = H) | H | 5-Cl | OCF₂H | CH₃ | |
| J-1 | S | Q-122 (R₇ = H, R₈ = H, R₉ = H, R₂ = H) | H | H | OCH₃ | OCH₃ | |
| J-2 | S | Q-122 (R₇ = CH₃, R₈ = H, R₉ = H, R₂ = CH₃) | CH₃ | 5-CH₃ | CH₃ | OCH₃ | |
| J-1 | S | Q-123 (R₇ = H, R₈ = H, R₉ = H) | H | H | CH₃ | OCH₃ | |
| J-3 | S | Q-123 (R₇ = CH₃, R₈ = H, R₉ = CH₃) | H | H | OCH₃ | OCH₃ | |
| J-1 | S | Q-124 (R₇ = H, R₈ = H, R₉ = H) | H | H | Cl | OCH₃ | |
| J-2 | S | Q-124 (R₇ = C₂H₅, R₈ = H, R₉ = C₂H₅) | H | H | CH₃ | OCH₃ | |
| J-1 | S | Q-125 (R₇ = H, R₈ = H, R₉ = H) | H | H | CH₃ | OCH₃ | |
| J-2 | O | Q-125 (R₇ = H, R₈ = H, R₉ = n-C₄H₉) | CH₃ | H | OCH₃ | OCH₃ | |
| J-1 | S | Q-126 (R₇ = H, R₈ = CH₃, R₉ = H) | H | H | OCH₃ | OCH₃ | |
| J-2 | S | Q-126 (R₇ = H, R₈ = H, R₉ = H) | H | H | OCH₃ | OCH₃ | |
| J-1 | S | Q-126 (R₇ = H, R₈ = H, R₉ = s-C₃H₇) | H | H | OCH₃ | OCH₃ | |
| J-1 | S | Q-126 (R₇ = n-C₃H₇, R₈ = H, R₉ = H) | H | 5-CH₃ | OCH₃ | OCH₃ | |
| J-1 | S | Q-127 (R₇ = H, R₈ = H, R₉ = H, R₃ = CH₃) | H | H | OCH₃ | OCF₂H | |
| J-2 | S | Q-127 (R₇ = CH₃, R₈ = H, R₉ = H, R₃ = C₂H₅) | H | 5-Cl | OCH₃ | OCH₃ | |
| J-1 | S | Q-128 (R₇ = H, R₈ = H, R₉ = H, R₃ = CH₃) | CH₃ | H | OCH₃ | OCH₃ | |
| J-1 | S | Q-128 (R₇ = H, R₈ = H, R₉ = CH₃, R₃ = C₂H₅) | H | 5-CH₃ | OCF₂H | OCH₃ | |
| J-2 | O | Q-129 (R₇ = H, R₈ = CH₃, R₉ = H, R₃ = CH₃) | H | H | OCH₃ | OCH₃ | |
| J-1 | S | Q-129 (R₇ = H, R₈ = H, R₉ = CH₃, R₃ = i-C₃H₇) | H | 5-Cl | OCH₃ | OCH₃ | |
| J-1 | S | Q-130 (R₇ = H, R₈ = H, R₉ = CH₃, R₃ = CH₃) | H | H | CH₃ | CH₃ | |
| J-1 | S | Q-130 (R₇ = CH₃, R₈ = H, R₉ = CH₃, R₃ = H) | H | H | CH₃ | CH₃ | |
| J-2 | S | Q-130 (R₇ = H, R₈ = H, R₉ = C₂H₅, R₃ = CH₃) | H | 5-CH₃ | CH₃ | OCH₃ | |
| J-1 | S | Q-131 (R₇ = H, R₈ = H, R₉ = H, R₁₀ = CH₃) | CH₃ | H | OCH₃ | OCH₃ | |
| J-1 | S | Q-131 (R₇ = CH₃, R₈ = H, R₉ = H, R₁₀ = H) | CH₃ | H | Cl | OCH₃ | |
| J-2 | S | Q-132 (R₇ = H, R₈ = H, R₉ = CH₃) | CH₃ | H | CH₃ | OCH₃ | |
| J-3 | O | Q-132 (R₇ = H, R₈ = H, R₉ = H) | H | H | OCH₃ | OCH₃ | |
| J-1 | S | Q-133 (R₇ = H, R₈ = C₂H₅, R₉ = H) | H | H | OCH₃ | OCH₃ | |
| J-2 | S | Q-133 (R₇ = CH₃, R₈ = H, R₉ = H) | H | H | OCH₃ | OCH₃ | |

TABLE 1-continued

General Formula 1

| J | $W_1$ | Q | R | $R_1$ | X | Y | m.p. (°C.) |
|---|---|---|---|---|---|---|---|
| J-1 | S | Q-133 ($R_7$ = H, $R_8$ = H, $R_9$ = $C_2H_5$) | H | 5-$CH_3$ | $OCH_3$ | $OCH_3$ | |
| J-2 | S | Q-134 ($R_7$ = H, $R_8$ = H, $R_9$ = H) | H | H | $OCH_3$ | $OCH_3$ | |
| J-1 | S | Q-134 ($R_7$ = $CH_3$, $R_8$ = H, $R_9$ = $C_2H_5$) | H | H | $OCH_3$ | $OCF_2H$ | |
| J-2 | S | Q-134 ($R_7$ = H, $R_8$ = H, $R_9$ = $C_2H_5$) | H | 5-Cl | $OCH_3$ | $OCH_3$ | |
| J-3 | S | Q-135 ($R_7$ = H, $R_8$ = H, R = H) | $CH_3$ | H | $OCH_3$ | $OCH_3$ | |
| J-2 | O | Q-135 ($R_7$ = $CH_3$, $R_8$ = H, R = $CH_3$) | H | 5-$CH_3$ | $OCH_3$ | $OCH_3$ | |
| J-1 | S | Q-136 ($R_7$ = H, $R_8$ = H, $R_9$ = H) | H | H | $OCF_2H$ | $CH_3$ | |
| J-2 | S | Q-136 ($R_7$ = H, $R_8$ = $CH_3$, $R_9$ = $C_2H_5$) | H | 5-Cl | $OCH_3$ | $CH_3$ | |
| J-1 | S | Q-137 ($R_7$ = H, $R_8$ = H, $R_9$ = H) | H | H | $CH_3$ | $OCH_3$ | |
| J-2 | S | Q-137 ($R_7$ = $CH_3$, $R_8$ = H, $R_9$ = H) | H | 5-$CH_3$ | $CH_3$ | $OCH_3$ | |
| J-1 | S | Q-138 ($R_7$ = H, $R_8$ = H, $R_9$ = $CH_3$) | H | H | $OCH_3$ | $OCH_3$ | |
| J-2 | S | Q-138 ($R_7$ = H, $R_8$ = H, $R_9$ = H) | H | H | $CH_3$ | $CH_3$ | 87-95 |
| J-1 | S | Q-138 ($R_7$ = H, $R_8$ = H, $R_9$ = H) | H | H | $OCH_3$ | $CH_3$ | 73-84 |
| J-2 | S | Q-138 ($R_7$ = H, $R_8$ = H, $R_9$ = H) | H | H | $OCH_3$ | $CH_3$ | 89-93 |
| J-1 | S | Q-138 ($R_7$ = $CH_3$, $R_8$ = H, $R_9$ = H) | H | H | $OCH_3$ | Cl | 85-93 |
| J-2 | O | Q-138 ($R_7$ = H, $R_8$ = H, $R_9$ = $CH_3$) | H | H | Cl | $OCH_3$ | |
| J-1 | S | Q-139 ($R_7$ = H, $R_8$ = H, $R_9$ = H) | $CH_3$ | H | $CH_3$ | $OCH_3$ | |
| J-2 | S | Q-139 ($R_7$ = $CH_3$, $R_8$ = $CH_3$, $R_9$ = H) | H | H | $CH_3$ | $OCH_3$ | |
| J-1 | S | Q-140 ($R_7$ = H, $R_8$ = H, $R_9$ = H) | H | 5-$CH_3$ | $OCH_3$ | $OCH_3$ | |
| J-2 | S | Q-140 ($R_7$ = H, $R_8$ = $CH_3$, $R_9$ = H) | H | H | $OCH_3$ | $OCH_3$ | |
| J-1 | S | Q-140 ($R_7$ = $CH_3$, $R_8$ = H, $R_9$ = $C_2H_5$) | H | H | $OCH_3$ | $OCH_3$ | |
| J-2 | S | Q-141 ($R_7$ = H, $R_8$ = H, $R_9$ = H) | H | H | $OCH_3$ | $OCH_3$ | |
| J-1 | S | Q-141 ($R_7$ = H, $R_8$ = H, $R_9$ = $CH_3$) | H | 5-Cl | $OCH_3$ | $OCH_3$ | |
| J-2 | S | Q-142 ($R_7$ = H, $R_8$ = H, $R_{10}$ = H) | H | H | $OCH_3$ | $OCH_3$ | |
| J-1 | O | Q-142 ($R_7$ = $CH_3$, $R_8$ = H, $R_{10}$ = $CH_3$) | $CH_3$ | H | $OCH_3$ | $CH_3$ | |
| J-2 | S | Q-143 ($R_7$ = H, $R_8$ = H, $R_3$ = H) | H | 5-$CH_3$ | $OCH_3$ | $OCH_3$ | |
| J-3 | S | Q-143 ($R_7$ = $CH_3$, $R_8$ = $CH_3$, $R_9$ = H) | H | H | $OCF_2H$ | $CH_3$ | |
| J-1 | S | Q-144 ($R_7$ = $CH_3$, $R_8$ = H, $R_9$ = $CH_3$, $R_3$ = $CH_3$) | H | 5-Cl | $OCH_3$ | $CH_3$ | |
| J-2 | NH | Q-144 ($R_7$ = H, $R_8$ = H, $R_9$ = H, $R_3$ = $CH_3$) | $CH_3$ | H | $CH_3$ | $OCH_3$ | |
| J-1 | S | Q-144 ($R_7$ = H, $R_8$ = $CH_3$, $R_9$ = H, $R_3$ = H) | H | H | $CH_3$ | $OCH_3$ | |
| J-2 | S | Q-144 ($R_7$ = H, $R_8$ = $CH_3$, $R_9$ = H, $R_3$ = $C_2H_5$) | H | H | $CH_3$ | $OCH_3$ | |
| J-1 | S | Q-145 ($R_7$ = H, $R_8$ = H, $R_9$ = H) | H | 5-$CH_3$ | Cl | $OCH_3$ | |
| J-2 | O | Q-145 ($R_7$ = H, $R_8$ = $CH_3$, $R_9$ = $CH_3$) | H | H | $CH_3$ | $OCH_3$ | |
| J-1 | S | Q-146 ($R_7$ = H, $R_8$ = H, $R_9$ = H) | H | 5-$CH_3$ | $CH_3$ | $OCH_3$ | |
| J-2 | S | Q-146 ($R_7$ = $CH_3$, $R_8$ = H, $R_9$ = n-$C_4H_9$) | H | H | $CH_3$ | $OCH_3$ | |
| J-1 | S | Q-147 ($R_7$ = H, $R_8$ = H, $R_9$ = H) | H | H | $OCH_3$ | $OCH_3$ | |
| J-2 | S | Q-147 ($R_7$ = $CH_3$, $R_8$ = H, $R_9$ = n-$C_4H_9$) | H | 5-$CH_3$ | $OCH_3$ | $OCH_3$ | |
| J-1 | S | Q-148 ($R_7$ = H, $R_8$ = H, $R_9$ = H) | H | H | $OCH_3$ | $OCH_3$ | |
| J-2 | S | Q-148 ($R_7$ = $CH_3$, $R_8$ = H, $R_9$ = $CH_3$) | H | H | $OCH_3$ | $OCF_2H$ | |
| J-1 | S | Q-148 ($R_7$ = H, $R_8$ = H, $R_9$ = H) | H | 5-Cl | $OCH_3$ | $OCH_3$ | |
| J-1 | O | Q-149 ($R_7$ = H, $R_8$ = H, $R_9$ = H) | H | H | $OCH_3$ | $OCH_3$ | |

TABLE 1-continued

General Formula 1

| J | W₁ | Q | R | R₁ | X | Y | m.p. (°C.) |
|---|---|---|---|---|---|---|---|
| J-2 | S | Q-149 (R₇ = H, R₈ = H, R₉ = CH₃) | CH₃ | H | OCH₃ | OCH₃ | |
| J-3 | S | Q-149 (R₇ = CH₃, R₈ = H, R₉ = H) | H | 5-CH₃ | OCH₃ | OCH₃ | |
| J-1 | S | Q-150 (R₇ = H, R₈ = H, R₉ = H) | H | H | OCH₃ | OCH₃ | |
| J-2 | S | Q-150 (R₇ = H, R₈ = CH₃, R₉ = CH₃) | H | H | OCF₂H | CH₃ | |
| J-1 | S | Q-150 (R₇ = H, R₈ = H, R₉ = H) | H | 5-Cl | CH₃ | CH₃ | |
| J-2 | S | Q-151 (R₇ = H, R₈ = H, R₉ = H) | H | H | CH₃ | CH₃ | |
| J-1 | S | Q-151 (R₇ = CH₃, R₈ = H, R₉ = H) | H | 5-CH₃ | OCH₃ | OCH₃ | |
| J-2 | S | Q-151 (R₇ = CH₃, R₈ = CH₃, R₉ = H) | H | H | OCH₃ | OCH₃ | |
| J-1 | O | Q-152 (R₇ = H, R₈ = H, R₉ = H) | H | H | OCH₃ | OCH₃ | |
| J-2 | S | Q-152 (R₇ = C₂H₅, R₈ = H, R₉ = H) | H | H | Cl | OCH₃ | |
| J-1 | S | Q-152 (R₇ = CH₃, R₈ = CH₃, R₉ = H) | CH₃ | H | CH₃ | CH₃ | |
| J-3 | S | Q-153 (R₇ = H, R₈ = H, R₉ = H, R₁₁ = CH₃) | H | H | CH₃ | CH₃ | |
| J-1 | S | Q-153 (R₇ = CH₃, R₈ = H, R₉ = H, R₁₁ = H) | H | H | CH₃ | CH₃ | |
| J-2 | S | Q-153 (R₇ = H, R₈ = H, R₉ = H, R₁₁ = CH₃) | H | H | OCH₃ | OCH₃ | |
| J-1 | S | Q-154 (R₇ = CH₃, R₈ = H, R₉ = H) | H | H | OCH₃ | OCH₃ | |
| J-2 | S | Q-154 (R₇ = CH₃, R₈ = H, R₉ = H) | H | 5-CH₃ | OCH₃ | OCH₃ | |
| J-1 | S | Q-154 (R₇ = H, R₈ = CH₃, R₉ = CH₃) | H | H | OCH₃ | OCH₃ | |
| J-2 | S | Q-155 (R₇ = H, R₈ = H, R₉ = H) | H | H | OCH₃ | OCH₃ | |
| J-1 | S | Q-155 (R₇ = CH₃, R₈ = CH₃, R₉ = H) | H | 5-Cl | OCH₃ | OCF₂H | |
| J-2 | O | Q-155 (R₇ = H, R₈ = H, R₉ = H) | H | H | OCH₃ | OCH₃ | |
| J-1 | S | Q-156 (R₇ = H, R₈ = H, R₉ = H) | H | 5-CH₃ | OCH₃ | OCH₃ | |
| J-2 | S | Q-156 (R₇ = C₂H₅, R₈ = H, R₉ = H) | CH₃ | H | OCH₃ | OCH₃ | |
| J-3 | NCH₃ | Q-156 (R₇ = CH₃, R₈ = CH₃, R₉ = H) | H | H | OCH₃ | OCH₃ | |
| J-1 | S | Q-157 (R₇ = H, R₈ = H, R₉ = H, R₁₀ = H) | H | H | OCH₃ | OCH₃ | |
| J-2 | S | Q-157 (R₇ = CH₃, R₈ = H, R₉ = H, R₁₀ = H) | H | 5-Cl | OCF₂H | CH₃ | |
| J-1 | S | Q-158 (R₇ = H, R₈ = H, R₉ = H) | H | H | OCH₃ | OCH₃ | |
| J-2 | S | Q-158 (R₇ = H, R₈ = H, R₉ = CH₃) | H | H | CH₃ | CH₃ | |
| J-1 | S | Q-158 (R₇ = CH₃, R₈ = H, R₉ = H) | H | H | CH₃ | CH₃ | |
| J-2 | O | Q-159 (R₇ = H, R₈ = H, R₉ = CH₃) | H | H | OCH₃ | OCH₃ | |
| J-1 | S | Q-159 (R₇ = H, R₈ = H, R₉ = H) | H | 5-CH₃ | Cl | OCH₃ | |
| J-2 | S | Q-160 (R₇ = H, R₈ = H, R₉ = CH₃, R₁₁ = H) | CH₃ | H | CH₃ | CH₃ | |
| J-1 | S | Q-160 (R₇ = H, R₈ = H, R₉ = H, R₁₁ = i-C₃H₇) | H | H | CH₃ | CH₃ | |
| J-2 | S | Q-160 (R₇ = H, R₈ = H, R₉ = H, R₁₁ = CH₃) | H | H | OCH₃ | OCH₃ | |
| J-1 | S | Q-161 (R₇ = H, R₈ = H, R₉ = H, R₁₁ = H) | H | H | OCH₃ | OCH₃ | |
| J-2 | S | Q-161 (R₇ = CH₃, R₈ = H, R₉ = CH₃R₁₁ = CH₃) | H | 5-CH₃ | OCH₃ | OCH₃ | |
| J-1 | S | Q-162 (R₇ = H, R₈ = H, R₉ = H, R₁₀ = H) | H | H | OCH₃ | OCH₃ | |
| J-2 | O | Q-162 (R₇ = CH₃, R₈ = H, R₉ = H, R₁₀ = CH₃) | H | 5-Cl | OCH₃ | OCF₂H | |
| J-1 | S | Q-163 (R₇ = H, R₈ = H, R₉ = H, R₂ = H) | H | H | OCH₃ | OCH₃ | |
| J-2 | O | Q-163 (R₇ = H, R₈ = H, R₉ = H, R₂ = H) | H | H | OCH₃ | OCH₃ | |
| J-1 | S | Q-164 (R₇ = H) | H | H | CH₃ | CH₃ | |
| J-2 | O | Q-164 (R₇ = H) | H | H | OCH₃ | OCH₃ | |
| J-1 | S | Q-165 (R₇ = H, R₃ = CH₃) | H | H | OCH₃ | OCH₃ | |
| J-2 | O | Q-165 (R₇ = H, R₃ = CH₃) | H | H | OCH₃ | OCH₃ | |
| J-2 | O | Q-165 (R₇ = H, R₃ = CH₃) | H | H | OCH₃ | OCH₃ | |
| J-1 | S | Q-166 (R₇ = H, R₃ = CH₃) | H | H | OCH₃ | OCH₃ | |

TABLE 1-continued

General Formula 1

| J | $W_1$ | Q | R | $R_1$ | X | Y | m.p. (°C.) |
|---|---|---|---|---|---|---|---|
| J-2 | O | Q-166 ($R_7$ = H, $R_3$ = $CH_3$) | H | H | $OCH_3$ | $OCH_3$ | |
| J-2 | S | Q-166 ($R_7$ = H, $R_3$ = $CH_3$) | H | H | $OCH_3$ | $OCH_3$ | |
| J-1* | S | Q-1 ($R_7$ = H, $R_8$ = H) | H | H | $OCH_3$ | $OCH_3$ | |
| J-1* | S | Q-1 ($R_7$ = H, $R_8$ = H) | H | H | $OCH_3$ | $CH_3$ | |
| J-2* | S | Q-1 ($R_7$ = H, $R_8$ = H) | H | H | $OCH_3$ | $OCH_3$ | |
| J-3* | S | Q-1 ($R_7$ = H, $R_8$ = H) | H | H | $OCH_3$ | $OCH_3$ | |
| J-2* | S | Q-37 ($R_7$ = H, $R_8$ = H, $R_2$ = H) | H | H | $OCH_3$ | $OCH_3$ | |
| J-2* | S | Q-60 ($R_7$ = H, $R_8$ = H, $R_9$ = H, $R_2$ = H) | H | H | $OCH_3$ | $OCH_3$ | |
| J-2* | S | Q-105 ($R_7$ = H, $R_8$ = H, $R_9$ = H, $R_2$ = H) | H | H | $OCH_3$ | $OCH_3$ | |
| J-2* | S | Q-138 ($R_7$ = H, $R_8$ = H, $R_9$ = H) | H | H | $OCH_3$ | $OCH_3$ | |

TABLE 2

| J | W₁ | Q | General Formula 2 R | R₁ | X | Y | m.p.(°C.) |
|---|----|---|---|----|---|---|---|
| J-1 | S | Q-1 (R₇ = H, R₈ = H) | H | H | CH₃ | CH₃ | |
| J-2 | S | Q-1 (R₇ = H, R₈ = H) | H | H | CH₃ | CH₃ | |
| J-1 | S | Q-1 (R₇ = H, R₈ = H) | H | H | OCH₃ | OCH₃ | |
| J-2 | S | Q-1 (R₇ = H, R₈ = H) | CH₃ | H | OCH₃ | OCH₃ | |
| J-1 | S | Q-1 (R₇ = H, R₈ = H) | CH₃ | H | OCH₃ | CH₃ | |
| J-2 | S | Q-1 (R₇ = H, R₈ = H) | H | 5-CH₃ | OCH₃ | OCH₃ | |
| J-1 | S | Q-1 (R₇ = H, R₈ = H) | H | 5-CH₂F | OCH₃ | OCH₃ | |
| J-2 | S | Q-1 (R₇ = H, R₈ = H) | H | 5-CH₂CH₂Br | OCH₃ | OCH₃ | |
| J-1 | O | Q-1 (R₇ = H, R₈ = H) | H | 5-CH(CH₃)(CH₂Cl) | OCH₃ | OCH₃ | |
| J-2 | S | Q-1 (R₇ = H, R₈ = H) | H | 4-NH₂ | OCH₃ | OCH₃ | |
| J-1 | S | Q-1 (R₇ = H, R₈ = H) | H | 4-N(CH₃)₂ | OCH₃ | OCH₃ | |
| J-3 | S | Q-1 (R₇ = H, R₈ = H) | H | 5-Cl | OCH₃ | OCH₃ | |
| J-1 | S | Q-1 (R₇ = H, R₈ = H) | H | 4-F | OCH₃ | OCH₃ | |
| J-2 | S | Q-1 (R₇ = H, R₈ = H) | H | 5-I | OCH₃ | OCH₃ | |
| J-1 | S | Q-1 (R₇ = H, R₈ = H) | H | 4-NO₂ | OCH₃ | OCH₃ | |
| J-2 | S | Q-1 (R₇ = H, R₈ = H) | H | 5-CF₃ | OCH₃ | OCH₃ | |
| J-1 | O | Q-1 (R₇ = H, R₈ = H) | H | H | OCH₃ | CH₂CH₃ | |
| J-2 | S | Q-1 (R₇ = H, R₈ = H) | H | H | OCH₃ | CH(CH₃)₂ | |
| J-1 | O | Q-1 (R₇ = H, R₈ = H) | H | H | OCH₃ | (CH₂)₃CH₃ | |
| J-2 | S | Q-1 (R₇ = H, R₈ = H) | H | H | OCH₃ | OCH₂CH₃ | |
| J-1 | S | Q-1 (R₇ = H, R₈ = H) | H | H | OCH₃ | OCH(CH₃)₂ | |
| J-2 | S | Q-1 (R₇ = H, R₈ = H) | H | H | OCH₃ | O(CH₂)₃CH₃ | |
| J-1 | S | Q-1 (R₇ = H, R₈ = H) | H | H | OCH₂CH₂F | OCH₃ | |
| J-2 | S | Q-1 (R₇ = H, R₈ = H) | H | H | OCH₂CHF₂ | OCH₃ | |
| J-1 | S | Q-1 (R₇ = H, R₈ = H) | H | H | OCH₂CF₃ | OCH₃ | |
| J-2 | S | Q-1 (R₇ = H, R₈ = H) | H | H | OCH(CH₃)(CH₂Cl) | OCH₃ | |
| J-1 | S | Q-1 (R₇ = H, R₈ = H) | H | H | O(CH₂)₃CH₂Br | OCH₃ | |
| J-2 | S | Q-1 (R₇ = H, R₈ = H) | H | H | CH₂F | OCH₃ | |
| J-1 | S | Q-1 (R₇ = H, R₈ = H) | H | H | CH₂Cl | OCH₃ | |
| J-2 | O | Q-1 (R₇ = H, R₈ = H) | H | H | CH₂Br | OCH₃ | |
| J-1 | S | Q-1 (R₇ = H, R₈ = H) | H | H | CF₃ | OCH₃ | |
| J-2 | S | Q-1 (R₇ = H, R₈ = H) | H | H | CH₂CH₂Br | OCH₃ | |
| J-1 | S | Q-1 (R₇ = H, R₈ = H) | H | H | CH(CH₃)(CH₂Cl) | OCH₃ | |
| J-2 | S | Q-1 (R₇ = H, R₈ = H) | H | H | (CH₂)₃CH₂I | OCH₃ | |
| J-1 | NH | Q-1 (R₇ = H, R₈ = H) | H | H | SCH₃ | OCH₃ | |
| J-2 | S | Q-1 (R₇ = H, R₈ = H) | H | H | SCH₂CH₃ | OCH₃ | |
| J-1 | S | Q-1 (R₇ = H, R₈ = H) | H | H | SCH(CH₃)₂ | OCH₃ | |
| J-2 | O | Q-1 (R₇ = H, R₈ = H) | H | H | S(CH₂)₃CH₃ | OCH₃ | |
| J-1 | S | Q-1 (R₇ = H, R₈ = H) | H | H | SCHF₂ | OCH₃ | |
| J-2 | S | Q-1 (R₇ = H, R₈ = H) | H | H | SCH₂CH₂Br | OCH₃ | |
| J-1 | S | Q-1 (R₇ = H, R₈ = H) | H | H | SCH(CH₃)(CH₂Br) | OCH₃ | |
| J-2 | O | Q-1 (R₇ = H, R₈ = H) | H | H | S(CH₂)₃CH₂F | OCH₃ | |
| J-1 | S | Q-1 (R₇ = H, R₈ = H) | H | H | OCH₃ | CH₂OCH₃ | |
| J-2 | S | Q-1 (R₇ = H, R₈ = H) | H | H | OCH₃ | CH₂CH₂OCH(CH₃)₂ | |
| J-1 | S | Q-1 (R₇ = H, R₈ = H) | H | H | OCH₃ | CH(CH₃)(CH₂OCH₃) | |
| J-3 | S | Q-1 (R₇ = H, R₈ = H) | H | H | OCH₃ | (CH₂)₄CH₂OCH₂CH₃ | |
| J-2 | S | Q-1 (R₇ = H, R₈ = H) | H | H | OCH₂O(CH₂)₃CH₃ | OCH₃ | |
| J-1 | O | Q-1 (R₇ = H, R₈ = H) | H | H | OCH₂CH₂OCH(CH₃)₂ | OCH₃ | |
| J-2 | S | Q-1 (R₇ = H, R₈ = H) | H | H | OCH(CH₃)(CH₂OCH₃) | OCH₃ | |
| J-1 | O | Q-1 (R₇ = H, R₈ = H) | H | H | O(CH₂)₄CH₂OCH₂CH₃ | OCH₃ | |
| J-1 | S | Q-1 (R₇ = H, R₈ = H) | H | H | OCH₃ | NH₂ | |

TABLE 2-continued

| | | | General Formula 2 | | | | |
|---|---|---|---|---|---|---|---|
| J | W₁ | Q | R | R₁ | X | Y | m.p.(°C.) |
| J-2 | S | Q-1 (R₇ = H, R₈ = H) | H | H | OCH₃ | NHCH₃ | |
| J-1 | S | Q-1 (R₇ = H, R₈ = H) | H | H | OCH₃ | NHCH₂CH₃ | |
| J-2 | S | Q-1 (R₇ = H, R₈ = H) | H | H | OCH₃ | NHCH(CH₃)₂ | |
| J-3 | S | Q-1 (R₇ = H, R₈ = H) | H | H | OCH₃ | N(CH₃)₂ | |
| J-1 | S | Q-1 (R₇ = H, R₈ = H) | H | H | OCH₃ | N(CH₃)(CH₂CH₃) | |
| J-2 | S | Q-1 (R₇ = H, R₈ = H) | H | H | OCH₃ | N(CH₃)(CH(CH₃)₂) | |
| J-1 | O | Q-1 (R₇ = H, R₈ = H) | H | H | OCH₃ | (CH₂)₄CH₂OCH₂CH₃ | |
| J-1 | S | Q-1 (R₇ = H, R₈ = H) | H | H | H | OCH₃ | |
| J-2 | S | Q-1 (R₇ = H, R₈ = H) | H | H | OCH₃ | OCH₂CH=CH₂ | |
| J-1 | S | Q-1 (R₇ = H, R₈ = H) | H | H | OCH₃ | OCH₂C(CH₃)=CH₂ | |
| J-2 | S | Q-1 (R₇ = H, R₈ = H) | H | H | OCH₃ | OCH₂C≡CH | |
| J-1 | S | Q-1 (R₇ = H, R₈ = H) | H | H | OCH₃ | OCH₂C≡CCH₃ | |
| J-2 | S | Q-1 (R₇ = H, R₈ = H) | H | H | OCH₃ | CH₂S(CH₂)₃CH₃ | |
| J-3 | S | Q-1 (R₇ = H, R₈ = H) | H | H | OCH₃ | CH₂CH₂SCH(CH₃)₂ | |
| J-1 | S | Q-1 (R₇ = H, R₈ = H) | H | H | OCH₃ | CH(CH₃)(CH₂SCH₃) | |
| J-2 | S | Q-1 (R₇ = H, R₈ = H) | H | H | OCH₃ | (CH₂)₄CH₂SCH₂CH₃ | |
| J-1 | O | Q-1 (R₇ = H, R₈ = H) | H | H | OCH₃ | cyclopropyl | |
| J-2 | S | Q-1 (R₇ = H, R₈ = H) | H | H | OCH₃ | 2-methylcyclopropyl | |
| J-1 | S | Q-1 (R₇ = H, R₈ = H) | H | H | OCH₃ | cyclopentyl | |
| J-2 | S | Q-1 (R₇ = H, R₈ = H) | H | H | OCH₃ | C≡CH | |
| J-1 | S | Q-1 (R₇ = H, R₈ = H) | H | H | OCH₃ | C≡CCH₃ | |
| J-2 | S | Q-1 (R₇ = H, R₈ = H) | H | H | OCH₃ | —CHO | |
| J-1 | S | Q-1 (R₇ = H, R₈ = H) | H | H | OCH₃ | —COCH₃ | |
| J-2 | S | Q-1 (R₇ = H, R₈ = H) | H | H | OCH₃ | —CH(OCH₃)₂ | |
| J-3 | S | Q-1 (R₇ = H, R₈ = H) | H | H | OCH₃ | —CH(SCH₃)(OCH₂CH₃) | |
| J-1 | S | Q-1 (R₇ = H, R₈ = H) | H | H | OCH₃ | —C(CH₃)(SCH₃) | |
| J-2 | O | Q-1 (R₇ = H, R₈ = H) | H | H | OCH₃ | —CH(SCH₂CH₃)₂ | |
| J-1 | S | Q-1 (R₇ = H, R₈ = H) | H | H | OCH₃ | 1,3-dioxolan-2-yl | |
| J-2 | S | Q-1 (R₇ = H, R₈ = H) | H | H | OCH₃ | 2-methyl-1,3-oxa-thiolan-2-yl | |
| J-1 | S | Q-1 (R₇ = H, R₈ = H) | H | H | OCH₃ | 1,3-oxathian-2-yl | |
| J-2 | S | Q-1 (R₇ = H, R₈ = H) | H | H | OCH₃ | 2-methyl-1,3-dithian-2-yl | |
| J-1 | S | Q-1 (R₇ = H, R₈ = H) | H | H | OCH₃ | 4-methyl-1,3-dioxolan-2-yl | |
| J-2 | S | Q-1 (R₇ = H, R₈ = H) | H | H | OCH₃ | 4-methyl-1,3-oxathiolan-2-yl | |
| J-1 | S | Q-1 (R₇ = H, R₈ = H) | H | H | OCH₃ | 2,4-dimethyl-1,3-dithiolan-2-yl | |
| J-2 | S | Q-1 (R₇ = H, R₈ = CH₃) | H | H | OCH₃ | N(OCH₃)(CH₃)₂ | |
| J-1 | S | Q-1 (R₇ = H, R₈ = CH₃) | H | H | OCH₃ | OCH₃ | |
| J-2 | S | Q-1 (R₇ = H, R₈ = CH₃) | H | H | CH₃ | CH₃ | |
| J-1 | O | Q-1 (R₇ = H, R₈ = CH₂CH₃) | H | H | CH₃ | OCH₃ | |
| J-2 | S | Q-1 (R₇ = H, R₈ = CH₂CH₃) | H | H | OCH₃ | OCH₃ | |
| J-1 | S | Q-1 (R₇ = H, R₈ = CH(CH₃)₂) | H | H | OCH₃ | OCH₃ | |
| J-2 | S | Q-1 (R₇ = H, R₈ = (CH₂)₃CH₃) | H | H | OCH₃ | OCH₃ | |
| J-3 | S | Q-1 (R₇ = CH₃, R₈ = CH₃) | H | H | OCH₃ | OCH₃ | |
| J-1 | S | Q-2 (R₇ = H, R₈ = H) | CH₃ | H | OCH₃ | OCH₃ | |
| J-2 | O | Q-2 (R₇ = H, R₈ = CH₃) | H | 5-CH₃ | OCH₃ | OCH₃ | |
| J-1 | S | Q-3 (R₇ = H, R₈ = H) | H | H | OCH₃ | OCH₃ | |

TABLE 2-continued

| | | | General Formula 2 | | | | |
|---|---|---|---|---|---|---|---|
| J | W$_1$ | Q | R | R$_1$ | X | Y | m.p.(°C.) |
| J-2 | S | Q-3 (R$_7$ = C$_2$H$_5$, R$_8$ = H) | H | H | OCH$_3$ | CH$_3$ | |
| J-1 | O | Q-3 (R$_7$ = CH$_3$, R$_8$ = H) | H | 5-Cl | OCH$_3$ | CH$_3$ | |
| J-2 | S | Q-4 (R$_7$ = H, R$_8$ = H, R$_3$ = CH$_3$) | H | H | CH$_3$ | OCH$_3$ | |
| J-3 | S | Q-4 (R$_7$ = H, R$_8$ = H, R$_3$ = C$_2$H$_5$) | H | H | OCH$_3$ | OCH$_3$ | |
| J-2 | S | Q-4 (R$_7$ = H, R$_8$ = H, R$_3$ = i-C$_3$H$_7$) | H | 5-CH$_3$ | OCH$_3$ | OCH$_3$ | |
| J-1 | S | Q-5 (R$_7$ = H, R$_8$ = H, R$_3$ = H) | H | H | CH$_3$ | OCH$_3$ | |
| J-1 | S | Q-5 (R$_7$ = H, R$_8$ = H, R$_3$ = CH$_3$) | H | H | CH$_3$ | OCH$_3$ | |
| J-2 | S | Q-5 (R$_7$ = CH$_3$, R$_8$ = H, R$_3$ = CH$_3$) | H | H | CH$_3$ | OCH$_3$ | |
| J-1 | S | Q-6 (R$_7$ = H, R$_8$ = H, R$_3$ = CH$_3$) | CH$_3$ | H | CH$_3$ | OCH$_3$ | |
| J-2 | S | Q-6 (R$_7$ = C$_2$H$_5$, R$_8$ = H, R$_3$ = C$_2$H$_5$) | H | H | OCH$_3$ | OCH$_3$ | |
| J-2 | O | Q-7 (R$_7$ = H, R$_8$ = H, R$_9$ = H) | H | H | OCH$_3$ | OCH$_3$ | |
| J-1 | S | Q-7 (R$_7$ = i-C$_3$H$_7$, R$_8$ = H, R$_9$ = CH$_3$) | H | 5-CH$_3$ | OCH$_3$ | OCH$_3$ | |
| J-3 | S | Q-8 (R$_7$ = H, R$_8$ = H, R$_2$ = H) | H | H | OCH$_3$ | OCH$_3$ | |
| J-1 | S | Q-8 (R$_7$ = H, R$_8$ = H, R$_2$ = OCH$_3$) | H | H | OCH$_3$ | OCH$_3$ | |
| J-1 | S | Q-8 (R$_7$ = CH$_3$, R$_8$ = H, R$_2$ = OCH(CH$_3$)CH$_2$CH$_3$) | H | H | OCH$_3$ | OCH$_3$ | |
| J-1 | S | Q-9 (R$_7$ = H, R$_8$ = H, R$_2$ = H) | H | 5-Cl | OCH$_3$ | OCH$_3$ | |
| J-2 | S | Q-9 (R$_7$ = CH$_3$, R$_8$ = H, R$_2$ = CH$_3$) | CH$_3$ | 5-CH$_3$ | OCH$_3$ | OCH$_3$ | |
| J-1 | S | Q-9 (R$_7$ = H, R$_8$ = H, R$_2$ = Cl) | H | H | OCH$_3$ | OCH$_3$ | |
| J-1 | S | Q-10 (R$_7$ = CH$_3$, R$_8$ = H) | H | 5-Cl | OCH$_3$ | OCH$_3$ | |
| J-1 | O | Q-10 (R$_7$ = H, R$_8$ = CH$_3$) | H | H | CH$_3$ | CH$_3$ | |
| J-1 | S | Q-10 (R$_7$ = H, R$_8$ = H) | H | 5-CH$_3$ | CH$_3$ | CH$_3$ | |
| J-2 | S | Q-11 (R$_7$ = n-C$_4$H$_9$, R$_8$ = H) | H | H | CH$_3$ | OCH$_3$ | |
| J-1 | S | Q-11 (R$_7$ = CH$_3$, R$_8$ = CH$_3$) | H | 5-Cl | OCH$_3$ | OCH$_3$ | |
| J-2 | S | Q-12 (R$_7$ = H, R$_8$ = H) | H | H | OCH$_3$ | OCH$_3$ | |
| J-1 | S | Q-12 (R$_7$ = H, R$_8$ = C$_2$H$_5$) | H | 5-CH$_3$ | OCH$_3$ | OCH$_3$ | |
| J-2 | S | Q-13 (R$_7$ = H, R$_8$ = H, R$_3$ = H) | H | H | OCH$_3$ | OCH$_3$ | |
| J-1 | O | Q-13 (R$_7$ = CH$_3$, R$_8$ = H, R$_3$ = CH$_3$) | H | 5-Cl | OCH$_3$ | OCH$_3$ | |
| J-1 | S | Q-14 (R$_7$ = H, R$_8$ = H, R$_3$ = CH$_3$) | H | H | OCH$_3$ | OCH$_3$ | |
| J-2 | S | Q-14 (R$_7$ = CH$_3$, R$_8$ = CH$_3$, R$_3$ = C$_2$H$_5$) | H | 5-CH$_3$ | CH$_3$ | OCH$_3$ | |
| J-1 | S | Q-15 (R$_7$ = H, R$_8$ = H, R$_3$ = CH$_3$) | CH$_3$ | H | OCH$_3$ | OCH$_3$ | |
| J-1 | S | Q-15 (R$_7$ = C$_2$H$_5$, R$_8$ = H, R$_3$ = CH$_3$) | H | H | OCH$_3$ | OCH$_3$ | |
| J-2 | S | Q-15 (R$_7$ = CH$_3$, R$_8$ = CH$_3$, R$_3$ = CH$_3$) | H | 5-Cl | OCH$_3$ | OCH$_3$ | |
| J-1 | S | Q-16 (R$_7$ = H, R$_8$ = H, R$_9$ = H) | H | H | OCH$_3$ | OCH$_3$ | |
| J-2 | O | Q-16 (R$_7$ = CH$_3$, R$_8$ = H, R$_9$ = H) | H | 5-CH$_3$ | OCH$_3$ | OCH$_3$ | |
| J-3 | S | Q-16 (R$_7$ = CH$_3$, R$_8$ = CH$_3$, R$_9$ = H) | H | H | OCH$_3$ | OCH$_3$ | |
| J-1 | S | Q-17 (R$_7$ = H, R$_8$ = H, R$_2$ = H) | H | 5-Cl | CH$_3$ | CH$_3$ | |
| J-2 | S | Q-17 (R$_7$ = CH$_3$, R$_8$ = H, R$_2$ = CH$_3$) | H | 5-CH$_3$ | OCH$_3$ | CH$_3$ | |
| J-1 | S | Q-17 (R$_7$ = H, R$_8$ = H, R$_2$ = C$_2$H$_5$) | H | H | CH$_3$ | OCH$_3$ | |
| J-2 | S | Q-18 (R$_7$ = H, R$_8$ = H, R$_2$ = H) | H | H | OCH$_3$ | OCH$_3$ | |
| J-1 | S | Q-18 (R$_7$ = H, R$_8$ = OH$_2$H$_5$, R$_2$ = H) | H | 5-Cl | OCH$_3$ | OCH$_3$ | |
| J-3 | S | Q-18 (R$_7$ = H, R$_8$ = OCH(CH$_3$)$_2$, R$_2$ = CH$_3$) | H | 5-CH$_3$ | CH$_3$ | CH$_3$ | |
| J-2 | S | Q-19 (R$_7$ = H, R$_8$ = H) | H | H | CH$_3$ | CH$_3$ | |
| J-1 | S | Q-19 (R$_7$ = CH$_3$, R$_8$ = CH$_3$) | H | H | CH$_3$ | OCH$_3$ | |
| J-2 | NCH$_3$ | Q-19 (R$_7$ = CH$_3$, R$_8$ = H) | H | H | OCH$_3$ | OCH$_3$ | |
| J-1 | S | Q-20 (R$_7$ = H, R$_8$ = H) | H | H | OCH$_3$ | OCH$_3$ | |

TABLE 2-continued

| | | | General Formula 2 | | | | |
|---|---|---|---|---|---|---|---|
| J | W$_1$ | Q | R | R$_1$ | X | Y | m.p.(°C.) |
| J-2 | O | Q-20 (R$_7$ = CH$_3$, R$_8$ = H) | CH$_3$ | H | CH$_3$ | OCH$_3$ | |
| J-2 | S | Q-20 (R$_7$ = H, R$_8$ = CH$_3$) | H | H | OCH$_3$ | OCH$_3$ | |
| J-2 | S | Q-21 (R$_7$ = CH$_3$, R$_8$ = H) | H | H | OCH$_3$ | OCH$_3$ | |
| J-1 | S | Q-21 (R$_7$ = H, R$_8$ = CH$_3$) | H | H | OCH$_3$ | OCH$_3$ | |
| J-2 | S | Q-21 (R$_7$ = H, R$_8$ = H, R$_3$ = CH$_3$) | H | 5-CH$_3$ | OCH$_3$ | OCH$_3$ | |
| J-1 | S | Q-22 (R$_7$ = H, R$_8$ = H, R$_3$ = CH$_3$) | H | H | OCH$_3$ | OCH$_3$ | |
| J-2 | S | Q-22 (R$_7$ = CH$_3$, R$_8$ = CH$_3$, R$_3$ = C$_2$H$_5$) | H | H | OCH$_3$ | OCH$_3$ | |
| J-3 | S | Q-22 (R$_7$ = H, R$_8$ = H, R$_3$ = CH$_3$) | H | 5-Cl | OCH$_3$ | OCH$_3$ | |
| J-1 | O | Q-23 (R$_7$ = CH$_3$, R$_8$ = H, R$_3$ = CH$_3$) | CH$_3$ | H | OCH$_3$ | OCH$_3$ | |
| J-2 | S | Q-23 (R$_7$ = H, R$_8$ = H, R$_3$ = CH$_3$) | H | 5-CH$_3$ | OCH$_3$ | OCH$_3$ | |
| J-2 | S | Q-23 (R$_7$ = H, R$_8$ = H, R$_3$ = n-C$_4$H$_9$) | H | H | CH$_3$ | CH$_3$ | |
| J-2 | S | Q-24 (R$_7$ = CH$_3$, R$_8$ = CH$_3$, R$_3$ = C$_2$H$_5$) | H | 5-Cl | CH$_3$ | CH$_3$ | |
| J-1 | S | Q-24 (R$_7$ = CH$_3$, R$_8$ = CH$_3$, R$_3$ = i-C$_3$H$_7$) | H | H | OCH$_3$ | OCH$_3$ | |
| J-2 | S | Q-25 (R$_7$ = H, R$_8$ = H, R$_9$ = H) | H | 5-CH$_3$ | OCH$_3$ | OCH$_3$ | |
| J-1 | S | Q-25 (R$_7$ = H, R$_8$ = H, R$_9$ = C$_2$H$_5$) | H | H | OCH$_3$ | OCH$_3$ | |
| J-1 | S | Q-25 (R$_7$ = H, R$_8$ = H) | H | H | OCH$_3$ | OCH$_3$ | |
| J-3 | S | Q-26 (R$_7$ = CH$_3$, R$_8$ = H) | H | H | OCH$_3$ | OCH$_3$ | |
| J-1 | S | Q-26 (R$_7$ = CH$_3$, R$_8$ = CH$_3$) | H | H | OCH$_3$ | OCH$_3$ | |
| J-1 | O | Q-27 (R$_7$ = H, R$_8$ = H) | CH$_3$ | H | OCH$_3$ | OCH$_3$ | |
| J-2 | S | Q-27 (R$_7$ = CH$_3$, R$_8$ = CH$_3$) | H | H | OCH$_3$ | OCH$_3$ | |
| J-1 | S | Q-28 (R$_7$ = CH$_3$, R$_8$ = H) | H | H | CH$_3$ | CH$_3$ | |
| J-2 | S | Q-28 (R$_7$ = H, R$_8$ = CH$_3$) | H | 5-CH$_3$ | CH$_3$ | CH$_3$ | |
| J-1 | S | Q-29 (R$_7$ = CH$_3$, R$_8$ = H) | H | H | CH$_3$ | CH$_3$ | |
| J-2 | S | Q-29 (R$_7$ = H, R$_8$ = CH$_3$) | H | H | OCH$_3$ | OCH$_3$ | |
| J-3 | S | Q-30 (R$_7$ = CH$_3$, R$_8$ = H) | H | 5-Cl | OCH$_3$ | OCH$_3$ | |
| J-1 | O | Q-30 (R$_7$ = CH$_3$, R$_8$ = CH$_3$) | CH$_3$ | 5-CH$_3$ | OCH$_3$ | OCH$_3$ | |
| J-1 | S | Q-30 (R$_7$ = C$_2$H$_5$, R$_8$ = H) | H | H | OCH$_3$ | OCH$_3$ | |
| J-2 | S | Q-31 (R$_7$ = H, R$_8$ = H) | H | H | OCH$_3$ | OCH$_3$ | |
| J-2 | S | Q-31 (R$_7$ = i-C$_3$H$_7$, R$_8$ = H) | H | 5-Cl | OCH$_3$ | OCH$_3$ | |
| J-1 | S | Q-31 (R$_7$ = H, R$_8$ = n-C$_4$H$_9$) | H | H | OCH$_3$ | OCH$_3$ | |
| J-1 | S | Q-32 (R$_7$ = H, R$_8$ = H, R$_3$ = CH$_3$) | H | H | OCH$_3$ | OCH$_3$ | |
| J-1 | S | Q-32 (R$_7$ = CH$_3$, R$_8$ = H, R$_3$ = CH$_3$) | H | 5-CH$_3$ | OCH$_3$ | OCH$_3$ | |
| J-2 | S | Q-32 (R$_7$ = H, R$_8$ = CH$_3$, R$_3$ = C$_2$H$_5$) | H | H | OCH$_3$ | OCH$_3$ | |
| J-1 | S | Q-33 (R$_7$ = H, R$_8$ = H, R$_3$ = CH$_3$) | H | 5-CH$_3$ | OCH$_3$ | OCH$_3$ | |
| J-3 | O | Q-33 (R$_7$ = CH$_3$, R$_8$ = CH$_3$, R$_3$ = i-C$_3$H$_7$) | H | H | OCH$_3$ | OCH$_3$ | |
| J-1 | S | Q-33 (R$_7$ = C$_2$H$_5$, R$_8$ = H, R$_3$ = n-C$_4$H$_9$) | H | 5-Cl | OCH$_3$ | OCH$_3$ | |
| J-1 | S | Q-34 (R$_7$ = H, R$_8$ = H, R$_3$ = H) | H | H | OCH$_3$ | OCH$_3$ | |
| J-2 | O | Q-34 (R$_7$ = i-C$_3$H$_7$, R$_8$ = H, R$_3$ = CH$_3$) | CH$_3$ | H | OCH$_3$ | OCH$_3$ | |
| J-1 | S | Q-34 (R$_7$ = H, R$_8$ = n-C$_4$H$_9$, R$_3$ = CH$_3$) | H | H | OCH$_3$ | OCH$_3$ | |
| J-2 | S | Q-35 (R$_7$ = H, R$_8$ = H, R$_9$ = H) | H | 5-CH$_3$ | OCH$_3$ | OCH$_3$ | |
| J-1 | S | Q-35 (R$_7$ = CH$_3$, R$_8$ = CH$_3$, R$_9$ = CH$_3$) | H | H | OCH$_3$ | OCH$_3$ | |
| J-1 | S | Q-36 (R$_7$ = H, R$_8$ = H, R$_2$ = H) | H | H | OCH$_3$ | OCH$_3$ | |
| J-1 | S | Q-36 (R$_7$ = CH$_3$, R$_8$ = H, R$_2$ = CH$_3$) | H | 5-CH$_3$ | OCH$_3$ | OCH$_3$ | |
| J-2 | S | Q-36 (R$_7$ = H, R$_8$ = H, R$_2$ = C$_2$H$_5$) | H | 5-Cl | OCH$_3$ | OCH$_3$ | |
| J-2 | O | Q-37 (R$_7$ = H, R$_8$ = H, R$_2$ = H) | H | H | OCH$_3$ | OCH$_3$ | |

TABLE 2-continued

General Formula 2

| J | W₁ | Q | R | R₁ | X | Y | m.p.(°C.) |
|---|---|---|---|---|---|---|---|
| J-2 | S | Q-37 (R₇ = H, R₈ = H, R₂ = H) | H | H | OCH₃ | CH₃ | 162-165 |
| J-3 | S | Q-37 (R₇ = H, R₈ = H, R₂ = i-C₃H₇) | CH₃ | H | OCH₃ | OCH₃ | |
| J-1 | S | Q-37 (R₇ = H, R₈ = H, R₂ = n-C₄H₉) | H | 5-CH₃ | OCH₃ | OCH₃ | |
| J-2 | S | Q-38 (R₇ = H, R₈ = H, R₂ = OCF₂H) | H | H | OCH₃ | CH₃ | |
| J-1 | S | Q-38 (R₇ = CH₃, R₈ = H, R₂ = OCH₂CH₂F) | H | H | CH₃ | CH₃ | |
| J-2 | S | Q-39 (R₇ = H, R₈ = H, R₂ = Cl) | H | 5-Cl | CH₃ | CH₃ | |
| J-1 | S | Q-39 (R₇ = H, R₈ = H, R₉ = H) | H | H | OCH₃ | OCH₃ | |
| J-2 | S | Q-39 (R₇ = C₂H₅, R₈ = H, R₉ = H) | H | 5-CH₃ | OCH₃ | OCH₃ | |
| J-1 | S | Q-40 (R₇ = H, R₈ = H, R₉ = CH₃) | H | H | OCH₃ | OCH₃ | |
| J-1 | O | Q-40 (R₇ = H, R₈ = H) | H | H | CH₃ | CH₃ | |
| J-2 | S | Q-40 (R₇ = CH₃, R₈ = H) | H | H | OCH₃ | OCH₃ | |
| J-3 | S | Q-41 (R₇ = H, R₈ = CH₃) | H | H | OCH₃ | OCH₃ | |
| J-2 | S | Q-41 (R₇ = CH₃, R₈ = CH₃) | H | H | OCH₃ | OCH₃ | |
| J-1 | S | Q-41 (R₇ = H, R₈ = C₂H₅) | H | 5-CH₃ | OCH₃ | OCH₃ | |
| J-2 | S | Q-42 (R₇ = CH₃, R₈ = H) | H | 5-Cl | OCH₃ | OCH₃ | |
| J-1 | S | Q-42 (R₇ = H, R₈ = H) | H | H | OCH₃ | OCH₃ | |
| J-2 | S | Q-42 (R₇ = CH₃, R₈ = CH₃) | H | H | OCH₃ | OCH₃ | |
| J-1 | S | Q-42 (R₇ = C₂H₅, R₈ = C₂H₅) | H | H | OCH₃ | CH₃ | |
| J-2 | S | Q-43 (R₇ = H, R₈ = H, R₃ = H) | H | H | OCH₃ | CH₃ | |
| J-1 | S | Q-43 (R₇ = CH₃, R₈ = H, R₃ = CH₃) | H | H | OCH₃ | OCH₃ | |
| J-2 | S | Q-43 (R₇ = H, R₈ = H, R₃ = CH₃) | H | 5-Cl | OCH₃ | OCH₃ | |
| J-1 | S | Q-44 (R₇ = CH₃, R₈ = H, R₃ = C₂H₅) | CH₃ | H | OCH₃ | OCH₃ | |
| J-2 | S | Q-44 (R₇ = H, R₈ = CH₃, R₃ = CH₃) | H | H | OCH₃ | OCH₃ | |
| J-3 | S | Q-45 (R₇ = C₂H₅, R₈ = H, R₃ = CH₃) | H | 5-CH₃ | OCH₃ | OCH₃ | |
| J-1 | S | Q-45 (R₇ = CH₃, R₈ = CH₃, R₃ = CH₃) | H | 5-Cl | OCH₃ | CH₃ | |
| J-2 | S | Q-46 (R₇ = H, R₈ = H, R₉ = H) | H | H | OCH₃ | CH₃ | |
| J-1 | O | Q-46 (R₇ = CH₃, R₈ = H, R₉ = H) | H | 5-CH₃ | CH₃ | CH₃ | |
| J-2 | S | Q-46 (R₇ = CH₃, R₈ = H, R₉ = H) | H | H | CH₃ | OCH₃ | |
| J-1 | S | Q-47 (R₇ = H, R₈ = H, R₂ = CH₃) | H | H | OCH₃ | OCH₃ | |
| J-2 | S | Q-47 (R₇ = H, R₈ = H, R₂ = C₂H₅) | H | H | OCH₃ | OCH₃ | |
| J-3 | NH | Q-48 (R₇ = H, R₈ = CH₃, R₂ = H) | CH₃ | H | CH₃ | CH₃ | |
| J-1 | S | Q-48 (R₇ = H, R₈ = C₂H₅, R₂ = C₂H₅) | H | H | OCH₃ | OCH₃ | |
| J-2 | S | Q-49 (R₇ = CH₃, R₈ = H, R₂ = H) | H | 5-CH₃ | OCH₃ | OCH₃ | |
| J-1 | S | Q-49 (R₇ = CH₃, R₈ = H, R₂ = CH₃) | H | H | OCH₃ | OCH₃ | |
| J-2 | O | Q-50 (R₇ = CH₃, R₈ = H, R₂ = H) | H | H | CH₃ | OCH₃ | |
| J-1 | S | Q-50 (R₇ = CH₃, R₈ = H, R₂ = CH₃) | H | 5-Cl | OCH₃ | OCH₃ | |
| J-2 | S | Q-50 (R₇ = CH₃, R₈ = H, R₂ = H) | CH₃ | 5-CH₃ | OCH₃ | OCH₃ | |
| J-1 | S | Q-51 (R₇ = H, R₈ = H, R₉ = H) | H | H | OCH₃ | OCH₃ | |
| J-2 | S | Q-51 (R₇ = H, R₈ = H, R₉ = s-C₄H₉) | H | 5-CH₃ | OCH₃ | OCH₃ | |
| J-1 | S | Q-52 (R₇ = H, R₈ = H, R₉ = H) | H | H | OCH₃ | OCH₃ | |
| J-3 | S | Q-52 (R₇ = H, R₈ = H, R₉ = CH₃) | H | 5-Cl | OCH₃ | CH₃ | |
| J-2 | S | Q-53 (R₇ = H, R₈ = CH₃, R₉ = H) | H | H | CH₃ | CH₃ | |
| J-1 | O | Q-53 (R₇ = H, R₈ = H, R₉ = CH₃) | H | 5-CH₃ | OCH₃ | OCH₃ | |

TABLE 2-continued

General Formula 2

| J | W₁ | Q | R | R₁ | X | Y | m.p.(°C.) |
|---|----|---|---|----|----|---|---|
| J-2 | S | Q-54 (R₇ = H, R₈ = H, R₉ = H) | H | H | OCH₃ | OCH₃ | |
| J-2 | S | Q-54 (R₇ = CH₃, R₈ = H, R₉ = H) | H | H | CH₃ | OCH₃ | |
| J-2 | S | Q-54 (R₇ = H, R₈ = H, R₉ = i-C₃H₇) | H | H | CH₃ | OCH₃ | |
| J-1 | S | Q-55 (R₇ = H, R₈ = H, R₉ = CH₃, R₃ = H) | CH₃ | H | CH₃ | OCH₃ | |
| J-3 | S | Q-55 (R₇ = H, R₈ = H, R₉ = s-C₄H₉, R₃ = H) | H | H | CH₃ | OCH₃ | |
| J-1 | S | Q-56 (R₇ = H, R₈ = H, R₉ = H, R₃ = C₂H₅) | H | H | OCH₃ | OCH₃ | |
| J-2 | S | Q-56 (R₇ = CH₃, R₈ = H, R₉ = CH₃, R₃ = H) | H | 5-CH₃ | OCH₃ | OCH₃ | |
| J-1 | O | Q-56 (R₇ = H, R₈ = H, R₉ = H, R₃ = i-C₃H₇) | H | H | OCH₃ | OCH₃ | |
| J-2 | S | Q-57 (R₇ = CH₃, R₈ = H, R₉ = CH₃, R₉ = CH₃, R₃ = H) | H | 5-CH₃ | OCH₃ | OCH₃ | |
| J-1 | S | Q-57 (R₇ = H, R₈ = H, R₉ = CH₃, R₃ = CH₃) | H | 5-Cl | OCH₃ | OCH₃ | |
| J-2 | S | Q-58 (R₇ = H, R₉ = H, R₃ = H) | CH₃ | H | OCH₃ | OCH₃ | |
| J-1 | S | Q-58 (R₇ = CH₃, R₈ = H, R₉ = H, R₃ = H) | H | 5-CH₃ | OCH₃ | OCH₃ | |
| J-3 | S | Q-58 (R₇ = H, R₈ = H, R₉ = H, R₁₀ = CH₃) | H | H | OCH₃ | CH₃ | |
| J-2 | S | Q-59 (R₇ = CH₃, R₈ = H, R₉ = H, R₁₀ = H) | H | H | OCH | CH₃ | |
| J-3 | S | Q-59 (R₇ = H, R₈ = H, R₉ = H, R₁₀ = s-C₄H₉) | H | 5-Cl | OCH₃ | OCH₃ | 118-128 |
| J-2 | S | Q-60 (R₇ = H, R₈ = H, R₉ = H, R₂ = H) | H | H | CH₃ | OCH₃ | 120-133 |
| J-1 | O | Q-60 (R₇ = CH₃, R₈ = H, R₉ = H, R₂ = O(CH₂)₃CH₂Br) | H | 5-CH₃ | CH₃ | OCH₃ | |
| J-2 | S | Q-60 (R₇ = H, R₈ = H, R₉ = H, R₂ = Br) | H | H | OCH₃ | OCH₃ | |
| J-1 | S | Q-61 (R₇ = H, R₈ = H, R₉ = H, R₂ = H) | H | H | OCH₃ | OCH₃ | |
| J-1 | S | Q-61 (R₇ = H, R₈ = CH₃, R₉ = H, R₂ = OCH₂F) | H | 5-CH₃ | CH₃ | OCH₃ | |
| J-2 | S | Q-61 (R₇ = H, R₈ = H, R₉ = H, R₂ = O(CH₂)₃CH₃) | H | 5-Cl | CH₃ | OCH₃ | |
| J-1 | S | Q-62 (R₇ = CH₃, R₈ = H, R₉ = H, R₂ = CH₃) | CH₃ | H | CH₃ | OCH₃ | |
| J-2 | S | Q-62 (R₇ = Cl, R₈ = H, R₉ = H, R₂ = H) | H | H | OCH | OCH₃ | |
| J-3 | S | Q-63 (R₇ = H, R₈ = H, R₉ = H) | H | H | OCH₃ | OCH₃ | |
| J-1 | O | Q-63 (R₇ = CH₃, R₈ = H, R₉ = CH₃) | H | H | CH₃ | OCH₃ | |
| J-2 | S | Q-64 (R₇ = H, R₈ = H, R₉ = H) | H | 5-CH₃ | CH₃ | OCH₃ | |
| J-1 | S | Q-64 (R₇ = H, R₈ = C₂H₅, R₈ = H, R₉ = H) | H | H | OCH₃ | OCH₃ | |
| J-1 | S | Q-64 (R₇ = H, R₈ = H, R₉ = C₂H₅) | H | H | OCH₃ | OCH₃ | |
| J-2 | S | Q-65 (R₇ = H, R₈ = H, R₉ = H) | H | H | OCH | OCH₃ | |
| J-1 | S | Q-65 (R₇ = H, R₈ = n-C₄H₉, R₈ = H, R₉ = H) | H | H | OCH₃ | OCH₃ | |
| J-1 | S | Q-66 (R₇ = H, R₈ = CH₃, R₉ = i-C₃H₇) | CH₃ | H | CH₃ | OCH₃ | |
| J-2 | S | Q-66 (R₇ = H, R₈ = H, R₉ = H) | H | 5-CH₃ | OCH₃ | OCH₃ | |
| J-1 | S | Q-67 (R₇ = i-C₃H₇, R₈ = C₂H₅, R₉ = H) | H | 5-Cl | OCH₃ | OCH₃ | |
| J-1 | O | Q-67 (R₇ = H, R₈ = H, R₉ = H, R₃ = CH₃) | H | H | CH₃ | OCH₃ | |
| J-2 | S | Q-67 (R₇ = CH₃, R₈ = H, R₉ = H, R₃ = H) | H | 5-CH₃ | CH₃ | OCH₃ | |
| J-1 | S | Q-68 (R₇ = H, R₈ = H, R₉ = CH₃, R₃ = C₂H₅) | H | H | OCH₃ | OCH₃ | |
| J-1 | S | Q-68 (R₇ = H, R₈ = H, R₉ = H, R₃ = i-C₃H₇) | H | H | OCH₃ | OCH₃ | |
| J-1 | S | Q-68 (R₇ = C₂H₅, R₈ = H, R₉ = C₂H₅, R₃ = n-C₄H₉) | H | H | OCH₃ | OCH₃ | |
| J-1 | S | Q-69 (R₇ = H, R₈ = H, R₉ = H, R₃ = CH₃) | CH₃ | H | CH₃ | OCH₃ | |
| J-2 | S | Q-69 (R₇ = n-C₄H₉, R₈ = H, R₉ = H, R₃ = C₂H₅) | H | H | OCH₃ | OCH₃ | |
| J-1 | S | Q-69 (R₇ = H, R₈ = CH₃, R₉ = i-C₃H₇, R₃ = H) | H | H | CH₃ | OCH₃ | |
| J-2 | S | Q-70 (R₇ = H, R₈ = H, R₉ = H, R₃ = CH₃) | H | H | CH₃ | OCH₃ | |
| J-3 | O | Q-70 (R₇ = i-C₃H₇, R₈ = H, R₉ = H, R₃ = CH₃) | H | H | OCH₃ | OCH₃ | |

TABLE 2-continued

General Formula 2

| J | W₁ | Q | R | R₁ | X | Y | m.p.(°C.) |
|---|----|---|---|----|---|---|-----------|
| J-1 | S | Q-70 (R₇ = H, R₈ = C₂H₅, R₉ = CH₃, R₃ = H) | H | 5-CH₃ | OCH₃ | OCH₃ | |
| J-2 | S | Q-71 (R₇ = H, R₈ = H, R₉ = H, R₁₀ = H) | H | H | OCH₃ | OCH₃ | |
| J-1 | S | Q-71 (R₇ = CH₃, R₈ = H, R₉ = H, R₁₀ = CH₃) | H | H | OCH₃ | OCH₃ | |
| J-2 | S | Q-71 (R₇ = H, R₈ = H, R₉ = H, R₁₀ = CH₃) | H | 5-Cl | OCH₃ | OCH₃ | |
| J-1 | S | Q-72 (R₇ = H, R₈ = H, R₉ = H, R₂ = CH₃) | CH₃ | H | CH₃ | CH₃ | |
| J-2 | S | Q-72 (R₇ = H, R₈ = H, R₉ = H, R₂ = H) | H | 5-CH₃ | OCH₃ | OCH₃ | |
| J-1 | S | Q-73 (R₇ = CH₃, R₈ = H, R₉ = H, R₂ = H) | H | H | OCH₃ | OCH₃ | |
| J-2 | O | Q-73 (R₇ = H, R₈ = CH₃, R₉ = H, R₂ = C₂H₅) | H | H | OCH₃ | CH₃ | |
| J-1 | S | Q-73 (R₇ = CH₃, R₈ = H, R₉ = CH₃, R₂ = H) | H | 5-Cl | OCH₃ | OCH₃ | |
| J-3 | S | Q-74 (R₇ = H, R₈ = H, R₉ = H, R₂ = H) | H | H | CH₃ | CH₃ | |
| J-1 | S | Q-74 (R₇ = CH₃, R₈ = H, R₉ = H, R₂ = H) | H | 5-CH₃ | OCH₃ | OCH₃ | |
| J-2 | S | Q-74 (R₇ = H, R₈ = H, R₉ = H, R₂ = CH₃) | H | H | OCH₃ | OCH₃ | |
| J-1 | S | Q-75 (R₇ = H, R₈ = H, R₉ = H) | H | H | OCH₃ | OCH₃ | |
| J-2 | S | Q-75 (R₇ = H, R₈ = H, R₉ = CH₃) | H | H | CH₃ | CH₃ | |
| J-1 | S | Q-76 (R₇ = H, R₈ = H, R₉ = H) | H | H | OCH₃ | OCH₃ | |
| J-2 | S | Q-76 (R₇ = C₂H₅, R₈ = H, R₉ = C₂H₅) | H | H | OCH₃ | OCH₃ | |
| J-1 | S | Q-77 (R₇ = H, R₈ = H, R₉ = H) | H | 5-CH₃ | OCH₃ | OCH₃ | |
| J-2 | S | Q-77 (R₇ = H, R₈ = H, R₉ = n-C₃H₇) | H | H | OCH₃ | OCH₃ | |
| J-1 | S | Q-77 (R₇ = H, R₈ = CH₃, R₉ = H) | H | H | OCH₃ | OCH₃ | |
| J-2 | S | Q-78 (R₇ = n-C₃H₇, R₈ = H, R₉ = H) | H | 5-Cl | OCH₃ | OCH₃ | |
| J-1 | S | Q-78 (R₇ = H, R₈ = H, R₉ = H, R₃ = H) | H | H | OCH₃ | OCH₃ | |
| J-2 | S | Q-78 (R₇ = H, R₈ = H, R₉ = H, R₃ = C₂H₅) | H | 5-CH₃ | OCH₃ | OCH₃ | |
| J-1 | S | Q-79 (R₇ = H, R₈ = H, R₉ = CH₃, R₃ = CH₃) | H | H | OCH₃ | OCH₃ | |
| J-2 | S | Q-79 (R₇ = H, R₈ = H, R₉ = H, R₃ = CH₃) | H | H | OCH₃ | OCH₃ | |
| J-1 | S | Q-80 (R₇ = CH₃, R₈ = H, R₉ = H, R₃ = C₂H₅) | CH₃ | H | CH₃ | CH₃ | |
| J-2 | O | Q-80 (R₇ = H, R₈ = H, R₉ = CH₃, R₃ = C₂H₅) | H | 5-Cl | CH₃ | CH₃ | |
| J-1 | S | Q-81 (R₇ = H, R₈ = CH₃, R₉ = H, R₃ = CH₃) | H | H | OCH₃ | OCH₃ | |
| J-2 | S | Q-81 (R₇ = CH₃, R₈ = H, R₉ = H, R₃ = i-C₃H₇) | H | 5-CH₃ | OCH₃ | OCH₃ | |
| J-1 | S | Q-82 (R₇ = H, R₈ = H, R₉ = CH₃, R₃ = CH₃) | H | H | OCH₃ | OCH₃ | |
| J-2 | S | Q-82 (R₇ = CH₃, R₈ = H, R₉ = H, R₃ = CH₃) | CH₃ | H | CH₃ | CH₃ | |
| J-1 | S | Q-82 (R₇ = H, R₈ = H, R₉ = CH₃, R₃ = CH₃) | H | H | OCH₃ | OCH₃ | |
| J-2 | S | Q-83 (R₇ = H, R₈ = H, R₉ = C₂H₅, R₃ = CH₃) | H | H | OCH₃ | OCH₃ | |
| J-1 | NCH₃ | Q-83 (R₇ = CH₃, R₈ = H, R₉ = H, R₁₀ = H) | CH₃ | H | CH₃ | CH₃ | |
| J-2 | S | Q-83 (R₇ = CH₃, R₈ = H, R₉ = H, R₁₀ = CH₃) | H | H | OCH₃ | OCH₃ | |
| J-1 | O | Q-83 (R₇ = CH₃, R₈ = CH₃, R₉ = H, R₁₀ = H) | H | H | OCH₃ | OCH₃ | |
| J-2 | S | Q-84 (R₇ = H, R₈ = H, R₉ = H) | H | H | OCH₃ | OCH₃ | |
| J-1 | S | Q-84 (R₇ = CH₃, R₈ = H, R₉ = CH₃) | H | H | OCH₃ | OCH₃ | |
| J-2 | S | Q-84 (R₇ = H, R₈ = C₂H₅, R₉ = H) | H | H | OCH₃ | OCH₃ | |
| J-1 | S | Q-85 (R₇ = CH₃, R₈ = H, R₉ = H) | H | H | OCH₃ | OCH₃ | |
| J-2 | S | Q-85 (R₇ = H, R₈ = H, R₉ = C₂H₅) | H | H | OCH₃ | OCH₃ | |
| J-1 | S | Q-86 (R₇ = CH₃, R₈ = H, R₉ = H) | CH₃ | H | OCH₃ | OCH₃ | |
| J-2 | S | Q-86 (R₇ = H, R₈ = H, R₉ = C₂H₅) | H | H | OCH₃ | OCH₃ | |
| J-1 | S | Q-87 (R₇ = H, R₈ = H, R₉ = H) | H | 5-CH₃ | OCH₃ | OCH₃ | |
| J-1 | O | Q-87 (R₇ = H, R₈ = H, R₉ = CH₃) | H | H | OCH | CH₃ | |

TABLE 2-continued

| | | | General Formula 2 | | | | | |
|---|---|---|---|---|---|---|---|---|
| J | $W_1$ | Q | R | $R_1$ | X | Y | m.p.(°C) |
| J-2 | S | Q-87 ($R_7$ = $CH_3$, $R_8$ = H, $R_9$ = H) | H | 5-Cl | $OCH_3$ | $CH_3$ | |
| J-1 | S | Q-88 ($R_7$ = H, $R_8$ = H, $R_9$ = H) | H | H | $CH_3$ | $OCH_3$ | |
| J-2 | S | Q-88 ($R_7$ = $CH_3$, $R_8$ = H, $R_9$ = H) | H | H | $CH_3$ | $OCH_3$ | |
| J-3 | S | Q-88 ($R_7$ = H, $R_8$ = H, $R_9$ = $CH_3$) | H | H | $OCH_3$ | $OCH_3$ | |
| J-1 | S | Q-89 ($R_7$ = H, $R_8$ = H, $R_9$ = H) | H | H | $OCH_3$ | $OCH_3$ | |
| J-2 | S | Q-89 ($R_7$ = $CH_3$, $R_8$ = H, $R_9$ = $C_2H_5$) | H | H | $CH_3$ | $OCH_3$ | |
| J-1 | S | Q-89 ($R_7$ = H, $R_8$ = $CH_3$, $R_9$ = H) | H | H | $CH_3$ | $OCH_3$ | |
| J-2 | S | Q-90 ($R_7$ = H, $R_8$ = H, $R_9$ = H, $R_3$ = $CH_3$) | $CH_3$ | H | $CH_3$ | $OCH_3$ | |
| J-1 | O | Q-90 ($R_7$ = $CH_3$, $R_8$ = H, $R_9$ = H, $R_3$ = $C_2H_5$) | H | H | $OCH_3$ | $OCH_3$ | |
| J-1 | S | Q-90 ($R_7$ = H, $R_8$ = H, $R_9$ = $CH_3$, $R_3$ = $CH_3$) | H | H | $OCH_3$ | $OCH_3$ | |
| J-1 | S | Q-91 ($R_7$ = H, $R_8$ = H, $R_3$ = H) | H | H | $OCH_3$ | $OCH_3$ | |
| J-2 | S | Q-91 ($R_7$ = $CH_3$, $R_8$ = H, $R_3$ = H) | H | 5-$CH_3$ | $OCH_3$ | $OCH_3$ | |
| J-1 | S | Q-91 ($R_7$ = H, $R_8$ = $CH_3$, $R_3$ = $CH_3$) | H | H | $CH_3$ | $CH_3$ | |
| J-2 | S | Q-92 ($R_7$ = H, $R_8$ = H, $R_{10}$ = H) | H | 5-Cl | $OCH_3$ | $OCH_3$ | |
| J-1 | S | Q-92 ($R_7$ = H, $R_8$ = $CH_3$, $R_{10}$ = $CH_3$) | H | H | $CH_3$ | $OCH_3$ | |
| J-3 | S | Q-92 ($R_7$ = H, $R_8$ = $CH_3$, $R_9$ = H, $R_{10}$ = H) | H | H | $OCH_3$ | $OCH_3$ | |
| J-2 | S | Q-93 ($R_7$ = H, $R_8$ = H, $R_9$ = $CH_3$) | $CH_3$ | H | $CH_3$ | $CH_3$ | |
| J-1 | S | Q-93 ($R_7$ = $CH_3$, $R_8$ = H, $R_9$ = H) | H | 5-$CH_3$ | $CH_3$ | $CH_3$ | |
| J-1 | O | Q-94 ($R_7$ = $CH_3$, $R_8$ = H, $R_9$ = H) | H | H | $OCH_3$ | $OCH_3$ | |
| J-1 | S | Q-94 ($R_7$ = H, $R_8$ = H, $R_9$ = n-$C_4H_9$) | H | H | $CH_3$ | $OCH_3$ | |
| J-2 | S | Q-95 ($R_7$ = H, $R_8$ = H, $R_9$ = H) | H | 5-Cl | $OCH_3$ | $OCH_3$ | |
| J-1 | S | Q-95 ($R_7$ = $CH_3$, $R_8$ = H, $R_9$ = $CH_3$) | H | H | $OCH_3$ | $OCH_3$ | |
| J-2 | S | Q-95 ($R_7$ = H, $R_8$ = H, $R_9$ = s-$C_4H_9$) | H | 5-$CH_3$ | $CH_3$ | $OCH_3$ | |
| J-1 | S | Q-96 ($R_7$ = H, $R_8$ = H, $R_9$ = H) | H | 5-Cl | $OCH_3$ | $OCH_3$ | |
| J-2 | S | Q-96 ($R_7$ = $CH_3$, $R_8$ = H, $R_9$ = H) | H | H | $OCH_3$ | $OCH_3$ | |
| J-1 | S | Q-96 ($R_7$ = H, $R_8$ = $CH_3$, $R_9$ = $CH_3$) | H | H | $CH_3$ | $OCH_3$ | |
| J-1 | O | Q-97 ($R_7$ = $CH_3$, $R_8$ = $CH_3$, $R_9$ = $CH_3$) | H | H | $OCH_3$ | $OCH_3$ | |
| J-2 | S | Q-97 ($R_7$ = H, $R_8$ = H, $R_9$ = $CH_3$) | H | 5-$CH_3$ | $OCH_3$ | $OCH_3$ | |
| J-1 | S | Q-98 ($R_7$ = H, $R_8$ = H, $R_9$ = H) | H | H | $OCH_3$ | $OCH_3$ | |
| J-2 | S | Q-98 ($R_7$ = $CH_3$, $R_8$ = H, $R_9$ = H) | H | H | $CH_3$ | $OCH_3$ | |
| J-1 | S | Q-98 ($R_7$ = H, $R_8$ = H, $R_9$ = i-$C_3H_7$) | H | H | $OCH_3$ | $OCH_3$ | |
| J-2 | S | Q-99 ($R_7$ = H, $R_8$ = H, $R_9$ = H, $R_3$ = H) | H | 5-$CH_3$ | $CH_3$ | $OCH_3$ | |
| J-1 | S | Q-99 ($R_7$ = H, $R_8$ = H, $R_9$ = $CH_3$, $R_3$ = $CH_3$) | H | H | $OCH_3$ | $OCH_3$ | |
| J-3 | S | Q-99 ($R_7$ = H, $R_8$ = H, $R_9$ = s-$C_4H_9$, $R_3$ = H) | H | H | $CH_3$ | $OCH_3$ | |
| J-2 | S | Q-100 ($R_7$ = H, $R_8$ = $CH_3$, $R_9$ = H, $R_3$ = $C_2H_5$) | H | H | $OCH_3$ | $OCH_3$ | |
| J-1 | S | Q-100 ($R_7$ = $CH_3$, $R_8$ = H, $R_9$ = H, $R_3$ = H) | $CH_3$ | H | $OCH_3$ | $CH_3$ | |
| J-2 | S | Q-100 ($R_7$ = H, $R_8$ = H, $R_9$ = $CH_3$, $R_3$ = $CH_3$) | H | 5-$CH_3$ | $OCH_3$ | $OCH_3$ | |
| J-1 | S | Q-101 ($R_7$ = H, $R_8$ = H, $R_9$ = H, $R_3$ = i-$C_3H_7$) | H | H | $OCH_3$ | $OCH_3$ | |
| J-1 | S | Q-101 ($R_7$ = $CH_3$, $R_8$ = H, $R_9$ = $CH_3$, $R_3$ = $CH_3$) | H | 5-Cl | $CH_3$ | $CH_3$ | |
| J-2 | S | Q-101 ($R_7$ = H, $R_8$ = $CH_3$, $R_9$ = $CH_3$, $R_3$ = H) | H | H | $OCH_3$ | $OCH_3$ | |
| J-1 | S | Q-102 ($R_7$ = H, $R_8$ = $CH_3$, $R_9$ = $CH_3$, $R_3$ = $CH_3$) | H | 5-$CH_3$ | $OCH_3$ | $OCH_3$ | |
| J-2 | S | Q-102 ($R_7$ = H, $R_8$ = H, $R_9$ = H, $R_3$ = H) | H | H | $CH_3$ | $CH_3$ | |
| J-1 | S | Q-103 ($R_7$ = H, $R_8$ = H, $R_9$ = H, $R_{10}$ = H) | H | 5-Cl | $CH_3$ | $CH_3$ | |
| J-2 | S | Q-103 ($R_7$ = H, $R_8$ = H, $R_9$ = H, $R_{10}$ = $CH_3$) | H | H | $OCH_3$ | $OCH_3$ | |
| J-1 | O | Q-103 ($R_7$ = H, $R_8$ = H, $R_9$ = H, $R_{10}$ = s-$C_4H_9$) | H | 5-$CH_3$ | $CH_3$ | $OCH_3$ | |
| J-2 | S | Q-104 ($R_7$ = H, $R_8$ = H, $R_9$ = H, $R_{10}$ = H) | $CH_3$ | H | $CH_3$ | $OCH_3$ | |
| J-1 | S | Q-104 ($R_7$ = $CH_3$, $R_8$ = H, $R_9$ = H, $R_2$ = $OC_2H_5$) | $CH_3$ | H | $CH_3$ | $OCH_3$ | |

TABLE 2-continued

General Formula 2

| J | W₁ | Q | R | R₁ | X | Y | m.p.(°C.) |
|---|---|---|---|---|---|---|---|
| J-2 | S | Q-104 (R₇ = H, R₈ = H, R₉ = H, R₂ = Br) | H | H | OCH₃ | OCH₃ | |
| J-1 | S | Q-105 (R₇ = H, R₈ = H, R₉ = H, R₂ = H) | H | H | OCH₃ | OCH₃ | 175-180 |
| J-2 | S | Q-105 (R₇ = H, R₈ = H, R₉ = H, R₂ = H) | H | H | CH₃ | CH₃ | 162-167 |
| J-1 | S | Q-105 (R₇ = CH₃, R₈ = H, R₉ = H, R₂ = CH₃) | H | H | OCH₃ | OCH₃ | |
| J-2 | S | Q-105 (R₇ = H, R₈ = CH₃, R₉ = H, R₂ = C₂H₅) | H | 5-CH₃ | OCH₃ | OCH₃ | |
| J-1 | S | Q-106 (R₇ = H, R₈ = H, R₉ = H, R₂ = H) | H | H | OCH₃ | OCH₃ | |
| J-2 | S | Q-106 (R₇ = CH₃, R₈ = H, R₉ = H, R₂ = CH₃) | H | H | OCH₃ | OCH₃ | |
| J-1 | S | Q-106 (R₇ = Cl, R₈ = H, R₉ = H, R₂ = H) | H | 5-Cl | OCH₃ | OCH₃ | |
| J-3 | S | Q-107 (R₇ = H, R₈ = H, R₉ = H, R₂ = H) | H | H | OCH₃ | OCH₃ | |
| J-1 | O | Q-107 (R₇ = CH₃, R₈ = H, R₉ = H, R₂ = CH₃) | CH₃ | H | OCH₃ | OCH₃ | |
| J-2 | S | Q-107 (R₇ = H, R₈ = H, R₉ = H, R₂ = CH₃) | H | 5-CH₃ | OCH₃ | OCH₃ | |
| J-1 | S | Q-108 (R₇ = H, R₈ = H, R₉ = H, R₂ = H) | H | H | OCH₃ | OCH₃ | |
| J-2 | S | Q-108 (R₇ = CH₃, R₈ = H, R₉ = H, R₂ = Cl) | H' | 5-Cl | CH₃ | CH₃ | |
| J-1 | S | Q-108 (R₇ = H, R₈ = H, R₉ = H, R₂ = CH₃) | H | H | CH₃ | CH₃ | |
| J-2 | S | Q-109 (R₇ = H, R₈ = H, R₉ = H) | H | H | CH₃ | CH₃ | |
| J-1 | S | Q-109 (R₇ = CH₃, R₈ = H, R₉ = H) | H | H | OCH₃ | OCH₃ | |
| J-2 | S | Q-109 (R₇ = H, R₈ = H, R₉ = CH₃) | H | 5-CH₃ | OCH₃ | OCH₃ | |
| J-1 | S | Q-110 (R₇ = H, R₈ = H, R₉ = H) | H | H | OCH₃ | OCH₃ | |
| J-2 | S | Q-110 (R₇ = CH₃, R₈ = H, R₉ = H) | H | H | OCH₃ | OCH₃ | |
| J-3 | O | Q-110 (R₇ = H, R₈ = CH₃, R₉ = H) | H | H | OCH₃ | OCH₃ | |
| J-2 | S | Q-111 (R₇ = H, R₈ = H, R₉ = H) | H | H | OCH₃ | OCH₃ | |
| J-1 | S | Q-111 (R₇ = CH₃, R₈ = H, R₉ = H) | CH₃ | H | OCH₃ | OCH₃ | |
| J-2 | S | Q-112 (R₇ = H, R₈ = H, R₉ = H) | H | H | OCH₃ | OCH₃ | |
| J-1 | S | Q-112 (R₇ = CH₃, R₈ = CH₃, R₉ = H) | H | 5-CH₃ | OCH₃ | OCH₃ | |
| J-2 | S | Q-112 (R₇ = H, R₈ = H, R₉ = H, R₃ = CH₃) | H | H | OCH₃ | OCH₃ | |
| J-1 | S | Q-113 (R₇ = C₂H₅, R₈ = H, R₉ = H, R₃ = i-C₃H₇) | H | H | OCH₃ | OCH₃ | |
| J-2 | S | Q-113 (R₇ = H, R₈ = H, R₉ = C₂H₅, R₃ = n-C₄H₉) | H | H | OCH₃ | OCH₃ | |
| J-1 | S | Q-113 (R₇ = H, R₈ = H, R₉ = H, R₃ = CH₃) | H | H | OCH₃ | OCH₃ | |
| J-2 | O | Q-114 (R₇ = n-C₄H₉, R₈ = H, R₉ = H, R₃ = C₂H₅) | CH₃ | H | OCH₃ | OCH₃ | |
| J-1 | S | Q-114 (R₇ = H, R₈ = CH₃, R₈ = i-C₃H₇, R₃ = H) | H | H | OCH₃ | OCH₃ | |
| J-2 | S | Q-115 (R₇ = H, R₈ = H, R₉ = H, R₃ = CH₃) | H | H | CH₃ | CH₃ | |
| J-1 | S | Q-115 (R₇ = i-C₃H₇, R₈ = C₂H₅, R₉ = CH₃, R₃ = H) | H | H | CH₃ | CH₃ | |
| J-2 | S | Q-116 (R₇ = H, R₈ = H, R₉ = H, R₁₀ = H) | H | 5-Cl | OCH₃ | OCH₃ | |
| J-1 | S | Q-116 (R₇ = CH₃, R₈ = H, R₉ = H, R₁₀ = CH₃) | H | 5-CH₃ | OCH₃ | OCH₃ | |
| J-2 | S | Q-117 (R₇ = H, R₈ = H, R₉ = H, R₂ = H) | H | H | OCH₃ | OCH₃ | |
| J-1 | O | Q-117 (R₇ = CH₃, R₈ = H, R₉ = H, R₂ = H) | H | H | OCH₃ | OCH₃ | |
| J-2 | NH | Q-118 (R₇ = H, R₈ = H, R₉ = H, R₁₀ = H) | CH₃ | H | OCH₃ | OCH₃ | |
| J-1 | S | Q-118 (R₇ = CH₃, R₈ = H, R₉ = H, R₁₀ = H) | H | 5-Cl | OCH₃ | OCH₃ | |
| J-2 | S | Q-119 (R₇ = H, R₈ = H, R₉ = H, R₂ = H) | H | 5-CH₃ | OCH₃ | OCH₃ | |
| J-1 | S | Q-119 (R₇ = H, R₈ = CH₃, R₉ = H, R₂ = C₂H₅) | H | H | OCH₃ | OCH₃ | |
| J-2 | S | Q-120 (R₇ = H, R₈ = H, R₉ = H, R₂ = H) | H | 5-CH₃ | OCH₃ | OCH₃ | |
| J-1 | S | Q-120 (R₇ = H, R₈ = H, R₉ = CH₃, R₂ = CH₃) | H | H | OCH₃ | OCH₃ | |
| J-2 | O | Q-120 (R₇ = H, R₈ = H, R₉ = H, R₂ = CH₃) | H | 5-Cl | OCH₃ | OCH₃ | |

TABLE 2-continued

| | | | General Formula 2 | | | | |
|---|---|---|---|---|---|---|---|
| J | W$_1$ | Q | R | R$_1$ | X | Y | m.p.(°C.) |
| J-1 | S | Q-121 (R$_7$ = H, R$_8$ = H, R$_9$ = H, R$_2$ = H) | H | H | OCH$_3$ | OCH$_3$ | |
| J-2 | S | Q-121 (R$_7$ = H, R$_8$ = H, R$_9$ = H, R$_2$ = C$_2$H$_5$) | CH$_3$ | H | OCH$_3$ | CH$_3$ | |
| J-3 | S | Q-121 (R$_7$ = CH$_3$, R$_8$ = H, R$_9$ = CH$_3$, R$_2$ = H) | H | 5-CH$_3$ | OCH$_3$ | OCH$_3$ | |
| J-1 | S | Q-122 (R$_7$ = H, R$_8$ = H, R$_9$ = H, R$_2$ = H) | H | H | OCH$_3$ | OCH$_3$ | |
| J-2 | S | Q-122 (R$_7$ = H, R$_8$ = H, R$_9$ = H, R$_2$ = CH$_3$) | H | H | OCH$_3$ | CH$_3$ | |
| J-1 | S | Q-122 (R$_7$ = CH$_3$, R$_8$ = H, R$_9$ = H, R$_2$ = CH$_3$) | H | 5-Cl | OCH$_3$ | CH$_3$ | |
| J-2 | S | Q-123 (R$_7$ = H, R$_8$ = H, R$_9$ = H) | H | H | CH$_3$ | OCH$_3$ | |
| J-1 | S | Q-123 (R$_7$ = CH$_3$, R$_8$ = H, R$_9$ = CH$_3$) | H | H | OCH$_3$ | OCH$_3$ | |
| J-2 | S | Q-123 (R$_7$ = CH$_3$, R$_8$ = H, R$_9$ = CH$_3$) | H | 5-CH$_3$ | CH$_3$ | OCH$_3$ | |
| J-1 | O | Q-124 (R$_7$ = H, R$_8$ = H, R$_9$ = CH$_3$) | H | H | OCH$_3$ | OCH$_3$ | |
| J-2 | S | Q-124 (R$_7$ = H, R$_8$ = H, R$_9$ = CH$_3$) | H | H | CH$_3$ | OCH$_3$ | |
| J-1 | S | Q-124 (R$_7$ = C$_2$H$_5$, R$_8$ = H, R$_9$ = C$_2$H$_5$) | H | 5-Cl | CH$_3$ | OCH$_3$ | |
| J-3 | S | Q-125 (R$_7$ = H, R$_8$ = H, R$_9$ = n-C$_4$H$_9$) | H | H | CH$_3$ | OCH$_3$ | |
| J-1 | S | Q-125 (R$_7$ = H, R$_8$ = CH$_3$, R$_9$ = H) | H | H | OCH$_3$ | OCH$_3$ | |
| J-2 | S | Q-125 (R$_7$ = H, R$_8$ = H, R$_9$ = s-C$_3$H$_7$) | H | H | OCH$_3$ | OCH$_3$ | |
| J-1 | S | Q-126 (R$_7$ = H, R$_8$ = H, R$_9$ = H) | H | H | OCH$_3$ | OCH$_3$ | |
| J-2 | S | Q-126 (R$_7$ = n-C$_3$H$_7$, R$_8$ = H, R$_9$ = H) | H | 5-CH$_3$ | OCH$_3$ | OCH$_3$ | |
| J-1 | S | Q-127 (R$_7$ = H, R$_8$ = H, R$_9$ = H, R$_3$ = H) | H | H | OCH | OCH$_3$ | |
| J-2 | O | Q-127 (R$_7$ = H, R$_8$ = H, R$_9$ = H, R$_3$ = CH$_3$) | H | H | OCH$_3$ | CH$_3$ | |
| J-1 | S | Q-127 (R$_7$ = H, R$_8$ = H, R$_9$ = H, R$_3$ = C$_2$H$_5$) | H | 5-Cl | CH$_3$ | CH$_3$ | |
| J-2 | S | Q-128 (R$_7$ = H, R$_8$ = H, R$_9$ = H, R$_3$ = CH$_3$) | H | H | OCH$_3$ | OCH$_3$ | |
| J-1 | S | Q-128 (R$_7$ = CH$_3$, R$_8$ = H, R$_9$ = H, R$_3$ = CH$_3$) | CH$_3$ | H | OCH$_3$ | OCH$_3$ | |
| J-3 | S | Q-128 (R$_7$ = H, R$_8$ = H, R$_9$ = H, R$_3$ = C$_2$H$_5$) | H | H | OCH$_3$ | OCH$_3$ | |
| J-1 | S | Q-129 (R$_7$ = H, R$_8$ = H, R$_9$ = H, R$_3$ = i-C$_3$H$_7$) | H | 5-CH$_3$ | OCH$_3$ | OCH$_3$ | |
| J-2 | S | Q-129 (R$_7$ = H, R$_8$ = CH$_3$, R$_9$ = H, R$_3$ = CH$_3$) | H | H | OCH$_3$ | OCH$_3$ | |
| J-1 | O | Q-130 (R$_7$ = CH$_3$, R$_8$ = H, R$_9$ = CH$_3$, R$_3$ = H) | H | 5-Cl | CH$_3$ | OCH$_3$ | |
| J-2 | S | Q-130 (R$_7$ = H, R$_8$ = H, R$_9$ = CH$_3$, R$_3$ = CH$_3$) | H | H | OCH$_3$ | OCH$_3$ | |
| J-3 | S | Q-130 (R$_7$ = H, R$_8$ = H, R$_9$ = C$_2$H$_5$, R$_3$ = CH$_3$) | H | H | OCH$_3$ | OCH$_3$ | |
| J-1 | S | Q-131 (R$_7$ = H, R$_8$ = H, R$_9$ = H, R$_{10}$ = H) | H | 5-CH$_3$ | OCH$_3$ | OCH$_3$ | |
| J-2 | O | Q-131 (R$_7$ = CH$_3$, R$_8$ = CH$_3$, R$_9$ = H, R$_{10}$ = CH$_3$) | H | H | OCH$_3$ | OCH$_3$ | |
| J-1 | S | Q-132 (R$_7$ = H, R$_8$ = H, R$_9$ = H, R$_{10}$ = H) | H | H | OCH | OCH$_3$ | |
| J-2 | S | Q-132 (R$_7$ = H, R$_8$ = H, R$_9$ = CH$_3$) | CH$_3$ | H | CH$_3$ | CH$_3$ | |
| J-1 | S | Q-132 (R$_7$ = H, R$_8$ = C$_2$H$_5$, R$_9$ = H) | H | 5-Cl | CH$_3$ | CH$_3$ | |
| J-2 | S | Q-133 (R$_7$ = H, R$_8$ = H, R$_9$ = H) | H | H | OCH$_3$ | OCH$_3$ | |
| J-3 | S | Q-133 (R$_7$ = CH$_3$, R$_8$ = H, R$_9$ = H) | H | H | OCH$_3$ | OCH$_3$ | |
| J-1 | S | Q-133 (R$_7$ = H, R$_8$ = H, R$_9$ = C$_2$H$_5$) | H | 5-CH$_3$ | OCH$_3$ | OCH$_3$ | |
| J-2 | O | Q-134 (R$_7$ = CH$_3$, R$_8$ = H, R$_9$ = H) | H | H | OCH$_3$ | OCH$_3$ | |
| J-1 | S | Q-134 (R$_7$ = H, R$_8$ = H, R$_9$ = C$_2$H$_5$) | H | 5-Cl | OCH$_3$ | OCH$_3$ | |
| J-2 | S | Q-135 (R$_7$ = H, R$_8$ = H, R = H) | H | H | OCH$_3$ | OCH$_3$ | |
| J-1 | S | Q-135 (R$_7$ = CH$_3$, R$_8$ = H, R$_9$ = CH$_3$) | CH$_3$ | H | OCH$_3$ | OCH$_3$ | |
| J-2 | S | Q-135 (R$_7$ = H, R$_8$ = H, R$_9$ = H) | H | 5-CH$_3$ | OCH$_3$ | OCH$_3$ | |
| J-1 | S | Q-136 (R$_7$ = H, R$_8$ = H, R$_9$ = CH$_3$) | H | H | OCH$_3$ | OCH$_3$ | |
| J-2 | S | Q-136 (R$_7$ = H, R$_8$ = CH$_3$, R$_9$ = C$_2$H$_5$) | H | 5-Cl | CH$_3$ | CH$_3$ | |
| J-3 | S | Q-137 (R$_7$ = CH$_3$, R$_8$ = H, R$_9$ = H) | H | H | CH$_3$ | CH$_3$ | |
| J-1 | O | Q-137 (R$_7$ = H, R$_8$ = H, R$_9$ = H) | H | H | CH$_3$ | OCH$_3$ | |
| J-2 | S | Q-137 (R$_7$ = H, R$_8$ = H, R$_9$ = CH$_3$) | H | 5-CH$_3$ | OCH$_3$ | OCH$_3$ | |

TABLE 2-continued

| | | | General Formula 2 | | | | |
|---|---|---|---|---|---|---|---|
| J | W₁ | Q | | R | R₁ | X | Y | m.p.(°C.) |
| J-1 | S | Q-138 (R₇ = H, R₈ = H, R₉ = H) | H | H | OCH₃ | OCH₃ | |
| J-2 | S | Q-138 (R₇ = H, R₈ = H, R₉ = H) | H | H | CH₃ | OCH₃ | 85-93 |
| J-2 | S | Q-138 (R₇ = H, R₈ = H, R₉ = H) | H | H | OCH₃ | OCH₃ | 118-127 |
| J-1 | NCH₃ | Q-138 (R₇ = CH₃, R₈ = H, R₉ = H) | H | H | CH₃ | OCH₃ | |
| J-1 | S | Q-138 (R₇ = H, R₈ = H, R₉ = CH₃) | H | H | CH₃ | OCH₃ | |
| J-2 | S | Q-139 (R₇ = H, R₈ = H, R₉ = H) | H | H | CH₃ | OCH₃ | |
| J-1 | S | Q-139 (R₇ = CH₃, R₈ = H, R₉ = H) | CH₃ | H | OCH₃ | OCH₃ | |
| J-3 | S | Q-139 (R₇ = CH₃, R₈ = H, R₉ = H) | H | H | OCH₃ | OCH₃ | |
| J-2 | S | Q-140 (R₇ = H, R₈ = H, R₉ = H, R₃ = CH₃) | H | H | OCH₃ | OCH₃ | |
| J-2 | O | Q-140 (R₇ = H, R₈ = H, R₉ = CH₃, R₃ = H) | H | H | OCH₃ | OCH₃ | |
| J-2 | S | Q-140 (R₇ = H, R₈ = CH₃, R₉ = H, R₃ = C₂H₅) | H | 5-CH₃ | OCH₃ | OCH₃ | |
| J-1 | S | Q-141 (R₇ = H, R₈ = H, R₉ = H, R₃ = CH₃) | H | H | OCH₃ | OCH₃ | |
| J-2 | S | Q-141 (R₇ = H, R₈ = H, R₉ = H, R₃ = H) | H | H | OCH₃ | OCH₃ | |
| J-1 | S | Q-141 (R₇ = H, R₈ = H, R₉ = CH₃, R₃ = CH₃) | H | 5-CH₃ | OCH₃ | OCH₃ | |
| J-2 | S | Q-142 (R₇ = H, R₈ = H, R₉ = H, R₁₀ = H) | H | 5-Cl | OCH₃ | OCH₃ | |
| J-1 | S | Q-142 (R₇ = CH₃, R₈ = H, R₉ = H, R₁₀ = H) | CH₃ | H | OCH₃ | CH₃ | |
| J-1 | S | Q-143 (R₇ = H, R₈ = H, R₉ = H, R₁₀ = CH₃) | H | 5-CH₃ | OCH₃ | OCH₃ | |
| J-2 | S | Q-143 (R₇ = H, R₈ = H, R₉ = H, R₃ = H) | H | H | CH₃ | CH₃ | |
| J-1 | O | Q-143 (R₇ = CH₃, R₈ = H, R₉ = H, R₃ = CH₃) | H | 5-Cl | CH₃ | CH₃ | |
| J-2 | S | Q-144 (R₇ = CH₃, R₈ = H, R₉ = H, R₃ = CH₃) | H | H | OCH₃ | OCH₃ | |
| J-1 | S | Q-144 (R₇ = H, R₈ = C₂H₅, R₉ = H, R₃ = CH₃) | H | H | OCH₃ | OCH₃ | |
| J-2 | S | Q-145 (R₇ = H, R₈ = H, R₉ = H) | H | H | OCH₃ | OCH₃ | |
| J-1 | S | Q-145 (R₇ = CH₃, R₈ = H, R₉ = CH₃) | H | H | OCH₃ | OCH₃ | |
| J-2 | S | Q-146 (R₇ = H, R₈ = H, R₉ = H) | H | H | OCH₃ | OCH₃ | |
| J-1 | S | Q-146 (R₇ = H, R₈ = H, R₉ = n-C₄H₉) | H | H | OCH₃ | OCH₃ | |
| J-2 | S | Q-147 (R₇ = CH₃, R₈ = H, R₉ = H) | H | H | OCH₃ | OCH₃ | |
| J-1 | S | Q-147 (R₇ = H, R₈ = H, R₉ = n-C₄H₉) | H | H | OCH₃ | OCH₃ | |
| J-2 | S | Q-148 (R₇ = H, R₈ = H, R₉ = CH₃) | H | H | OCH₃ | OCH₃ | |
| J-1 | S | Q-148 (R₇ = CH₃, R₈ = H, R₉ = H) | H | 5-Cl | OCH₃ | OCH₃ | |
| J-2 | S | Q-149 (R₇ = H, R₈ = H, R₉ = H) | H | 5-CH₃ | OCH₃ | OCH₃ | |
| J-1 | S | Q-149 (R₇ = CH₃, R₈ = H, R₉ = CH₃) | H | H | OCH₃ | OCH₃ | |
| J-2 | S | Q-150 (R₇ = H, R₈ = H, R₉ = H) | H | 5-Cl | OCH₃ | OCH₃ | |
| J-1 | O | Q-150 (R₇ = CH₃, R₈ = CH₃, R₉ = CH₃) | H | H | OCH₃ | CH₃ | |
| J-1 | S | Q-151 (R₇ = CH₃, R₈ = H, R₉ = H) | H | 5-CH₃ | OCH₃ | CH₃ | |
| J-2 | S | Q-151 (R₇ = H, R₈ = CH₃, R₉ = H) | H | H | OCH₃ | CH₃ | |
| J-1 | S | Q-152 (R₇ = H, R₈ = H, R₉ = H) | H | 5-Cl | OCH₃ | OCH₃ | |
| J-2 | S | Q-152 (R₇ = C₂H₅, R₈ = H, R₉ = H) | H | H | OCH₃ | OCH₃ | |
| J-1 | S | Q-153 (R₇ = CH₃, R₈ = CH₃, R₉ = H) | CH₃ | 5-CH₃ | OCH₃ | OCH₃ | |
| J-2 | S | Q-153 (R₇ = H, R₈ = H, R₉ = H, R₁₁ = CH₃) | H | H | OCH₃ | OCH₃ | |
| J-1 | S | Q-153 (R₇ = H, R₈ = H, R₉ = H, R₁₁ = H) | H | H | OCH₃ | OCH₃ | |
| J-2 | S | Q-154 (R₇ = H, R₈ = H, R₉ = H, R₁₁ = CH₃) | H | H | OCH₃ | OCH₃ | |
| J-1 | O | Q-154 (R₇ = H, R₈ = H, R₉ = H, R₁₁ = CH₃) | H | H | OCH₃ | OCH₃ | |

TABLE 2-continued

| J | W$_1$ | Q | R | R$_1$ | X | Y | m.p.(°C.) |
|---|---|---|---|---|---|---|---|
| J-2 | S | Q-154 (R$_7$ = CH$_3$, R$_8$ = H, R$_9$ = H) | H | H | OCH$_3$ | OCH$_3$ | |
| J-3 | S | Q-154 (R$_7$ = H, R$_8$ = CH$_3$, R$_9$ = CH$_3$) | H | 5-CH$_3$ | OCH$_3$ | OCH$_3$ | |
| J-1 | S | Q-155 (R$_7$ = H, R$_8$ = H, R$_9$ = H) | H | H | OCH$_3$ | OCH$_3$ | |
| J-2 | S | Q-155 (R$_7$ = CH$_3$, R$_8$ = H, R$_9$ = H) | H | 5-Cl | OCH$_3$ | OCH$_3$ | |
| J-2 | S | Q-155 (R$_7$ = H, R$_8$ = CH$_3$, R$_9$ = H) | H | H | OCH$_3$ | OCH$_3$ | |
| J-1 | S | Q-156 (R$_7$ = H, R$_8$ = H, R$_9$ = H) | CH$_3$ | H | OCH$_3$ | OCH$_3$ | |
| J-2 | S | Q-156 (R$_7$ = C$_2$H$_5$, R$_8$ = H, R$_9$ = H) | H | 5-CH$_3$ | OCH$_3$ | OCH$_3$ | |
| J-2 | S | Q-156 (R$_7$ = CH$_3$, R$_8$ = CH$_3$, R$_9$ = H) | H | H | OCH$_3$ | OCH$_3$ | |
| J-1 | O | Q-157 (R$_7$ = H, R$_8$ = H, R$_9$ = H, R$_{10}$ = H) | H | H | OCH$_3$ | CH$_3$ | |
| J-2 | S | Q-157 (R$_7$ = CH$_3$, R$_8$ = H, R$_9$ = H, R$_{10}$ = CH$_3$) | H | 5-Cl | OCH$_3$ | CH$_3$ | |
| J-1 | S | Q-158 (R$_7$ = H, R$_8$ = H, R$_9$ = H) | H | H | CH$_3$ | OCH$_3$ | |
| J-2 | S | Q-158 (R$_7$ = H, R$_8$ = H, R$_9$ = CH$_3$) | H | H | CH$_3$ | OCH$_3$ | |
| J-3 | S | Q-158 (R$_7$ = CH$_3$, R$_8$ = H, R$_9$ = H) | H | 5-CH$_3$ | CH$_3$ | OCH$_3$ | |
| J-2 | S | Q-159 (R$_7$ = H, R$_8$ = H, R$_9$ = H) | H | H | OCH$_3$ | OCH$_3$ | |
| J-1 | NH | Q-159 (R$_7$ = CH$_3$, R$_8$ = H, R$_9$ = H) | H | H | OCH$_3$ | OCH$_3$ | |
| J-2 | S | Q-160 (R$_7$ = H, R$_8$ = H, R$_9$ = H, R$_{11}$ = CH$_3$) | H | H | OCH$_3$ | OCH$_3$ | |
| J-1 | O | Q-160 (R$_7$ = CH$_3$, R$_8$ = H, R$_9$ = CH$_3$, R$_{11}$ = H) | CH$_3$ | H | OCH$_3$ | OCH$_3$ | |
| J-1 | S | Q-161 (R$_7$ = H, R$_8$ = H, R$_9$ = H, R$_{11}$ = i-C$_3$H$_7$) | H | H | OCH$_3$ | OCH$_3$ | |
| J-1 | S | Q-161 (R$_7$ = CH$_3$, R$_8$ = H, R$_9$ = H, R$_{11}$ = H) | H | H | OCH$_3$ | OCH$_3$ | |
| J-3 | S | Q-161 (R$_7$ = H, R$_8$ = H, R$_9$ = CH$_3$, R$_{11}$ = CH$_3$) | H | 5-CH$_3$ | OCH$_3$ | OCH$_3$ | |
| J-1 | S | Q-162 (R$_7$ = CH$_3$, R$_8$ = H, R$_9$ = H, R$_{10}$ = H) | H | H | OCH$_3$ | OCH$_3$ | |
| J-2 | O | Q-162 (R$_7$ = H, R$_8$ = H, R$_9$ = CH$_3$, R$_{10}$ = CH$_3$) | H | H | OCH$_3$ | OCH$_3$ | |
| J-1 | S | Q-162 (R$_7$ = H, R$_8$ = H, R$_9$ = H, R$_{10}$ = CH$_3$) | H | 5-Cl | OCH$_3$ | OCH$_3$ | |
| J-1 | S | Q-163 (R$_7$ = H, R$_8$ = H, R$_9$ = H, R$_2$ = H) | H | H | OCH$_3$ | OCH$_3$ | |
| J-2 | O | Q-163 (R$_7$ = CH$_3$, R$_8$ = H, R$_9$ = H, R$_2$ = H) | H | H | OCH$_3$ | OCH$_3$ | |
| J-1 | S | Q-163 (R$_7$ = H, R$_8$ = H, R$_9$ = H, R$_2$ = H) | H | H | OCH$_3$ | OCH$_3$ | |
| J-1 | S | Q-164 (R$_7$ = H) | H | H | OCH$_3$ | OCH$_3$ | |
| J-2 | O | Q-164 (R$_7$ = H) | H | H | OCH$_3$ | OCH$_3$ | |
| J-1 | S | Q-165 (R$_7$ = H, R$_3$ = CH$_3$) | H | H | OCH$_3$ | OCH$_3$ | |
| J-2 | S | Q-165 (R$_7$ = H, R$_3$ = CH$_3$) | H | H | OCH$_3$ | OCH$_3$ | |
| J-2 | O | Q-165 (R$_7$ = H, R$_3$ = CH$_3$) | H | H | OCH$_3$ | OCH$_3$ | |
| J-1 | S | Q-166 (R$_7$ = H, R$_3$ = CH$_3$) | H | H | OCH$_3$ | OCH$_3$ | |
| J-2 | S | Q-166 (R$_7$ = H, R$_3$ = CH$_3$) | H | H | OCH$_3$ | OCH$_3$ | |
| J-2 | O | Q-166 (R$_7$ = H, R$_3$ = CH$_3$) | H | H | OCH$_3$ | OCH$_3$ | |
| J-1* | S | Q-1 (R$_7$ = H, R$_8$ = H) | H | H | OCH$_3$ | OCH$_3$ | |
| J-1* | S | Q-1 (R$_7$ = H, R$_8$ = H) | H | H | OCH$_3$ | CH$_3$ | |
| J-2* | S | Q-1 (R$_7$ = H, R$_8$ = H) | H | H | OCH$_3$ | OCH$_3$ | |
| J-2* | S | Q-1 (R$_7$ = H, R$_8$ = H) | H | H | OCH$_3$ | OCH$_3$ | |
| J-3* | S | Q-37 (R$_7$ = H, R$_8$ = H, R$_9$ = H, R$_2$ = H) | H | H | OCH$_3$ | OCH$_3$ | |
| J-2* | S | Q-60 (R$_7$ = H, R$_8$ = H, R$_9$ = H, R$_2$ = H) | H | H | OCH$_3$ | OCH$_3$ | |
| J-2* | S | Q-105 (R$_7$ = H, R$_8$ = H, R$_9$ = H, R$_2$ = H) | H | H | OCH$_3$ | OCH$_3$ | |
| J-2* | S | Q-138 (R$_7$ = H, R$_8$ = H, R$_9$ = H) | H | H | OCH$_3$ | OCH$_3$ | |

TABLE 3

General Formula 3

| J | W$_1$ | Q | R | R$_1$ | X$_1$ | Y$_1$ |
|---|---|---|---|---|---|---|
| J-1 | S | Q-1 (R$_7$ = H, R$_8$ = H) | H | H | CH$_3$ | CH$_2$ |
| J-2 | S | Q-1 (R$_7$ = H, R$_8$ = H) | H | H | CH$_3$ | CH$_2$ |
| J-1 | S | Q-1 (R$_7$ = H, R$_8$ = H) | CH$_3$ | H | OCH$_3$ | CH$_2$ |
| J-2 | S | Q-1 (R$_7$ = H, R$_8$ = H) | CH$_3$ | H | OC$_2$H$_5$ | CH$_2$ |
| J-1 | S | Q-1 (R$_7$ = H, R$_8$ = H) | CH$_3$ | H | OCF$_2$H | CH$_2$ |
| J-2 | S | Q-1 (R$_7$ = H, R$_8$ = H) | CH$_3$ | H | CH$_3$ | O |
| J-1 | S | Q-1 (R$_7$ = H, R$_8$ = H) | CH$_3$ | H | OCH$_3$ | O |
| J-2 | S | Q-1 (R$_7$ = H, R$_8$ = H) | CH$_3$ | H | OC$_2$H$_5$ | O |
| J-1 | S | Q-1 (R$_7$ = H, R$_8$ = H) | CH$_3$ | H | OCF$_2$H | O |
| J-2 | O | Q-1 (R$_7$ = H, R$_8$ = H) | H | H | CH$_3$ | CH$_2$ |
| J-3 | S | Q-1 (R$_7$ = H, R$_8$ = H) | H | 5-CH$_3$ | CH$_3$ | CH$_2$ |
| J-1 | S | Q-1 (R$_7$ = H, R$_8$ = H) | H | 5-CH$_2$F | CH$_3$ | CH$_2$ |
| J-2 | S | Q-1 (R$_7$ = H, R$_8$ = H) | H | 5-CH$_2$CH$_2$Br | CH$_3$ | CH$_2$ |
| J-1 | S | Q-1 (R$_7$ = H, R$_8$ = H) | H | 5-CH(CH$_3$)(CH$_2$Cl) | CH$_3$ | CH$_2$ |
| J-2 | S | Q-1 (R$_7$ = H, R$_8$ = H) | H | 4-NH$_2$ | CH$_3$ | CH$_2$ |
| J-1 | S | Q-1 (R$_7$ = H, R$_8$ = H) | H | 4-N(CH$_3$)$_2$ | CH$_3$ | CH$_2$ |
| J-1 | S | Q-1 (R$_7$ = H, R$_8$ = H) | H | 5-Cl | CH$_3$ | CH$_2$ |
| J-1 | S | Q-1 (R$_7$ = H, R$_8$ = H) | H | 4-F | CH$_3$ | CH$_2$ |
| J-1 | S | Q-1 (R$_7$ = H, R$_8$ = H) | H | 5-I | CH$_3$ | CH$_2$ |
| J-2 | S | Q-1 (R$_7$ = H, R$_8$ = H) | H | 4-NO$_2$ | CH$_3$ | CH$_2$ |
| J-2 | S | Q-1 (R$_7$ = H, R$_8$ = H) | H | 5-CF$_3$ | CH$_3$ | CH$_2$ |
| J-1 | S | Q-1 (R$_7$ = H, R$_8$ = H) | H | 5-CH$_3$ | CH$_3$ | O |
| J-1 | O | Q-1 (R$_7$ = H, R$_8$ = H) | H | 5-CH$_2$F | CH$_3$ | O |
| J-2 | S | Q-1 (R$_7$ = H, R$_8$ = H) | H | 5-CH$_2$CH$_2$Br | CH$_3$ | O |
| J-3 | S | Q-1 (R$_7$ = H, R$_8$ = H) | H | 5-CH(CH$_3$)(CH$_2$Cl) | CH$_3$ | O |
| J-1 | S | Q-1 (R$_7$ = H, R$_8$ = H) | H | 4-NH$_2$ | CH$_3$ | O |
| J-1 | S | Q-1 (R$_7$ = H, R$_8$ = H) | H | 4-N(CH$_3$)$_2$ | CH$_3$ | O |
| J-1 | S | Q-1 (R$_7$ = H, R$_8$ = H) | H | 5-Cl | CH$_3$ | O |
| J-2 | S | Q-1 (R$_7$ = H, R$_8$ = H) | H | 4-F | CH$_3$ | O |
| J-1 | S | Q-1 (R$_7$ = H, R$_8$ = H) | H | 5-I | CH$_3$ | O |
| J-2 | S | Q-1 (R$_7$ = H, R$_8$ = H) | H | 4-NO$_2$ | CH$_3$ | O |
| J-1 | S | Q-1 (R$_7$ = H, R$_8$ = H) | H | 5-CF$_3$ | CH$_3$ | O |
| J-2 | S | Q-1 (R$_7$ = H, R$_8$ = H) | H | H | CH$_3$ | O |
| J-1 | S | Q-1 (R$_7$ = H, R$_8$ = H) | H | H | OCH$_3$ | O |
| J-2 | O | Q-1 (R$_7$ = H, R$_8$ = H) | H | H | OC$_2$H$_5$ | O |
| J-1 | S | Q-1 (R$_7$ = H, R$_8$ = H) | H | H | OCF$_2$H | O |
| J-2 | S | Q-1 (R$_7$ = H, R$_8$ = H) | H | H | OCH$_3$ | CH$_2$ |
| J-3 | S | Q-1 (R$_7$ = H, R$_8$ = H) | H | H | OC$_2$H$_5$ | CH$_2$ |
| J-1 | S | Q-1 (R$_7$ = H, R$_8$ = H) | H | H | OCF$_2$H | CH$_2$ |
| J-2 | S | Q-1 (R$_7$ = H, R$_8$ = H) | H | H | CH$_3$ | O |
| J-1 | S | Q-1 (R$_7$ = H, R$_8$ = CH$_3$) | H | H | CH$_3$ | CH$_2$ |
| J-2 | S | Q-1 (R$_7$ = H, R$_8$ = CH$_3$) | H | H | CH$_3$ | CH$_2$ |
| J-1 | NH | Q-1 (R$_7$ = H, R$_8$ = CH(CH$_3$)$_2$) | H | H | OCH$_3$ | CH$_2$ |
| J-2 | S | Q-1 (R$_7$ = H, R$_8$ = n-C$_4$H$_9$) | H | H | OCH$_3$ | O |
| J-1 | O | Q-1 (R$_7$ = H, R$_8$ = CH$_3$) | H | H | OCH$_3$ | O |
| J-1 | S | Q-37 (R$_7$ = H, R$_8$ = H, R$_2$ = H) | H | H | CH$_3$ | CH$_2$ |
| J-2 | S | Q-37 (R$_7$ = H, R$_8$ = H, R$_2$ = i-C$_3$H$_7$) | H | H | CH$_3$ | O |
| J-1 | S | Q-37 (R$_7$ = H, R$_8$ = H, R$_2$ = n-C$_4$H$_9$) | H | 5-CH$_3$ | OCH$_3$ | CH$_2$ |
| J-2 | S | Q-98 (R$_7$ = H, R$_8$ = H, R$_9$ = H) | H | H | CH$_3$ | CH$_2$ |
| J-3 | O | Q-98 (R$_7$ = CH$_3$, R$_8$ = H, R$_9$ = H) | H | H | CH$_3$ | O |
| J-1 | S | Q-98 (R$_7$ = H, R$_8$ = H, R$_9$ = i-C$_3$H$_7$) | H | 5-CH$_3$ | OCH$_3$ | CH$_2$ |
| J-1 | O | Q-105 (R$_7$ = H, R$_8$ = H, R$_9$ = H, R$_2$ = H) | H | H | CH$_3$ | CH$_2$ |
| J-2 | S | Q-105 (R$_7$ = CH$_3$, R$_8$ = H, R$_9$ = H, R$_2$ = CH$_3$) | H | H | CH$_3$ | O |
| J-3 | NH | Q-105 (R$_7$ = H, R$_8$ = CH$_3$, R$_9$ = H, R$_2$ = C$_2$H$_5$) | H | 5-CH$_3$ | OCH$_3$ | CH$_2$ |
| J-1 | S | Q-138 (R$_7$ = H, R$_8$ = H, R$_9$ = H) | H | H | CH$_3$ | CH$_2$ |
| J-2 | O | Q-138 (R$_7$ = CH$_3$, R$_8$ = H, R$_9$ = H) | H | H | CH$_3$ | O |
| J-3 | S | Q-138 (R$_7$ = H, R$_8$ = H, R$_9$ = CH$_3$) | H | H | OCH$_3$ | CH$_2$ |
| J-2 | S | Q-143 (R$_7$ = H, R$_8$ = H, R$_9$ = H, R$_3$ = CH$_3$) | H | H | CH$_3$ | CH$_2$ |
| J-1 | S | Q-143 (R$_7$ = H, R$_8$ = H, R$_9$ = H, R$_3$ = H) | H | H | CH$_3$ | O |
| J-2 | S | Q-143 (R$_7$ = CH$_3$, R$_8$ = H, R$_9$ = CH$_3$, R$_3$ = CH$_3$) | H | 5-Cl | OCH$_3$ | CH$_2$ |

TABLE 4

General Formula 4

| J | W$_1$ | Q | R | R$_1$ | X$_1$ |
|---|---|---|---|---|---|
| J-1 | S | Q-1 (R$_7$ = H, R$_8$ = H) | H | H | CH$_3$ |
| J-2 | S | Q-1 (R$_7$ = H, R$_8$ = H) | H | H | CH$_3$ |
| J-1 | S | Q-1 (R$_7$ = H, R$_8$ = H) | CH$_3$ | H | OCH$_3$ |
| J-2 | S | Q-1 (R$_7$ = H, R$_8$ = H) | CH$_3$ | H | OC$_2$H$_5$ |
| J-1 | S | Q-1 (R$_7$ = H, R$_8$ = H) | CH$_3$ | H | OCF$_2$H |
| J-2 | S | Q-1 (R$_7$ = H, R$_8$ = H) | H | 5-CH$_3$ | CH$_3$ |
| J-1 | S | Q-1 (R$_7$ = H, R$_8$ = H) | H | 5-CH$_2$F | CH$_3$ |
| J-2 | S | Q-1 (R$_7$ = H, R$_8$ = H) | H | 5-CH$_2$CH$_2$Br | CH$_3$ |
| J-3 | S | Q-1 (R$_7$ = H, R$_8$ = H) | H | 5-CH(CH$_3$)(CH$_2$Cl) | CH$_3$ |
| J-1 | O | Q-1 (R$_7$ = H, R$_8$ = H) | H | 4-NH$_2$ | CH$_3$ |
| J-2 | S | Q-1 (R$_7$ = H, R$_8$ = H) | H | 4-N(CH$_3$)$_2$ | CH$_3$ |
| J-1 | NH | Q-1 (R$_7$ = H, R$_8$ = H) | H | 5-Cl | CH$_3$ |
| J-2 | S | Q-1 (R$_7$ = H, R$_8$ = H) | H | 4-F | CH$_3$ |

TABLE 4-continued

General Formula 4

| J | W₁ | Q | R | R₁ | X₁ |
|---|---|---|---|---|---|
| J-1 | S | Q-1 ($R_7$ = H, $R_8$ = H) | H | 5-I | $CH_3$ |
| J-2 | S | Q-1 ($R_7$ = H, $R_8$ = H) | H | 4-$NO_2$ | $CH_3$ |
| J-1 | S | Q-1 ($R_7$ = H, $R_8$ = H) | H | 5-$CF_3$ | $CH_3$ |
| J-2 | S | Q-1 ($R_7$ = H, $R_8$ = H) | H | H | $OCH_3$ |
| J-1 | S | Q-1 ($R_7$ = H, $R_8$ = H) | H | H | $OC_2H_5$ |
| J-2 | S | Q-1 ($R_7$ = H, $R_8$ = H) | H | H | $OCF_2H$ |
| J-3 | O | Q-1 ($R_7$ = H, $R_8$ = $CH_3$) | H | H | $CH_3$ |
| J-1 | S | Q-1 ($R_7$ = H, $R_8$ = $CH_2CH_3$) | H | H | $CH_3$ |
| J-2 | S | Q-1 ($R_7$ = H, $R_8$ = $CH(CH_3)_2$) | H | H | $OCH_3$ |
| J-1 | S | Q-1 ($R_7$ = H, $R_8$ = n-$C_4H_9$) | H | H | $OCH_3$ |
| J-2 | S | Q-1 ($R_7$ = H, $R_8$ = $CH_3$) | H | H | $OCH_3$ |
| J-3 | O | Q-37 ($R_7$ = H, $R_8$ = H, $R_2$ = H) | H | H | $CH_3$ |
| J-1 | S | Q-37 ($R_7$ = H, $R_8$ = H, $R_2$ = i-$C_3H_7$) | H | H | $CH_3$ |
| J-2 | S | Q-37 ($R_7$ = H, $R_8$ = H, $R_2$ = n-$C_4H_9$) | H | 5-$CH_3$ | $OCH_3$ |
| J-1 | NH | Q-98 ($R_7$ = H, $R_8$ = H, $R_9$ = H) | H | H | $CH_3$ |
| J-2 | S | Q-98 ($R_7$ = $CH_3$, $R_8$ = H, $R_9$ = H) | H | H | $CH_3$ |
| J-1 | S | Q-98 ($R_7$ = H, $R_8$ = H, $R_9$ = i-$C_3H_7$) | H | 5-$CH_3$ | $OCH_3$ |
| J-2 | S | Q-105 ($R_7$ = H, $R_8$ = H, $R_9$ = H, $R_2$ = H) | H | H | $CH_3$ |
| J-1 | S | Q-105 ($R_7$ = $CH_3$, $R_8$ = H, $R_9$ = H, $R_2$ = $CH_3$) | H | H | $CH_3$ |
| J-2 | S | Q-105 ($R_7$ = H, $R_8$ = $CH_3$, $R_9$ = H, $R_2$ = $C_2H_5$) | H | 5-$CH_3$ | $OCH_3$ |
| J-2 | S | Q-138 ($R_7$ = H, $R_8$ = H, $R_9$ = H) | H | H | $CH_3$ |
| J-1 | S | Q-138 ($R_7$ = $CH_3$, $R_8$ = H, $R_9$ = H) | H | H | $CH_3$ |
| J-2 | S | Q-138 ($R_7$ = H, $R_8$ = H, $R_9$ = $CH_3$) | H | H | $OCH_3$ |
| J-2 | S | Q-143 ($R_7$ = H, $R_8$ = H, $R_9$ = H, $R_3$ = $CH_3$) | H | H | $CH_3$ |
| J-3 | S | Q-143 ($R_7$ = H, $R_8$ = H, $R_9$ = H, $R_3$ = H) | H | H | $CH_3$ |
| J-1 | S | Q-143 ($R_7$ = $CH_3$, $R_8$ = H, $R_9$ = $CH_3$, $R_3$ = $CH_3$) | H | 5-Cl | $OCH_3$ |

TABLE 5

General Formula 5

| J | W₁ | Q | R | R₁ | X₁ | Y₂ |
|---|---|---|---|---|---|---|
| J-1 | S | Q-1 ($R_7$ = H, $R_8$ = H) | H | H | $CH_3$ | $CH_3$ |
| J-2 | S | Q-1 ($R_7$ = H, $R_8$ = H) | H | H | $CH_3$ | H |
| J-1 | S | Q-1 ($R_7$ = H, $R_8$ = H) | H | H | $OCH_3$ | $CH_3$ |
| J-2 | S | Q-1 ($R_7$ = H, $R_8$ = H) | H | H | $OC_2H_5$ | $CH_3$ |
| J-1 | S | Q-1 ($R_7$ = H, $R_8$ = H) | H | H | $OCF_2H$ | $CH_3$ |
| J-2 | S | Q-1 ($R_7$ = H, $R_8$ = H) | H | H | $OCH_3$ | H |
| J-1 | NH | Q-1 ($R_7$ = H, $R_8$ = H) | H | H | $OC_2H_5$ | H |
| J-2 | S | Q-1 ($R_7$ = H, $R_8$ = H) | H | H | $OCF_2H$ | H |
| J-1 | S | Q-1 ($R_7$ = H, $R_8$ = H) | $CH_3$ | H | $CH_3$ | $CH_3$ |
| J-2 | O | Q-1 ($R_7$ = H, $R_8$ = H) | $CH_3$ | H | $OCH_3$ | $CH_3$ |
| J-3 | S | Q-1 ($R_7$ = H, $R_8$ = H) | $CH_3$ | H | $CH_3$ | H |
| J-1 | S | Q-1 ($R_7$ = H, $R_8$ = H) | H | 5-$CH_3$ | $OCH_3$ | H |
| J-2 | S | Q-1 ($R_7$ = H, $R_8$ = H) | H | 5-$CH_2F$ | $OCH_3$ | H |
| J-1 | S | Q-1 ($R_7$ = H, $R_8$ = H) | H | 5-$CH_2CH_2Br$ | $OCH_3$ | H |
| J-2 | S | Q-1 ($R_7$ = H, $R_8$ = H) | H | 5-$CH(CH_3)(CH_2Cl)$ | $OCH_3$ | H |
| J-1 | S | Q-1 ($R_7$ = H, $R_8$ = H) | H | 4-$NH_2$ | $OCH_3$ | H |
| J-1 | S | Q-1 ($R_7$ = H, $R_8$ = H) | H | 4-$N(CH_3)_2$ | $OCH_3$ | H |
| J-1 | S | Q-1 ($R_7$ = H, $R_8$ = H) | H | 5-Cl | $OCH_3$ | H |
| J-2 | S | Q-1 ($R_7$ = H, $R_8$ = H) | H | 4-F | $OCH_3$ | H |
| J-1 | S | Q-1 ($R_7$ = H, $R_8$ = H) | H | 5-I | $OCH_3$ | H |
| J-2 | S | Q-1 ($R_7$ = H, $R_8$ = H) | H | 4-$NO_2$ | $OCH_3$ | H |
| J-3 | O | Q-1 ($R_7$ = H, $R_8$ = H) | H | 5-$CF_3$ | $OCH_3$ | H |
| J-1 | S | Q-1 ($R_7$ = H, $R_8$ = $CH_3$) | H | H | $OCH_3$ | H |
| J-2 | S | Q-1 ($R_7$ = H, $R_8$ = $CH_3$) | H | H | $OCH_3$ | $CH_3$ |
| J-1 | S | Q-1 ($R_7$ = H, $R_8$ = $CH_2CH_3$) | H | H | $CH_3$ | H |
| J-2 | S | Q-1 ($R_7$ = H, $R_8$ = $CH(CH_3)_2$) | H | H | $CH_3$ | $CH_3$ |
| J-1 | S | Q-1 ($R_7$ = H, $R_8$ = n-$C_4H_9$) | H | H | $OCF_2H$ | H |
| J-2 | S | Q-1 ($R_7$ = $CH_3$, $R_8$ = $CH_3$) | H | H | $OCH_3$ | H |
| J-3 | S | Q-37 ($R_7$ = H, $R_8$ = H, $R_2$ = H) | H | H | $OCH_3$ | H |
| J-1 | S | Q-37 ($R_7$ = H, $R_8$ = H, $R_2$ = i-$C_3H_7$) | H | H | $OCH_3$ | $CH_3$ |
| J-2 | S | Q-37 ($R_7$ = H, $R_8$ = H, $R_2$ = n-$C_4H_9$) | H | 5-$CH_3$ | $OCF_2H$ | H |
| J-1 | S | Q-98 ($R_7$ = H, $R_8$ = H, $R_9$ = H) | H | H | $OCH_3$ | H |
| J-2 | S | Q-98 ($R_7$ = $CH_3$, $R_8$ = H, $R_9$ = H) | H | H | $OCH_3$ | H |
| J-1 | S | Q-98 ($R_7$ = H, $R_8$ = H, $R_9$ = i-$C_3H_7$) | H | 5-$CH_3$ | $OCH_3$ | H |
| J-2 | S | Q-105 ($R_7$ = H, $R_8$ = H, $R_9$ = H, $R_2$ = H) | H | H | $OCH_3$ | H |
| J-1 | S | Q-105 ($R_7$ = $CH_3$, $R_8$ = H, $R_9$ = H, $R_2$ = $CH_3$) | H | H | $OCH_3$ | H |
| J-2 | S | Q-105 ($R_7$ = H, $R_8$ = $CH_3$, $R_9$ = H, $R_2$ = $C_2H_5$) | H | 5-$CH_3$ | $OCH_3$ | H |
| J-2 | S | Q-138 ($R_7$ = H, $R_8$ = H, $R_9$ = H) | H | H | $OCH_3$ | H |
| J-1 | S | Q-138 ($R_7$ = $CH_3$, $R_8$ = H, $R_9$ = H) | H | H | $OCH_3$ | H |
| J-2 | S | Q-138 ($R_7$ = H, $R_8$ = H, $R_9$ = H) | H | H | $OCH_3$ | H |
| J-2 | S | Q-143 ($R_7$ = H, $R_8$ = H, $R_9$ = $CH_3$) | H | H | $OCH_3$ | H |
| J-1 | O | Q-143 ($R_7$ = H, $R_8$ = H, $R_9$ = H, $R_3$ = H) | H | H | $OCH_3$ | $CH_3$ |
| J-2 | S | Q-143 ($R_7$ = $CH_3$, $R_8$ = H, $R_9$ = $CH_3$, $R_3$ = $CH_3$) | H | 5-Cl | $CH_3$ | H |

TABLE 6

General Formula 6

| J | $W_1$ | Q | R | $R_1$ | $X_2$ | $Y_3$ |
|---|---|---|---|---|---|---|
| J-1 | S | Q-1 ($R_7$ = H, $R_8$ = H) | H | H | $CH_3$ | $CH_3$ |
| J-2 | S | Q-1 ($R_7$ = H, $R_8$ = H) | H | H | $OCH_3$ | $CH_3$ |
| J-1 | S | Q-1 ($R_7$ = H, $R_8$ = H) | H | H | $SCH_3$ | $CH_3$ |
| J-2 | S | Q-1 ($R_7$ = H, $R_8$ = H) | H | H | $CH_3$ | $CH_2CH_3$ |
| J-1 | S | Q-1 ($R_7$ = H, $R_8$ = H) | H | H | $OCH_3$ | $CH_2CH_3$ |
| J-2 | S | Q-1 ($R_7$ = H, $R_8$ = H) | H | H | $SCH_3$ | $CH_2CH_3$ |
| J-1 | S | Q-1 ($R_7$ = H, $R_8$ = H) | H | H | $CH_3$ | $CH_2CF_3$ |
| J-2 | S | Q-1 ($R_7$ = H, $R_8$ = H) | H | H | $OCH_3$ | $CH_2CF_3$ |
| J-1 | S | Q-1 ($R_7$ = H, $R_8$ = H) | H | H | $SCH_3$ | $CH_2CF_3$ |
| J-2 | O | Q-1 ($R_7$ = H, $R_8$ = H) | $CH_3$ | 5-$CH_3$ | $CH_3$ | $CH_3$ |
| J-3 | S | Q-1 ($R_7$ = H, $R_8$ = H) | H | 5-$CH_2F$ | $OCH_3$ | $CH_3$ |
| J-1 | S | Q-1 ($R_7$ = H, $R_8$ = H) | H | 5-$CH_2CH_2Br$ | $OCH_3$ | $CH_3$ |
| J-2 | S | Q-1 ($R_7$ = H, $R_8$ = H) | H | 5-$CH(CH_3)(CH_2Cl)$ | $OCH_3$ | $CH_3$ |
| J-1 | S | Q-1 ($R_7$ = H, $R_8$ = H) | H | 4-$NH_2$ | $OCH_3$ | $CH_3$ |
| J-2 | S | Q-1 ($R_7$ = H, $R_8$ = H) | H | 4-$N(CH_3)_2$ | $OCH_3$ | $CH_3$ |
| J-1 | S | Q-1 ($R_7$ = H, $R_8$ = H) | H | 5-Cl | $OCH_3$ | $CH_3$ |
| J-2 | S | Q-1 ($R_7$ = H, $R_8$ = H) | H | 4-F | $OCH_3$ | $CH_3$ |
| J-1 | S | Q-1 ($R_7$ = H, $R_8$ = H) | H | 5-I | $OCH_3$ | $CH_3$ |
| J-2 | S | Q-1 ($R_7$ = H, $R_8$ = H) | H | 4-$NO_2$ | $OCH_3$ | $CH_3$ |
| J-1 | O | Q-1 ($R_7$ = H, $R_8$ = H) | H | 5-$CF_3$ | $OCH_3$ | $CH_3$ |
| J-2 | NH | Q-1 ($R_7$ = H, $R_8$ = $CH_3$) | H | H | $OCH_3$ | $CH_3$ |
| J-3 | S | Q-1 ($R_7$ = H, $R_8$ = $CH_3$) | H | H | $CH_3$ | $CH_2CF_3$ |
| J-1 | S | Q-1 ($R_7$ = H, $R_8$ = $CH_2CH_3$) | H | H | $CH_3$ | $CH_3$ |
| J-2 | S | Q-1 ($R_7$ = H, $R_8$ = $CH(CH_3)_2$) | H | H | $OCH_3$ | $CH_3$ |
| J-1 | S | Q-1 ($R_7$ = H, $R_8$ = n-$C_4H_9$) | H | H | $SCH_3$ | $CH_3$ |
| J-2 | S | Q-1 ($R_7$ = $CH_3$, $R_8$ = $CH_3$) | H | H | $OCH_3$ | $CH_3$ |
| J-3 | S | Q-37 ($R_7$ = H, $R_8$ = H, $R_2$ = H) | H | H | $OCH_3$ | $CH_3$ |
| J-1 | S | Q-37 ($R_7$ = H, $R_8$ = H, $R_2$ = i-$C_3H_7$) | H | H | $OCH_3$ | $CH_3$ |
| J-2 | S | Q-37 ($R_7$ = H, $R_8$ = H, $R_2$ = n-$C_4H_9$) | H | 5-$CH_3$ | $CH_3$ | $CH_2CF_3$ |
| J-1 | S | Q-98 ($R_7$ = H, $R_8$ = H, $R_9$ = H) | H | H | $OCH_3$ | $CH_3$ |
| J-2 | $NCH_3$ | Q-98 ($R_7$ = $CH_3$, $R_8$ = H, $R_9$ = H) | H | H | $OCH_3$ | $CH_3$ |
| J-1 | S | Q-98 ($R_7$ = H, $R_8$ = H, $R_9$ = i-$C_3H_7$) | H | 5-$CH_3$ | $CH_3$ | $CH_2CF_3$ |
| J-2 | S | Q-105 ($R_7$ = H, $R_8$ = H, $R_9$ = H, $R_2$ = H) | H | H | $OCH_3$ | $CH_3$ |
| J-1 | S | Q-105 ($R_7$ = $CH_3$, $R_8$ = H, $R_9$ = H, $R_2$ = $CH_3$) | H | H | $OCH_3$ | $CH_3$ |
| J-2 | S | Q-105 ($R_7$ = H, $R_8$ = $CH_3$, $R_9$ = H, $R_2$ = $C_2H_5$) | H | 5-$CH_3$ | $CH_3$ | $CH_2CF_3$ |
| J-2 | S | Q-138 ($R_7$ = H, $R_8$ = H, $R_9$ = H) | H | H | $OCH_3$ | $CH_3$ |
| J-1 | S | Q-138 ($R_7$ = $CH_3$, $R_8$ = H, $R_9$ = H) | H | H | $OCH_3$ | $CH_3$ |
| J-2 | S | Q-138 ($R_7$ = H, $R_8$ = H, $R_9$ = $CH_3$) | H | H | $OCH_3$ | $CH_3$ |
| J-2 | O | Q-143 ($R_7$ = H, $R_8$ = H, $R_9$ = H, $R_3$ = $CH_3$) | H | H | $OCH_3$ | $CH_3$ |
| J-3 | S | Q-143 ($R_7$ = H, $R_8$ = H, $R_9$ = H, $R_3$ = H) | H | H | $OCH_3$ | $CH_3$ |
| J-1 | S | Q-143 ($R_7$ = $CH_3$, $R_8$ = H, $R_9$ = $CH_3$, $R_3$ = $CH_3$) | H | 5-Cl | $CH_3$ | $CH_3$ |

TABLE 7

General Formula 7

| J | $W_1$ | Q | R | $R_1$ | $X_3$ |
|---|---|---|---|---|---|
| J-1 | S | Q-1 ($R_7$ = H, $R_8$ = H) | H | H | $CH_3$ |
| J-2 | S | Q-1 ($R_7$ = H, $R_8$ = H) | H | H | $OCH_3$ |
| J-1 | S | Q-1 ($R_7$ = H, $R_8$ = H) | $CH_3$ | H | $OCH_3$ |
| J-2 | S | Q-1 ($R_7$ = H, $R_8$ = $CH_3$) | H | H | $CH_3$ |
| J-1 | S | Q-1 ($R_7$ = H, $R_8$ = H) | H | 5-$CH_3$ | $OCH_3$ |
| J-2 | S | Q-2 ($R_7$ = H, $R_8$ = H) | H | H | $OCH_3$ |
| J-1 | S | Q-3 ($R_7$ = $C_2H_5$, $R_8$ = H) | H | H | $OCH_3$ |
| J-2 | S | Q-4 ($R_3$ = $CH_3$, $R_7$ = H, $R_8$ = H) | H | H | $OCH_3$ |
| J-1 | S | Q-5 ($R_3$ = H, $R_7$ = H, $R_8$ = H) | H | H | $OCH_3$ |
| J-2 | O | Q-7 ($R_7$ = H, $R_8$ = H, $R_9$ = H) | H | H | $OCH_3$ |
| J-3 | S | Q-8 ($R_2$ = H, $R_7$ = H, $R_8$ = H) | H | H | $OCH_3$ |
| J-1 | S | Q-9 ($R_2$ = H, $R_7$ = H, $R_8$ = H) | H | 5-$CH_2F$ | $OCH_3$ |
| J-2 | S | Q-9 ($R_2$ = H, $R_7$ = H, $R_8$ = H) | H | H | $OCH_3$ |
| J-1 | S | Q-11 ($R_7$ = H, $R_8$ = H) | H | 5-$CH_2CH_2Br$ | $OCH_3$ |
| J-2 | S | Q-11 ($R_7$ = H, $R_8$ = H) | H | H | $OCH_3$ |
| J-1 | S | Q-13 ($R_3$ = $CH_3$, $R_7$ = H, $R_8$ = H) | H | 5-$CH(CH_3)(CH_2Cl)$ | $OCH_3$ |
| J-2 | S | Q-13 ($R_3$ = $CH_3$, $R_7$ = H, $R_8$ = H) | H | H | $OCH_3$ |
| J-1 | NH | Q-14 ($R_3$ = $CH_3$, $R_7$ = H, $R_8$ = H) | H | H | $OCH_3$ |
| J-2 | S | Q-16 ($R_7$ = H, $R_8$ = H, $R_9$ = H) | H | H | $OCH_3$ |
| J-1 | O | Q-17 ($R_2$ = H, $R_7$ = H, $R_8$ = H) | H | H | $OCH_3$ |
| J-2 | S | Q-18 ($R_2$ = H, $R_7$ = H, $R_8$ = H) | H | H | $OCH_3$ |
| J-3 | S | Q-29 ($R_7$ = H, $R_8$ = H) | H | H | $OCH_3$ |
| J-1 | S | Q-30 ($R_7$ = H, $R_8$ = H) | H | H | $OCH_3$ |
| J-2 | S | Q-32 ($R_3$ = $CH_3$, $R_7$ = H, $R_8$ = H) | H | 4-$NH_2$ | $OCH_3$ |
| J-1 | S | Q-32 ($R_3$ = $CH_3$, $R_7$ = H, $R_8$ = H) | H | H | $OCH_3$ |
| J-2 | S | Q-36 ($R_2$ = H, $R_7$ = H, $R_8$ = H) | H | H | $OCH_3$ |
| J-1 | S | Q-51 ($R_7$ = H, $R_8$ = H, $R_9$ = H) | H | H | $OCH_3$ |
| J-2 | S | Q-52 ($R_7$ = H, $R_8$ = H, $R_9$ = H) | H | H | $OCH_3$ |
| J-1 | S | Q-55 ($R_3$ = $CH_3$, $R_7$ = H, $R_8$ = H, $R_9$ = H) | H | 4-$N(CH_3)_2$ | $OCH_3$ |
| J-2 | O | Q-55 ($R_3$ = $CH_3$, $R_7$ = H, $R_8$ = H, $R_9$ = H) | H | H | $OCH_3$ |
| J-1 | S | Q-59 ($R_7$ = H, $R_8$ = H, $R_9$ = H, $R_{10}$ = H) | H | H | $OCH_3$ |
| J-2 | S | Q-60 ($R_2$ = H, $R_7$ = H, $R_8$ = H, $R_9$ = H) | H | H | $OCH_3$ |

TABLE 7-continued

General Formula 7

| J | $W_1$ | Q | R | $R_1$ | $X_3$ |
|---|---|---|---|---|---|
| J-3 | S | Q-69 ($R_3$ = $CH_3$, $R_7$ = H, $R_8$ = H, $R_9$ = H) | H | 5-Cl | $OCH_3$ |
| J-1 | S | Q-69 ($R_3$ = $CH_3$, $R_7$ = H, $R_8$ = H, $R_9$ = H) | H | H | $OCH_3$ |
| J-2 | S | Q-70 ($R_3$ = $CH_3$, $R_7$ = H, $R_8$ = H, $R_9$ = H) | H | H | $OCH_3$ |
| J-1 | S | Q-71 ($R_7$ = H, $R_8$ = H, $R_9$ = H, $R_{10}$ = H) | H | 4-F | $OCH_3$ |
| J-2 | S | Q-71 ($R_7$ = H, $R_8$ = H, $R_9$ = H, $R_{10}$ = H) | H | H | $OCH_3$ |
| J-1 | S | Q-72 ($R_2$ = H, $R_7$ = H, $R_8$ = H, $R_9$ = H) | H | 5-I | $OCH_3$ |
| J-2 | S | Q-72 ($R_2$ = H, $R_7$ = H, $R_8$ = H, $R_9$ = H) | H | H | $OCH_3$ |
| J-1 | O | Q-74 ($R_2$ = H, $R_7$ = H, $R_8$ = H, $R_9$ = H) | H | 5-$NO_2$ | $OCH_3$ |
| J-2 | S | Q-74 ($R_2$ = H, $R_7$ = H, $R_8$ = H, $R_9$ = H) | H | H | $OCH_3$ |
| J-1 | S | Q-95 ($R_7$ = H, $R_8$ = H, $R_9$ = H) | H | 5-$CF_3$ | $OCH_3$ |
| J-2 | S | Q-95 ($R_7$ = H, $R_8$ = H, $R_9$ = H) | H | H | $OCH_3$ |
| J-3 | S | Q-104 ($R_2$ = H, $R_7$ = H, $R_8$ = H, $R_9$ = H) | H | H | $OCH_3$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active Ingredient | Weight Percent* Diluent(s) | Surfactant(s) |
|---|---|---|---|
| Wettable Powders | 20–90 | 0–74 | 1–10 |
| Oil Suspensions | 3–50 | 40–95 | 1–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described is Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 4

| Wettable Powder | |
|---|---|
| N—[(4-methoxy-6-methyl-1,3,5-triazin-2-yl)aminocarbonyl]-3-(tetrahydro-2-oxo-3-furanyl)-2-thiophenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 5

| Wettable Powder | |
|---|---|
| N—[(4,6-dimethoxypyrimidin-2-yl)amino-carbonyl]-3-(tetrahydro-2-oxo-3-furanyl)-2-thiophenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 6

| Granule | |
|---|---|
| Wettable Powder of Example 5 | 5% |
| attapulgite granules (U.S.S. 20–40 mesh; 0.84–0.42 mm) | 95% |

A slurry of wettable powder containing 25% solids is sprayed on the surface of attapulgite granules while tumbling in a double-cone blender. The granules are dried and packaged.

EXAMPLE 7

| Extruded Pellet | |
|---|---|
| N—[(4-methoxy-6-methyl-1,3,5-triazin-2-yl)amino-carbonyl]-3-(tetrahydro-2-oxo-3-furanyl)-2-thiophenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

| Oil Suspension | |
|---|---|
| N—[(4,6-dimethoxypyrimidin-2-yl)amino-carbonyl]-3-(tetrahydro-2-oxo-3-furanyl)-2-thiophenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

| Wettable Powder | |
|---|---|
| N—[(4-methoxy-6-methyl-1,3,5-triazin-2-yl)amino-carbonyl]-3-(tetrahydro-2-oxo-3-furanyl)-2-thiophenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 10

| Low Strength Granule | |
|---|---|
| N—[(4,6-dimethoxypyrimidin-2-yl)amino-carbonyl]-3-(tetrahydro-2-oxo-3-furanyl)-2-thiophenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 11

| Aqueous Suspension | |
|---|---|
| N—[(4-methoxy-6-methyl-1,3,5-triazin-2-yl)amino-carbonyl]-3-(tetrahydro-2-oxo-3-furanyl)-2-thiophenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 12

| Low Strength Granule | |
|---|---|
| N—[(4,6-dimethoxypyrimidin-2-yl)amino-carbonyl]-3-(tetrahydro-2-oxo-3-furanyl)-2-thiophenesulfonamide | 0.1% |
| attapulgite granules (U.S.S. 20–40 mesh) | 99.9% |

The active ingredients is dissolved in a solvent and the solution is sprayed upon dedusted granules in a double-cone blender. After spraying of the solution has been completed, the material is warmed to evaporate the solvent. THe material is allowed to cool and then packaged.

EXAMPLE 13

| Granule | |
|---|---|
| N—[(4-methoxy-6-methyl-1,3,5-triazin-2-yl)amino-carbonyl]-3-(tetrahydro-2-oxo-3-furanyl)-2-thiophenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 14

| High Strength Concentrate | |
|---|---|
| N—[(4,6-dimethoxypyrimidin-2-yl)amino-carbonyl]-3-(tetrahydro-2-oxo-3-furanyl)-2-thiophenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 15

| Wettable Powder | |
|---|---|
| N—[(4-methoxy-6-methyl-1,3,5-triazin-2-yl)amino-carbonyl]-3-(tetrahydro-2-oxo-3-furanyl)-2-thiophenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 16

| Wettable Powder | |
|---|---|
| N—[(4,6-dimethoxypyrimidin-2-yl)amino-carbonyl]-3-(tetrahydro-2-oxo-3-furanyl)-2-thiophenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 17

| Oil Suspension | |
|---|---|
| N—[(4-methoxy-6-methyl-1,3,5-triazin-2-yl)amino-carbonyl]-3-(tetrahydro-2-oxo-3-furanyl)-2-thiophenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 18

| Dust | |
|---|---|
| N—[(4,6-dimethoxypyrimidin-2-yl)amino-carbonyl]-3-(tetrahydro-2-oxo-3-furanyl)-2-thiophenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Compounds of the present invention are highly active preemergent or postemergent herbicides or plant growth regulators. Many of them should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds are expected to have utility for selective herbicides in crops. Alternatively, the subject compounds may be useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foilage present, etc. In general terms, the subject compounds should be applied at levels of around 0.01 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp.), barnyardgrass (*Echinochloa crusgalli*), wild oats (*Avena fatua*), cheatgrass (*Bromus secalinus*), velvetleaf (*Abutilon theophrasti*), morningglory (Ipomoea spp.), cocklebur (*Xanthium pensylvanicum*), sorghum, corn, soybean, sugarbeet, cotton, rice, wheat and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to &=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axiliary stimulation;
S=albinism; and
6Y=abscised buds or flowers.

| Compound No. | X | Y | Z |
|---|---|---|---|
| 1 | CH₃ | CH₃ | CH |
| 2 | OCH₃ | CH₃ | CH |
| 3 | OCH₃ | OCH₃ | CH |
| 4 | OCH₃ | CH₃ | N |
| 5 | OCH₃ | OCH₃ | N |
| 6 | CH₃ | CH₃ | CH |
| 7 | OCH₃ | CH₃ | CH |
| 8 | OCH₃ | OCH₃ | CH |
| 9 | OCH₃ | CH₃ | N |
| 10 | Cl | OCH₃ | CH |
| 11 | CH₃ | CH₃ | CH |
| 12 | OCH₃ | CH₃ | CH |
| 13 | OCH₃ | OCH₃ | CH |
| 14 | OCH₃ | CH₃ | N |
| 15 | OCH₃ | OCH₃ | N |
| 16 | Cl | OCH₃ | CH |
| 17 | CH₃ | CH₃ | CH |
| 18 | OCH₃ | CH₃ | CH |
| 19 | OCH₃ | OCH₃ | CH |
| 20 | OCH₃ | CH₃ | N |
| 21 | OCH₃ | OCH₃ | N |
| 22 | OCH₃ | Cl | CH |

Compound 23

TABLE A

| | TYPE TEST | RATE K/HA | MORN-ING GLORY | COCKLE BUR | VELVET LEAF | NUT SEDGE | CRAB GRASS | BARN-YARD GRASS | CHEAT GRASS | WILD OATS | SICKLE POD | WHEAT | CORN | SOY-BEAN | RICE | SORGHUM | SUGAR-BEET | COT-TON |
|---|---|---|---|---|---|---|---|---|---|---|---|---|---|---|---|---|---|---|
| Compound 1 | POST | 0.05 | 0 | 0 | 0 | 0 | 0 | 0 | 0 | 0 | | 0 | 0 | 0 | 0 | 0 | 0 | 0 |
| | PRE | 0.05 | 0 | 0 | 0 | 0 | 0 | 0 | 0 | 0 | | 0 | 0 | 0 | 0 | 0 | 0 | 0 |
| Compound 2 | POST | 0.05 | 2C | 2C | 3C | 2C | 2G | 3C | 0 | 0 | | 0 | 3C | 3C | 2C | 3C | 3C | 3C |
| | POST | 0.05 | 5G | 3G | 8G | 5G | | 9H | | | | | 9H | 8G | 8G | 9H | 8G | 8H |
| | PRE | 0.05 | 0 | | 2G | 0 | 0 | 0 | 0 | 0 | | 0 | 2C | 0 | 2C | 2C | 3C | 3G |
| | PRE | 0.05 | | | | | | | | | | | 5G | | 5G | 3G | 6G | |
| Compound 3 | POST | 0.05 | 0 | 0 | 0 | 0 | 0 | 3C | 0 | 2C | | 0 | 2C | 2C | 2G | 3C | 4C | 2C |
| | POST | 0.05 | | | | | | 8H | | 4G | | | 5G | 5H | | 8H | 8G | |
| | PRE | 0.05 | 0 | 0 | 4G | 0 | 0 | 0 | 0 | 0 | | 0 | 0 | 2H | 2G | 2G | 4G | 0 |
| Compound 4 | POST | 0.05 | 0 | 0 | 0 | 0 | 0 | 0 | 0 | 0 | | 0 | 0 | 0 | 0 | 0 | 2C | 2C |
| | PRE | 0.05 | 0 | | 0 | 0 | 0 | 0 | 0 | 0 | | 0 | 0 | 0 | 0 | 0 | 5G | |
| Compound 5 | POST | 0.05 | 0 | 4G | 0 | 0 | 0 | 0 | 0 | 0 | | 0 | 0 | 0 | 0 | 0 | 0 | 0 |
| | POST | 0.05 | 0 | 0 | 5G | 5G | 0 | 2C | 0 | 0 | | 0 | 0 | 1H | 0 | 0 | 2C | 2C |
| | PRE | 0.05 | | | | | | 4H | | | | | | | | | 5G | |
| Compound 6 | POST | 0.05 | 0 | 2G | 2G | 0 | 0 | 0 | 0 | 2C | | 0 | 0 | 0 | 0 | 0 | 4H | 0 |
| | POST | 0.05 | 2G | 0 | 0 | 5G | 0 | 7H | 4G | 8G | | 0 | 7H | 1H | 7G | 4C | 3C | 3G |
| | PRE | 0.05 | | | | | | | | 3G | | | | 7G | | 8H | 5G | |
| Compound 7 | POST | 0.05 | 5G | 0 | 5G | 0 | 0 | 0 | 4G | 4G | | 0 | 3C | 1H | 4G | 4G | 5H | 2G |
| | POST | 0.05 | 2G | 7G | 7G | 9G | 5G | 9H | 9H | | | 0 | 8H | 5C | 3C | 3C | 9C | 4C |
| | PRE | 0.05 | | | | | | | | | | | 3C | 9G | 6G | 9H | | 8G |
| | PRE | 0.05 | | | | | | | | | | | 7H | 2H | 2H | | | 2G |
| Compound 8 | POST | 0.05 | 3G | 2H | 8G | 6E | 3G | 8H | 7G | 5G | | 2G | 2C | 5C | 0 | 2C | 5C | 4G |
| | POST | 0.05 | | | | | | | | | | | 7H | 9G | | 8G | 9G | |
| Compound 9 | POST | 0.05 | 5G | 3C | 5G | 8G | 0 | 4H | 0 | 0 | | 0 | 2G | 0 | 0 | 7G | 4C | 2G |
| | PRE | 0.05 | | 9H | | | | | | | | | | | | 3G | 8G | |
| | PRE | 0.05 | | 2H | | | | | | | | | | 1H | | 1H | | |
| Compound 10 | POST | 0.05 | 5G | 0 | 7G | 0 | 0 | 0 | 0 | 0 | | 0 | 0 | 0 | 0 | 0 | 7G | 2G |
| | POST | 0.05 | 0 | 0 | 0 | 0 | 0 | 0 | 0 | 0 | | 0 | 0 | 0 | 0 | 0 | 0 | 0 |
| | PRE | 0.05 | 0 | 0 | 0 | 0 | 0 | 0 | 0 | 0 | | 0 | 0 | 0 | 0 | 2C | 0 | 0 |
| | PRE | 0.05 | | | | | | | | | | | | | | 7G | | |
| Compound 11 | POST | 2 | 3C | 0 | 0 | 0 | 0 | 0 | 4C | 4C | | 0 | 0 | 0 | 0 | 0 | 5C | 5C |
| | POST | 2 | 9G | 9C | &C | 9G | 2C | 9C | 9G | 9C | | 9G | 3C | 8G | 9C | 2C | 9G | 9G |
| | PRE | 2 | 9G | | | &E | 7G | 3C | 4C | 3C | | | 9H | | | 7G | 5C | 9G |
| | PRE | 2 | | | | | 5G | 9H | 9H | 9G | | | 2G | | | 3G | 9C | |
| Compound 12 | POST | 0.05 | 7G | 9H | 9C | &E | 2C | 3C | 7G | 2C | | 3C | 2C | 2C | 9C | &E | 5C | 5C |
| | POST | 0.05 | | | | | | 9H | | 6G | | 9H | 9G | 8G | 8G | | 9G | 9G |
| Compound 13 | POST | 0.05 | 9G | 9H | &C | 2C | 2C | 3C | 7G | 0 | | 4G | 7G | 6G | 3C | 3C | 2C | 2C |
| | POST | 0.05 | | 6H | 5C | 8G | 4G | 8H | | | | | 5H | | 9G | 8H | 8G | 8H |
| | PRE | 0.05 | | | 9C | 3C | 5H | 9H | | | | | | 3C | 6G | 2C | 9C | 9C |
| Compound 14 | POST | 0.05 | 2C | 3C | 5C | 2C | 2G | 3C | 4G | 2C | | 0 | 0 | 2C | 2C | 8G | 4G | |
| | POST | 0.05 | 7G | 9G | 9C | 3C | 4G | 8H | | 6G | | 0 | 3C | 8G | 7G | 2C | 9G | 9C |
| | PRE | 0.05 | 8G | 8H | &C | 9G | 5H | 9H | | | | | 9H | 3G | 4G | 5H | 4C | 2C |
| | PRE | 0.05 | | | | | | | | | | | 5H | | | 3C | | 8H |
| Compound 15 | POST | 0.05 | 3G | 3C | 9G | 2C | 2G | 3C | 6G | 0 | | 0 | 2G | 1H | 3G | 3C | 4C | 5G |
| | PRE | 0.05 | 3C | 3C | 2G | 9G | | 5G | | | | | | 0 | | 7G | 9G | 0 |
| | PRE | 0.05 | 7G | 3C | | 9G | | | | | | | | 2C | 0 | | 3C | |
| | PRE | 0.05 | 5H | 8H | | 9G | | | | | | | | 7G | 4G | | 7H | 0 |
| | PRE | 0.05 | | 5G | | | | | | | | | | 1C | 2G | | 4H | 2C |
| Compound 16 | POST | 0.05 | 0 | | 2G | 0 | 0 | 0 | 0 | 0 | | 0 | 0 | 0 | 0 | 0 | 3C | 2C |
| | POST | 0.05 | | 4G | 2G | 0 | 0 | 0 | 0 | 0 | | 0 | 0 | 0 | 2G | 2G | 5H | 2C |
| | | | | | | | | | | | | | | | | | 5G | 3G |
| | | | | | | | | | | | | | | | | | 2G | 4C |

TABLE A-continued

| | TYPE TEST | RATE K/HA | MORN ING GLORY | COCKLE BUR | VELVET LEAF | NUT SEDGE | CRAB GRASS | BARN YARD GRASS | CHEAT GRASS | WILD OATS | SICKLE POD | WHEAT | CORN | SOY BEAN | RICE | SORGHUM | SUGAR BEET | COT TON |
|---|---|---|---|---|---|---|---|---|---|---|---|---|---|---|---|---|---|---|
| Compound 17 | POST | 0.05 | 8G | 0 | 5G | 0 | 0 | 0 | 0 | 0 | | 0 | 0 | 0 | 3G | 3G | 4G | 9G |
| | PRE | 0.05 | 0 | 2C | 5G | 0 | 0 | 0 | 0 | 0 | | 0 | 0 | 0 | 8G | 3G | 3C | 3G |
| | POST | 0.05 | 1H | 6G | 0 | 0 | 0 | 0 | | | | | | | | | 8H | 1C |
| | PRE | 0.05 | 1H | 1H | 9C | 4C | 2G | 2C | 0 | 2G | | 2G | 2C | 4C | 1C | 0 | 6G | 0 |
| Compound 18 | POST | 0.05 | | 2C | | 9G | | 7H | | | | | 9H | 9G | 2C | 3C | 8C | 4C |
| | POST | 0.05 | | 8G | | 0 | | 0 | | | | | 2C | 3C | 9G | 9H | | 9H |
| | PRE | 0.05 | 8H | 8H | 8G | | | | | | | | 7G | 3G | 6G | 2C | | 2C |
| | PRE | 0.05 | | | | | | | | | | | 2H | | | | | 5G |
| Compound 19 | POST | 0.05 | 7G | 8H | 5C | &C | 0 | 0 | 0 | 0 | | 0 | 0 | 5C | 3G | 0 | 4C | 4C |
| | POST | 0.05 | | | 9G | 0 | | | | | | | | 9G | | | 9G | 9H |
| | PRE | 0.05 | 5G | 8H | 5G | 3G | 0 | 0 | 0 | 0 | | 0 | 0 | 2C | 2G | 0 | 9C | 3G |
| Compound 20 | POST | 0.05 | 2H | 2C | 3C | 0 | 0 | 0 | 0 | 0 | | 0 | 0 | 2C | 0 | 0 | 6G | 3C |
| | POST | 0.05 | | 8G | 7G | | | | | | | | | 8G | | | 3C | 3C |
| | PRE | 0.05 | 0 | 0 | 0 | 0 | 0 | 1C | 0 | 0 | | 0 | 0 | 0 | 2C | 0 | 8G | 8H |
| Compound 21 | POST | 0.05 | 1H | 0 | 3C | 0 | 0 | 0 | 0 | 0 | | 0 | 0 | 2C | 0 | 0 | 2H | 0 |
| | POST | 0.05 | | | 8H | | | | | | | | | 8G | | | 3C | 3C |
| | PRE | 0.05 | 0 | 0 | 0 | 0 | 0 | 0 | 0 | 0 | | 0 | 0 | 0 | 0 | 0 | 7G | 8H |
| Compound 22 | POST | 0.05 | 0 | 0 | 0 | 0 | 0 | 0 | 0 | 0 | | 0 | 0 | 0 | 0 | 0 | 2H | 0 |
| | PRE | 0.05 | 1H | 0 | 0 | 0 | 0 | 0 | 0 | 0 | | 0 | 2C | 1H | 5G | 3C | 4G | 1H |
| Compound 23 | POST | 0.05 | | 2H | | | | | | | | | 8H | | | 9H | 0 | 0 |
| | POST | 0.05 | | | | | | | | | | | | | | | 3C | 2C |
| | PRE | 0.05 | 0 | 7G | 2G | 0 | 0 | 0 | 0 | 0 | | 0 | 0 | 0 | 0 | 5G | 5G | 0 |

What is claimed is:

1. A compound of the formula:

$$JSO_2NHCNA \overset{W_2}{\underset{R}{\|}} \quad I$$

wherein

J is or ;

R is H or $CH_3$;

$R_1$ is H, $C_1$-$C_3$ alkyl, $C_1$-$C_3$ haloalkyl, halogen, nitro, $C_1$-$C_3$ alkoxy, $SO_2NR^IR^{II}$, $C_1$-$C_3$ alkylthio, $C_1$-$C_3$ alkylsulfinyl, $C_1$-$C_3$ haloalkoxy, $C_1$-$C_3$ haloalkylthio, amino, $C_1$-$C_3$ alkylamino, di($C_1$-$C_3$)alkylamino, $C_1$-$C_3$ alkylsulfonyl, $CO_2R^{III}$, $CH_2CN$, $CH_2OCH_3$ or $CH_2SCH_3$;

$W_1$ is O, S or $NR^{II}$;

$W_2$ is O or S;

$R^I$ is H, $C_1$-$C_4$ alkyl, $C_2$-$C_3$ cyanoalkyl, methoxy or ethoxy;

$R^{II}$ is H, $C_1$-$C_4$ alkyl or $C_3$-$C_4$ alkenyl; or $R^I$ and $R^{II}$ may be taken together as $-(CH_2)_3-$, $-(CH_2)_4-$, $-(CH_2)_5-$ or $-CH_2CH_2OCH_2CH_2-$;

$R^{III}$ is $C_1$-$C_4$ alkyl, $C_3$-$C_4$ alkenyl, $C_3$-$C_4$ alkynyl, $C_2$-$C_4$ haloalkyl, $C_2$-$C_3$ cyanoalkyl, $C_5$-$C_6$ cycloalkyl, $C_4$-$C_7$ cycloalkylalkyl or $C_2$-$C_4$ alkoxyalkyl;

Q is

Q1, Q2, Q3, Q4 (structural diagrams)

G is C=O or $SO_2$;

W is O, S, $CHR_2$ or $NR_3$;

$W_3$ is O, S, $SO_2$, $CHR_2$ or $NR_3$;

$R_2$ is H, $C_1$-$C_2$ alkyl, Cl, F or Br;

$R_3$ is H, $C_1$-$C_4$ alkyl, $C_1$-$C_4$ haloalkyl, $C_2$-$C_4$ alkoxyalkyl, $C_2$-$C_4$ cyanoalkyl, $C_3$-$C_4$ alkenyl or $C_3$-$C_4$ alkynyl;

E and $E_1$ are independently $C_3$-$C_4$ alkylene, $C_3$-$C_4$ alkenylene or $C_4$ alkenyldienyl;

$E_2$ and $E_4$ are independently $C_1$-$C_2$ alkylene or $C_2$ alkenylene;

$E_3$ and $E_5$ are independently $C_2$-$C_3$ alkylene or $C_2$-$C_3$ alkenylene; and E, $E_1$, $E_2$, $E_3$, $E_4$ and $E_5$ may optionally be substituted by 1-4 groups selected from $C_1$-$C_4$ alkyl, $C_1$-$C_4$ alkoxy, $C_1$-$C_4$ alkenyl, OH, halogen or $C_1$-$C_4$ haloalkoxy, further, when W is O, $CHR_2$ or $NR_3$, one of the carbon atoms of E may be in the form of a carbonyl group, and when $W_3$ is O, $CHR_2$ or $NR_3$, one of the carbon atoms of $E_4$ or $E_5$ may be in the form of a carbonyl group, provided that said carbonyl groups are not bonded directly to G;

A is

A-1, A-2, A-3, A-4, A-5 (structural diagrams)

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_3$-$C_5$ cycloalkyl, $C_2$-$C_4$ alkynyl, $C(O)R_6$, (three substituent structures)

or $N(OCH_3)CH_3$;

m is 2 or 3;

$L_1$ and $L_2$ are independently O or S;

$R_4$ and $R_5$ are independently $C_1$-$C_2$ alkyl;

$R_6$ is H or $CH_3$;

Z is CH;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $OCH_3$ or $SCH_3$; and

Y is $CH_3$, $CH_2CH_3$ or $CH_2CF_3$;

and their agriculturally suitable salts; provided that (a) when G is $SO_2$, then W is O, $CHR_2$ or $NR_3$;

(b) when $E_2$ or $E_4$ is $C_2$ alkylene or $C_2$ alkenylene, then $E_3$ or $E_5$ is $C_2$ alkylene or $C_2$ alkenylene;

(c) when X is Cl, F, Br or I, then Y is $OCH_3$, $OC_2H_5$, $N(OCH_3)CH_3$, $NHCH_3$, $N(CH_3)_2$ or $OCF_2H$;

(d) when the total number of carbon atoms of X and Y is greater than four, then the number of carbons of $R_1$ is less than or equal to two and the number of carbons of Q is less than or equal to eight; and (e) when $W_2$ is S, then R is H, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2=CH$, $OCH_2CH_2OCH_3$, $CH(OCH_3)_2$ or

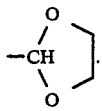

2. The compounds of claim 1 where $W_2$ is O and R is H.

3. The compounds of claim 2 where
$W_1$ is S;
$R_1$ is H, Cl, Br, $NO_2$, $CH_3$, $OCH_3$ or $CF_3$;
X is $CH_3$, $OCH_3$, $OCH_2CH_3$, Cl, F, Br, I, $OCF_2H$, $CH_2F$, $OCH_2F$, $OCH_2CHF_2$, $OCH_2CF_3$, $CF_3$, $CH_2Cl$ or $CH_2Br$;
Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $CH(CH_3)_2$, $OCH_2CH=CH_2$, $OCH_2C\equiv CH$, $CH_2OCH_2CH_3$, $OCH_2CH_2OCH_3$, $CH_2SCH_3$, $-C(O)R_6$,

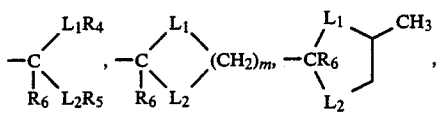

$OCF_2H$, $SCF_2H$, cyclopropyl, $C\equiv CH$ or $C\equiv CCH_3$.

4. The compounds of claim 3 where Q is $Q_1$.
5. The compounds of claim 3 where Q is $Q_2$.
6. The compounds of claim 3 where Q is $Q_3$.
7. The compounds of claim 3 where Q is $Q_4$.
8. The compounds of claim 3 where Q is

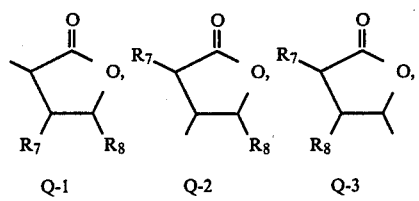

Q-1  Q-2  Q-3

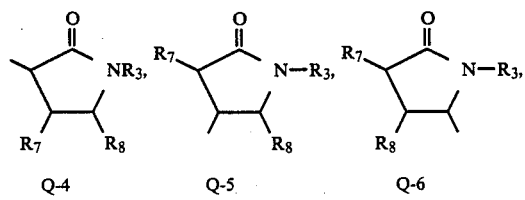

Q-4  Q-5  Q-6

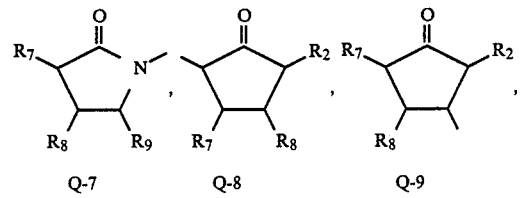

Q-7  Q-8  Q-9

-continued

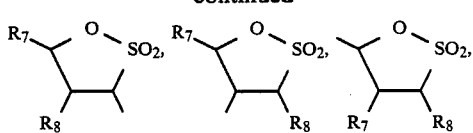

Q-10  Q-11  Q-12

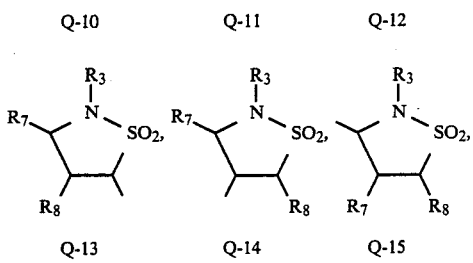

Q-13  Q-14  Q-15

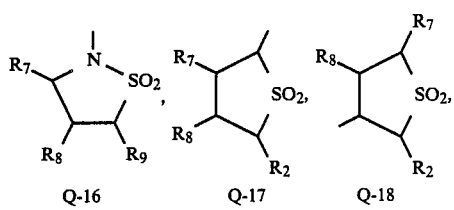

Q-16  Q-17  Q-18

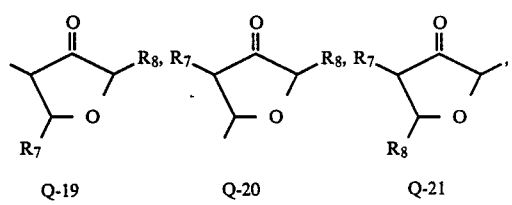

Q-19  Q-20  Q-21

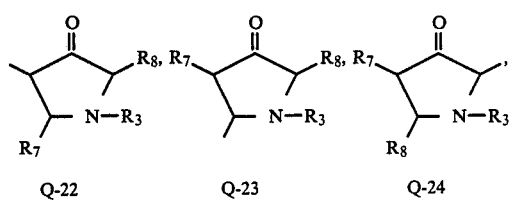

Q-22  Q-23  Q-24

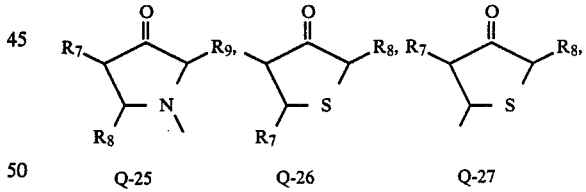

Q-25  Q-26  Q-27

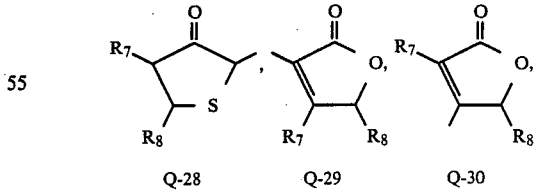

Q-28  Q-29  Q-30

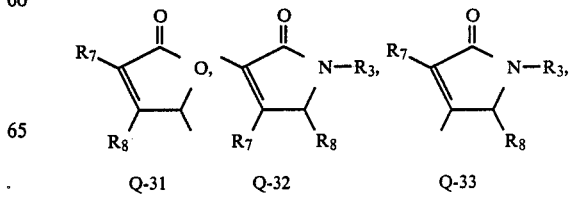

Q-31  Q-32  Q-33

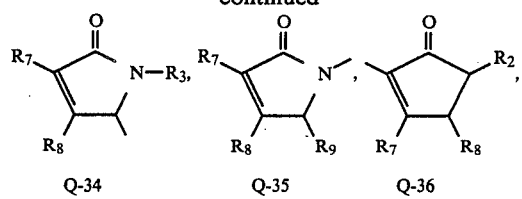
Q-34, Q-35, Q-36
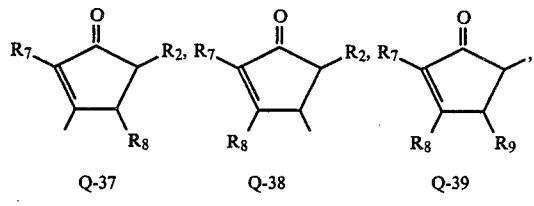
Q-37, Q-38, Q-39
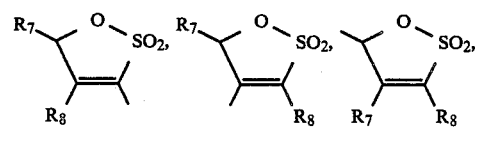
Q-40, Q-41, Q-42
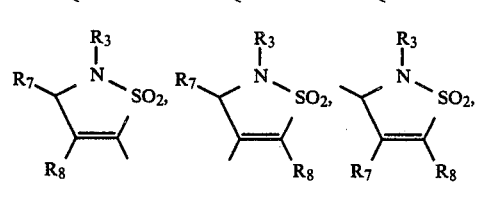
Q-43, Q-44, Q-45
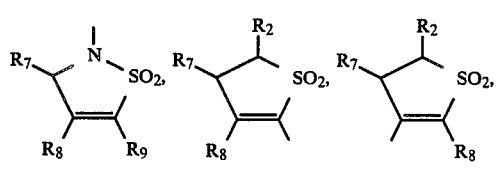
Q-46, Q-47, Q-48
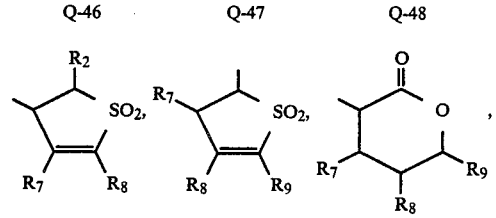
Q-49, Q-50, Q-51
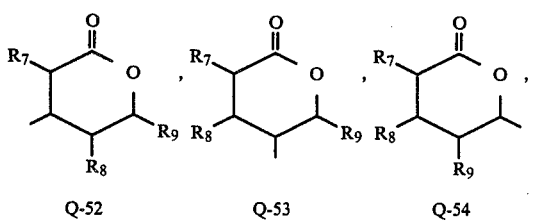
Q-52, Q-53, Q-54
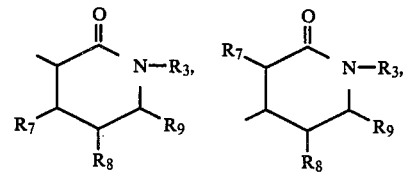
Q-55, Q-56
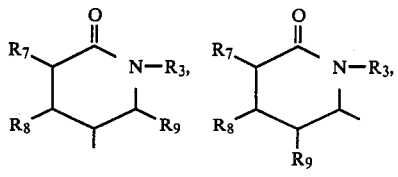
Q-57, Q-58
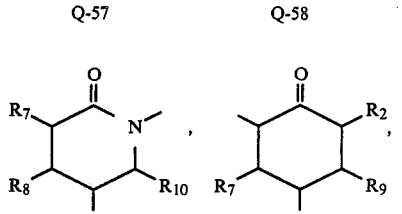
Q-59, Q-60
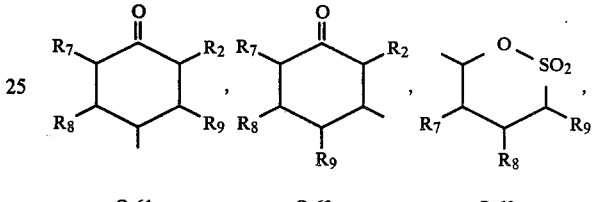
Q-61, Q-62, Q-63
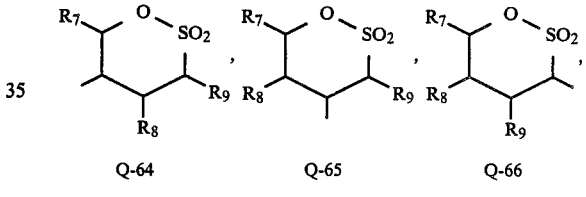
Q-64, Q-65, Q-66
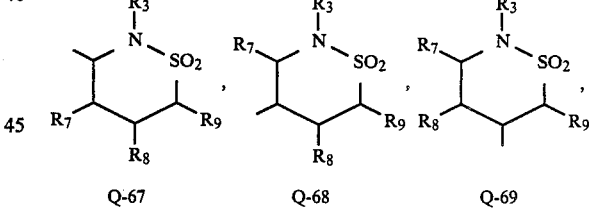
Q-67, Q-68, Q-69
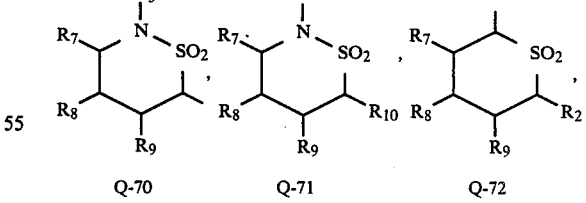
Q-70, Q-71, Q-72
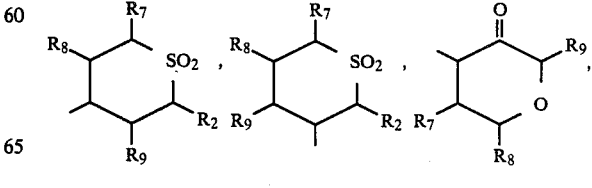
Q-73, Q-74, Q-75

-continued
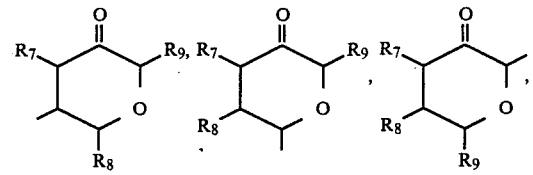
Q-76, Q-77, Q-78
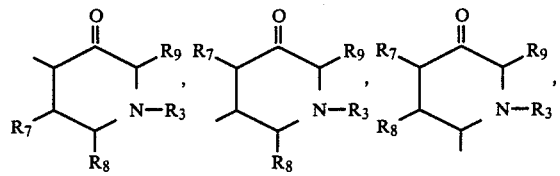
Q-79, Q-80, Q-81
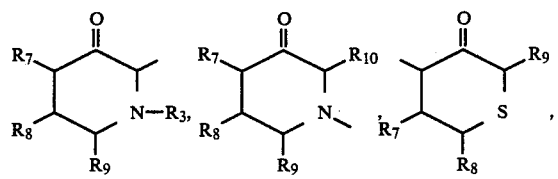
Q-82, Q-83, Q-84
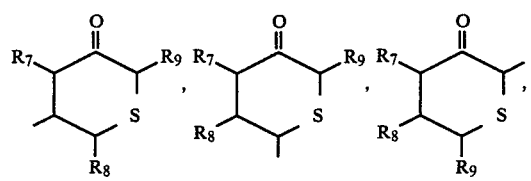
Q-85, Q-86, Q-87
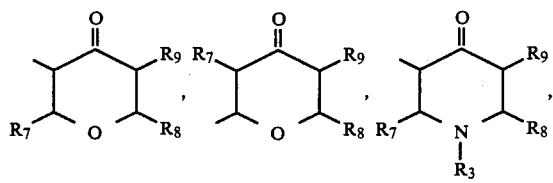
Q-88, Q-89, Q-90
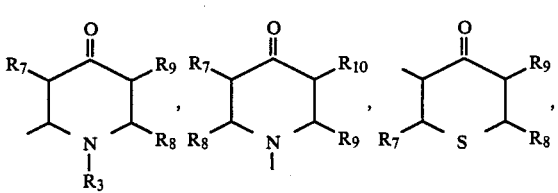
Q-91, Q-92, Q-93
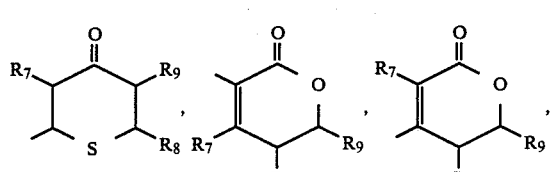
Q-94, Q-95, Q-96
-continued
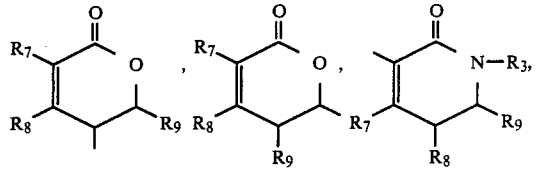
Q-97, Q-98, Q-99
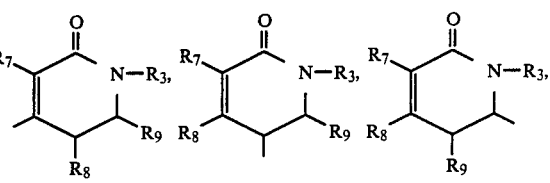
Q-100, Q-101, Q-102
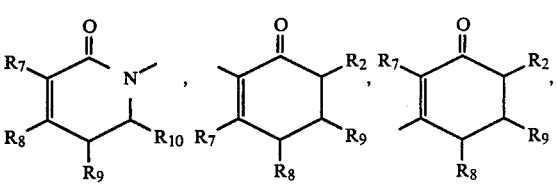
Q-103, Q-104, Q-105
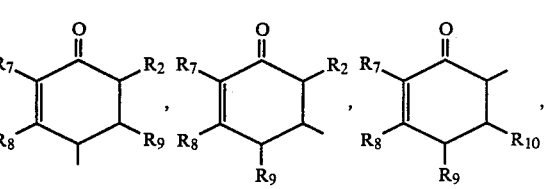
Q-106, Q-107, Q-108
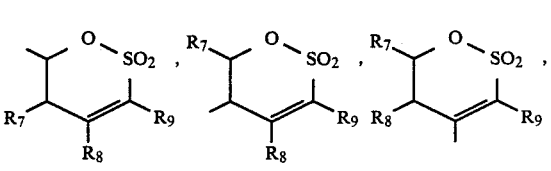
Q-109, Q-110, Q-111
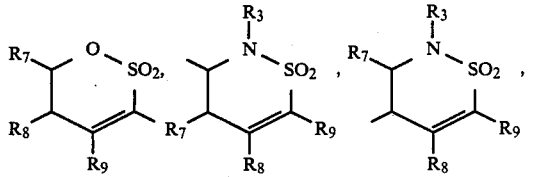
Q-112, Q-113, Q-114
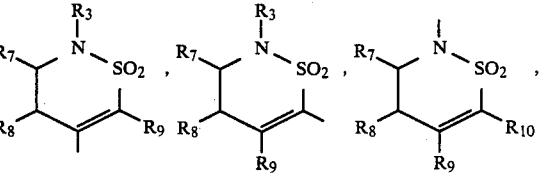
Q-115, Q-116, Q-117

-continued
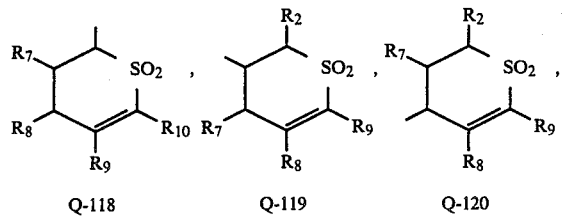
Q-118, Q-119, Q-120
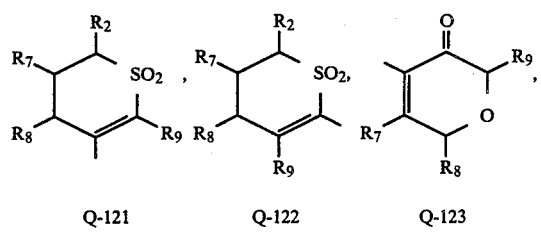
Q-121, Q-122, Q-123
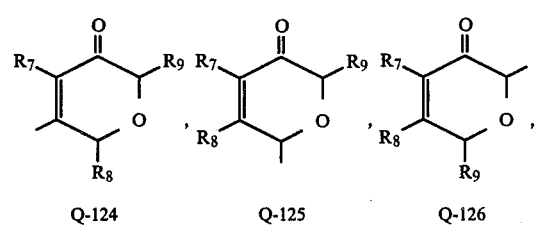
Q-124, Q-125, Q-126
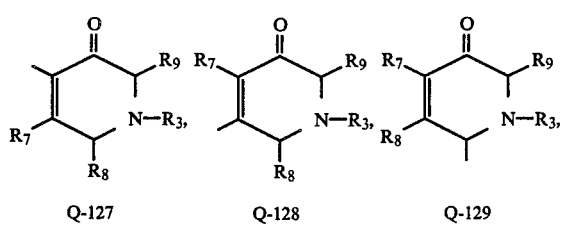
Q-127, Q-128, Q-129
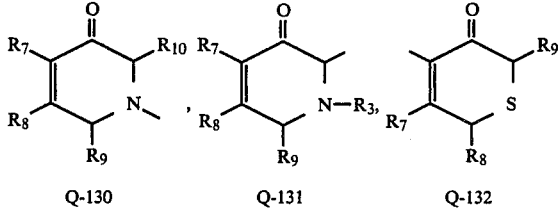
Q-130, Q-131, Q-132
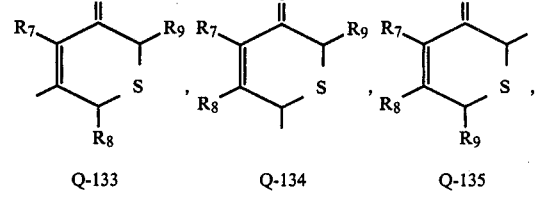
Q-133, Q-134, Q-135
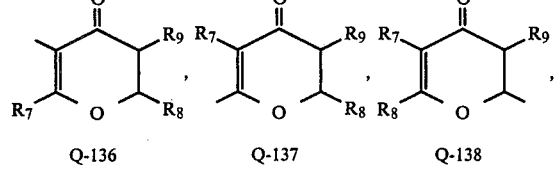
Q-136, Q-137, Q-138
-continued
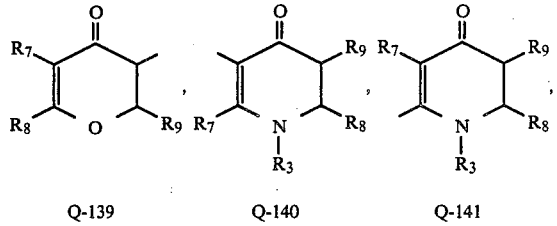
Q-139, Q-140, Q-141
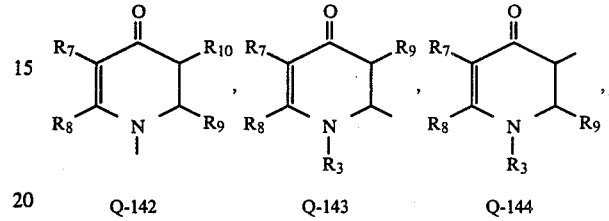
Q-142, Q-143, Q-144
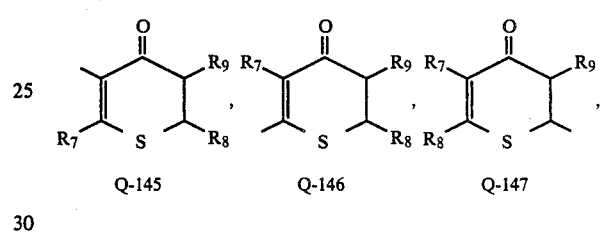
Q-145, Q-146, Q-147
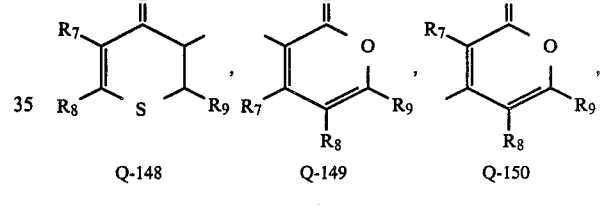
Q-148, Q-149, Q-150
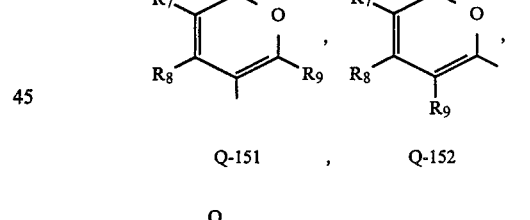
Q-151, Q-152
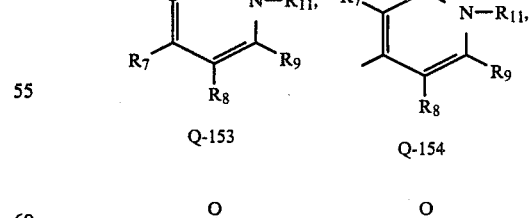
Q-153, Q-154
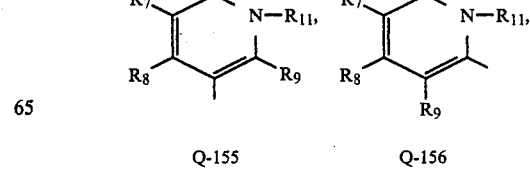
Q-155, Q-156

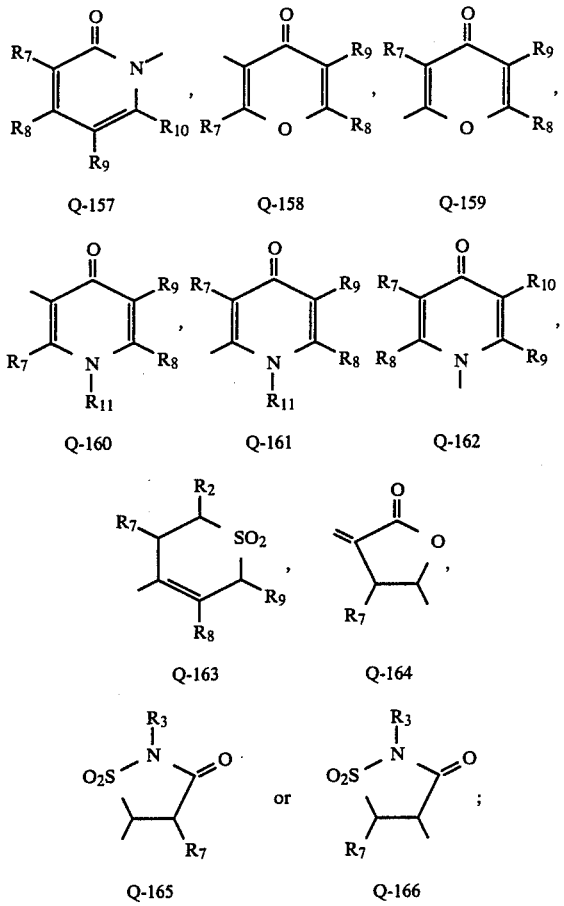

$R_7$, $R_8$, $R_9$ and $R_{10}$ are independently H or $CH_3$; and $R_{11}$ is H, $CH_3$ or $CH_2CH_3$;

9. The compounds of claim 8 where J is J-1 or J-2.

10. The compounds of claim 9 where $R_1$ is H, $CH_3$ or Cl and Y is $CH_3$, $OCH_3$, $C_2H_5$, $OC_2H_5$, $CH_2OCH_3$, $NHCH_3$, $CH(CH_3)_2$, $CH(OCH_3)_2$ or cyclopropyl.

11. The compounds of claim 10 where $R_2$ is H or $CH_3$ and $R_3$ is H, $CH_3$ or $C_2H_5$.

12. The compounds of claim 11 where X is $CH_3$, $OCH_3$, Cl or $OCF_2H$.

13. The compounds of claim 12 where Q is Q-1, Q-2, Q-3, Q-4, Q-7, Q-13, Q-14, Q-17, Q-18, Q-29, Q-37, Q-51, Q-60 or Q-105.

14. The compound of claim 1 which is N-[(4,6-dimethoxypyrimidin-2-yl)aminocarbonyl]-2-(tetrahydro-2-oxofuran-3-yl)-3-thiophenesulfonamide.

15. The compound of claim 1 which is N-[(4,6-dimethylpyrimidin-2-yl)aminocarbonyl]-2-(3-oxo-1-cyclohexen-1-yl)-3-thiophenesulfonamide.

16. A composition suitable for controlling the growth of undesired vegetation which comprises an effective amount of a compound of claim 1 and at least one of the following: sufactant, solid or liquid diluent.

17. A composition suitable for controlling the growth of undesired vegetation which comprises an effective amount of a compound of claim 2 and at least one of the following: surfactant, solid or liquid diluent.

18. A composition suitable for controlling the growth of undesired vegetation which comprises an effective amount of a compound of claim 3 and at least one of the following: surfactant, solid or liquid diluent.

19. A composition suitable for controlling the growth of undesired vegetation which comprises an effective amount of a compound of claim 4 and at least one of the following: surfactant, solid or liquid diluent.

20. A composition suitable for controlling the growth of undesired vegetation which comprises an effective amount of a compound of claim 5 and at least one of the following: surfactant, solid or liquid diluent.

21. A composition suitable for controlling the growth of undesired vegetation which comprises an effective amount of a compound of claim 6 and at least one of the following: surfactant, solid or liquid diluent.

22. A composition suitable for controlling the growth of undesired vegetation which comprises an effective amount of a compound of claim 7 and at least one of the following: surfactant, solid or liquid diluent.

23. A composition suitable for controlling the growth of undesired vegetation which comprises an effective amount of the compound of claim 8 and at least one of the following: surfactant, solid or liquid diluent.

24. A method for controlling the growth of undesired vegetation which comprises applying to the locus to be protected an effective amount of a compound of claim 1.

25. A method for controlling the growth of undesired vegetation which comprises applying to the locus to be protected an effective amount of a compound of claim 2.

26. A method for controlling the growth of undesired vegetation which comprises applying to the locus to be protected an effective amount of a compound of claim 3.

27. A method for controlling the growth of undesired vegetation which comprises applying to the locus to be protected an effective amount of a compound of claim 4.

28. A method for controlling the growth of undesired vegetation which comprises applying to the locus to be protected an effective amount of a compound of claim 5.

29. A method for controlling the growth of undesired vegetation which comprises applying to the locus to be protected an effective amount of a compound of claim 6.

30. A method for controlling the growth of undesired vegetation which comprises applying to the locus to be protected an effective amount of a compound of claim 7.

31. A method for controlling the growth of undesired vegetation which comprises applying to the locus to be protected an effective amount of the compound of claim 8.

* * * * *

UNITED STATES PATENT AND TRADEMARK OFFICE
CERTIFICATE OF CORRECTION

PATENT NO. : 4,756,742

DATED : July 12, 1988

INVENTOR(S) : Mark E. Thompson

It is certified that error appears in the above-identified patent and that said Letters Patent is hereby corrected as shown below:

Col. 177, line 20: "$OCH_2F$," should be -- $OCH_2CH_2F$ --.

Signed and Sealed this

Twenty-eighth Day of November 1989

*Attest:*

JEFFREY M. SAMUELS

*Attesting Officer*   *Acting Commissioner of Patents and Trademarks*